US007012098B2

(12) United States Patent
Manning et al.

(10) Patent No.: US 7,012,098 B2
(45) Date of Patent: Mar. 14, 2006

(54) INHIBITORS OF INDUCIBLE NITRIC OXIDE SYNTHASE FOR CHEMOPREVENTION AND TREATMENT OF CANCERS

(75) Inventors: Pamela T. Manning, Labadie, MO (US); Jane R. Connor, University City, MO (US); Karen Seibert, St. Louis, MO (US); Chinthalapally V. Rao, Croton-on-Hudson, NY (US); Bandaru S. Reddy, Suffern, NY (US)

(73) Assignee: Pharmacia Corporation, Chesterfield, MO (US)

(*) Notice: Subject to any disclaimer, the term of this patent is extended or adjusted under 35 U.S.C. 154(b) by 0 days.

(21) Appl. No.: 09/961,969

(22) Filed: Sep. 24, 2001

(65) Prior Publication Data

US 2003/0013702 A1 Jan. 16, 2003

Related U.S. Application Data

(60) Provisional application No. 60/278,512, filed on Mar. 23, 2001.

(51) Int. Cl.
*A61K 31/195* (2006.01)

(52) U.S. Cl. .................................................. 514/562
(58) Field of Classification Search ............ 514/233.8, 514/300.19, 235.2, 301, 300, 310, 562, 369
See application file for complete search history.

(56) References Cited

U.S. PATENT DOCUMENTS

| 4,769,498 | A | | 9/1988 | Billing et al. |
| 5,132,453 | A | | 7/1992 | Griffith |
| 5,466,823 | A | | 11/1995 | Talley et al. |
| 5,474,955 | A | | 12/1995 | Thakur |
| 5,684,008 | A | | 11/1997 | Hallinan et al. |
| 5,830,917 | A | | 11/1998 | Moore et al. |
| 5,854,251 | A | | 12/1998 | Hallinan et al. |
| 5,863,931 | A | | 1/1999 | Beams et al. |
| 5,919,787 | A | | 7/1999 | Hallinan et al. |
| 5,945,408 | A | | 8/1999 | Webber et al. |
| 5,981,511 | A | | 11/1999 | Gapud et al. |
| 6,034,256 | A | | 3/2000 | Carter et al. |
| 6,046,191 | A | * | 4/2000 | Hamley et al. ........... 514/232.8 |
| 6,046,211 | A | | 4/2000 | Hansen et al. |
| 6,063,789 | A | | 5/2000 | Hamley et al. |
| 6,077,850 | A | | 6/2000 | Carter et al. |
| 6,248,745 | B1 | * | 6/2001 | Hamley et al. ........... 514/266.2 |
| 6,403,830 | B2 | * | 6/2002 | Webber et al. ............. 562/557 |
| 6,498,166 | B1 | * | 12/2002 | Campbell et al. ........... 514/300 |
| 2002/0010190 | A1 | * | 1/2002 | Davey et al. ............... 514/269 |
| 2002/0111493 | A1 | * | 8/2002 | Webber et al. ............. 546/231 |

FOREIGN PATENT DOCUMENTS

| EP | 0446699 A1 | 2/1991 |
| WO | 9313055 | 7/1993 |
| WO | 9412165 | 6/1994 |
| WO | 9414780 | 7/1994 |
| WO | 9511014 | 4/1995 |
| WO | 9511231 | 4/1995 |
| WO | 9524382 | 9/1995 |
| WO | 9525717 | 9/1995 |
| WO | 9615120 | 5/1996 |
| WO | 9633175 | 10/1996 |
| WO | 9635677 | 11/1996 |
| WO | 9946240 | 9/1999 |
| WO | 9962875 | 12/1999 |
| WO | 0023433 | 4/2000 |
| WO | 0024719 | 5/2000 |
| WO | 0026195 | 5/2000 |

* cited by examiner

*Primary Examiner*—Rebecca Cook
(74) *Attorney, Agent, or Firm*—Philip B. Polster, II

(57) ABSTRACT

Agents and methods for chemoprevention and treatment of neoplasia are described, the agents including a selective inhibitor of inducible nitric oxide synthase and a combination of a selective inhibitor of inducible nitric oxide synthase and an inhibitor of cylcooxygenase-2 in a pharmaceutical composition. The agents and methods are used for chemoprevention and treatment of neoplasia including colorectal cancer and other cancers affecting epithelial cells throughout the body. The agents can also be used to treat the fibrosis that occurs with radiation therapy, as well as adenomatous polyps, including those with familial adenomatous polyposis (FAP).

5 Claims, No Drawings

INHIBITORS OF INDUCIBLE NITRIC OXIDE SYNTHASE FOR CHEMOPREVENTION AND TREATMENT OF CANCERS

CROSS REFERENCE TO RELATED APPLICATIONS

Priority is claimed from U.S. provisional application Ser. No. 60/278,512, filed Mar. 23, 2001.

BACKGROUND OF THE INVENTION

The present invention relates in general to agents and methods for treating tumor cell growth progression and metastasis, and more particularly to combinations of an inhibitor of inducible nitric oxide synthase and an inhibitor of cylcooxygenase-2 for chemoprevention and treatment of cancers and methods of using the agents in medicine.

Cancers continue to be a leading cause of death in developed nations, and in particular colorectal cancer is one of the leading causes of cancer deaths in both men and women in Western countries, including the United States (Landis et al. (2000) *CA-A Cancer J. Clinicians*, 48: 6–27.).

Epidemiological and experimental studies indicate that the risk of development of colon and rectal cancer may be attributable to combined actions of environmental factors and endogenous promoting agents (Potter (1996)*Eur. J. Cancer*, 31A: 1033–1038). Thus, endogenous factors, which appear to be directly responsible for tumor cell growth, spreading and invasion (progression and metastasis) have been the focus of much attention in the pharmaceutical industry.

Among the endogenous factors that have been implicated in the development of colorectal cancer is nitric oxide. Nitric oxide is produced endogenously as a consequence of arginine metabolism by the family of nitric oxide synthase enzymes, which possess a wide range of physiological and pathophysiological actions (Moncada et al. (1991) *Pharmacol. Rev.*, 43: 109–142).

Only one distinct form of nitric oxide synthase, known as $Ca^{+2}$-independent inducible nitric oxide synthase (iNOS), a 130 Kd protein, is expressed in response to pro-inflammatory agents. Inducible nitric oxide synthase produces high, but sustained concentrations of nitric oxide when compared to the low levels produced by the $Ca^{+2}$-dependent neuronal and endothelial isoforms of the enzyme (Nathan et al. (1994) *Cell*, 78: 915–918; Forstermann et al. (1995) *Naunyn.-Schmiedebergs. Arch. Pharmakol.*, 352: 351–364).

Studies suggest that iNOS may also play a role in tumor development (Rao et al. (2000) *Carcinogenesis*, 21: 617–621). Increased iNOS expression and/or activity was reported in human gynecological (Thomsen et al. (1994) *Cancer Res.*, 54: 1352–1354), breast (Thomsen et al. (1995) *Br. J. Cancer*, 72: 41–44), and central nervous system (Cobbs et al. (1995) *Cancer Res.*, 55: 727–730) tumors. In addition, human colon adenomas exhibit increased expression and activity of iNOS (Ambs et al. (1998) *Cancer Res.*, 58: 334–341).

Studies in experimental models of colon cancer indicate that azoxymethane-induced colon tumors have higher expression and activity, or both higher expression and activity, of iNOS by comparison to levels found in adjacent colonic tissue (Rao et al. (1998) *Proc. Am. Assoc. Cancer Res.*, 39: 197; Takahashi et al. (1997) *Cancer Res.*, 57: 1233–1237).

Inducible nitric oxide synthase has also been shown to be involved in the regulation of COX-2, which is believed to play a substantial role in colon tumorigenesis (Landino et al. (1996) *Proc. Natl. Acad. Sci. USA*, 93: 15069–15074). Together these observations suggest that an iNOS may play an important role in colon tumorigenesis. In this connection, it is noteworthy that an iNOS-selective inhibitor, PBIT, prevented azoxymethane-induced colonic aberrant crypt foci development and iNOS activity in laboratory rodents (Rao et al. (1998) *Proc. Am. Assoc. Cancer Res.*, 39: 197).

Also among the endogenous factors that have been implicated in the development of colorectal cancer are the cyclooxygenase (COX) enzymes. The involvement of COX enzymes in colorectal cancer has been revealed in work that has established the inhibitory effect of non-steroidal anti-inflammatory drugs (NSAIDs) such as aspirin, piroxicam and sulindac on colon cancer development. The collective results of epidemiological and animal studies present an inverse relationship between the use of NSAIDs and colon cancer (Thun et al. (1991) *N. Engl. J. Med.*, 325: 1593–1596).

Additional evidence suggests that colon tumor inhibition by NSAIDs may be mediated through the modulation of arachidonic acid metabolism via cyclooxygenase enzymes which, in turn, inhibits immune responsiveness (Marnett (1992) *Cancer Res.*, 52: 5575–5589; Smith (1992) *Am. J. Physiol.*, 263: F181–F191).

However, cyclooxygenase enzymes include both a constitutive form, COX-1, which has a protective effect in the gastrointestinal system, and COX-2, which is an inducible form of the enzyme that is involved in pain, inflammation, edema, angiogenesis and tumor-related processes. Since NSAIDs do not selectively inhibit COX-2, prolonged administration of NSAIDs at therapeutic doses can cause gastrointestinal bleeding and ulceration, and also renal toxicity by blocking the activity of constitutive COX-1 activity.

Thus, NSAIDs probably render chemopreventive effects by blocking COX-2, but also produce adverse side effects by blocking the activity of COX-1. A need therefore existed for selective COX-2 inhibitors that act on inducible COX-2 enzyme but spare COX-1 activity and normal physiological functions of this enzyme. COX-2 selective inhibitors have since been developed, including, for example, celecoxib, rofecoxib, valdecoxib, parecoxib and related compounds. Some COX-2 selective inhibitors appear to have tumor-suppressive effects. The COX-2 selective inhibitor celecoxib has been shown to suppress induction of the colonic aberrant crypt foci (ACF) by azoxymethane and inhibit colon tumor formation (Reddy et al. (1996) *Cancer Res.*, 56: 4566–4569; Kawamori et al. (1998) *Cancer Res.*, 58: 409–412).

In addition, COX-2 inhibitors such as nemisulide and nabumetone inhibit formation of colonic aberrant crypt foci in male F344 rats (Rao et al. (1999) *Proc. Am. Assoc. Cancer Res.*, 40: 373).

Additional evidence supporting a tumor-suppressive role for COX-2 comes from studies showing that MF-Tricyclic, a COX-2 inhibitor, blocks intestinal tumorigenesis in $APC^{\Delta 716}$ mice (Oshima et al. (1996) *Cell*, 87: 803–809).

Based on preclinical and clinical efficacy studies, celecoxib has been approved for the treatment of patients with familial adenomatous polyps, a precancerous condition that precedes colon cancer in certain individuals. Additional recent studies on COX-2 have greatly improved the understanding of its role in colorectal cancer and other diseases (Taketo (1998) *J. Natl. Cancer Inst.*, 90: 1609–1620). However, mechanistic studies support the hypothesis that COX-2 regulation is highly complex and influenced by various exogenous and endogenous factors.

Against this background, increasing interest has developed in finding combinations of low doses of two or more chemopreventive agents, each with different modes of action, so that overall treatment efficacy is improved while toxicity and adverse side effects of each agent are minimized. In this regard, preliminary work has examined a combination of an NSAID and an omithine decarboxylase inhibitor. More specifically, preliminary data suggests that lowest dose levels of piroxicam (an NSAID), and difluoromethylomithine (an omithine decarboxylase inhibitor) administered together are more effective in inhibiting colon tumorigenesis than when these agents are given individually even at higher levels (Reddy et al. (1990) Cancer Res., 50: 2562–2568).

A need however continues for new and effective combinations, and particularly for combinations that exploit the advantages of COX-2 selective inhibitors over NSAIDs.

Additional evidence suggests that aberrant crypt foci are especially suitable for use as a model system in which to test proposed chemopreventive combinations, and particularly those including COX-2 selective inhibitors. Aberrant crypt foci are recognized as early preneoplastic lesions and have consistently been observed in experimentally-induced colon carcinogenesis in laboratory animals (McLellan et al. (1991) Cancer Res., 51: 5270–5274).

Additional work has shown the presence of such lesions in the colonic mucosa of patients with colon cancer and have suggested that aberrant crypts are putative precursor lesions from which adenomas and carcinomas develop in the colon (Pretlow et al. (1992) J. Cell. Biochem., 16G (Suppl.): 55–62).

Aberrant crypt foci express mutations in the apc gene and ras oncogene that appear to be biomarkers of colon cancer development (Jen et al. (1994) Cancer Res., 54: 5523–5526).

Other preliminary studies indicate that both COX-2 and iNOS are over-expressed in the azoxymethane-induced colonic aberrant crypt foci (Rao et al. (1999) Proc. Am. Assoc. Cancer Res., 40: 373; Rao et al. (1998) Proc. Am. Assoc. Cancer Res., 39: 197). Additional evidence indicates that several inhibitors of aberrant crypt foci development reduce colon tumorigenesis in laboratory animals (Rao et al. (1995) Cancer Res., 55: 2310–2315; Rao et al. (1993) Cancer Res., 53: 4182–4188).

Thus, while COX-2 and iNOS have been separately implicated in tumor growth and development, known methods of treating and preventing tumor growth do not include the use of novel combinations of COX-2 selective inhibitors and iNOS-selective inhibitors. It would therefore be advantageous to find and describe new combinations of chemopreventive agents that allow reduced dosages of individual chemopreventive agents while maintaining or improving efficacy of the agents in the prophylaxis and treatment of cancers.

SUMMARY OF THE INVENTION

In a broad sense, the present invention is directed to treating or preventing a neoplasia-related condition in a subject in need of such treatment or prevention, by administering to the subject an amount of an inducible nitric oxide synthase selective inhibitor or pharmaceutically acceptable salt thereof or prodrug thereof, wherein the amount of the inducible nitric oxide synthase selective inhibitor constitutes a neoplasia-related condition treatment effective amount.

Cancers treatable with the present methods include, without limitation, acute lymphoblastic leukemia, acute myeloid leukemia, adrenocortical carcinoma, aids-related lymphoma, aids-related malignancies, anal cancer, cerebellar astrocytoma, extrahepatic bile duct cancer, bladder cancer, osteosarcoma/malignant fibrous histiocytoma, brain stem glioma, ependymoma, medulloblastoma, supratentorial primitive neuroectodermal and pineal tumors, visual pathway and hypothalamic gliomas, breast cancer, breast cancer and pregnancy, breast cancer, childhood, breast cancer, male, bronchial adenomas/carcinoids, carcinoid tumors, gastrointestinal carcinoid tumors, carcinoma, adrenocortical, islet cell carcinoma, carcinoma of unknown primary, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, ovarian epithelial cancer, esophageal cancer, ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastric (stomach) cancer, gastrointestinal carcinoid tumor, ovarian germ cell tumor, gestational trophoblastic tumor, hairy cell leukemia, head and neck cancer, primary hepatocellular cancer, Hodgkin's disease, including Hodgkin's disease during pregnancy, hypopharyngeal cancer, hypothalamic and visual pathway glioma, intraocular melanoma, islet cell carcinoma (endocrine pancreas), Kaposi's sarcoma, kidney cancer, laryngeal cancer, acute lymphoblastic leukemia, acute myeloid leukemia, chronic lymphocytic, leukemia, chronic myelogenous leukemia, hairy cell, lip and oral cavity cancer, liver cancer, non-small cell lung cancer, small cell lung cancer, Hodgkin's disease, non-Hodgkin's lymphoma, Waldenström's macroglobulinemia, male breast cancer, malignant mesothelioma, malignant thymoma, medulloblastoma, melanoma, intraocular melanoma, merkel cell carcinoma, malignant mesothelioma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian epithelial cancer, ovarian low malignant potential tumor, pancreatic cancer, pancreatic cancer, islet cell, paranasal sinus and nasal cavity cancer, parathyroid cancer, penile cancer, pheochromocytoma, pineal and supratentorial primitive neuroectodermal tumors, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, Ewing's family of tumors/primitive neuroectodermal tumor (pnet), malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous t-cell lymphoma, testicular cancer, malignant thymoma, thyroid cancer, transitional cell cancer of the renal pelvis and ureter, gestational trophoblastic tumor, cancer of unknown primary site, unusual cancers of childhood, urethral cancer, uterine sarcoma, vaginal cancer, vulvar cancer, and Wilms' tumor.

The cancers that will be treatable or preventable by the methods of the present invention include, without limitation, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

In another embodiment of the present invention, a neoplasia is selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present methods can also be used to treat the fibrosis which occurs with radiation therapy.

In addition, the present methods can be used to treat subjects having adenomatous polyps, including those with familial adenomatous polyposis (FAP). Additionally, the present compounds and methods can be used to prevent polyps from forming in patients at risk of FAP.

In another embodiment, the present invention is directed to treating or preventing a neoplasia-related condition in a subject in need of such treatment or prevention, by administering to the subject an amount of an inducible nitric oxide synthase selective inhibitor or pharmaceutically acceptable salt thereof or prodrug thereof, and an amount of a cyclooxygenase-2 inhibitor or pharmaceutically acceptable salt thereof or prodrug thereof, wherein the amount of the inducible nitric oxide synthase selective inhibitor and the amount of the cyclooxygenase-2 inhibitor together constitute a neoplasia-related condition treatment effective amount.

In another embodiment, the invention relates to a pharmaceutical composition comprising an amount of an inducible nitric oxide synthase selective inhibitor or pharmaceutically acceptable salt thereof or prodrug thereof, wherein the amount of the inducible nitric oxide synthase selective inhibitor constitutes a neoplasia-related condition treatment effective amount.

In another embodiment, the invention relates to a pharmaceutical composition comprising an amount of an inducible nitric oxide synthase selective inhibitor or pharmaceutically acceptable salt thereof or prodrug thereof, and an amount of a cyclooxygenase-2 inhibitor or pharmaceutically acceptable salt thereof or prodrug thereof, wherein the amount of the inducible nitric oxide synthase selective inhibitor and the amount of the cyclooxygenase-2 selective inhibitor or prodrug together constitute a neoplasia-related condition effective amount.

In another embodiment, the invention relates to a pharmaceutical composition comprising an amount of an inducible nitric oxide synthase selective inhibitor or pharmaceutically acceptable salt thereof or prodrug thereof, and an amount of a cyclooxygenase-2 inhibitor or pharmaceutically acceptable salt thereof or prodrug thereof, wherein the inducible nitric oxide synthase selective inhibitor is selected from the group consisting of the compound of formulas I–X, below.

In one illustrative example of a selective iNOS inhibitor, treatment is facilitated through compounds having Formula I:

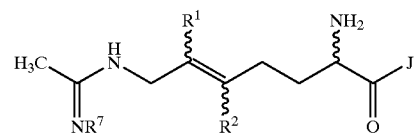

or a pharmaceutically acceptable salt thereof, wherein:

$R^1$ is selected from the group consisting of H, halo and alkyl which may be optionally substituted by one or more halo;

$R^2$ is selected from the group consisting of H, halo and alkyl which may be optionally substituted by one or more halo; with the proviso that at least one of $R^1$ or $R^2$ contains a halo;

$R^7$ is selected from the group consisting of H and hydroxy; and

J is selected from the group consisting of hydroxy, alkoxy, and $NR^3R^4$ wherein;

$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

In another embodiment, the present invention provides treatment utilizing a compound or a salt thereof, the compound having a structure corresponding to Formula II:

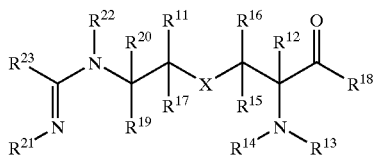

II

In the structure of Formula II, X is selected from the group consisting of —S—, —S(O)—, and —S(O)$_2$—. Preferably, X is —S—. $R^{12}$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl wherein each of these groups is optionally substituted by one or more substituent selected from the group consisting of —OH, alkoxy, and halogen. Preferably, $R^{12}$ is $C_1$–$C_6$ alkyl optionally substituted with a substituent selected from the group consisting of —OH, alkoxy, and halogen. With respect to $R^{13}$ and $R^{18}$, $R^{18}$ is selected from the group consisting of —O$R^{24}$ and —N($R^{25}$)($R^{26}$), and $R^{13}$ is selected from the group consisting of —H, —OH, —C(O)—$R^{27}$, —C(O)—O—$R^{28}$, and —C(O)—S—$R^{29}$; or $R^{18}$ is —N($R^{30}$)—, and $R^{13}$ is —C(O)—, wherein $R^{18}$ and $R^{13}$ together with the atoms to which they are attached form a ring; or $R^{18}$ is —O—, and $R^{13}$ is —C($R^{31}$)($R^{32}$)—, wherein $R^{18}$ and $R^{13}$ together with the atoms to which they are attached form a ring. If $R^{13}$ is —C(R3$^{21}$)($R^{32}$)—, then $R^{14}$ is —C(O)—O—$R^{33}$; otherwise $R^{14}$ is —H. $R^{11}$, $R^{15}$, $R^{16}$, and $R^{17}$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$ alkyl. $R^{19}$ and $R^{20}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl. With respect to $R^{21}$ and $R^{22}$, $R^{21}$ is selected from the group consisting of —H, —OH, —C(O)—O—$R^{34}$, and —C(O)—S—$R^{35}$, and $R^{22}$ is selected from the group consisting of —H, —OH, —C(O)—O—$R^{36}$, and —C(O)—S—$R^{37}$; or $R^{21}$ is —O—, and $R^{22}$ is —C(O)—, wherein $R^{21}$ and $R^{22}$ together with the atoms to which they are attached form a ring; or $R^{21}$ is —C(O)—, and $R^{22}$ is —O—, wherein $R^{21}$ and $R^{22}$ together with the atoms to which they are attached form a ring. $R^{23}$ is $C_1$ alkyl. $R^{24}$ is selected from the group consisting of —H and $C_1$–$C_6$ alkyl, wherein when $R^{24}$ is $C_1$–$C_6$ alkyl, $R^{24}$ is optionally substituted by one or more moieties selected from the group consisting of cycloalkyl, heterocyclyl, aryl, and heteroaryl. With respect to $R^{25}$ and $R^{26}$, $R^{25}$ is selected from the group consisting of —H, alkyl, and alkoxy, and $R^{26}$ is selected from the group consisting of —H, —OH, alkyl, alkoxy, —C(O)—$R^{38}$, —C(O)—O—$R^{39}$, and —C(O)—S—$R^{40}$; wherein when $R^{25}$ and $R^{26}$ independently are alkyl or alkoxy, $R^{25}$ and $R^{26}$ independently are optionally substituted with one or more moieties selected from the group consisting of cycloalkyl, heterocyclyl, aryl, and heteroaryl; or $R^{25}$ is —H; and $R^{26}$ is selected from the group consisting of cycloalkyl, heterocyclyl, aryl, and heteroaryl. $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, and $R^{40}$ independently are selected from the group consisting of —H and alkyl, wherein alkyl is optionally substituted by one or more moieties selected from the group consisting of cycloalkyl, heterocyclyl, aryl, and heteroaryl. When any of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$ $R^{36}$, $R^{37}$, $R^{38}$, $R^{39}$, and $R^{40}$ independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen.

In a preferred compound, $R^{18}$ is —OH. When $R^{18}$ is —OH, preferably X is S. In a further compound, $R^{11}$, $R^{15}$, $R^{16}$, $R^{17}$, $R^{19}$, and $R^{20}$ independently are selected from the group consisting of —H and $C_1$–$C_3$ alkyl. Preferably $R^{15}$, $R^{16}$, $R^{17}$, $R^{19}$, $R^{20}$ each are —H. $R^{23}$ can be a variety of groups, for example fluoromethyl or methyl. $R^{11}$ can be $C_1$–$C_6$ alkyl optionally substituted with a substituent selected from the group consisting of —OH and halogen; preferably $R^{11}$ is $C_1$ alkyl optionally substituted with halogen; more preferably $R^{11}$ is selected from the group consisting of fluoromethyl, hydroxymethyl, and methyl. In one important compound, $R^{11}$ can be methyl. Alternatively, $R^{11}$ can be fluoromethyl. In another alternative $R^{11}$ can be hydroxymethyl. In another compound, $R^{12}$ is $C_1$–$C_6$ alkyl optionally substituted with a substituent selected from the group consisting of —OH, alkoxy, and halogen. In one preferred compound $R^{12}$ is $C_1$ alkyl optionally substituted with halogen. For example, $R^{12}$ can be methyl. Alternatively, $R^{12}$ can be fluoromethyl. In yet another example, $R^{12}$ can be hydroxymethyl. In still another example, $R^{12}$ can be methoxymethyl.

In this exemplary compound, it is preferred that $R^{13}$, $R^{14}$, $R^{21}$ and $R^{22}$ each is —H. In this compound, it is further preferred that $R^{11}$, $R^{15}$, $R^{16}$, $R^{17}$, $R^{19}$, and $R^{20}$ independently are selected from the group consisting of —H and $C_1$–$C_3$ alkyl. Preferably $R^{15}$, $R^{16}$, $R^{17}$, $R^{19}$, $R^{20}$ each is —H. In this further compound, $R^{23}$ can be, for example, fluoromethyl, or in another example $R^{23}$ can be methyl. In preferred compounds of these examples, $R^{12}$ is $C_1$–$C_6$ alkyl optionally substituted with a substituent selected from the group consisting of —OH, alkoxy, and halogen. Preferably $R^{12}$ is $C_1$ alkyl optionally substituted with halogen. In one such example $R^{12}$ is fluoromethyl. In another example $R^{12}$ is methyl. Alternatively $R^{12}$ can be hydroxymethyl. In another alternative, $R^{12}$ can be methoxymethyl.

When $R^{23}$ is methyl, $R^{11}$ can be, for example, —H or $C_1$–$C_6$ alkyl optionally substituted with a substituent selected from the group consisting of —OH and halogen. In a preferred compound $R^{11}$ is —H. Alternatively, $R^{11}$ can be $C_1$–$C_6$ alkyl optionally substituted with a substituent selected from the group consisting of —OH and halogen. For example $R^{11}$ can be methyl, ethyl, n-propyl, i-propyl, n-butyl, sec-butyl, isobutyl, t-butyl, a pentyl isomer, or a hexyl isomer. For example, $R^{11}$ can be ethyl. Alternatively, $R^{11}$ can be $C_1$ alkyl optionally substituted with a substituent selected from the group consisting of —OH and halogen; for example $R^{11}$ can be methyl. Alternatively, $R^{11}$ can be fluoromethyl. In another alternative, $R^{11}$ can be hydroxymethyl.

In another compound $R^{18}$ can be —O$R^{24}$. $R^{24}$ can be as defined above. Preferably $R^{24}$ is $C_1$–$C_6$ alkyl optionally substituted by one or more moieties selected from the group consisting of cycloalkyl, heterocyclyl, aryl, and heteroaryl; more preferably $R^{24}$ is $C_1$–$C_3$ alkyl; and more preferably still $R^{24}$ is methyl. In yet another example of compound II, $R^{18}$ can be —N($R^{25}$)($R^{26}$), wherein $R^{25}$ and $R^{26}$ are as defined above. In still another compound, $R^{18}$ can be —N($R^{30}$)—, and $R^{13}$ can be —C(O)—, wherein $R^{18}$ and $R^{13}$ together with the atoms to which they are attached form a ring. In another example still, $R^{18}$ can be —O—, and $R^{13}$ can be —C($R^{31}$)($R^{32}$)—, wherein $R^{18}$ and $R^{13}$ together with the atoms to which they are attached form a ring.

In a compound of Formula II, $R^{21}$ can be selected from the group consisting of —OH, —C(O)—O—$R^{34}$, and —C(O)—S—$R^{35}$. Preferably $R^{21}$ is —OH. In a further example, $R^{22}$ is —H when $R^{21}$ is —OH.

However, the present example also provides useful compounds of Formula II in which $R^{21}$ is —O—, and $R^{22}$ is —C(O)—, wherein $R^{21}$ and $R^{22}$ together with the atoms to which they are attached form a ring. In another useful compound, $R^{21}$ is —C(O)—, and $R^{22}$ is —O—, wherein $R^{21}$ and $R^{22}$ together with the atoms to which they are attached form a ring. Alternatively, $R^{22}$ can be selected from the group consisting of —OH, —C(O)—O—$R^{36}$, and —C(O)—S—$R^{37}$. In this alternative, $R^{21}$ is preferably —H.

In another selective iNOS inhibitor useful in the practice of the present invention, a compound is represented by Formula III:

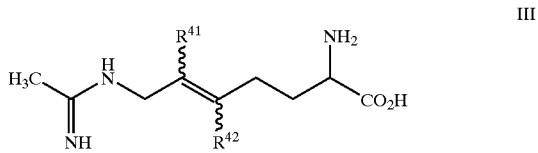

III or a pharmaceutically acceptable salt thereof, wherein:

$R^{41}$ is H or methyl; and
$R^{42}$ is H or methyl.

Another selective iNOS inhibitor useful in the practice of the present invention is represented by a compound of formula IV

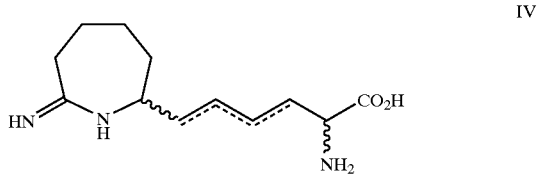

IV or a pharmaceutically acceptable salt thereof.

Another exemplary selective iNOS inhibitor useful in the present invention is represented by Formula V:

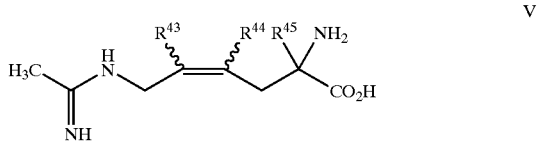

V or a pharmaceutically acceptable salt thereof, wherein:

$R^{43}$ is selected from the group consisting of hydrogen, halo, $C_1$–$C_5$ alkyl and $C_1$–$C_5$ alkyl substituted by alkoxy or one or more halo;
$R^{44}$ is selected from the group consisting of hydrogen, halo, $C_1$–$C_5$ alkyl and $C_1$–$C_5$ alkyl substituted by alkoxy or one or more halo;
$R^{45}$ is $C_1$–$C_5$ alkyl or $C_1$–$C_5$ alkyl be substituted by alkoxy or one or more halo.

A further illustrative selective iNOS inhibitor is represented by Formula VI:

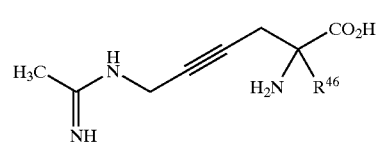

VI or a pharmaceutically acceptable salt thereof, wherein:
$R^{46}$ is $C_1$–$C_5$ alkyl, said $C_1$–$C_5$ alkyl optionally substituted by halo or alkoxy, said alkoxy optionally substituted by one or more halo.

Another exemplary selective iNOS inhibitor useful in the present invention is represented by Formula VII

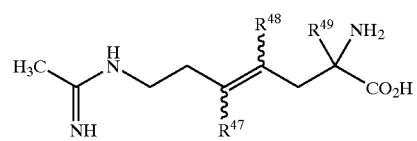

VII or a pharmaceutically acceptable salt thereof, wherein:
$R^{47}$ is selected from the group consisting of hydrogen, halo, $C_1$–$C_5$ alkyl and $C_1$–$C_5$ alkyl substituted by alkoxy or one or more halo;
$R^{48}$ is selected from the group consisting of hydrogen, halo, $C_1$–$C_5$ alkyl and $C_1$–$C_5$ alkyl substituted by alkoxy or one or more halo;
$R^{49}$ is $C_1$–$C_5$ alkyl or $C_1$–$C_5$ alkyl be substituted by alkoxy or one or more halo.

Another exemplary selective iNOS inhibitor useful in the present invention is represented by Formula VIII

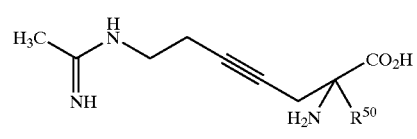

VIII or a pharmaceutically acceptable salt thereof, wherein:
$R^{50}$ is $C_1$–$C_5$ alkyl, said $C_1$–$C_5$ alkyl optionally substituted by halo or alkoxy, said alkoxy optionally substituted by one or more halo.

Another selective iNOS inhibitor useful in the practice of the present invention is represented by a compound of formula IX

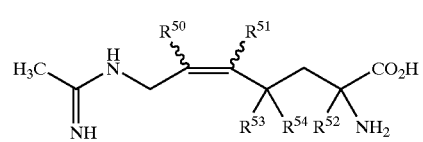

IX or a pharmaceutically acceptable salt thereof, wherein:
$R^{50}$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^{51}$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^{52}$ is $C_1$–$C_5$ alkyl, said $C_1$–$C_5$ alkyl optionally substituted by halo or alkoxy, said alkoxy optionally substituted by one or more halo;

R[53] is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and R[54] is selected from the group consisting of halo and $C_1$–$C_5$ alkyl, said $C_1$–$C_5$ alkyl optionally substituted by halo or alkoxy, said alkoxy optionally substituted by one or more halo.

Yet another selective iNOS inhibitor useful in the practice of the present invention is represented by a compound of formula X

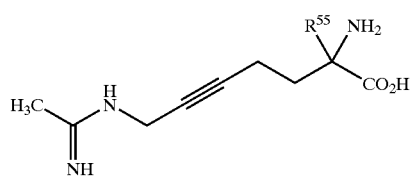

or a pharmaceutically acceptable salt thereof, wherein:
R[55] is $C_1$–$C_5$ alkyl, said $C_1$–$C_5$ alkyl optionally substituted by halo or alkoxy, said alkoxy optionally substituted by one or more halo.

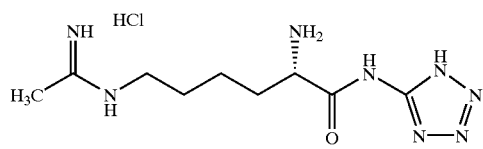

and aminoguanidine.

The compositions and methods described above are useful in the treatment and prophylaxis of neoplasia and neoplasia—related conditions including cancers and adenomatous polyposis. These compositions also reduce the dosages of individual chemopreventive agents while maintaining or improving efficacy of the agents in the prophylaxis and treatment of cancer.

DETAILED DESCRIPTION OF INVENTION

The following detailed description is provided to aid those skilled in the art to practice the present invention. However, this detailed description should not be construed to unduly limit the present invention, inasmuch as modifications and variations in the exemplary embodiments discussed herein can be made by those of ordinary skill in the art without departing from the scope of the appended claims.

The contents of each of the primary references cited herein in Table I, including the contents of the references cited within the primary references, are herein incorporated by reference in their entirety.

Generally, the present invention encompasses therapeutic combinations of chemopreventive agents, and their methods of use in medicine for preventing and treating tumor cell growth, progression and metastasis. The therapeutic combinations include an inhibitor of inducible nitric oxide synthase and an inhibitor of cylcooxygenase-2. The novel combinations of the present invention demonstrate improved efficacy, improved potency and reduced dosing requirements for each active compound as compared to therapeutic agents using the active compounds individually, for the treatment of colon and rectal cancer and other types of epithelial cell-derived cancers, as well as polyposis, including adenomatous polyps and especially familial adenomatous polyps.

a. Definitions

The following definitions are provided in order to aid an understanding of the detailed description of the present invention:

The term "combination therapy" as used herein refers to the administration of two or more therapeutic compounds to treat neoplasias, including cancer such as colorectal cancer, esophageal cancer, breast cancer and other known cancers that effect epithelial cells throughout the body, as well as to treat adenomatous polyps, including subjects with familial adenomatous polyposis (FAP).

The term "subject" as used herein refers to an animal, in one embodiment a mammal, and in an exemplary embodiment particularly a human being, who is the object of treatment, observation or experiment.

The terms "dosing" and "treatment" as used herein refer to any process, action, application, therapy or the like, wherein a subject, particularly a human being, is rendered medical aid with the object of improving the subject's condition, either directly or indirectly.

The term "therapeutic compound" as used herein refers to a compound useful in the prophylaxis or treatment of neoplasia including colorectal cancer, including colon cancer, rectal cancer, esophageal cancer, breast cancer and other known cancers that effect epithelial cells throughout the body, and adenomatous polyps including familial adenomatous polyps.

The term "therapeutic combination" as used herein refers to the administered therapeutic compounds when administered in combination therapy, and to any pharmaceutically acceptable carriers used to provide dosage forms such that the beneficial effect of each therapeutic compound is realized by the subject at the desired time, whether the compounds are administered substantially simultaneously, or sequentially.

The term "therapeutically effective" as used herein refers to a characteristic of the combined amount of therapeutic compounds in the combination therapy. The combined amount achieves the goal of preventing, avoiding, reducing or eliminating the colorectal cancer-related condition.

The terms "inducible nitric oxide synthase" and "iNOS" as used interchangeably herein refer to the $Ca^{+2}$-independent, inducible isoform of the enzyme nitric oxide synthase.

The terms "inducible nitric oxide synthase selective inhibitor" and "iNOS selective inhibitor" as used interchangeably herein refer to a therapeutic compound that selectively inhibits the $Ca^{+2}$-independent, inducible isoform of the enzyme nitric oxide synthase. A selective iNOS inhibitor is defined as producing the selective inhibition of iNOS compared to either endothelial NOS or neuronal NOS such that in vivo administration results in efficacy ($ED_{50}$ less than 100 mg/kg, but preferably less than 10 mg/kg in a rodent endotoxin model) and selectivity of at least 20-fold, but preferably 100-fold or greater with respect to eNOS as measured by elevation in mean arterial blood pressure and selectivity of at least 20-fold, but preferably 100-fold or greater with respect to nNOS as measured by reductions in gastrointestinal transit or penile erection.

The terms "cyclooxygenase-1" and "COX-1" as used interchangeably herein refer to the constitutive isoform of the enzyme cyclooxygenase.

The terms "cyclooxygenase-2" and "COX-2" as used interchangeably herein refer to the inducible isoform of the enzyme cyclooxygenase.

The terms "cyclooxygenase inhibitor" and "COX inhibitor" as used interchangeably herein refer to a therapeutic compound that inhibits both the constitutive COX-1 isoform of the enzyme cyclooxygenase, and the inducible COX-2 isoform of the enzyme cycloxygenase.

The terms "cyclooxygenase-2 selective inhibitor", "COX-2 selective inhibitor" and "COX-2 inhibitor" as used interchangeably herein refer to a therapeutic compound that selectively inhibits cyclooxygenase-2 relative to inhibition of cyclooxygenase-1. Especially suitable as cyclooxygenase-2 selective inhibitors are those compounds that have a cyclooxygenase-2 $IC_{50}$ of less than about 0.2 $\mu$M, and also have a selectivity ratio of cyclooxygenase-2 inhibition over cyclooxygenase-1 inhibition of at least 50, and more preferably of at least 100. Even more preferably, the cyclooxygenase-2 selective inhibitor compounds have a cyclooxygenase-1 $IC_{50}$ of greater than about 1 $\mu$M, and more preferably of greater than 10 $\mu$M.

The term "prodrug" refers to a compound that is a drug precursor which, following administration to a subject and subsequent absorption, is converted to an active species in vivo via some process, such as a metabolic process. Other products from the conversion process are easily disposed of by the body. The more preferred prodrugs are those involving a conversion process that produces products that are generally accepted as safe.

b. Inducible Nitric Oxide Synthase Inhibitors

In the combinations of the present invention, the inducible nitric oxide synthase selective inhibitor can be any known iNOS selective inhibitor or a pharmaceutically acceptable salt or derivative or prodrug thereof. For example, compounds that selectively inhibit iNOS include aminoguanidine, compounds previously described in U.S. Pat. No. 6,046,211 (which is herein incorporated by reference) and U.S. Pat. No. 6,063,789 (WO97/3897).

In one illustrative example of a selective iNOS inhibitor, treatment is facilitated through a compound having Formula I:

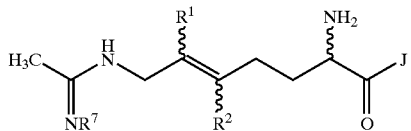

I or a pharmaceutically acceptable salt thereof, wherein:

$R^1$ is selected from the group consisting of H, halo and alkyl which may be optionally substituted by one or more halo;

$R^2$ is selected from the group consisting of H, halo and alkyl which may be optionally substituted by one or more halo;

with the proviso that at least one of $R^1$ or $R^2$ contains a halo;

$R^7$ is selected from the group consisting of H and hydroxy; and

J is selected from the group consisting of hydroxy, alkoxy, and $NR^3R^4$ wherein;

$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydmxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

In another embodiment, the present invention provides treatment utilizing a compound or a salt thereof, the compound having a structure corresponding to Formula II:

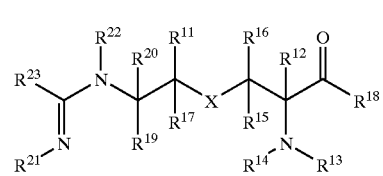

II

In the structure of Formula II, X is selected from the group consisting of —S—, —S(O)—, and —S(O)$_2$—. Preferably, X is —S—. $R^{12}$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl wherein each of these groups is optionally substituted by one or more substituent selected from the group consisting of —OH, alkoxy, and halogen. Preferably, $R^{12}$ is $C_1$–$C_6$ alkyl optionally substituted with a substituent selected from the group consisting of —OH, alkoxy, and halogen. With respect to $R^{13}$ and $R^{18}$, $R^{18}$ is selected from the group consisting of —OR$^{24}$ and —N(R$^{25}$)(R$^{26}$), and $R^{13}$ is selected from the group consisting of —H, —OH, —C(O)—R$^{27}$, —C(O)—O—R$^{28}$, and —C(O)—S—R$^{29}$; or $R^{18}$ is —N(R$^{30}$)—, and $R^{13}$ is —C(O)—, wherein $R^{18}$ and $R^{13}$ together with the atoms to which they are attached form a ring; or $R^{18}$ is —O—, and $R^{13}$ is —C(R$^{31}$)(R$^{32}$)—, wherein $R^{18}$ and $R^{13}$ together with the atoms to which they are attached form a ring. If $R^{13}$ is —C(R3$^{21}$)(R$^{32}$)—, then $R^{14}$ is —C(O)—O—R$^{33}$; otherwise $R^{14}$ is —H. $R^{11}$, $R^{15}$, $R^{16}$, and $R^{17}$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$ alkyl. $R^{19}$ and $R^{20}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl. With respect to $R^{21}$ and $R^{22}$, $R^{21}$ is selected from the group consisting of —H, —OH, —C(O)—O—$R^{34}$, and —C(O)—S—$R^{35}$, and $R^{22}$ is selected from the group consisting of —H, —OH, —C(O)—O—$R^{36}$, and —C(O)—S—$R^{37}$; or $R^{21}$ is —O—, and $R^{22}$ is —C(O)—, wherein $R^{21}$ and $R^{22}$ together with the atoms to which they are attached form a ring; or $R^{21}$ is —C(O)—, and $R^{22}$ is —O—, wherein $R^{21}$ and $R^{22}$ together with the atoms to which they are attached form a ring. $R^{23}$ is $C_1$ alkyl. $R^{24}$ is selected from the group consisting of —H and $C_1$–$C_6$ alkyl, wherein when $R^{24}$ is $C_1$–$C_6$ alkyl, $R^{24}$ is optionally substituted by one or more moieties selected from the group consisting of cycloalkyl, heterocyclyl, aryl, and heteroaryl. With respect to $R^{25}$ and $R^{26}$, $R^{25}$ is selected from the group consisting of —H, alkyl, and alkoxy, and $R^{26}$ is selected from the group consisting of —H, —OH, alkyl, alkoxy, —C(O)—$R^{38}$, —C(O)—O—$R^{39}$, and —C(O)—S—$R^{40}$; wherein when $R^{25}$ and $R^{26}$ independently are alkyl or alkoxy, $R^{25}$ and $R^{26}$ independently are optionally substituted with one or more moieties selected from the group consisting of cycloalkyl, heterocyclyl, aryl, and heteroaryl; or $R^{25}$ is —H; and $R^{26}$ is selected from the group consisting of cycloalkyl, heterocyclyl, aryl, and heteroaryl. $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, and $R^{40}$ independently are selected from the group consisting of —H, and alkyl, wherein alkyl is optionally substituted by one or more moieties selected from the group consisting of cycloalkyl, heterocyclyl, aryl, and heteroaryl. When any of $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, and $R^{40}$ independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen.

In a preferred compound, $R^{18}$ is —OH. When $R^{18}$ is —OH, preferably X is S. In a further compound, $R^{11}$, $R^{15}$, $R^{16}$, $R^{17}$, $R^{19}$, and $R^{20}$ independently are selected from the group consisting of —H and $C_1$–$C_3$ alkyl. Preferably $R^{15}$, $R^{16}$, $R^{17}$, $R^{19}$, $R^{20}$ each are —H. $R^{23}$ can be a variety of groups, for example fluoromethyl or methyl. $R^{11}$ can be $C_1$–$C_6$ alkyl optionally substituted with a substituent selected from the group consisting of —OH and halogen; preferably $R^{11}$ is $C_1$ alkyl optionally substituted with halogen; more preferably $R^{11}$ is selected from the group consisting of fluoromethyl, hydroxymethyl, and methyl. In one important compound, $R^{11}$ can be methyl. Alternatively, $R^{11}$ can be fluoromethyl. In another alternative $R^{11}$ can be hydroxymethyl. In another compound, $R^{12}$ is $C_1$–$C_6$ alkyl optionally substituted with a substituent selected from the group consisting of —OH, alkoxy, and halogen. In one preferred compound $R^{12}$ is $C_1$ alkyl optionally substituted with halogen. For example, $R^{12}$ can be methyl. Alternatively, $R^{12}$ can be fluoromethyl. In yet another example, $R^{12}$ can be hydroxymethyl. In still another example, $R^{12}$ can be methoxymethyl.

In this exemplary compound, it is preferred that $R^{13}$, $R^{14}$, $R^{21}$ and $R^{22}$ each is —H. In this compound, it is further preferred that $R^{11}$, $R^{15}$, $R^{16}$, $R^{17}$, $R^{19}$, and $R^{20}$ independently are selected from the group consisting of —H and $C_1$–$C_3$ alkyl. Preferably $R^{15}$, $R^{16}$, $R^{17}$, $R^{19}$, $R^{20}$ each is —H. In this further compound, $R^{23}$ can be, for example, fluoromethyl, or in another example $R^{23}$ can be methyl. In preferred compounds of these examples, $R^{12}$ is $C_1$–$C_6$ alkyl optionally substituted with a substituent selected from the group consisting of —OH, alkoxy, and halogen. Preferably $R^{12}$ is $C_1$ alkyl optionally substituted with halogen. In one such example $R^{12}$ is fluoromethyl. In another example $R^{12}$ is methyl. Alternatively $R^{12}$ can be hydroxymethyl. In another alternative, $R^{12}$ can be methoxymethyl.

When $R^{23}$ is methyl, $R^{11}$ can be, for example, —H or $C_1$–$C_6$ alkyl optionally substituted with a substituent selected from the group consisting of —OH and halogen. In a preferred compound $R^{11}$ is —H. Alternatively, $R^{11}$ can be $C_1$–$C_6$ alkyl optionally substituted with a substituent selected from the group consisting of —OH and halogen. For example $R^{11}$ can be methyl, ethyl, n-propyl, i-propyl, n-butyl, sec-butyl, isobutyl, t-butyl, a pentyl isomer, or a hexyl isomer. For example, $R^{11}$ can be ethyl. Alternatively, $R^{11}$ can be $C_1$ alkyl optionally substituted with a substituent selected from the group consisting of —OH and halogen; for example $R^{11}$ can be methyl. Alternatively, $R^{11}$ can be fluoromethyl. In another alternative, $R^{11}$ can be hydroxymethyl.

In another compound $R^{18}$ can be —O$R^{24}$. $R^{24}$ can be as defined above. Preferably $R^{24}$ is $C_1$–$C_6$ alkyl optionally substituted by one or more moieties selected from the group consisting of cycloalkyl, heterocyclyl, aryl, and heteroaryl; more preferably $R^{24}$ is $C_1$–$C_3$ alkyl; and more preferably still $R^{24}$ is methyl. In yet another example of compound II, $R^{18}$ can be —N($R^{25}$)($R^{26}$), wherein $R^{25}$ and $R^{26}$ are as defined above. In still another compound, $R^{18}$ can be —N($R^{30}$)—, and $R^{13}$ can be —C(O)—, wherein $R^{18}$ and $R^{13}$ together with the atoms to which they are attached form a ring. In another example still, $R^{18}$ can be —O—, and $R^{13}$ can be —C($R^{31}$)($R^{32}$)—, wherein $R^{18}$ and $R^{13}$ together with the atoms to which they are attached form a ring.

In a compound of Formula II, $R^{21}$ can be selected from the group consisting of —OH, —C(O)—O—$R^{34}$, and —C(O)—S—$R^{35}$. Preferably $R^{21}$ is —OH. In a further example, $R^{22}$ is —H when $R^{21}$ is —OH.

However, the present example also provides useful compounds of Formula II in which $R^{21}$ is —O—, and $R^{22}$ is —C(O)—, wherein $R^{21}$ and $R^{22}$ together with the atoms to which they are attached form a ring. In another useful compound, $R^{21}$ is —C(O)—, and $R^{22}$ is —O—, wherein $R^{21}$ and $R^{22}$ together with the atoms to which they are attached form a ring. Alternatively, $R^{22}$ can be selected from the group consisting of —OH, —C(O)—O—$R^{36}$, and —C(O)—S—$R^{37}$. In this alternative, $R^{21}$ is preferably —H.

In another selective iNOS inhibitor useful in the practice of the present invention, a compound is represented by Formula III:

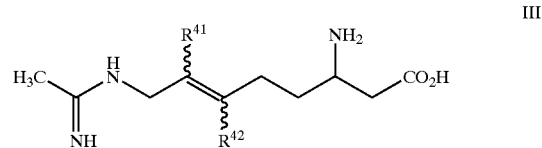

III or a pharmaceutically acceptable salt thereof, wherein:
$R^{41}$ is H or methyl; and
$R^{42}$ is H or methyl.

Another selective iNOS inhibitor useful in the practice of the present invention is represented by a compound of formula IV

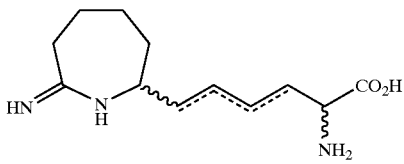

IV or a pharmaceutically acceptable salt thereof.

Another exemplary selective iNOS inhibitor useful in the present invention is represented by Formula V:

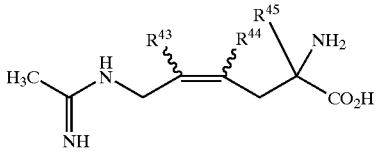

V or a pharmaceutically acceptable salt thereof, wherein:
$R^{43}$ is selected from the group consisting of hydrogen, halo, $C_1$–$C_5$ alkyl and $C_1$–$C_5$ alkyl substituted by alkoxy or one or more halo;
$R^{44}$ is selected from the group consisting of hydrogen, halo, $C_1$–$C_5$ alkyl and $C_1$–$C_5$ alkyl substituted by alkoxy or one or more halo;
$R^{45}$ is $C_1$–$C_5$ alkyl or $C_1$–$C_5$ alkyl be substituted by alkoxy or one or more halo.

A further illustrative selective iNOS inhibitor is represented by Formula VI:

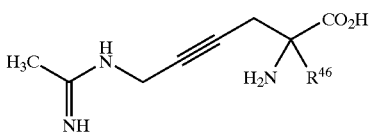

VI or a pharmaceutically acceptable salt thereof, wherein:
$R^{46}$ is $C_1$–$C_5$ alkyl, said $C_1$–$C_5$ alkyl optionally substituted by halo or alkoxy, said alkoxy optionally substituted by one or more halo.

Another exemplary selective iNOS inhibitor useful in the present invention is represented by Formula VII

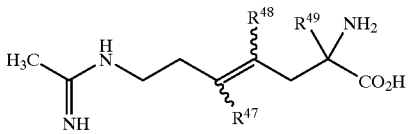

VII or a pharmaceutically acceptable salt thereof, wherein:
$R^{47}$ is selected from the group consisting of hydrogen, halo, $C_1$–$C_5$ alkyl and $C_1$–$C_5$ alkyl substituted by alkoxy or one or more halo;
$R^{48}$ is selected from the group consisting of hydrogen, halo, $C_1$–$C_5$ alkyl and $C_1$–$C_5$ alkyl substituted by alkoxy or one or more halo;
$R^{49}$ is $C_1$–$C_5$ alkyl or $C_1$–$C_5$ alkyl be substituted by alkoxy or one or more halo.

Another exemplary selective iNOS inhibitor useful in the present invention is represented by Formula VIII

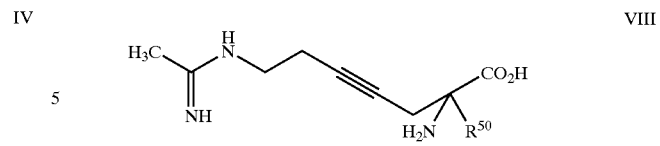

VIII or a pharmaceutically acceptable salt thereof, wherein:
$R^{50}$ is $C_1$–$C_5$ alkyl, said $C_1$–$C_5$ alkyl optionally substituted by halo or alkoxy, said alkoxy optionally substituted by one or more halo.

Another selective iNOS inhibitor useful in the practice of the present invention is represented by a compound of formula IX

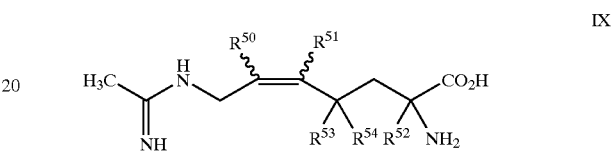

IX or a pharmaceutically acceptable salt thereof, wherein:
$R^{50}$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^{51}$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo;
$R^{52}$ is $C_1$–$C_5$ alkyl, said $C_1$–$C_5$ alkyl optionally substituted by halo or alkoxy, said alkoxy optionally substituted by one or more halo;
$R^{53}$ is selected from the group consisting of hydrogen, halo, and $C_1$–$C_5$ alkyl, said $C_1$–$C_5$ alkyl optionally substituted by halo or alkoxy, said alkoxy optionally substituted by one or more halo; and
$R^{54}$ is selected from the group consisting of halo and $C_1$–$C_5$ alkyl, said $C_1$–$C_5$ alkyl optionally substituted by halo or alkoxy, said alkoxy optionally substituted by one or more halo.

Yet another selective iNOS inhibitor useful in the practice of the present invention is represented by a compound of formula X

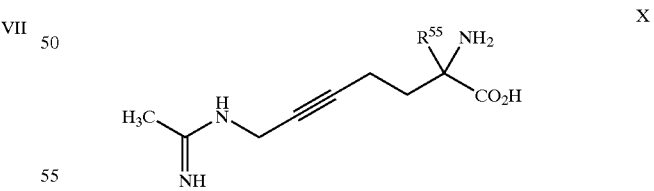

X or a pharmaceutically acceptable salt thereof, wherein:
$R^{55}$ is $C_1$–$C_5$ alkyl, said $C_1$–$C_5$ alkyl optionally substituted by halo or alkoxy, said alkoxy optionally substituted by one or more halo.

In another exemplary compound, the inducible nitric oxide synthase selective inhibitor is the compound having the formula XI, or a pharmaceutically acceptable thereof. Compound XI has previously been described in International Publication Number WO 00/26195, published May 11, 2000, which is herein incorporated by reference.

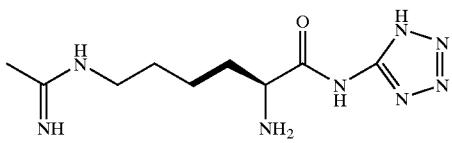

2S-amino-6-[(1-iminoethyl)amino]-N-(1H-tetrazol-5-yl)hexanamide, hydrate, dihydrochloride

ILLUSTRATIVE EXAMPLES

The following synthesis examples are shown for illustrative purposes and in no way intended to limit the scope of the invention. Where isomers are not defined, utilization of appropriate chromatography methods will afford single isomers.

Example A

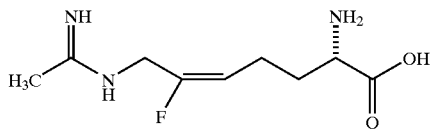

(2S,5E)-2-amino-6-fluoro-7-[(1-iminoethyl)amino] 5-heptenoic acid, dihydrochloride, monohydrate

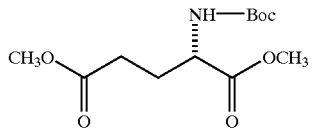

EX-A-1) Trimethylsilyl chloride (107.8 g, 1.00 mol) was added dropwise to a cooled solution of L-glutamic acid (30.00 g, 0.20 mol) in 300 mL of methanol at 0° C. The resulting clear, colorless solution was allowed to stir at room temperature. After 18 h, analysis by thin layer chromatography (30% ethyl acetate in hexane) showed that no starting material remained. The reaction was then cooled to 0° C., triethylamine (134 g, 1.33 mol) was added, and a white precipitate formed. Di-tert-butyldicarbonate (49 g, 0.23 mol) was added, and the mixture was allowed to warm to room temperature. After 3 h the solvent was removed, and 700 mL of diethyl ether was added. The solution was filtered, and the filter cake was rinsed with an additional 500 mL of diethyl ether. The filtrate was concentrated to 60.8 g (>95%) of a tan oil which was carried onto the next step without further purification. LCMS: m/z=298.1 [M+Na]$^+$. HRMS calcd. for $C_{12}H_{21}NO_6$: 276.1447 [M+H]$^+$, found: 276.1462. $^1$H NMR (CDCl$_3$)? 1.45 (s, 9H), 1.95 (m, 1H), 2.50 (m, 1H), 2.40 (m, 2H), 3.69 (s, 3H), 3.75 (s, 3H), 4.32 (m, 1H), 5.15 (m, 1H).

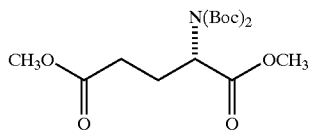

EX-A-2) To a solution of the crude product from EX-A-1 (60 g, 0.22 mol) in 300 mL of acetonitrile at room temperature was added 4-dimethylaminopyridine (5.3 g, 0.44 mol) and di-tert-butyldicarbonate (79.2 g, 0.36 mol). The resulting mixture was stirred for 2 days at room temperature, at which time analysis by thin layer chromatography (25% ethyl acetate in hexane) showed that most of the starting material was consumed. The solvent was removed in vacuo affording 85 g of a red oil. The crude material was purified by flash column chromatography on silica gel eluting with 1:10 ethyl acetate in hexane to give 66.4 g (81%) of the desired di-Boc product as a pale-yellow solid. LCMS: m/z=398.2 [M+Na]$^+$. HRMS calcd. for $C_{17}H_{29}NO_8$: 398.1791 [M+Na]$^+$, found: 398.1790. $^1$H NMR (CDCl$_3$)? 1.48 (s, 18H), 2.19 (m, 1H), 2.41 (m, 2H), 2.46 (m, 1H), 3.66 (s, 3H), 3.70 (s, 3H), 4.91 (dd, 1H).

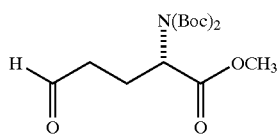

EX-A-3) A solution of DIBAL (64 mL of 1.0 M solution in hexanes, 63.9 mmol) was added dropwise to a cold solution of EX-A-2 (20 g, 53.3 mmol) in 400 mL of anhydrous diethyl ether at −78° C. over 30 min. After an additional 30 min at −78° C., the solution was quenched with water (12 mL, 666 mmol) and allowed to warm to room temperature. The cloudy mixture was diluted with 350 mL of ethyl acetate, dried over MgSO$_4$ and filtered through a pad of celite. The filtrate was concentrated to a yellow oil. The crude material, 18.9 g of yellow oil, was purified by flash column chromatography on silica gel eluting with 1:4 ethyl acetate in hexane to give 13.8 g (75%) of the desired aldehyde product as a clear oil. LCMS: m/z=368.2 [M+Na]$^+$. $^1$H NMR (CDCl$_3$)? 1.48 (s, 18H), 2.19 (m, 1H), 2.41 (m, 2H), 2.46 (m, 1H), 3.70 (s, 3H), 4.91 (dd, 1H), 9.8 (s, 1H).

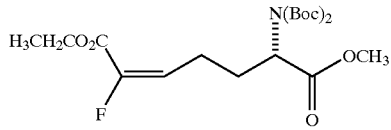

EX-A-4) To a cold (−78° C.) solution of triethyl 2-fluorophosphonoacetate (4.67 g, 19.3 mmol) in 20 mL of THF was added n-butyl lithium (10.9 mL of 1.6 M in hexane, 17.5 mmol). This mixture was stirred at −78° C. for 20 min producing a bright yellow solution. A solution of the product from EX-A-3 (6.0 g, 17.5 mmol) in 5 mL of THF was then added via syringe, and the resulting mixture was stirred for 2 h at −78° C., at which time analysis by thin layer chromatography (30% ethyl acetate in hexane) showed that no starting material remained. The reaction was quenched at −78° C. with sat. aqueous NH$_4$Cl (30 mL). The organic layer was collected, and the aqueous layer was extracted with diethyl ether (2×50 mL). The combined organics were washed with water (100 mL) and brine (100 mL), dried over MgSO$_4$, filtered and concentrated. The crude material, 8.6 g of a yellow oil, was purified by flash column chromatography on silica gel eluting with 1:4 ethyl acetate in hexane to give 6.05 g (79%) of the desired fluoro olefin product as a clear oil. $^1$H NMR and $^{19}$F NMR indicated that the isolated product had an approximate E:Z ratio of 95:5. LCMS: m/z=456.2 [M+Na]$^+$. HRMS calcd. for $C_{20}H_{32}NO_8F$: 456.2010 [M+Na]$^+$, found: 456.2094. $^1$H NMR (CDCl$_3$)?

1.48 (s, 18H), 2.0 (m, 1H), 2.25 (m, 1H), 2.6 (m, 2H), 3.7 (s, 3H), 4.25 (m, 2H), 4.9 (m, 1H), 5.9 (dt, vinyl, 1H,J=20 Hz), 6.2 (dt, vinyl, 1H,J=30 Hz). $^{19}$F NMR (CDCl$_3$)? −129.12 (d, 0.09F,J=31 Hz, 9% Z-isomer), −121.6 (d, 0.91F, J=20 Hz, 91% E-isomer).

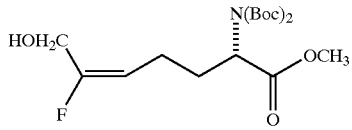

EX-A-5) To a solution of EX-A-4 (805 mg, 1.86 mmol) in 20 mL of methanol at room temperature was added solid NaBH$_4$ (844 mg, 22.3 mmol) in 200 mg portions. The reaction was stirred for 18 h at ambient temperature, at which time analysis by thin layer chromatography (30% ethyl acetate in hexane) showed that most of the starting material was consumed. The reaction was quenched with 20 mL of sat. aqueous NH$_4$Cl and extracted with ethyl acetate (2×35 mL). The organic layers were combined, dried over MgSO$_4$, filtered and concentrated. The crude material, 700 mg of clear oil, was purified by flash column chromatography on silica gel eluting with 1:4 ethyl acetate in hexane to give 353 mg (48%) of the desired allylic alcohol product as a clear oil, that contained primarily the desired E-isomer by $^{19}$F NMR. LCMS: m/z=414.2 [M+Na]$^+$. $^1$HNMR (CDCl$_3$)? 1.48 (s, 18H), 1.95 (m, 1H), 2.1 (m, 1H), 2.2 (m, 1H), 2.35 (t, 1H), 3.7 (s, 3H), 4.25 (m, 2H), 4.8 (m, 1H), 5.15 (dt, 1H,J=20 Hz). $^{19}$F NMR (CDCl$_3$)? −119.1 (d, 0.02F,J=37 Hz, 2% Z-isomer), −111.8 (d, 0.98F,J=24 Hz, 98% E-isomer).

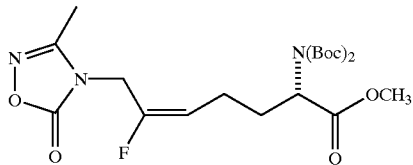

EX-A-6) To a mixture of EX-A-5 (1.37 g, 3.5 mmol), polymer-supported triphenylphosphine (3 mmol/g, 1.86 g, 5.6 mmol) and 3-methyl-1,2,4-oxadiazolin-5-one (450 mg, 4.55 mmol) in 50 mL of THF was added dropwise dimethylazodicarboxylate (820 mg, 5.6 mmol). The reaction was stirred for 1 h at room temperature, at which time analysis by thin layer chromatography (40% ethyl acetate in hexane) showed that no starting material remained. The mixture was filtered through celite, and the filtrate was concentrated. The resulting yellow oil was partitioned between 30 mL of methylene chloride and 30 mL of water. The organic layer was separated, washed with water (1×30 mL) and brine (1×30 mL), dried over MgSO$_4$, filtered and concentrated. The crude material, 1.8 g of a yellow oil, was purified by flash column chromatography on silica gel eluting with 1:4 ethyl acetate in hexane to give 670 mg (40%) of the desired protected E-allylic amidine product as a clear oil, that contained only the desired E-isomer by $^{19}$F NMR. LCMS: m/z=496.2 [M+Na]$^+$. $^1$H NMR (CDCl$_3$)? 1.48 (s, 18H), 1.85 (m, 1H), 2.2 (m, 3H), 2.25 (s, 3H), 3.64 (s, 3H), 4.25 (m, 2H), 4.8 (m, 1H), 5.3 (dt, 1H,J=20 Hz). $^{19}$F NMR (CDCl$_3$)? −110.8 (q, 1F,J=20 Hz).

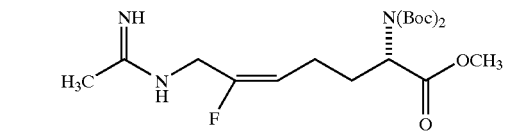

EX-A-7) The product from EX-A-6 (670 mg, 1.4 mmol) was dissolved in 25 mL of methanol and 25 mL of 25% acetic acid in water. Zinc dust (830 mg, 12.7 mmol) was added, and the mixture was agitated under sonication for 8 h, at which time HPLC analysis showed that only 20% of the starting material remained. The Zn dust was filtered from the reaction mixture, and the filtrate was stored at −20° C. for 12 h. The filtrate was warmed to room temperature, additional glacial acetic acid (7 mL) and zinc dust (400 mg, 6.1 mmol) were added, and the mixture was sonicated for 1 h at room temperature, at which time HPLC analysis showed 96% product. The mixture was filtered through celite, and the filtrate was concentrated. The crude material was purified by reverse-phase HPLC column chromatography on a YMC Combiprep column eluting over 8 min using a gradient of 20–95% A (A: 100% acetonitrile with 0.01% trifluoroacetic acid, B: 100% H$_2$O with 0.01% trifluoroacetic acid). Fractions containing product were combined and concentrated affording 344 mg (45%) of the desired acetamidine product as a trifluoroacetate salt, that contained only the desired E-isomer by $^{19}$F NMR. LCMS: m/z=432.3 [M+H]$^+$. $^1$H NMR (CD$_3$OD)? 1.52 (s, 18H), 2.9 (m, 1H), 2.2 (m, 3H), 2.27 (s, 3H), 4.2 (d, 1H), 5.4 (dt, vinyl, 1H,J=20 Hz). $^{19}$F NMR (CD$_3$OD)? −110.83 (m, 1F,J=20 Hz).

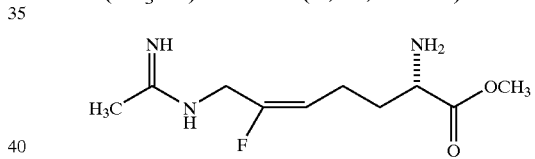

EX-A-8) A sample of the product of EX-A-7 is dissolved in glacial acetic acid. To this stirred solution is added 10 equivalents of 1N HCl in dioxane. After stirring this solution for ten minutes at room temperature, all solvent is removed in vacuo to generate the illustrated methyl ester dihydrochloride salt.

Example A

A solution of EX-A-7 (344 mg, 1.4 mmol) in 6 mL of 6.0 N HCl was refluxed for 1 h. The solvent was removed in vacuo. The resulting solid was dissolved in water and concentrated three additional times, followed by 5 subsequent times in 1.0 N HCl to remove any remaining TFA salts. Upon completion, 160 mg (37%) of the desired (2S,5E)-2-amino-6-fluoro-7-[(1-iminoethyl)amino]-5-heptenoic acid, dihydrochloride product was obtained as a white solid, m.p. 51.5–56.3° C., that contained only the desired E-isomer by $^{19}$F NMR. LCMS: m/z=218.1 [M+H]$^+$. HRMS calcd. for C$_9$H$_{16}$FN$_3$O$_2$: 218.1305 [M+H]$^+$, found: 218.1325. $^1$H NMR (D$_2$O)? 1.8 (m, 2H), 2.05 (m, 2H), 2.1 (s, 3H), 3.7 (t, 1H), 4.00 (d, 2H), 5.3 (dt, vinyl, 1H,J=21 Hz). $^{19}$F NMR (D$_2$O)? −109.9 (m, 1F,J=20 Hz).

Example B

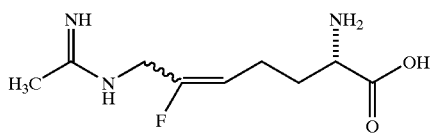

(2S,5E/Z)-2-amino-6-fluoro-7-[(1-iminoethyl)
amino]-5-heptenoic acid, dihydrochloride

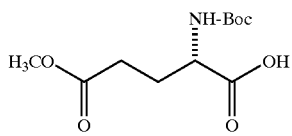

EX-B-1) To a cooled (0° C.) solution of L-glutamic acid 5-methyl ester (50.00 g, 0.31 mol) in 400 mL of 1:1 H$_2$O in dioxane was added triethylamine (38.35 g, 0.38 mol) followed by di-tert-butyldicarbonate (80.00 g, 0.37 mol). The resulting clear, colorless solution was allowed to stir at room temperature. After 18 h, analysis by thin layer chromatography (30% ethyl acetate in hexane) showed that no starting material remained. The reaction mixture was quenched with 200 mL of 1.0 N aqueous KHSO$_4$. The organic layer was removed, and the aqueous layer was extracted with ethyl acetate (3×100 mL). The organic layers were combined, dried over MgSO$_4$, filtered and concentrated to give 72.00 g (89%) of the desired product as a pale yellow oil. LCMS: m/z=284.1 [M+Na]$^+$. $^1$H NMR (CDCl$_3$)? 1.50 (s, 9H), 2.00 (m, 1H), 2.20 (m, 1H), 2.42 (m, 2H), 3.66 (s, 3H), 4.34 (d, 1H), 5.24 (d, 1H).

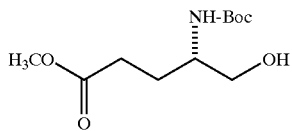

EX-B-2) To a solution of the product from EX-B-1 (72.60 g, 0.28 mol) in 300 mL of THF at −10° C. was quickly added 4-methylmorpholine (28.11 g, 0.28 mol) and isobutylchloroformate (37.95 g, 0.28 mol). The clear yellow solution immediately formed a white precipitate. After 4 min, the resulting cloudy yellow mixture was filtered, the filtrate was cooled to −10° C. and a solution of NaBH$_4$ (15.77 g, 0.42 mol) in 200 mL of H$_2$O was added dropwise while maintaining a subzero temperature. Once all of the NaBH$_4$ was added, the ice bath was removed, and the reaction was allowed to stir at room temperature for 1.5 h. The reaction mixture was quenched with 200 mL of H$_2$O. The organic layer was separated, and the aqueous layer was extracted with ethyl acetate (3×100 mL). The organic layers were combined, washed with brine, dried over MgSO$_4$, filtered and concentrated to give 58 g (85%) of the desired product as a yellow oil. LCMS: m/z=270.1 [M+Na]$^+$. $^1$H NMR (CDCl$_3$)? 1.42 (s, 9H), 1.65 (m, 1H), 1.85 (m, 2H), 2.42 (t, 2H), 3.66 (s, 3H), 4.8 (d, 1H).

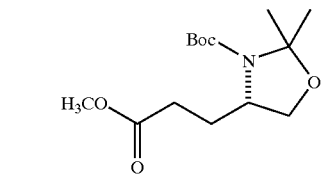

EX-B-3) To a solution of EX-B-2 (30.95 g, 0.13 mol) in 100 mL of benzene was added 2,2-dimethoxy propane (65.00 g, 0.63 mol) followed by p-toluenesulfonic acid (2.40 g, 12.5 mmol) and 5 g of 3 Å molecular sieves. The resulting mixture was refluxed for 2 h, at which time analysis by thin layer chromatography (30% ethyl acetate in hexane) showed complete reaction. The mixture was cooled to room temperature, diluted with diethyl ether (150 mL) and washed with sat. aqueous NaHCO$_3$ (100 mL) followed by brine (100 mL). The organic layer was dried over MgSO$_4$, filtered and concentrated. The crude material, 30.5 g of a yellow oil, was purified by flash column chromatography on silica gel eluting with 1:10 ethyl acetate in hexane to give 15.40 g (42%) of the desired product as a pale-yellow oil. LCMS: m/z=310.1 [M+Na]$^+$. $^1$H NMR (CDCl$_3$)? 1.42 (s, 12H), 1.56 (d, 3H), 1.85 (m, 2H), 2.38 (m, 2H), 3.66 (s, 3H), 3.7 (d, 1H), 3.95 (m, 2H).

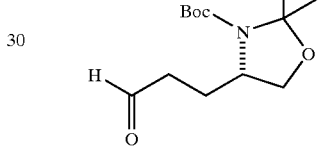

EX-B-4) DIBAL (6.0 mL of 1.0 M solution in toluene) was added dropwise to a cold (−78° C.) solution of the product from EX-B-3 (1.00 g, 3.00 mmol) in 10 mL of methylene chloride. After 30 min, the reaction was quenched with 5 mL sat. potassium sodium tartrate (Rochelle salt), then allowed to warm to room temperature. The mixture was then filtered through a pad of celite, dried over MgSO$_4$, re-filtered and concentrated to give a yellow oil. The crude material, 610 mg of a yellow oil, was purified by flash column chromatography on silica gel eluting with 1:4 ethyl acetate in hexane to give 550 mg (71%) of the desired product as a clear oil. $^1$H NMR (CDCl$_3$)? 1.50 (s, 12H), 1.58 (d, 3H), 2.00 (m, 2H), 2.5 (m, 2H), 3.7 (d, 1H), 3.95 (m, 2H), 9.8 (s, 1H).

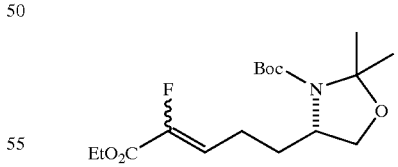

EX-B-5) To an ice cold (0° C.) solution of triethyl 2-fluoro-phosphonoacetate (6.70 g, 27.6 mmol) in 100 mL of methylene chloride was added 1,8-diazabicyclo[5.4.0]undec-7-ene (4.70 g, 31.0 mmol). The mixture was stirred at 0° C. for 1 h resulting in an orange solution. Then, a ice cold (0° C.) solution of the product from EX-B-4 (5.71 g, 22.2 mmol) in 15 mL of methylene chloride was added via syringe, and the resulting mixture was stirred for 18 h at ambient temperature, at which time analysis by thin layer chromatography (30% ethyl acetate in hexane) showed that no starting material remained. The solvent was removed in vacuo, and the resulting mixture was partitioned between 200 mL of ethyl acetate and 100 mL of water. The organic layer was collected, and the aqueous layer was extracted with ethyl acetate (2×50 mL). The combined organic layers were washed with 1.0 M aqueous KHSO$_4$ (100 mL), water (100 mL) and brine (100 mL), dried over MgSO$_4$, filtered and concentrated to give the desired fluoro olefin product as a yellow oil (8.0 g). $^1$H NMR and $^{19}$F NMR indicated that the isolated product had an approximate Z:E ratio of 70:30. LCMS: m/z=368.2 [M+Na]$^+$. $^1$H NMR (CDCl$_3$)? 5.9–6.0 (dt, 1H,J=20 Hz), 6.05–6.20 (dt, 1H,J=33 Hz). $^{19}$F NMR (CDCl$_3$)? −129.89 (d, 0.7F,J=38 Hz, 70% Z-isomer), −122.05 (d, 0.3F,J=20 Hz, 30% E-isomer). This mixture was carried on crude without further purification.

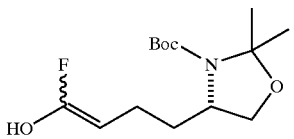

EX-B-6) To an ice cold (0° C.) solution of the product from EX-B-5 (8.0 g, 23.0 mmol) in 70 mL of THF was added LiBH$_4$ (12.7 mL of 2.0 M in THF, 25.0 mmol) via syringe. The reaction mixture was stirred for 18 h at ambient temperature at which time analysis by thin layer chromatography (30% ethyl acetate in hexane) showed that no starting material remained. The THF was removed, and the resulting mixture was dissolved in methylene chloride. After cooling to 0° C., 1.0 M aqueous KHSO$_4$ was slowly added to quench the reaction. The mixture was then extracted with ethyl acetate (3×50 mL). The organic layers were combined, dried over MgSO$_4$, filtered and concentrated. The crude material, 8.0 g of a clear oil, was purified by flash column chromatography on silica gel eluting with 1:4 ethyl acetate in hexane to give 900 mg (13%) of the desired product as a clear oil. LCMS: m/z=326.2 [M+Na]$^+$. $^1$H NMR (CDCl$_3$)? 4.79–4.94 (dm, 1H), 5.10–5.25 (dt, 1H). $^{19}$F NMR (CDCl$_3$)? −119.82 (dt, 0.7F,J=38 Hz, 70% Z-isomer), −111.09 (dt, 0.3F,J=27 Hz, 30% E-isomer).

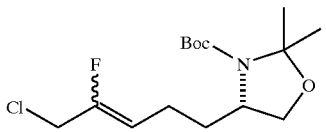

EX-B-7) To an ice cold (0° C.) solution of the product from EX-B-6 (950 mg, 3.1 mmol) in 5 mL of pyridine was added methanesulfonyl chloride (390 mg, 3.4 mmol). The reaction was stirred for 5 min at 0° C., then warmed to room temperature and stirred for 3 h, at which time analysis by thin layer chromatography (30% ethyl acetate in hexane) showed that no starting material remained. The reaction was diluted with diethyl ether (10 mL) and washed with sat. aqueous NaHCO$_3$ (20 mL) followed by 1.0 Mcitric acid (20 mL). The organic layer was dried over MgSO$_4$, filtered and concentrated to give 500 mg (51%) of the desired allylic chloride product as a white solid. This product was carried forward without further purification. LCMS: m/z=344.1 [M+Na]$^+$.

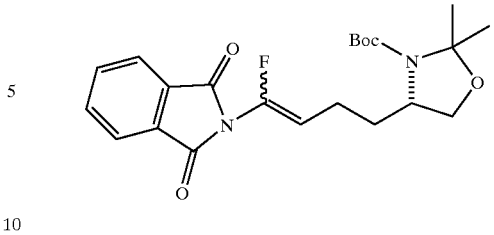

EX-B-8) To a stirring solution of the product from EX-B-7 (440 mg, 1.37 mmol) in 10 mL of DMF was added potassium phthalimide (290 mg, 1.57 mmol). The resulting mixture was heated under reflux for 18 h, at which time analysis by thin layer chromatography (30% ethyl acetate in hexane) showed that no starting material remained. The cooled mixture was diluted with 30 mL of water, extracted twice with ethyl acetate (30 mL), dried over MgSO$_4$, filtered and concentrated to give 540 mg (91%) of the desired product as a yellow oil. LCMS: m/z=455.2 [M+Na]$^+$. HRMS calcd. for: 433.2139 [M+H]$^+$, found: 433.2144. $^1$H NMR (CDCl$_3$)? 1.4 (s, 18H), 1.6 (m, 6H), 2.05 (m, 2H), 3.6–4.42 (m, 4H), 4.9 (dt, vinyl, 1H), 5.2, (m, vinyl, 1H), 7.7 (m, 2H), 7.9 (m, 2H). $^{19}$F NMR (CDCl$_3$)? −117.09 (m, 0.7F,J=38 Hz, 70% Z-isomer), −111.61 (m, 0.3F,J=22 Hz, 30% E-isomer).

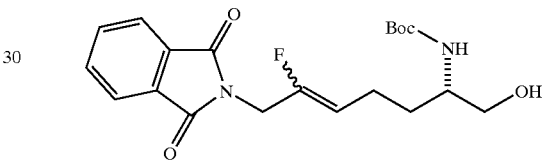

EX-B-9) The product from EX-B-8 (600 mg, 1.38 mmol) was dissolved in 8 mL of acetic acid and 2 mL of water. The mixture was stirred at room temperature overnight at which time analysis by thin layer chromatography (30% ethyl acetate in hexane) showed that no starting material remained. The solution was concentrated under a stream of nitrogen, and the crude product was purified by flash column chromatography on silica gel eluting with 1:2 ethyl acetate in hexane to give 248 mg (63%) of the desired product as a white solid. LCMS: m/z=415.1 [M+Na]$^+$. $^1$H NMR (CDCl$_3$)? 1.41 (s, 9H), 1.56 (m, 2H), 2.15 (m, 1H), 3.64 (m, 2H), 4.35 (d, 2H), 4.9 (dt, vinyl, 1H,J=37 Hz), 7.73 (m, 2H), 7.86 (m, 2H). $^{19}$F NMR (CDCl$_3$)? −116.96 (dt, 0.8F,J=37 Hz, 80% Z-isomer), −111.09 (dt, 0.2F,J=22 Hz, 20% E-isomer).

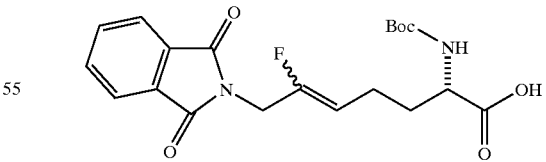

EX-B-10) To a stirring solution of the product from EX-B-9 (237 mg, 0.605 mmol) in 6 mL of DMF was added pyridinium dichromate (1.14 g, 3.03 mmol). The solution turned dark orange and was allowed to stir at room temperature for 18 H, at which time it was poured into 20 mL of H$_2$O. The mixture was extracted with ethyl acetate (4×25 mL). The combined organic layers were washed with 5% aqueous KHCO$_3$ (3×25 mL). The aqueous layer was acidified with 1.0 M KHSO₄ to pH=3 followed by extraction with ethyl acetate (3×50 mL). The combined organic layers were concentrated to yield 235 mg (95%) of the desired amino acid product. The resulting white solid was carried on crude without further purification. LCMS: m/z=429.1 [M+Na]⁺.

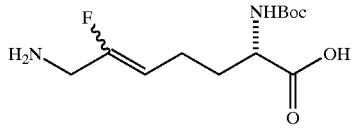

EX-B-11) To stirring solution of the product from EX-B-10 (230 mg, 0.56 mmol) in 7 mL of ethanol was added hydrazine hydrate (70 mg, 1.13 mmol), and the resulting solution was refluxed for 2 h forming a white precipitate. The solvent was removed in vacuo. The resulting white solid was dissolved in 8 mL of water and acidified to pH=4 with glacial acetic acid. It was then cooled in an ice bath and filtered. The filtrate was concentrated to give 136 mg (87%) of the desired allyl amine product as yellow crystals which were carried onto the next step without purification. LCMS: m/z=277.1 [M+H]⁺.

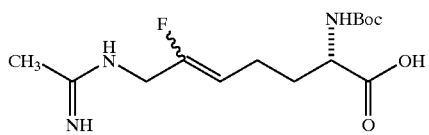

EX-B-12) To a stirring solution of the product from EX-B-11 (136 mg, 0.50 mmol) in 6 mL of DMF was added ethyl acetimidate (252 mg, 2.04 mmol) in 3 portions over 1.5 h intervals. After the addition was complete, the mixture was stirred overnight at room temperature. The pink solution was filtered, and the filter cake was washed with water. The solvent was removed in vacuo, and the resulting yellow oil was purified by reverse-phase HPLC using a YMC Combi-prep ODS-A semi-prep column eluting with a 7 minute gradient of 1–50% A (A: 100 acetonitrile with 0.05% TFA, B: 100 water with 0.05% TFA). Fractions containing product were combined and concentrated to afford approximately 50 mg of the desired acetamidine product as a trifluoroacetate salt which was carried onto the next step. LCMS: m/z=318.2 [M+H]⁺.

Example B

The product from EX-B-12 was dissolved in 6 mL of 6.0 N HCl and stirred for 1 h at room temperature. The solvent was removed in vacuo. The resulting solid was dissolved in water and concentrated three additional times to remove TFA salts. When ¹⁹F NMR indicated that all of the TFA was removed, the product was dried in vacuo to give 30 mg (20%, combined yield over two steps) of a 20:80 E:Z mixture containing the desired (2S,5E)-2-amino-6-fluoro-7-[(1-iminoethyl)amino]-5-heptenoic acid, dihydrochloride and (2S,5Z)-2-amino-6-fluoro-7-[(1-iminoethyl)amino]-5-heptenoic acid, dihydrochloride as a foamy clear solid. HRMS calcd. for C₉H₁₆FN₃O₂: 218.1305 [M+H]⁺, found: 218.1309. ¹H NMR (D₂O) 2.01 (m, 2H), 2.21 (s, 3H), 2.24 (m, 2H), 3.96 (t, 1H), 4.00 (d, 2H), 5.07 (dt, vinyl, 1H,J=37 Hz), 5.4 (dt, vinyl, 1H,J=37 Hz). ¹⁹F NMR (D₂O)? −116.8 (m, 0.8F,J=37 Hz, 80% Z-isomer), −109.6 (m, 0.2F,J=21 Hz, 20% E-isomer).

Example C

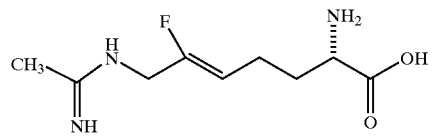

(2S,5Z)-2-amino-6-fluoro-7-[(1-iminoethyl)amino]-5-heptenoic acid, dihydrochloride

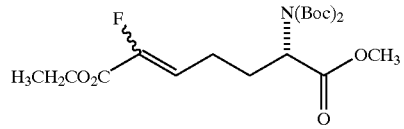

EX-C-1) Triethyl 2-fluoro-phosphonoacetate (3.54 g, 14.6 mmol) was dissolved in 20 mL of CH₂Cl₂ at 0° C., and 1,8-diazabicyclo[5.4.0]undec-7-ene (2.4 mL, 16.4 mmol) was added. The mixture was stirred at 0° C. for 20 min producing an orange solution. A solution of the aldehyde product from EX-A-3 (4.04 g, 11.7 mmol) was then added at 0° C., and the resulting brown mixture was stirred overnight at room temperature, at which time LCMS indicated that no starting material remained. The solvent was removed, and the residue was partitioned between water (60 mL) and ethyl acetate (120 mL). The organic layer was collected, and the aqueous layer was extracted with ethyl acetate (2×50 mL). The combined organic layers were washed with water (60 mL) and 10% aqueous KHSO₄ (60 mL), dried over MgSO₄, filtered and concentrated. The crude material, 5.7 g of an orange oil, was purified by flash column chromatography on silica gel eluting with 10% ethyl acetate in hexane to give 3.5 g (69%) of the desired fluoro olefin product as a clear oil. ¹H NMR and ¹⁹F NMR indicated that the isolated product had an Z/E ratio of 70:30. HRMS calcd. for C₂₀H₃₂O₈FN: 456.2010 [M+Na]⁺, found 456.2017. ¹H NMR (CDCl₃)? 1.48 (s, 18H), 2.0 (m, 1H), 2.25 (m, 1H), 2.6 (m, 2H), 3.7 (s, 3H), 4.25 (m, 2H), 4.9 (m, 1H), 5.9 (dt, vinyl, 1H,J=21.2 Hz), 6.1 (dt, vinyl, 1H,J=32.4 Hz). ¹⁹F NMR (CDCl₃)?: −129.4 (d, 0.7F,J=34 Hz, 70% Z isomer), −121.6 (d, 0.3F,J=22 Hz, 30% E isomer).

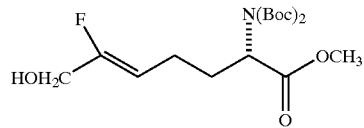

EX-C-2) The ester product from EX-C-1 (3.5 g, 8.1 mmol) was dissolved in 80 mL of methanol at room temperature, solid NaBH₄ (3 g, 80 mmol) was then added in portions. The mixture was stirred at room temperature for 18 h, at which time HPLC analysis indicated that the reaction was >90% complete. The reaction was quenched with sat NH₄Cl. The product was extracted with ethyl acetate and dried over Na₂SO₄. The organic layer was evaporated to give 3.2 g of crude product as a colorless oil, which was purified by Biotage flash column chromatography eluting with 20%–30% ethyl acetate in hexane to give 2.11 g (67%) of a Z/E mixture of the fluoro olefin product as a clear oil along with 0.41 g (13%) of the desired pure (Z:E=97:3 by ¹⁹F NMR) Z-isomer product as a clear oil. HRMS calcd. for C₁₈H₃₀NO₇F: 414.1904 [M+Na]⁺, found 414.1911. ¹H NMR (CDCl₃)? 1.48 (s, 18H), 2.0 (m, 1H), 2.2 (m, 3H), 3.7 (s, 3H), 4.1 (dd,2H,J=17Hz), 4.8 (dt, 1H,J=39 Hz), 4.9 (m, 1H). ¹⁹F NMR (CDCl₃)? –119.1 (dt, 1F,J=17 Hz).

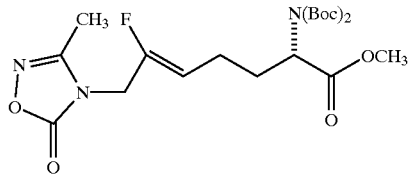

EX-C-3) The Z-alcohol product from EX-C-2 (390 mg, 1 mmol) and 3-methyl-1,2,4-oxadiazolin-5-one (130 mg, 1.3 mmol) were dissolved in 20 mL of THF. Then polymer supported-PPh₃ was added into the solution, and the mixture was gently stirred for 10 min. Then diethyl azodicarboxylate was added dropwise, and the mixture was stirred for 1 h at room temperature, at which time LCMS analysis indicated product formation and that no starting material was present. The polymer was filtered off through a celite pad, and the pad was washed with THF. The filtrate was evaporated to give 1.0 g of crude product which was purified by Biotage flash column chromatography eluting with 20% to 30% ethyl acetate in hexane to give 500 mg of product, contaminated with some hydrazide by-product. This material was further purified by Biotage flash column chromatography eluting with 98:2:0.01 of methylene chloride:methanol:ammon-ium hydroxide to give 180 mg (38%) of the desired protected amidine product as a clear oil, that contained only the desired Z-isomer by ¹⁹F NMR. HRMS calcd. for C₂₁H₃₂N₃O₈F: 491.2517 [M+NH₄]⁺, found 491.2523. ¹H NMR (CDCl₃)? 1.5 (s, 18H), 1.9 (m, 1H), 2.1 (m, 3H), 2.3 (s, 3H), 3.7 (s, 3H), 4.2 (d, 2H), 4.8 (m, 1H), 5.0 (dt, 1H,J=36 Hz). ¹⁹F NMR (CDCl₃)? –116.5 (dt, 1F,J=38 Hz).

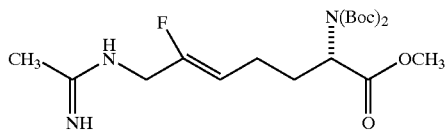

EX-C-4) The product from EX-C-3 (88 mg, 0.19 mmol) was dissolved in 4 mL of 25% acetic acid in water containing a few drops of methanol, and then Zn dust (109 mg, 1.67 mmol) was added. The mixture was agitated under sonication for 3 h. The Zn was filtered off through a celite pad, and the pad was washed with water. The filtrate was evaporated to dryness to give crude product which was purified by reverse-phase HPLC column chromatography on a YMC Combiprep column eluting over 8 min with a gradient of 20–80% A (A: 100% ACN with 0.01% TFA, B: 100% H₂O with 0.01% TFA). The desired product was collected in two fractions, and the combined fractions were concentrated. The product was obtained as a colorless oil as a mixture of trifluoroacetate salts that contained only the desired Z-isomer by ¹⁹F NMR: 30% was mono Boc-protected product: HRMS calcd. for C₁₅H₂₆N₃O₄F: 332.1986 [M+H]⁺, found 332.2001, and 70% was di-Boc-protected product: HRMS calcd. for C₂₀H₃₄N₃O₆F: 432.2510 [M+H]⁺, found 432.2503. ¹H NMR of the di-Boc product (D₂O)? 1.3 (s, 18H), 1.8 (m, 1H), 2.1 (m, 3H), 2.1 (s, 3H), 3.6 (s, 3H), 3.9 (d, 2H), 4.9 (dt, vinyl, 1H,J=37 Hz). ¹⁹F NMR (D₂O)? –117.3 (dt, 1F,J=37 Hz).

Example C

The combined mono- and di-BOC products from EX-C-4 were dissolved in 30 mL of 6N HCl, and the solution was refluxed for 4 h, at which time LCMS analysis indicated complete reaction. The excess HCl and water was removed in vacuo. Upon completion, 9 mg (40% combined yield for two steps) of the desired (2S,5Z)-2-amino-6-fluoro-7-[(1-iminoethyl)amino]-5-heptenoic acid, dihydrochloride product was obtained as a light yellow, very hygroscopic foam, that contained only the desired Zisomer by ¹⁹F NMR. HRMS calcd. for C₉H₁₆N₃O₂F: 218.1305 [M+H]⁺, found 218.1320. ¹H NMR (D₂O)? 1.3 (s, 18H), 1.9 (m, 2H) 2.1 (m, 2H), 2.1 (s, 3H), 3.8 (t, 1H), 3.9 (d, 2H), 4.9 (dt, vinyl, 1H,J=37 Hz). ¹⁹F NMR (D₂O)? –117.3 (dt, 1F,J=37 Hz).

Example D

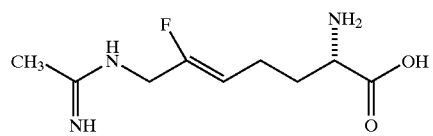

(2S,5Z)-2-amino-6-fluoro-7-[(1-iminoethyl)amino]-5-heptenoic acid, trihydrochloride, dihydrate

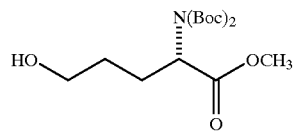

EX-D-1) The product from EX-D-2 (3.75 g, 10 mmol) was dissolved in 60 mL of methanol, and solid NaBH₄ (4 g, 106 mmol) was added in portions at room temperature over 10 h, at which time HPLC analysis indicated approximately 84% reduction. The reaction mixture was quenched with sat. NH₄Cl, and was then extracted with ethyl acetate three times. The combined organic layers were dried over MgSO₄, filtered, and evaporated to give 3.2 g of crude product as a yellow oil. HRMS calcd. for C₁₆H₂₉NO₇: 348.2022 [M+H]⁺, found: 348.2034. ¹H NMR (CD₃OD)? 4.9 (q, 1H), 3.7 (s, 3H), 3.5 (t, 2H), 3.2 (m, 1H), 2.1 (m, 1H), 1.9 (m, 1H), 1.9 (m, 2H), 1.5 (s, 18H).

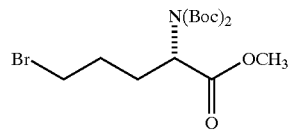

EX-D-2) The alcohol product from EX-D-1 (3.2 g, 9.0 mmol) was dissolved in 100 mL of THF and cooled in an ice bath. Carbon tetrabromide (4.27 g, 12.9 mmol) was added, and the resulting solution was stirred at 0° C. for 30 min under nitrogen. Polymer-supported PPh₃ was added, and the mixture was gently stirred at 0° C. for 1 h and then overnight at room temperature. The polymer was removed by filtration through celite, and the celite pad was washed with THF. The filtrate was evaporated to give crude product, which was purified by Biotage flash column chromatography eluting with 1:3 ethyl acetate in hexane to give 2.0 g (54%, combined yield over 2 steps) of the desired bromo product as a colorless oil. HRMS calcd. for C₁₆H₂₈NO₆Br: 410.1178 [M+H]⁺, found: 410.1137. ¹H NMR (CDCl₃)? 4.9 (q, 1H), 3.7 (s, 3H), 3.4 (m, 2H), 2.2 (m, 2H), 1.9 (m, 2H), 1.5 (s, 18H).

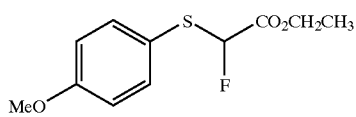

EX-D-3) A solution of NaOEt (21% in EtOH, 41.1 mL, 0.11 mol) in 60 mL of ethanol was treated with p-methoxy benzenethiol (14.0 g, 0.1 mol), followed by ethyl chlorofluoroacetate (18.3 g, 0.13 mol). The mixture was stirred at room temperature for 2 h and diluted with 250 mL of 1:1 hexane in ethyl acetate. The organic layer was washed with water three times, and dried over $Na_2SO_4$ The dried organic layer was evaporated to give 25 g of crude product which was carried forward without further purification. LCMS for $C_{11}H_{13}O_3SF$: m/z=267.10 [M+Na]$^+$. $^1$H NMR (CDCl$_3$)? 7.5 (d, 2H), 6.9 (d, 2H), 6.0 (d, 1H,J=51.9 Hz), 4.2 (q, 2H), 3.8 (s, 3H), 1.2 (t, 3H). $^{19}$F NMR (CDCl$_3$)? −146.2 (d, 1F,J=53.6 Hz).

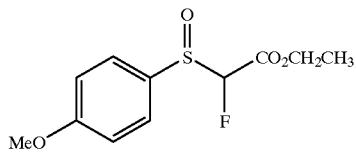

EX-D-4) A solution of the crude product from EX-D-3 (24 g, 0.1 mol) in 200 mL of methylene chloride was cooled to −78° C. and treated with 3-chloroperbenzoic acid (27 g, 0.12 mol) in 200 mL of methylene chloride. The reaction mixture was slowly warmed to room temperature and stirred overnight, at which time LCMS analysis indicated product formation and that no starting material remained. The solid was filtered off, and the filtrate was washed with sat. NaHCO$_3$ and NH$_4$Cl. The organic layer was dried over MgSO$_4$ and evaporated to give 30 g of an orange oil, which was purified by Biotage flash column chromatography eluting with 2:1 hexane in ethyl acetate to give 17.5 g (70%) of the desired sulfoxide product as an off-white oil. HRMS calcd. for $C_{11}H_{13}O_4FS$: 261.0597 [M+H]$^+$, found: 261.0598. $^1$H NMR (CDCl$_3$)? 7.6 (m, 2H), 7.0 (m, 2H), 5.6 (d, 1H,J=50 Hz major diastereomer), 5.4 (d, 1H,J=49 Hz minor diastereomer), 4.2 (q, 2H), 3.8 (s, 3H), 1.2 (t, 3H). $^{19}$F NMR (CDCl$_3$)? −194.3 (d, 1F,J=53.6 Hz major diastereomer), −191.7 (d, 1F,J=50.4 Hz minor diastereomer).

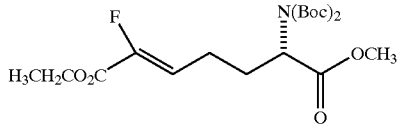

EX-D-5) A suspension of NaH (60% in mineral oil, 212 mg, 5.3 mmol) in 6 mL of dried DMF was cooled to 0° C. under nitrogen and treated with a solution of the sulfoxide product from EX-D-4 (1.25 g, 4.8 mmol) in 2 mL of DMF. After stirring at room temperature for 20 min, the mixture was cooled to 5° C., and the bromo product from EX-D-2 (2.17 g, 5.3 mmol) was added in one portion. The reaction was stirred at room temperature for 3 h, then heated at reflux at 95 ° C. for 1 h, at which time LCMS analysis indicated product formation. The mixture was poured into an ice/aqueous NH$_4$Cl mixture. The product was extracted with 1:1 hexane in ethyl acetate. The organic layer was dried over Na$_2$SO$_4$ and evaporated to give 3.17 g of a crude yellow oil, which was purified by Biotage flash column chromatography eluting with 10% ethyl acetate in hexane to give 1.05 g (50%) of the desired fluoro olefin ester product as a colorless oil. $^{19}$F NMR indicated that the isolated product contained 95:5 the desired Z-isomer. HRMS calcd. for $C_{20}H_{32}O_8FN$: 456.2010 [M+Na]$^+$, found: 456.2017. $^1$H NMR (CDCl$_3$)? 1.5 (s, 18H), 2.0 (m, 1H), 2.3 (m, 4H), 3.7 (s, 3H), 4.3 (m, 2H), 4.9 (m, 1H), 6.1 (dt, vinyl, 1H,J=32.4 Hz, Z isomer). $^{19}$F NMR (CDCl$_3$)? −129.4 (d, 0.95F,J=34.8 Hz, 95% Z isomer), −121.6 (d, 0.005F,J=21.6 Hz, 5% E isomer).

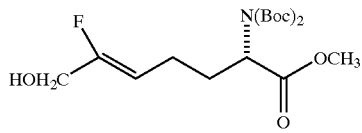

EX-D-6) The ester product from EX-D-5 (1.05 g, 2.4 mmol) was dissolved in methanol at room temperature, and solid NaBH$_4$ was added in portions. The mixture was stirred at room temperature for 18 h, then 2 mL of water was added, and the mixture was stirred for an additional 3 h, at which time HPLC analysis indicated the reaction was >95% complete. The reaction was quenched with sat NH$_4$Cl. The product was extracted with ethyl acetate, and the organic layer was dried over Na$_2$SO$_4$ and evaporated to give 0.95 g of crude product as colorless oil. $^{19}$F NMR indicated that the isolated crude product contained only the desired Z-isomer. HRMS calcd. for $C_{18}H_{30}NO_7F$: 414.1904 [M+Na]$^+$, found: 414.1949. $^1$H NMR (CDCl$_3$)? 1.48 (s, 18H), 2.0 (m, 1H), 2.2 (m, 3H), 3.7 (s, 3H), 4.1 (dd, 2H,J=17 Hz), 4.8 (dt, 1H,J=36 Hz), 4.9 (m, 1H). $^{19}$F NMR (CDCl$_3$)? −119.1 (dt, 1F,J=38 Hz,J=17 Hz).

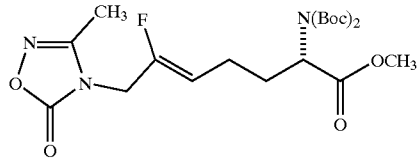

EX-D-7) The alcohol product from EX-D-6 (0.95 g, 2.4 mmol) and 3-methyl-1,2,4-oxadiazolin-5-one (290 mg, 2.9 mmol) were dissolved in 60 mL of THF. Polymer-bound triphenyl phosphine was added, and the mixture was gently stirred for 10 min. Then dimethyl azodicarboxylate was added dropwise, and the mixture was stirred for 1 h at room temperature, at which time LCMS analysis indicated product formation and that no starting material remained. The polymer was filtered off through a celite pad, and the pad was washed with THF. The filtrate was evaporated to give a residue which was partitioned between methylene chloride and water. The organic layer was washed with water twice, dried over MgSO$_4$, and evaporated to give 1.3 g of crude product which was purified by Biotage flash column chromatography eluting with 20% to 30% ethyl acetate in hexane to give 390 mg (34%, combined yield over 2 steps) of the desired protected amidine product as a colorless oil. $^{19}$F NMR indicated that the isolated product contained only the desired Z-isomer. HRMS calcd. for $C_{21}H_{32}N_3O_8F$: 491.2517 [M+NH$_4$]$^+$, found: 491.2523. $^1$H NMR (CDCl$_3$)? 1.5 (s, 18H), 1.9 (m, 1H), 2.1 (m, 3H), 2.3 (s, 3H), 3.7 (s, 3H), 4.2 (d, 2H), 4.8 (m, 1H), 5.0 (dt, 1H,J=36 Hz). $^{19}$F NMR (CDCl$_3$)? −116.5 (dt, 1F,J=38Hz).

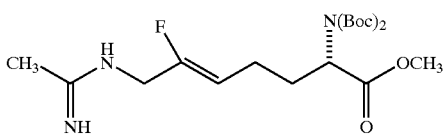

EX-D-8) The product from EX-D-7 (390 mg, 0.82 mmol) was dissolved in 20 mL of 25% HOAc in water containing 4 mL of methanol, and Zn dust (482 mg, 7.42 mmol) was added in two portions. The mixture was agitated under sonication for 3 h. The Zn was filtered off through a celite pad, and the pad was washed with water. The filtrate was evaporated to dryness to give crude product which was purified by reverse-phase-HPLC. Fractions containing the desired products were collected, combined and concentrated. The products were obtained as colorless oils as a mixture of trifluoroacetate salts, that contained only the desired Z-isomer by $^{19}$F NMR: 30% was mono-Boc protected product: HRMS calcd. for $C_{15}H_{26}N_3O_4F$: 332.1986 [M+H]$^+$, found 332.2001; 70% was diBoc protected product: HRMS calcd. for $C_{20}H_{34}N_3O_6F$: 432.2510 [M+H]$^+$, 432.2503. $^1$H NMR of diBoc product (D$_2$O)? 1.3 (s, 18H), 1.8 (m, 1H), 2.1 (m, 3H), 2.1 (s, 3H), 3.6 (s, 3H), 3.9 (d, 2H), 4.9 (dt, vinyl, 1H,J=37Hz). $^{19}$F NMR (D$_2$O)? −117.3 (dt, 1F,J=37 Hz).

Example D

The mono and diBOC products from EX-D-8 were dissolved in 80 mL of 6N HCl and the solution was heated at reflux for 1 hour, at which time LCMS analysis indicated complete reaction. The excess HCl and water was removed in vacuo to give 150 mg (50% combined yield over 2 steps) of the desired (2S,5Z)-2-amino-6-fluoro-7-[(1-iminoethyl) amino]-5-heptenoic acid, trihydrochloride, dihydrate product as a light yellow very hygroscopic foam. HRMS calcd. for $C_9H_{16}N_3O_2F$: 218.1305 [M+H]$^+$, found 218.1290. $^1$H NMR (D$_2$O)? 1.3 (s, 18H), 1.9 (m, 2H), 2.1 (m, 2H), 2.1 (s, 3H), 3.8 (t, 1H), 3.9 (d, 2H), 4.9 (dt, vinyl, 1H,J=37 Hz). $^{19}$F NMR (D$_2$O)?? −117.3 (dt, 1F,J=37 Hz). Anal. Calcd. for $C_9H_6N_3O_2F \cdot 3HCl \cdot 2H_2O$: C, 29.81; H, 6.39; N, 11.59. found C, 29.80; H, 6.11; N, 11.20.

Example E

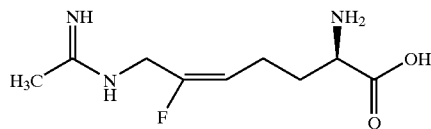

(2R,5E)-2-amino-6-fluoro-7-[(1-iminoethyl)amino]-5-heptenoic acid, dihydrochloride, monohydrate

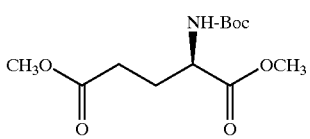

EX-E-1) Trimethylsilyl chloride is added dropwise to a cooled solution of D-glutamic acid in methanol at 0° C. The resulting clear, colorless solution is allowed to stir at room temperature until analysis by thin layer chromatography shows that no starting material remains. The reaction is then cooled to 0° C., triethylamine is added, and a white precipitate forms. Di-tert-butyldicarbonate is added, and the mixture is allowed to warm to room temperature. After 3 h the solvent is removed, and diethyl ether is added. The solution is filtered, and the filter cake is rinsed with additional diethyl ether. The filtrate is concentrated to give the desired mono-Boc diester product which is carried onto the next step without further purification.

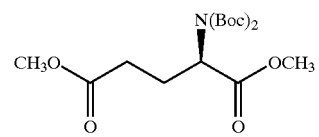

EX-E-2) To a solution of the crude product from EX-E-1 in acetonitrile at room temperature is added 4-dimethylaminopyridine and di-tert-butyldicarbonate. The resulting mixture is stirred at room temperature, until analysis by thin layer chromatography shows that most of the starting material is consumed. The solvent is removed in vacuo, and the resulting residue is purified by flash column chromatography on silica gel to give the desired di-Boc protected diester product.

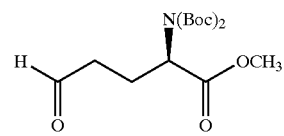

EX-E-3) A solution of DIBAL is added dropwise to a cold solution of EX-E-2 in anhydrous diethyl ether at −78° C. After 30 min at −78° C., the solution is quenched with water and allowed to warm to room temperature. The resulting cloudy mixture is diluted with ethyl acetate, dried over MgSO$_4$ and filtered through a pad of celite. The filtrate is concentrated, and the resulting residue is purified by flash column chromatography on silica gel to give the desired aldehyde product

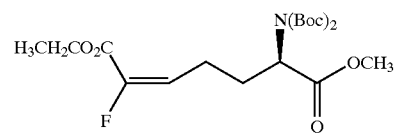

EX-E-4) To a cold (−78° C.) solution of triethyl 2-fluorophosphonoacetate in THF is added n-butyl lithium. This mixture is stirred at −78° C. producing a bright yellow solution. A solution of the product from EX-E-3 in THF is then added via syringe, and the resulting mixture is stirred at −78° C., until analysis by thin layer chromatography shows that no starting material remains. The reaction is quenched at −78° C. with sat. aqueous NH$_4$Cl. The organic layer is collected, and the aqueous layer is extracted with diethyl ether. The combined organics are washed with water and brine, dried over MgSO$_4$, filtered and concentrated. The crude material is then purified by flash column chromatography on silica gel to give the desired fluoro olefin product.

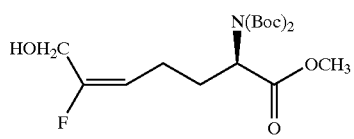

EX-E-5) To a solution of EX-E-4 in methanol at room temperature is added solid NaBH₄ in portions. The reaction is stirred at ambient temperature until analysis by thin layer chromatography shows that most of the starting material is consumed. The reaction is quenched with sat. aqueous NH₄Cl and extracted with ethyl acetate. The organic layers are combined, dried over MgSO₄, filtered and concentrated. The crude material is purified by flash column chromatography on silica gel to give the desired allylic alcohol product.

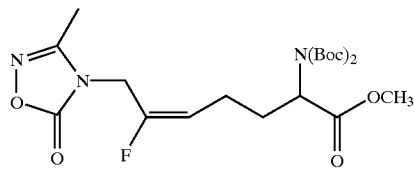

EX-E-6) To a mixture of EX-E-5, polymer-supported triphenylphosphine and 3-methyl-1,2,4-oxadiazolin-5-one in THF is added dropwise dimethylazodicarboxylate. The reaction mixture is stirred at room temperature until analysis by thin layer chromatography shows that no starting material remains. The mixture is filtered through celite, and the filtrate is concentrated. The resulting yellow oil is partitioned between methylene chloride and water. The organic layer is separated, washed with water and brine, dried over MgSO₄, filtered and concentrated. The crude material is purified by flash column chromatography on silica gel to give the desired protected E-allylic amidine product.

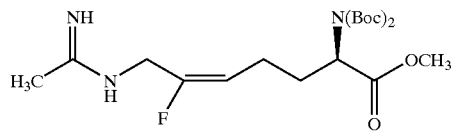

EX-E-7) The product from EX-E-6 is dissolved in methanol and acetic acid in water. Zinc dust is added, and the mixture is agitated under sonication until HPLC analysis shows that little of the starting material remains. The Zn dust is filtered through celite from the reaction mixture, and the filtrate is concentrated. The crude material is purified by reverse-phase HPLC column chromatography. Fractions containing product are combined and concentrated affording the desired acetamidine product as a trifluoroacetate salt.

Example E

A solution of EX-E-7 in 6.0 N HCl is refluxed for 1 h. The solvent is removed in vacuo. The resulting solid is dissolved in water and concentrated repeatedly from 1.0 N HCl to remove any remaining TFA salts to give the desired (2R, 5E)-2-amino-6-fluoro-7-[(1-iminoethyl)amino]-5-heptenoic acid, dihydrochloride product.

Example F

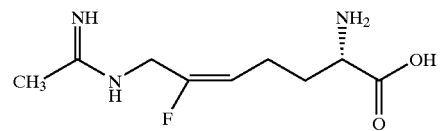

(2S,5E)-2-amino-6-fluoro-7-[(1-iminoethyl)amino]-5-heptenoic acid, dihydrochloride, monohydrate

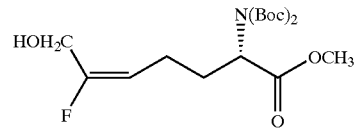

EX-F-1) To a THF (45 ml) solution of the product of EX-A-3 (5.0 g, 11.5 mmol) under nitrogen was added dropwise a solution of Red-Al (5.22ml, 17.4 mmol) in 5.6 mL THF over 30 minutes. The internal temperature was kept below −10° C. After 5 minutes, the reaction was quenched with 33.7 ml of 1.3M Na.K tartrate. Toluene (11 mL) was added to the mixture to improve separation. The organic layer was washed with 33.7 ml of 1.3M Na.K tartrate followed by brine (40 mL). The organic layers were combined, dried over MgSO4, filtered and concentrated. The crude material, 3.8 g (84%) of light yellow oil, was carried on directly into the next step. LCMS: m/z=414.2 [M+Na]⁺. ¹H NMR (CDCl₃)? 1.48 (s, 18H), 1.95 (m, 1H), 2.1 (m, 1H), 2.2 (m, 1H), 2.35 (t, 1H), 3.7 (s, 3H), 4.25 (m, 2H), 4.8 (m, 1H), 5.15 (dt, 1H,J=20 Hz). ¹⁹F NMR (CDCl₃)? −119.1 (d, 0.02F,J=37 Hz, 2% Z-isomer), −111.8 (d, 0.98F, J=24 Hz, 98% E-isomer).

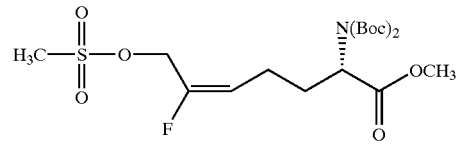

EX-F-2) To a solution of the product of EX-F-1 (50.0 g, 0.128 mol) in 500 mL of methylene chloride at −10° C. was added triethylamine (18.0 g, 0.179 mol). A solution of methanesulfonyl chloride (17.5 g, 0.153 mol) in 50 mL methylene chloride was added slowly to maintain temperature at −10° C. The reaction was stirred for 45 min at −10 ° C., at which time analysis by thin layer chromatography (50% ethyl acetate in hexane) and LCMS showed that most of the starting material was consumed. The reaction was quenched with 600 mL of 1.0 M citric acid and extracted with ethyl acetate (2×400 mL). The organic layers were combined, dried over MgSO₄, filtered and concentrated. The crude material, 70 g of yellow oil, was carried directly into the next step. LCMS: m/z=492.2 [M+Na].

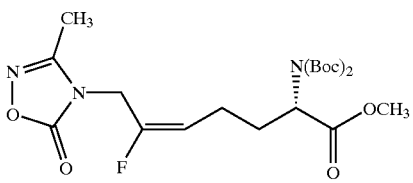

EX-F-3) To a solution of the product of EX-F-2 (70.0 g, 0.128 mol) in 400 mL of dimethyl formamide at room temperature was added potassium 3-methyl-1,2,4-oxadiazolin-5-onate (28.7 g, 0.192 mol). The reaction was stirred for 2.5 h at room temperature, at which time analysis by thin layer chromatography (30% ethyl acetate in hexane) and LCMS showed that the starting material was consumed. The reaction was diluted with 400 mL of water and extracted with ethyl acetate (5×400 mL). The organic layers were combined, washed with 400 mL water, 400 mL brine, dried over $MgSO_4$, filtered and concentrated. The crude material, 70 g of yellow oil, was purified by flash column chromatography on silica gel eluting with 1:4 ethyl acetate in hexane to give 38 g (63%) of a slightly yellow oil.

EX-F-4) A combination of product of several duplicate preparations of EX-F-3 was purified by HPLC column chromatography on Merk silica gel MODCOL column at a flow of 500 mL/min isocratic at 60:40 MtBE:heptane. A second purification on the 63 g recovered was a chiral HPLC column chromatography on a Chiral Pak-AD column running at a flow of 550 mL/min isocratic at 10:90 A:B (A: 100% ethanol, B: 100% heptane). Fractions containing product were combined and concentrated affording 41 g (68%) of the desired protected L,E-allylic amidine product as a clear oil, that contained only the desired L and E-isomer by $^{19}F$ NMR and chiral chromatography. LCMS: m/z=496.2 [M+Na]$^+$. [M+NH$_4$]$^+$. HRMS calcd. for $C_{21}H_{32}FN_3O_8$: 491.2507 [M+NH$_4$]$^+$, found: 491.2517. $^1H$ NMR (CDCl$_3$)? 1.48 (s, 18H), 1.85 (m, 1H), 2.2 (m, 3H), 2.25 (s, 3H), 3.64 (s, 3H), 4.25 (m, 2H), 4.8 (m, 1H), 5.3 (dt, 1H,J=20 Hz). $^{19}F$ NMR (CDCl$_3$)? −110.8 (q, 1F,J=20 Hz).

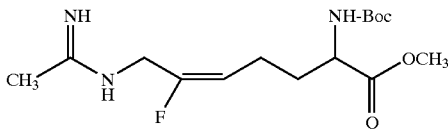

EX-F-5) The product from EX-F-4 (22.5 g, 0.047 mol) was dissolved in 112 mL of methanol. Vigorous stirring was begun and 225 mL of 40% acetic acid in water followed by zinc dust (11.5 g, 0.177 mmol) was added. The stirring reaction was placed under reflux (approx. 60° C.) for 2.5 h, at which time HPLC analysis showed that most of the starting material had been consumed. The reaction was cooled and the Zn was filtered from the reaction mixture through celite, washing the celite well with additional methanol. The filtrate and methanol washings were combined and concentrated. The resulting oily-white solid was washed with methylene chloride (2×500 mL) and filtered through a celite pad, an additional 500 mL methylene chloride wash was performed. The filtrates were combined and concentrated to provide a light yellow oil. The crude material, 39 g of a light-yellow oil, was purified by plug filtration on 200 mL silica gel eluting with 80:19:1 methanol: methylene chloride: acetic acid to give 13 g (83%) of the desired product. LCMS: m/z=432.3 [M+H]$^+$. 1 [M+H]$^+$.

HRMS calcd. for $C_{15}H_{26}FN_3O_4$: 332.1986 [M+H]$^+$, found: 332.1982. $^1H$ NMR (CD$_3$OD)? 1.42 (s, 9H), 1.7 (m, 1H), 1.9 (m, 1H), 2.17 (m, 2H), 2.22 (s, 3H), 3.3 (m, 1H), 3.7 (s, 3H), 4.2 (d, 2H), 5.1 (dt, vinyl, 1H,J=21 Hz). $^{19}F$ NMR (CD$_3$OD)? −110.83 (m, 1F,J=21 Hz).

Example F

A solution of the product of EX-F-5 (22 g, 0.066 mol) in 750 mL of 6.0 N HCl was refluxed for 45 min. The solvent was removed in vacuo. The resulting solid was dissolved in water and concentrated three additional times. The crude material was purified by reverse-phase HPLC column chromatography on a YMC ODS-AQ column eluting over 60 min pumping 100% isocratic B for 30 min followed by a gradient of 0–100% A for 10 min and a 100% A wash for 20 min (A: 100% acetonitrile, B: 100% H$_2$O with 0.0025% acetic acid). Fractions containing product were combined and concentrated affording 3.5 g (68%) of the desired acetamidine product as a dihydorchloride salt, that contained only the desired (2S,5E)-2-amino-6-fluoro-7-[(1-iminoethyl)amino]-5-heptenoic acid, dihydrochloride product was obtained as a white solid, m.p. 51.5–56.3° C., that contained only the desired E-isomer by $^{19}F$ NMR. LCMS: m/z=218.1 [M+H]$^+$. HRMS calcd. for $C_9H_{16}FN_3O_2$: 218.1305 [M+H]$^+$, found: 218.1325. $^1H$ NMR (D$_2$O) ? 1.8 (m, 2H), 2.05 (m, 2H), 2.1 (s, 3H), 3.7 (t, 1H), 4.00 (d, 2H), 5.3 (dt, vinyl, 1H,J=21 Hz). $^{19}F$ NMR (D$_2$O)? −109.9 (m, 1F,J=20 Hz). [?]$_{589}$ =+15.3 (C, 0.334, (H$_2$O);). [?]$_{365}$=+52.8 (C, 0.334, (H$_2$O))

Example G

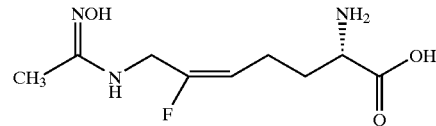

(2S,5E)-2-amino-6-fluoro-7-[(1-hydroximinoethyl) amino]-5-heptenoic acid

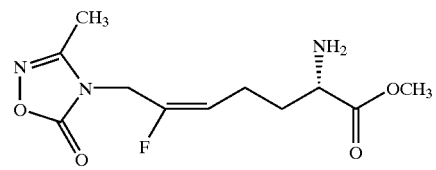

EX-G-1) Gaseous HCl was bubbled for 5 min through a stirring cold (0° C.) solution of the product of EX-F-3 (14 g, 30.0 mmol) in 100 mL of methanol. The resulting dark yellow solution was stirred an additional 30 min, at which time HPLC indicated complete consumption of starting material. The resulting mixture was neutralized with saturated NaHCO$_3$ to pH=8, and the product was extracted out with EtOAc. The organic layer was dried over MgSO$_4$ and concentrated to give the desired amino ester product as a dark yellow oil that was carried on crude to the next step. LCMS: m/z=274 [M+Na]$^+$. $^1H$ NMR (CDCl$_3$)? 1.8 (m, 4H), 2.25 (s, 3H), 3.42 (bm, 1H), 3.80 (s, 3H), 4.4 (dd, 2H), 5.40 (dt, vinyl, 1H,J=21 Hz). $^{19}F$ NMR (CDCl$_3$) ? −110.38 (m, 1F,J=21 Hz).

Example G

A solution of the product of EX-G-1 (8 g, 30 mmol) in 70 mL of 2.5N NaOH was stirred for 10 min, at which time HPLC analysis indicated the complete consumption of starting material. The resulting solution was neutralized with 12N HCl (approximately 50 mL) to pH=7–8 and concentrated. The resulting slurry was washed with methanol, filtered to remove salts and concentrated to a brownish oil. The crude material was purified by reverse-phase HPLC column chromatography on a YMC ODS-AQ column eluting over 60 min pumping 100% isocratic B for 30 min followed by a gradient of 0–100% A for 10 min and a 100% A wash for 20 min (A: 100% acetonitrile, B: 100%). Fractions containing product were combined and concentrated affording 1.0 g (14%) of the desired product as a white solid. The product was recrystallized from hot water and isopropyl alcohol and collected by filtration to afford pure (2S,5E)-2-amino-6-fluoro-7-[(1-hydroximinoethyl)amino]-5-heptenoic acid as a white crystalline solid. Melting point: 198.00–200.00° C. LCMS: m/z=234.1 [M+H]$^+$. $^1$H NMR (D$_2$O)? 1.8 (m, 4H), 2.05 (m, 2H), 3.6 (t, 1H), 3.9 (d, 2H), 5.2 (dt, vinyl, 1H,J=21 Hz). $^{19}$F NMR (D$_2$O)? −112.1 (m, 1F,J=20 Hz).). Anal. calcd. for C$_9$H$_{16}$FN$_3$O$_3$: C, 46.35; H, 6.91; N, 18.02; O, 20.58. Found: C, 46.44; H, 6.95; N, 17.94; O, 20.78. Chiral analysis>97.7%: CrownPak CR(+) at 0.8 mL/min isocratic with 100% A (A: aqueous HClO$_4$, pH=1.5).

Example H

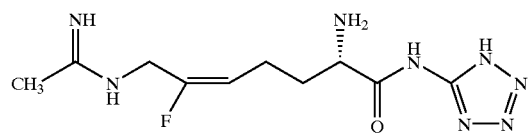

(2S,5E)-2-amino-6-fluoro-7-[(1-iminoethyl)amino]-N-(1H-tetrazol-5-yl)-5-heptenamide, dihydrochloride

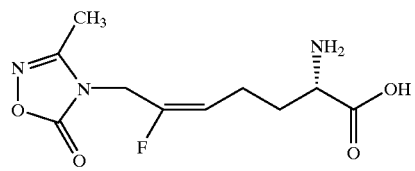

EX-H-1) The product from EX-F-3 (6.1 g, 0.013 mol) was dissolved in 4 mL of methanol. Vigorous stirring was begun and 10 mL of 6N HCl was added. The stirring reaction was placed under reflux (approx. 60° C.) for 18 h, at which time HPLC analysis showed that most of the starting material had been consumed. The reaction was cooled and concentrated to 3.3 g (100%) of orange oil. LCMS: m/z=282 [M+Na]$^+$.

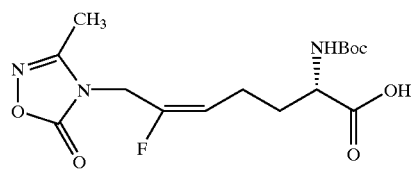

EX-H-2) The product from EX-H-1 (3.3 g, 0.013 mol) was dissolved in 12 mL of 1:1 H$_2$O: dioxane. Stirring was begun and triethylamine (1.95 g, 0.019 mol) was added. The reaction was cooled to 0° C. and di-tert-butyldicarbonate (3.4 g, 0.016 mol) was added. The reaction was allowed to warm to room temperature at which time acetonitrile (4 mL) was added to dissolve solids. The reaction was stirred at room temperature for 18 h at which time HPLC analysis showed that most of the starting material had been consumed. The reaction was quenched with 1.0N KHSO$_4$ (25 mL), extracted with ethyl acetate (3×50 mL) and the organic layers dried over MgSO$_4$ and concentrated. The crude material, 3.5 g of a dark oil, was purified by flash chromatography eluting with 4:95:1 methanol: methylene chloride: acetic acid to give 2.4 g (52%) of desired product as a light-yellow oil. LCMS: m/z=382 [M+Na]$^+$.

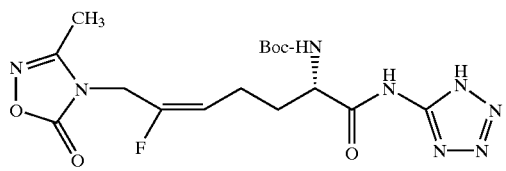

EX-H-3) The product from EX-H-2 (2.4 g, 0.007 mol) was dissolved in 13 mL THF. Stirring was begun and 5-aminotetrazole monohydrate (0.83 g, 0.008 mol) was added followed by 1,3-diisopropylcarbodiimide (1.0 g, 0.008 mol). The resulting mixture was allowed to stir at room temperature for 3 h at which time HPLC showed that most of the starting material had been consumed. To the reaction was added 12 mL water and the THF was removed by vaccum distillation. Ethanol (30 mL) was added and the reaction was heated to reflux. After 15 min at reflux, the reaction was cooled to −10° C. at which time the desired product precipitated from solution. The product was collected by filtration to afford 1.25 g (50%) of a white solid. LCMS: m/z=449 [M+Na]$^+$.

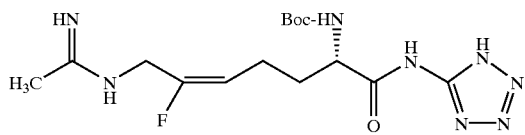

EX-H-4) The product from EX-H-3 (1.0 g, 0.0023 mol) was dissolved in 5 mL of methanol. Vigorous stirring was begun and 10 mL of 40% acetic acid in water followed by zinc dust (0.5 g, 0.008 mol) was added. The stirring reaction was placed under reflux (approx. 60° C.) for 1.5 h, at which time HPLC analysis showed that most of the starting material had been consumed. The reaction was cooled and the Zn was filtered from the reaction mixture through celite, washing the celite well with additional methanol. The filtrate and methanol washings were combined and concentrated. The resulting oily-white solid was purified by reverse-phase HPLC column chromatography on a YMC ODS-AQ column eluting over 60 min pumping 100% isocratic B for 30 min followed by a gradient of 0–100% A for 10 min and a 100% A wash for 20 min (A: 100% acetonitrile, B: 100% H$_2$O with 0.0025% acetic acid). Fractions containing product were combined and concentrated affording 0.390 g (44%) of the desired acetamidine product as a white solid. LCMS: m/z= 407.3 [M+Na].

Example H

The product from EX-H-4 (0.30 g, 0.780 mmol) was dissolved in 5 mL of conc HOAc. To this was added 1 mL of 4N HCl in dioxane. The reaction was stirred 5 min. at room temperature. The solvent was removed in vacuo. The resulting solid was dissolved in water and concentrated three additional times. HPLC indicated amounts of starting material. The solid was dissolved in 1N HCl and stirred 3 h at which time HPLC indicated that most of the starting material had been consumed. The solution was concentrated affording 290 mg (98%) of the desired acetamidine product as a dihydorchloride salt. LCMS: m/z=285.1 [M+H].

Example I

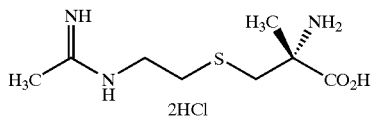

2HCl

S-[2-[(1-Iminoethyl)amino]ethyl]-2-methyl-L-cysteine, dihydrochloride

Example-I-1

(2R,4R)-Methyl-2-tert-butyl-1,3-thiazoline-3-formyl-4-carboxylate

See Jeanguenat and Seebach, *J. Chem. Soc. Perkin Trans.* 1, 2291 (1991) and Pattenden et al. *Tetrahedron*, 49, 2131 (1993): (R)-cysteine methyl ester hydrochloride (8.58 g, 50 mmol), pivalaldehyde (8.61 g, 100 mmol), and triethylamine (5.57 g, 55 mmol) were refluxed in pentane (800 ml) with continuous removal of water using a Dean-Stark trap. The mixture was filtered and evaporated. The resultant thiazolidine (9.15 g, 45 mmol) and sodium formate (3.37 g, 49.5 mmol) were stirred in formic acid (68 ml) and treated with acetic anhydride (13 mL, 138 mmol), dropwise over 1 hour at 0–5° C. The solution was allowed to warm to RT and stir overnight. The solvents were evaporated and the residue was neutralized with aqueous 5% $NaHCO_3$ and extracted with ether (3×). The combined organic layers were dried (anhy. $MgSO_4$), filtered, and evaporated to give the title compound which was crystallized from hexane-ether as white crystals (8.65 g) (80% overall, 8:1 mixture of conformers). $^1$H NMR ($CDCl_3$)??major conformer: 1.04 (s, 9H), 3.29 (d, 1H), 3.31 (d, 1H), 3.78 (s, 3H), 4.75 (s, 1H), 4.90 (t, 1H), 8.36 (s, 1H). MS m/z (electrospray) 232 (M+H)$^+$ (100%), 204 (10) 164 (24).

Example-I-2

(2R,4R)-Methyl-2-tert-butyl-1,3-thiazoline-3-formyl-4-methyl-4-carboxylate

To a solution of the product of Example-I-1, (2R,4R)-Methyl-2-tert-butyl-1,3-thiazoline-3-formyl-4-carboxylate (8.65 g, 37.4 mmol), in anhydrous tetrahydrofuran (130 mL) under $N_2$ at −78° C. was added DMPU (25 mL) and the mixture stirred for 5 min. Lithium bis(trimethylsilyl)amide, 1 M in tetrahydrofuran, (37.5 mL), was added, and the mixture stirred for 30 min. After methyl iodide (5.84 g, 41.1 mmol) was added, the mixture was held at −78° C. for 4 hr and then warmed to room temperature with continuous stirring. The solvents were evaporated in vacuo and brine and ethyl acetate was added. The aqueous phase was extracted 3×EtOAc, and the combined organic layers were washed with 10% $KHSO_4$, water, and brine. They were then dried (anhy. $MgSO_4$), filtered, and stripped of all solvent under reduced pressure. Chromatography of the residual oil on silica with 1–10% EtOAc/hexane yielded the title compound (5.78 g, 63%, 2.4:1 mixture of conformers). $^1$H NMR ($CDCl_3$)??major conformer, 1.08 (s, 9H), 1.77 (s, 3H), 2.72 (d, 1H), 3.31 (d, 1H), 3.77 (s, 3H), 4.63 (s, 1H), 8.27 (s, 1H), minor conformer, 0.97 (s, 9H), 1.79 (s, 3H), 2.84 (d, 1H), 3.63 (d, 1H), 3.81 (s, 3H), 5.29 (s, 1H), 8.40 (s, 1H); MS m/z (electrospray) 246 (M+H)$^+$ (100%), 188 (55) 160 (95). Retention time of 16.5 min on a Daicel Chemical Industries Chiracel OAS column, 10–40% IPA/hexane 0–25 min, >95% ee.

Example-I-3

(2R) 2-Methyl-L-cysteine hydrochloride

The product of Example-I-2, (2R,4R)-Methyl-2-tert-butyl-1,3-thiazoline-3-formyl-4-methyl-4-carboxylate, (5.7 g, 23.2 mmol) was stirred with 6N HCl (100 mL) under $N_2$ and held at vigorous reflux for 2 days. The solution was cooled, washed with EtOAc and evaporated to yield the product (2R) 2-methyl-cysteine hydrochloride (3.79 g, 95%) as a light yellow powder. $^1$H NMR (DMSO-$d_6$)?? 1.48 (s, 3H,) 2.82 (t, 1H), 2.96 (bs, 2H), 8.48 (s, 3H). MS m/z (electrospray) 136 [M+H$^+$].

Example-I-4

S-[2-[[(1,1-dimethylethoxy)carbonyl]amino]ethyl]-2-methyl-L-cysteine trifluoroacetate Sodium hydride (2.6 g, 60% in mineral oil, 65 mmol) was added to an oven-dried, vacuum-cooled RB flask, containing oxygen-free 1-methyl-2-pyrrolidinone (5 mL). The mixture was cooled to −10° C. and stirred under $N_2$. The product of Example-I-3, 2-Methyl-L-cysteine hydrochloride, (3.6 g, 21.0 mmol) dissolved in oxygen-free 1-methyl-2-pyrrolidinone (25 ml), was added in portions. After all $H_2$ evolution ceased, 2-[(1,1-dimethylethoxycarbonyl)-amino] ethyl bromide (4.94 g, 21 mmol) in oxygen-free 1-methyl-2-pyrrolidinone (15 mL) was added at −10° C. The reaction was then stirred for 4 hr allowing warming to room temperature. The solution was neutralized with 1 N HCl and the 1-methyl-2-pyrrolidinone was removed by evaporation in vacuo. Reverse-phase chromatography with 1–20% acetonitrile in 0.05% aqueous trifluoro acetic acid solution yielded the title compound (5.9 g), recovered by freeze-drying appropriate fractions. $^1$H NMR (DMSO-$d_6$/$D_2O$)? 1.31 (s, 9H), 1.39 (s, 3H), 2.55 (m, 2H), 2.78 (d, 1H), 3.04 (d, 1H), 3.06 (t, 2H). HRMS calc. for $C_{11}H_{22}N_2O_4S$: 279.1375 (M+H$^+$), found 279.1379.

Example-I-5

S-(2-aminoethyl)-2-methyl-L-cysteine hydrochloride

The product of Example-I-4, S-[2-[[(1,1-dimethylethoxy) carbonyl]amino]ethyl]-2-methyl-L-cysteine trifluoroacetate, (5.5 g, 14.0 mmol) was dissolved in 1 N HCl (100 mL) and stirred at room temperature under nitrogen overnight. The solution was removed by freeze-drying to give the title S-(2-aminoethyl)-2-methyl-L-cysteine hydrochloride, $^1$H NMR?(DMSO-$d_6$/$D_2O$)? 1.43 (s, 3H), 2.72 (m, 2H), 2.85 (d, 1H), 2.95 (t, 2H), 3.07 (d, 1H). m/z [M+H$^+$] 179.

Example I

The product of Example-I-5, was dissolved in $H_2O$, the pH adjusted to 10 with 1 N NaOH, and ethyl acetimidate hydrochloride (1.73 g, 14.0 mmol) was added. The reaction was stirred 15–30 min, the pH was raised to 10, and this process repeated 3 times. The pH was adjusted to 3 with HCl and the solution loaded onto a washed DOWEX 50WX4-200 column. The column was washed with $H_2O$ and 0.25 M $NH_4OH$, followed by 0.5 M $NH_4OH$. Fractions from the 0.5 M $NH_4OH$ wash were immediately frozen, combined and freeze-dried to give an oil that was dissolved in 1N HCl and evaporated to give the title compound as a white solid (2.7 g). $^1$H NMR (DMSO-$d_6$/$D_2$O)? 1.17 (s, 3H), 2.08 (s, 3H), 2.52 (d, 1H), 2.68 (m, 2H), 2.94 (d, 1H), 3.23 (t, 2H). HRMS calc. for $C_8H_{18}N_3O_2S$: 220.1120 [M+H$^+$], found 220.1133.

Example J

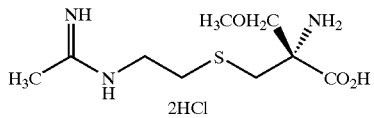

2-[[[2-[(1-Iminoethyl)amino]ethyl]thio]methyl]-O-methyl-D-serine, dihydrochloride The procedures and methods utilized in this example were identical to those of Example I except that in step Example-I-2 methoxymethyl iodide was used instead of methyl iodide. These procedures yielded the title product as a white solid (2.7 g). $^1$H NMR ($D_2$O)? 2.06 (s, 3H), 2.70 (m, 3H), 3.05 (d, 1H), 3.23 (s, 3H), 3.32 (t, 2H), 3.46 (d, 1H), 3.62 (d, 1H). HRMS calc. for $C_9H_{20}N_3O_3S$: 250.1225 [M+H$^+$], found 250.1228.

Example K

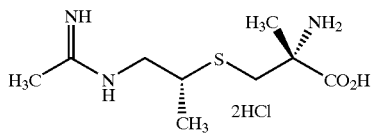

S-[(1R)-2-[(1-Iminoethyl)amino]-1-methylethyl]-2-methyl-L-cysteine, dihydrochloride Example-K-1

(S)-1-[(benzyloxycarbonyl)amino]-2-propanol

To a solution of (S)-1-amino-2-propanol (9.76 g, 130 mmol) in anhydrous benzene (60 mL) at 0° C. was added benzyl chloroformate (10.23 g, 60 mmol) in anhydrous benzene (120 mL) slowly, in portions, over a period of 20 min while vigorously stirring under an atmosphere of nitrogen. The mixture was stirred for 1 hour at 0° C., then allo/wed to warm to room temperature and stirred for a further 2 hours. The mixture was washed with water (2×) and brine (2×) before the organic layer was dried over anhydrous MgSO$_4$. Evaporation of all solvent gave the title product as an oil. $^1$H NMR (CDCl$_3$)? 1.22 (d, 3H,) 2.40 (bs, 1H), 3.07 (m, 1H), 3.37 (m, 1H), 3.94 (m, 1H), 5.16 (s, 2H), 5.27 (m, 1H), 7.38 (m, 5H). MS m/z (electrospray) 232 [M+23]$^{30}$ (100%), 166 (96).

Example-K-2

(S)-1-[(benzyloxycarbonyl)amino]-2-propanol tosylate

To a solution of the product of Example-K-1, (S)-1-[(benzyloxycarbonyl)amino]-2-propanol, (9.74 g, 46.7 mmol) and triethylamine 7.27 g, 72 mmol) in methylene chloride (60 mL) at 0° C. was added toluene sulfonyl chloride (9.15 g, 48 mmol) in methylene chloride (18 mL) slowly, in portions, over a period of 20 min while vigorously stirring under nitrogen. The mixture allowed to warm to room temperature and stirred for a further 36 hours under nitrogen. The organic layer was washed with 1N HCl, water, 5% NaHCO$_3$ solution, water and brine before it was dried over anhydrous MgSO$_4$. Evaporation of all solvent gave a white solid which was passed though a silica plug with ethyl acetate/hexane (1:4) to remove excess toluene sulfonyl chloride and then with ethyl acetate/hexane (1:3) to give the title product as white crystals. This material was recrystallized from ethyl acetate/hexane to give white needles (10.8 g). $^1$H NMR (CDCl$_3$)??1.22 (d, 3H,) 2.39 (s, 3H), 3.20 (m, 1H), 3.43 (dd, 1H) ), 4.66 (m, 1H), 5.02 (m, 1H), 5.04 (ABq, 2H), 7.34 (m, 7H), 7.77 (d, 2H). MS m/z (electrospray) 386 [M+23]$^+$ (100%), 320 (66). The product was examined on a Regis Technologies Inc. Perkle Covalent (R,R)?-GEM1 HPLC column using mobile phase of isopropanol/hexane and a gradient of 10% isopropanol for 5 min, then 10 to 40% isopropanol over a period of 25 min, and using both UV and Laser Polarimetry detectors. Retention time major peak: 22.2 min, >98% ee.

Example-K-3

S-[(1R)-2-(Benzyloxycarbonylamino)-1-methylethyl]-2-methyl-L-cysteine trifluoroacetate The product of Example-I-3, 2-methyl-L-cysteine hydrochloride, (1 g, 6.5 mmol) was added to an oven dried, N$_2$ flushed RB flask, dissolved in oxygen-free 1-methyl-2-pyrrolidinone (5 mL), and the system was cooled to 0° C. Sodium hydride (0.86 g, 60% in mineral oil, 20.1 mmol) was added and the mixture was stirred at 0° C. for 15 min. A solution of the product of Example-K-2, (2S)-1-[(N-benzyloxycarbonyl)amino]-2-propanol tosylate (2.5 g, 7 mmol) dissolved in oxygen-free 1-methyl-2-pyrrolidinone (10 mL) was added over 10 min. After 15 min at 0° C., the reaction mixture was stirred at room temperature for 4.5 hours. The solution was then acidified to pH 4 with 1N HCl and 1-methyl-2-pyrrolidinone was removed by evaporation in vacuo. Reverse phase chromatography with 20–40% acetonitrile in 0.05% aqueous trifluoro acetic acid solution yielded the title compound in (0.57 g), recovered by freeze-drying. $^1$H NMR (H$_2$O, 400 MHz)? 1.0 (d, 3H), 1.4 (s, 3H), 2.6 (m, 2H), 2.8 (m, 1H), 3.1 (m, 2H), 3.6 (s, 1 H), 5.0 (ABq, 2H), 7.3 (m, 5H). MS m/z (electrospray): 327 [M+H$^+$] (100%), 238 (20), 224 (10), and 100 (25).

Example-K-4

S-[(1R)-2-Amino-1-methylethyl]-2-methyl-L-cysteine hydrochloride

The product of Example-K-3, S-[(1R)-2-(Benzyloxycarbonylamino)-1-methylethyl]-2-methyl-L-cysteine trifluoroacetate, (0.5 g, 1.14 mmol) was dissolved in 6N HCl and refluxed for 1.5 hour. The mixture was then cooled to room temperature and extracted with EtOAc. The aqueous layer was concentrated in vacuo to give the title product, (2R,5R)-S-(1-amino-2-propyl)-2-methyl-cysteine hydrochloride (0.29 g), which was used without further purification. $^1$H NMR (H$_2$O, 400 MHz)? 1.2 (m, 3H), 1.4 (m, 3H), 2.7 (m, 1H), 2.8–3.2 (m, 2H), 3.4 (m, 1H). (some doubling of peaks due to rotameric forms). MS m/z (electrospray): 193 [M+H$^+$] (61%), 176 (53), 142 (34), 134 (100), and 102 (10).

Example K

The product of Example-K-4, S-[(1R)-2-Amino-1-methylethyl]-2-methyl-L-cysteine hydrochloride, (0.2 g, 0.76 mmol) was dissolved in 2 mL of H$_2$O, the pH was adjusted to 10.0 with 1N NaOH, and ethyl acetimidate hydrochloride (0.38 g, 3 mmol) was added in four portions over 10 minutes, adjusting the pH to 10.0 with 1N NaOH as necessary. After 1 h, the pH was adjusted to 3 with 1N HCl. The solution was loaded onto a water-washed DOWEX 50WX4-200 column. The column was washed with $H_2O$ and 0.5N $NH_4OH$. The basic fractions were pooled and concentrated to dryness in vacuo. The residue was acidified with 1N HCl and concentrated to the Example K title product, (49 mg). $^1H$ NMR ($H_2O$, 400 MHz)? 1.3–1.0 (m, 3H), 1.5 (m, 3H), 2.1–1.8 (m, 3H), 3.4–2.6 (m, 5H), 3.6 (m, 1H) (rotamers observed). MS m/z (electrospray): 234 [M+H$^+$] (100%), 176 (10), and 134 (10).

Example L

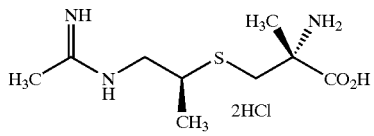

S-[(1S)-2-[(1-Iminoethyl)amino]-1-methylethyl]-2-methyl-L-cysteine, dihydrochloride The procedures and methods employed here were identical to those of Example K, except that in step Example-K-1 (R)-1-amino-2-propanol was used instead of (S)-1-amino-2-propanol to give the title material, S-[(1S)-2-[(1-Iminoethyl)amino]-1-methylethyl]-2-methyl-L-cysteine hydrochloride. $^1H$ NMR ($H_2O$, 400 MHz)? 3.6 (m, 1H), 3.4–2.6 (m, 5H), 2.1–1.8 (m, 3H), 1.5 (m, 3H), and 1.3–1.0 (m, 3H). HRMS calc for $C_9H_{19}N_3O_2S$ [M+H$^+$]: 234.1276. Found: 234.1286.

Example M

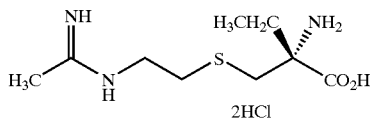

S-[2-[(1-Iminoethyl)amino]ethyl]-2-ethyl-L-cysteine, dihydrochloride

The procedures and methods used in this synthesis were the same as those used in Example I except that ethyl triflate was used in Example-I-2 instead of methyl iodide. Reverse phase chromatography, using a gradient of 10–40% acetonitrile in water, was used to purify the title product (20% yield). $^1H$ NMR ($D_2O$)?? 0.83 (t, 3H), 1.80 (m, 2H), 2.08 (s, 3H), 2.68 (m, 1H), 2.78 (m, 1H), 2.83 (m, 1H), 3.11 (m, 1H), 3.36 (t, 2H). HRMS calc. for $C_9H_{20}N_3O_2S$: 234.1276 [M+H$^+$], found 234.1284.

Example N

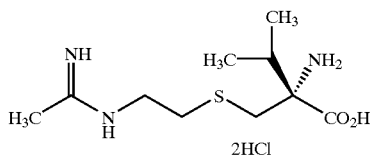

2-[[[[2-(1-Iminoethyl)amino]ethyl]thio]methyl]-D-valine, dihydrochloride

Example-N-1

Isopropyl triflate

Silver triflate (25.25 g, 98.3 mmol) stirred in diethyl ether (300 mL) under nitrogen was treated with isopropyl iodide (16.54 g, 98.5 mmol) in ether (200 mL) over 15 minutes. The mixture was stirred for 10 minutes and then filtered. The filtrate was distilled at reduced pressure. The distillate was redistilled at atmospheric pressure to remove the majority of the diethyl ether, leaving a mixture of the title isopropyl triflate-diethyl ether (84:16 by weight) (15.64 g, 70% corrected) as a colorless liquid. $^1H$ NMR (CDCl$_3$, 400 MHz)? 1.52 (d, 6H), 5.21 (septet, 1H).

The procedures and methods utilized here were the same as those used in Example I except that isopropyl triflate replaced methyl iodide in Example-I-2. The crude title product was purified by reversed phase chromatography using a gradient elution of 10–40% acetonitrile in water. $^1H$ NMR ($H_2O$, 400 MHz)?? 0.94 (dd, 6H), 2.04 (septet, 1H), 2.10 (s, 3H), 2.65, 2.80 (d m, 2H), 2.85, 3.10 (dd, 2H), 3.37 (t, 2H). HRMS calc. for $C_{10}H_{22}N_3O_2S$: 248.1433 [M+H$^+$], found 248.1450.

Example O

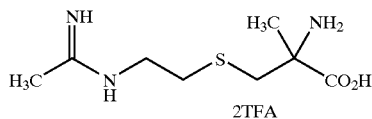

S-[2-(1-Iminoethylamino)ethyl]-2-methyl-(D/L)-cysteine, bistrifluoroacetate

Example-O-1

S-(2-aminoethyl)-L-cysteine, methyl ester

A 10 g (50 mmol) sample of S-(2-aminoethyl)-L-cysteine was dissolved in 400 mL of methanol. Into this cooled solution was bubbled in anhydrous HCl for 30 minutes. After stirring at room temperature overnight, the solution was concentrated to afford 12.7 g of the title compound.

Example-O-2

N-{4-chlorophenyl)methylene]-S-[2-[[(4-chlorophenyl)methylene]amino]ethyl}-L-cysteine, methyl ester A 12.7 g (50 mmol) sample of the product of Example-O-1, S-(2-aminoethyl)-L-cysteine methyl ester, was dissolved in acetonitrile. To this solution was added 12.2 g (100 mmol) of anhydrous MgSO$_4$, 14 g (100 mmol) of 4-chlorobenzaldehyde and 100 mmol of triethylamine. This mixture was stirred for 12 hours, concentrated to a small volume and diluted with 500 mL of ethyl acetate. The organic solution was washed successively with (0.1%) NaHCO$_3$, (2N) NaOH, and brine solution. The organic was dried (anhy. MgSO$_4$), filtered and concentrated to afford 7.5 g of the title compound. [M+H$^+$]=179.

Example-O-3

N-[4-chlorophenyl)methylene]-S-[2-[[(4-chlorophenyl)methylene]amino]ethyl]-2-methyl-D/L-cysteine methyl ester A sample of the product of Example-O-2, N-{4-chlorophenyl)methylene]-S-[2-[[(4-chlorophenyl)methylene]amino]ethyl]-L-cysteine methyl ester (7.5 g, 17 mmol), in anhydrous THF was treated with 17 mmol of sodium bis(trimethylsilyl)amide at −78° C. under nitrogen, followed by 2.4 g (17 mmol) of methyl iodide. The solution was held at −78° C. for 4 hr and then warmed to room temperature with continuous stirring. The solvents were evaporated in vacuo and brine and ethyl acetate was added. The aqueous phase was extracted 3×EtOAc, and the combined organic layers were washed with 10% KHSO$_4$, water, and brine before it was dried (anhy. MgSO$_4$), filtered, and evaporated to afford the title compound.

Example-O-4

S-(2-aminoethyl)-2-methyl-D/L-cysteine, hydrochloride

A sample of the product of Example-O-3, N-[4-chlorophenyl)methylene]-S-[2-[[(4-chlorophenyl)methylene]amino]ethyl]-2-methyl-D/L-cysteine methyl ester (4.37 g, 10 mmol), was stirred and heated (60° C.) with 2N HCl overnight and the solution washed (3×) with ethyl acetate. The aqueous solution was freeze-dried to give the title compound.

Example O

A sample of the product of Example-O-4, S-(2-aminoethyl)-2-methyl-D/L-cysteine dihydrochloride (2.5 g (10 mmol), was dissolved in H$_2$O and the pH was adjusted to 10 with 1 N NaOH. Ethyl acetimidate hydrochloride (1.24 g, 10.0 mmol) was then added to the reaction mixture. The reaction was stirred 15–30 min, the pH was raised to 10, and this process repeated 3 times. The pH was reduced to 4 with HCl solution and the solution evaporated. The residue was purified on reverse phase HPLC with H$_2$O containing 0.05% trifluoroacetic acid as the mobile phase to afford the Example O title product. M+H=220.

Example P

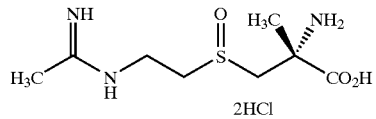

2HCl (2R)-2-Amino-3[[2-[(1-iminoethyl)amino]ethyl]sulfinyl]-2-methylpropanoic acid, dihydrochloride A solution of S-[2-[(1-iminoethyl)amino]ethyl]-2-methyl-L-cysteine, dihydrochloride (Example I, 0.2 g, 0.73 mmol) in 3 mL of water was stirred and cooled to 0° C. and a solution of 3% H$_2$O$_2$ (0.8 mL, 0.73 mmol) in formic acid (0.4 mL, 0.73 mmol) was added in 0.3 mL portions. The cold bath was removed and the reaction mixture was stirred at room temperature for 48 hours. The solution was concentrated in vacuo, diluted with of water (10 mL) and concentrated again to give the crude sulfone. This residue was chromatographed (C-18 reverse phase, with mobile phase H$_2$O containing 0.05% trifluoroacetic acid) to give the pure sulfone. The sulfone was treated with 1M HCl (10 mL) and concentrated in vacuo to give 140 mg of a mixture of 2 diastereomers of the title compound as a colorless oil of the HCl salts. $^1$H NMR (300 MHz, D$_2$O)? 1.5 (s, 2H), 1.6 (s, 1H), 2.0 (s, 3H), 3.1 (m, 2H), 3.3 (m, 2H), 3.6 (m, 2H). HRMS calc. for C$_8$H$_{18}$N$_3$O$_3$S: 236.1069 [M+H$^+$], found: 236.1024.

Example Q

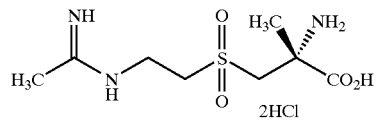

2HCl (2R)-2-Amino-3[[2-[(1-iminoethyl)amino]ethyl]sulfonyl]-2-methylpropanoic acid dihydrochloride A solution of S-[2-[(1-Iminoethyl)amino]ethyl]-2-methyl-L-cysteine dihydrochloride, the product of Example I, (0.15 g, 0.54 mmol) in 2 mL of water was cooled to 0° C. and a solution of 3% H$_2$O$_2$ (1.6 mL, 1.46 mmol) in formic acid (0.8 mL, 14.6 mmol) was added. The cold bath was removed and the reaction mixture was stirred at room temperature for 18 hours. The solution was concentrated in vacuo, diluted with 10 mL of water and concentrated again to give the crude sulfoxide. The residue was diluted with 4 mL of water and was adjusted to pH 9 with 2.5 N NaOH. Acetone (5 mL) was added, followed by Boc$_2$O (0.2 g), and the reaction was stirred for 48 h at room temperature. The reaction mixture was adjusted to pH 6 with 1M HCl and was concentrated in vacuo. This residue was chromatographed (C-18 reverse phase; 40 to 50% ACN: H$_2$O, 0.05% TFA) to give the pure Boc protected material. The fractions were concentrated in vacuo and the residue was treated with 1N HCl (3 mL) for 1 h. The solution was concentrated to give 30 mg of the title compound as colorless oil. $^1$H NMR (400 MHz, D$_2$O)? 4.0 (d, 1H), 3.7 (d, 1H), 3.6 (t, 2H), 3.5 (t, 2H), 2.1 (s, 3H), and 1.5 (s, 3H) ppm. HRMS calc. for C$_8$H$_{18}$N$_3$O$_4$S: 252.1018 [M+H$^+$], found: 252. 0992.

Example R

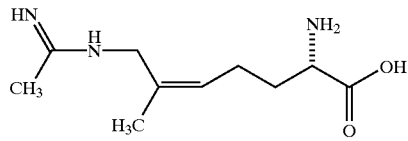

(2S,5Z)-2-amino-6-methyl-7-[(1-iminoethyl)amino]-5-heptenoic acid, dihydrochloride Example R-1

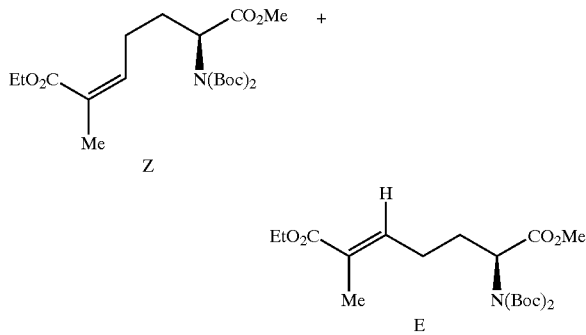

A solution of triethyl-2-phosphonopropionate (6.5 mg, 27.1 mmol) in toluene (60 ML) was treated with 0.5 M potassium bis(trimethylsilyl) amide (50.0 ML, in toluene) and the resulting anion was condensed with the aldehyde product of Example U-3 by the method of Example U-4 (see Example U infra). This produced, after chromatography, 8 g of a 3:7 mixture respectively of the desired Z and E diesters.

($^1$H)NMR (300 MHz, CDCl3) 6.7–6.8 ppm (m, 1H), 5.9 ppm (m, 1H), 4.9 ppm (m, 1H), 4.2 ppm (q, 2H), 3.7 ppm (s, 3H), 2.5 ppm (m, 1H), 2.2–2.3 ppm (m, 2H), 2.0 ppm (m, 1H), 1.9 ppm (s, 3H), 1.8 ppm (s, 3H), 1.5 ppm (s, 18H), 1.3 ppm (t, 3H).

Example R-2

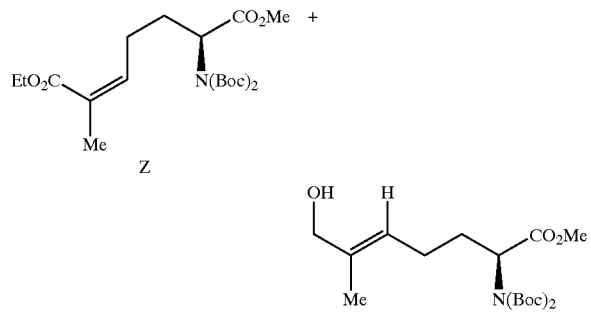

The product mixture of Example R-1 (850 mg, 2.0 mmol) in Et$_2$O (30 mL) was reduced over a period of twenty minutes with diisobutyl aluminum/hydride (DIBAL) by the method of Example U-5 to produce the crude illustrated desired mixture of E-alcohol and unreduced Z-ester. This mixture was chromatographed on silica gel eluting with n-hexane:EtOAc (9:1) to n-hexane:EtOAc (1:1) providing samples of the Z-ester (530 mg) and the E-alcohol desired materials.

Z-ester: ($^1$H)NMR (300 MHz, CDCl3) 5.9 ppm (m,1H), 4.9 ppm (m, 1H), 4.2 ppm (q, 2H), 3.7 ppm (s, 3H), 2.5 ppm (m, 1H), 2.2–2.3 ppm (m, 2H), 1.9 ppm (s, 3H), 1.5 ppm (s, 18H), 1.3 ppm (t, 3H).

E-alcohol: ($^1$H)NMR (300 MHz, CDCl3) 5.35 ppm (m, 1H), 4.9 ppm (m, 1H), 3.95 ppm (s, 1H), 3.7 ppm (s, 3H), 1.8–2.2 ppm (m, 6H), 1.6 ppm (s, 3H), 1.5 ppm (s, 18H).

Example R-3

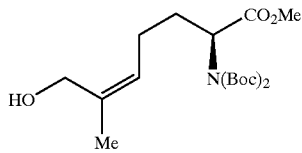

The product Z-ester of Example R-2 (510 mg, 1.2 mmol) in Et$_2$O (30 ML) was reduced over a period of two hours with diisobutyl aluminum/hydride (DIBAL) by the method of Example U-5 to produce the crude illustrated desired Z-alcohol. This material was chromatographed on silica gel eluting with n-hexane:EtOAc (9:1) to n-hexane:EtOAc (8:2) to yield 340 mg of the desired Z-alcohol product.

($^1$H)NMR (300 MHz, CDCl$_3$)? 5.3 ppm (m,1H), 4.9 ppm (m, 1H), 4.2 ppm (d, 1H), 4.0 ppm (d, 1H), 2.2 ppm (m, 3H), 1.95 ppm (m, 1H), 1.8 ppm (s, 3H), 1.5 ppm (s, 18H).

Example R-4

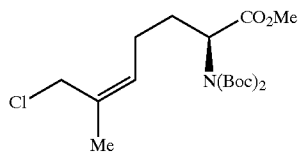

A CH$_2$Cl$_2$ solution (5 ML) of the product alcohol of Example R-3 (340 mg, 0.9 mmol) was treated with triethylamine (151 mg, 1.5 mmol). To this solution cooled in an ice bath was added a CH$_2$Cl$_2$ solution (1.5 ML) of methanesulfonyl chloride. After fifteen minutes the ice bath was removed and the reaction was stirred at ambient temperature for 20 h. The reaction mixture was then washed with 10% KHSO$_4$, dried over Na$_2$SO$_4$, and stripped of all solvent under reduced pressure to produce 350 mg of the desired Z-allylic chloride.

($^1$H)NMR (300 MHz, CDCl$_3$)? 5.4 ppm (m,1H), 4.9 ppm (m, 1H), 4.1 ppm (d, 1H), 4.0 ppm (d, 1H), 2.1 ppm (m, 3H), 1.95 ppm (m, 1H), 1.8 ppm (s, 3H), 1.5 ppm (s, 18H).

Example R-5

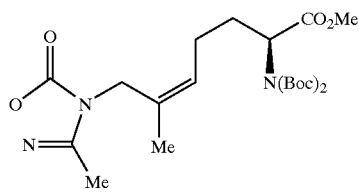

A suspension of potassium 3-methyl-1,2,4-oxa-diazoline-5-one in DMF is reacted with a DMF solution of the product of Example R-4 by the method of Example S-2 infra to produce the material.

Example R-6

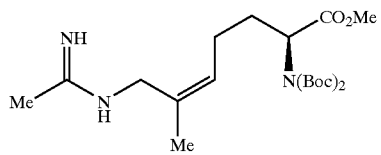

The product of Example R-5 is reacted with zinc in HOAc by the method of Example U-7 to yield the amidine.

Example R-7

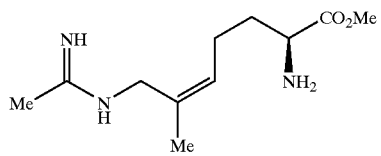

The product of Example R-6 was reacted with 4NHCl in dioxane in glacial HOAc to yield the amidine.

Example R

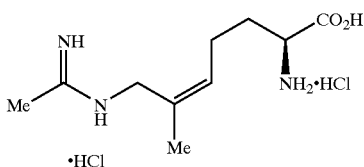

The product of Example R-7 is deprotected to yield the amino acid, dihydrochloride.

Example S

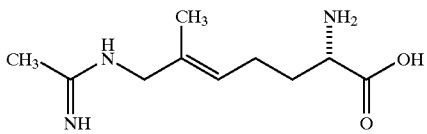

(2S,5E)-2-amino-6-methyl-7-[(1-iminoethyl)amino]-5-heptenoic acid, dihydrochloride

Example S-1

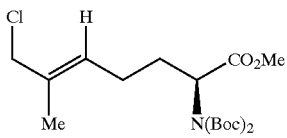

The E-alcohol product of Example R-2 (1.3 g, 3.3 mmol) was reacted with triethylamine (525 mg, 5.2 mmol) and methanesulfonyl chloride (560 mg, 5.2 mmol) by the method of Example R-4 to yield 1.4 g of the desired E-allylic chloride.

($^1$H)NMR (400 MHz, CDCl3) 5.5 ppm (m,1H), 4.9 ppm (m, 1H), 4.0 ppm (s, 2H), 3.7 ppm (s, 2H), 3.7 ppm (s, 3H), 2.1–2.3 ppm (m, 3H), 1.9 ppm (m, 1H), 1.7 ppm (s, 3H), 1.5 ppm (s, 18H).

Example S-2

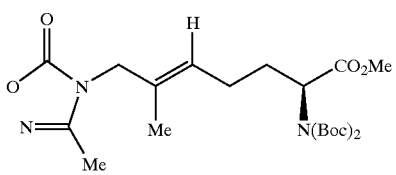

A suspension of potassium 3-methyl-1,2,4-oxa-diazoline-5-one (460 mg, 3.35 mmol) in 5 mL of DMF was treated with a DMF (15 mL) solution of the product of Example S-1. This reaction mixture was stirred at 50° C. for 17 h before an additional 50 mg (0.04 mmol) of the diazoline-5-one salt was added. Heating of the stirred reaction was continued for an additional 3 h before it was cooled to room temperature and diluted with 180 mL of water. This mixture was extracted with EtOAc and the extracts were diluted with 120 mL of n-hexane, washed with water, dried over Na$_2$SO$_4$ and stripped of all solvent under reduced pressure to yield 1.3 g of the material.

($^1$H)NMR (400 MHz, CDCl3) 5.5 ppm (m,1H), 4.9 ppm (m, 1H), 4.2 ppm (s, 3H),3.7 ppm (s, 3H), 2.2 ppm (m, 3H), 1.95 ppm (m, 1H), 1.8 ppm (s, 3H), 1.5 ppm (s, 18H).

Example S-3

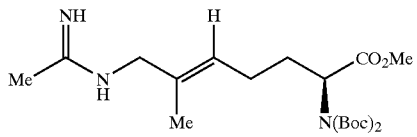

The product of Example S-2 (460 mg, 1.0 mmol) was reacted with zinc in HOAc by the method of Example U-7 (see Example U infra) to yield 312 mg of the desired amidine after HPLC purification.

Example S

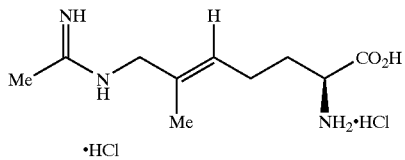

The product of Example S-3 (77 mg, 0.2 mmol) was deprotected with 2N HCl by the method of Example U to yield 63 mg the E-amino acid, dihydrochloride.

Example T

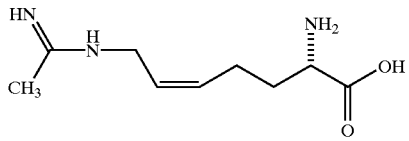

(2S,5Z)-2-amino-7-[(1-iminoethyl)amino]-5-heptenoic acid, dihydrochloride

Example T-1

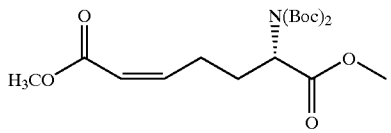

Methyl bis(trifluoroethyl)phosphonoacetate (4.77 g, 15 mmol) and 23.7 g (90 mmol) of 18-crown-6 were dissolved in 80 mL of anhydrous THF and cooled to –78° C. To this soution was added 30 mL (15 mmol) of potassium bis(trimethylsilyl) amide, followed by 5.1 g (14.7 mmol) of N,N-diBoc glutamic aldehyde methyl ester from Example U-3 (see Example U infra). After stirring for 30 minutes at –78° C., the reacion was quenched with aqueous KHSO$_4$. Extraction of the reaction mixture with EtOAc and concentration afforded 2.95 g (49%) of the desired compound. Mass spectra M+H=402.

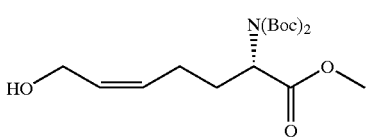

Example T-2

The product from Example T-1 was reduced by the method of Example U-5 to afford the desired compound.

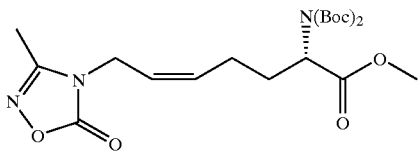

Example T-3

The product from Example T-2 was allowed to react with 3-methyl-1,2,4-oxadiazolin-5-one by the method of Example U-6 to afford the desired compound.

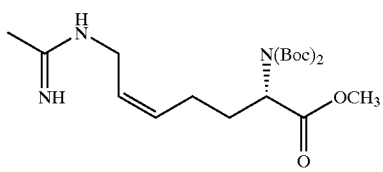

Example T-4

The product from Example T-3 was deprotected by the method of Example U-7 to afford the desired compound.

Example T

The product from Example T-4 was dissolved in 2 N HCl and heated at reflux. The reaction mixture was cooled and concentrated to afford 0.12 g of the desired product. H$^1$-NMR 1.8–2.0 (m, 2H); 2.05 (s, 3H); 2.15 (q, 2H); 3.75 (d, 2H); 3.9 (t, 1H); 5.45 (m, 1H); 5.6 (m, 1H)

Example U

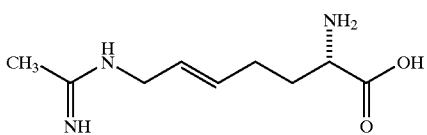

(2S,5E)-2-amino-7-[(1-iminoethyl)amino]-5-heptenoic acid, dihydrochloride

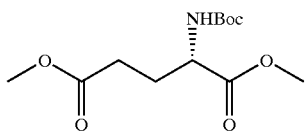

Example U-1

L-glutamic acid (6.0 g, 40.78 mmol) was dissolved in methanol (100 mL). To the reaction mixture trimethylsilyl chloride (22.9 mL, 180 mmol) was added at 0° C. under nitrogen and allowed to stir overnight. To the reaction mixture at 0° C. under nitrogen triethylamine (37 mL, 256 mmol) and di-tert-butyldicarbonate (9.8 g, 44.9 mmol) was added and stirred two hours. The solvent was removed and the residue was triturated with ether (200 mL). The triturated mixture was filtered. The filtrate was evaporated to an oil and chromatographed on silica, eluting with ethyl acetate and hexane, to give the mono boc L-glutamic diester (10.99 g, 98%).

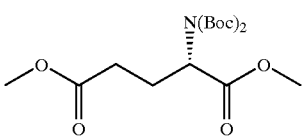

Example U-2

Mono boc L-glutamic acid (10.95 g, 39.8 mmol) was dissolved in acetonitrile (130 mL). To the reaction mixture 4-dimethylaminopyridine (450 mg, 3.68 mmol) and di-tert-butyldicarbonate (14.45 g, 66.2 mmol) was added and stirred for 20 hours. The solvent was evaporated and the residue chromatographed on silica and eluting with ethyl acetate and hexane to give the di-boc-L-glutamic diester (14.63 g, 98%).

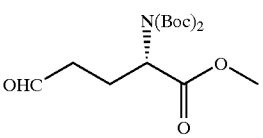

Example U-3

The product from Example U-2 (10.79 g, 28.7 mmol) was dissolved in diethyl ether (200 mL) and cooled in a dry ice bath to −80° C. To the reaction mixture Diisobutylaluminum hydride (32.0 mL, 32.0 mmol) was added and stirred 25 minutes. The reaction mixture was removed from the dry ice bath and water (7.0 mL) was added. Ethyl acetate (200 mL) was added to the reaction mixture and stirred 20 minutes. Magnesium sulfate (10 g) was added to the reaction mixture and stirred 10 minutes. The reaction mixture was filtered through celite and concentrated to give a clear yellow oil (11.19 g). The yellow oil was chromatographed on silica and eluting with ethyl acetate and hexane. The product (8.61, 87%) was a clear light yellow oil.

Mass Spectrometry: M+H 346, M+Na 378 ($^1$H)NMR (400 MHz, CDCl$_3$) 9.74 ppm (s, 1H), 4.85 ppm (m, 1H), 3.69 ppm (s, 3H), 2.49 ppm (m, 3H), 2.08 ppm (m, 1H), 1.48 ppm (s, 18H).

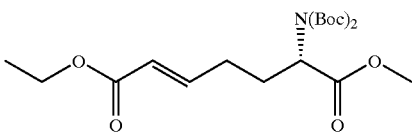

Example U-4

Triethyl phosphonoacetate (6.2 mL, 31.2 mmol) was dissolved in toluene (30 mL) and placed in an ice bath under nitrogen and cooled to 0° C. To the reaction mixture, potassium bis(trimethylsilyl) amide (70 mL, 34.9 mmol) was added and stirred 90 minutes. To the reaction mixture the product from Example U-3 (8.51 g, 24.6 mmol) dissolved in toluene (20 mL) was added and stirred 1 hour. The reaction mixture was warmed to room temperature. To the reaction mixture Potassium hydrogen sulfate (25 mL, 25 mmol) was added and stirred 20 minutes. The mixture was extracted with ethyl acetate (3×100 mL), dried over Magnesium sulfate and concentrated to give a cloudy brownish yellow oil (12.11 g). The oil was chromatographed on silica, eluted with ethyl acetate and toluene to give a light yellow oil (7.21 g, 70%).

Mass Spectrometry: M+H 416, M+NH₄ 433, -boc 316, -2 boc, 216. (¹H)NMR (400 MHz, CDCl₃) 6.88 ppm (m, 1H), 5.82 ppm (d, 1H), 4.81 ppm (m, 1H), 5.76 ppm (s, 3H), 2.50 ppm (m, 3H), 2.21 ppm (m, 1H), 1.45 ppm (s, 18H).

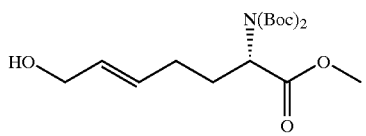

Example U-5

The product from Example U-4 (5.0 g, 12.03 mmol) was dissolved in diethyl ether (100 mL) and placed in a dry ice bath and cooled to −80° C. To the reaction mixture was added diisobutylaluminum hydride (21.0 mL, 21.0 mmol). And stirred 30 minutes. To the reaction mixture water (10 mL) was added, removed from dry ice bath, and stirred 60 minutes. To the reaction mixture magnesium sulfate (10 g) was added and stirred 10 minutes. The reaction mixture was filtered over celite and concentrated to give a yellow oil (5.0 g). The oil was chromatographed on silica, eluted with ethyl acetate and hexane, to give a light yellow oil (2.14 g, 47%).

Mass Spectrometry: M+H 374, M+NH₄ 391 (¹H)NMR (400 MHz, CDCl₃) 5.63 ppm (m, 2H), 4.88 ppm (m, 1H), 4.02 ppm (s, 2H), 3.68 ppm (s, 3H), 2.12 ppm (m, 4H), 1.47 ppm (s, 18H).

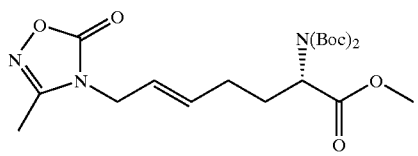

Example U-6

The product from Example U-5 was dissolved in tetrahydrofuran (50 mL). To the reaction mixture triphenyl phosphine on polymer (3.00 g, 8.84 mmol), oxadiazolinone (720 mg, 7.23 mmol), and azodicarboxylic acid dimethyl ester (1.17 g, 3.21 mmol) were added and stirred six hours at room temperature. The reaction mixture was filtered over celite and concentrated to give a cloudy yellow oil (2.81 g). The oil was chromatographed on silica, eluting with ethyl acetate in hexane, to give a clear colorless oil (1.66 g, 68%).

Mass Spectrometry: M+H 456, M+NH₄473, -boc 356, -2 boc 256 (¹H)NMR (400 MHz, CDCl₃) 5.65 ppm (m, 1H), 5.45 ppm (m, 1H), 4.79 ppm (m, 1H), 4.11 ppm (d, 2H), 3.68 ppm (s, 3H), 2.17 ppm (m, 4H), 1.47 ppm (s, 18H).

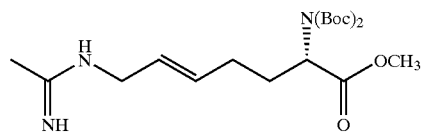

Example U-7

Product from Example U-6 (300 mg, 0.66 mmol) was dissolved in a solution of acetic acid and water (10 mL, 25/75) containing zinc metal and sonicated for 3 hours. The reaction mixture was filtered over celite and chromatographed on reverse phase HPLC to give a clear colorless residue (13 mg, 4%).

(¹H)NMR (400 MHz, CDCl₃) 8.89 ppm (m, 1H), 5.68 ppm (m, 1H), 5.47 ppm (m, 1H), 3.80 ppm (d, 2H), 3.71 ppm (s, 3H), 2.18 ppm (m, 4H), 1.41 ppm (s, 18H).

Example U

The product from Example U-7 (13.0 mg, 0.031 mmol) was dissolved in 2 N HCl (1.22 mL, 2.44 mmol) and refluxed 1 hour. The reaction mixture was cooled, concentrated, to give a clear colorless oil (6.6 mg, 95%)

Mass Spectrometry: M+H 200, (¹H)NMR (400 MHz, D₂O) 5.65 ppm (m, 1H), 5.47 ppm (m,1H), 3.80 ppm (t, 1H), 3.72 ppm (d, 2H), 2.0 ppm (m, 5H), 1.87 ppm (m, 2H).

Example V (αR,2S)-α-aminohexahydro-7-imino-1H-azepine-2-hexanoic acid, trihydrate hydrochloride

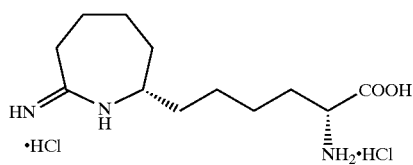

Example V-1

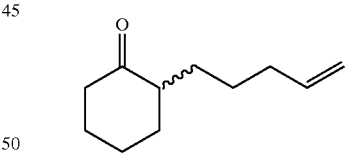

A three neck 3 L flask was purged with nitrogen before it was charged with cyclohexanone (1.27 mol, 132 mL) and 500 mL of toluene. This stirred mixture was cooled to 0° C. and 157.2 g (1.1 eq) of potassium t-butoxide was added. After stirring this mix for 1 hr, a color and texture change was noted before a solution of 5-pentenyl bromide (1.27 mol, 136 mL) in 100 mL toluene was added dropwise over 1 h to the mechanically stirred reaction mixture. The reaction mixture was allowed to warm to 25° C. and stir overnight. It was then diluted with 800 mL of 1 N KHSO₄ and the organic phase was dried (MgSO₄), filtered and evaporated to dryness to yield 208.5 g of crude product. This material was then purified by vacuum distillation (under water aspirator pressure) to give the title product in 47% yield.

$^1$HNMR (CDCl$_3$, δ ppm): 1.0–2.4 (m, 13H), 4.9–5.1 (m, 2H), 5.7–5.9 (m, 1H).

Example V-2

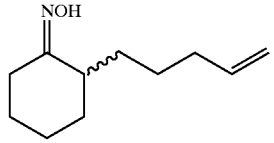

The product of Example V-1 (93.67 g, 0.563 mole) along with EtOH (600 mL), water (300 mL), NaOAc (101.67 g, 1.24 mole), and NH$_2$OH.HCl (78.31 g, 1.13 mole) were combined in a three neck 3 L flask. This stirred reaction mixture was refluxed for 16 h and then stirred at 25° C. for another 24 h. All solvent was removed under reduced pressure and the residue was partitioned between diethylether (Et$_2$O, 500 mL) and water (200 mL). The aqueous layer was extracted 3×200 mL ether. The combined organic layers were dried over MgSO$_4$, filtered, and stripped in vacuo to give the title oxime (121.3 g, 100% crude yield).

$^1$H NMR (CDCl$_3$, δ ppm): 1.2–2.6 (m, 13H), 4.9–5.1 (m, 2H), 5.7–5.9 (m, 1H).

Example V-3

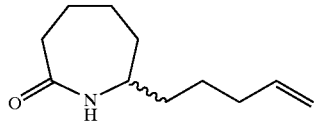

A three neck 3 L flask was purged with nitrogen and then charged with hexamethydisiloxane (471.7 mL, 2.2 moles), toluene (500 mL), and phosphorous pentoxide (203.88 g, 1.4 moles). This heterogeneous mixture was refluxed until a clear solution was obtained (about 1.5 h). After cooling this mixture to room temperature, the oxime product of Example V-1 (102.1 g, 0.563 moles) in 200 mL of toluene was added to the above reaction mixture over a 1 h period at 25° C. The reaction mixture was stirred for another 4–6 h (checked by TLC: 50% EA in Hex, I$_2$) before it was poured into ice water with thorough mixing. To this ice slurry mixture was added 250 g of NaCl and the resulting mixture was adjusted to pH 5 by adding solid potassium carbonate. This slurry was extracted with 3×500 mL of diethylether (Et$_2$O) and the combined organic fractions were dried over MgSO$_4$, filtered and stripped in vacuo to give the crude mixture of regioisomeric lactams (84.6 g).

Example V-4

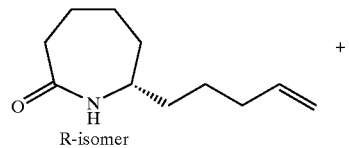
+

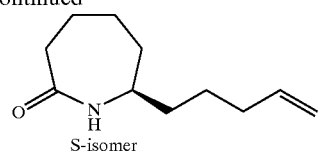

The product of Example V-3 was then subjected to chromatography (silica: acetonitrile) for purification and regioisomeric separation. From the crude sample, the 7-pentenyl regioisomer was isolated in 50% yield and after chiral chromatography, the desired single enantiomers were isolated in 43% yield each.

R-isomer:

Elemental analyses Calcd for C$_{11}$H$_{19}$NO: C, 71.99; H, 10.57; N, 7.63. Found: C, 71.97; H, 10.58; N, 7.52. $^1$H NMR (CDCl$_3$, δ ppm): 1.3–1.6 (m, 7H), 1.75–1.9 (m, 2H), 1.95–2.15 (m, 3H), 2.4–2.5 (m, 2H), 3.25–3.35 (m, 1H), 4.95–5.05 (m, 2H), 5.7–5.85 (m, 1H). $^{13}$C NMR (CDCl$_3$, δ ppm): 23.166, 25.169, 29.601, 33.209, 35.475, 35.624, 36.783, 53.600, 114.976, 137.923, 177.703 [α]$^{25}$=+26.9° (CHCl$_3$) at 365 nm.

S-isomer:

Elemental analyses Calcd for C$_{11}$H$_{19}$NO: C, 71.99; H, 10.57; N, 7.63. Found: C, 72.02; H, 10.61; N, 7.57. $^1$H NMR (CDCl$_3$, δ ppm): 1.3–1.6 (m, 7H), 1.75–1.9 (m, 2H), 1.95–2.15 (m, 3H), 2.4–2.5 (m, 2H), 3.25–3.35 (m, 1H), 4.95–5.05 (m, 2H), 5.7–5.85 (m, 1H). $^{13}$C NMR (CDCl$_3$, δ ppm): 23.187, 25.178, 29.630, 33.230, 35.526, 35.653, 36.778, 53.621, 115.032, 137.914, 177.703 [α]$^{25}$=−25.70° (CHCl$_3$) at 365 nm.

Example V-5

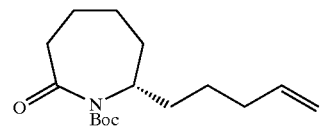

The R-isomer product of Example V-4 (102.1 g, 0.56 mol), dry THF (800 mL), DMAP (68.9 g, 0.56 mol), Di-t-butyl dicarbonate (Boc$_2$O, 99 g, 0.45 mol) were combined in a three neck 3 L flask purged with argon. The reaction mixture was warmed to 70° C. within 30 min before an additional 52.8 g of Boc$_2$O and 200 mL of dry THF were added. After 30 min. another 32 g of Boc$_2$O was added and the mixture was stirred for 1 h at 70° C. Another 36 g of Boc$_2$O was added and the mixture was stirred for 1 h. The reaction mixture was cooled to room temperature and stripped of THF at 18° C. to 20° C. under reduced pressure. A precipitate was filtered and washed with 100 mL of ethylacetate (EA) and discarded (~45 g). The EA filtrate was diluted with 500 mL of additional EA before it was washed with 500 mL of 1N KHSO$_4$, 500 mL of saturated aq. NaHCO$_3$, and 500 mL of brine and then dried over anhydrous Na$_2$SO$_4$ for 12 h. This EA extract was then treated with 20 g of DARCO, filtered through celite topped with MgSO$_4$, and concentrated in vacuo to give 150 g of title product as a dark brown oil.

$^1$H NMR (CDCl$_3$, δ ppm): 1.3–1.6 (m, 4H), 1.5 (s,9H), 1.6–1.9 (m, 6H), 1.95–2.05 (m, 2H), 2.5–2.7 (m, 2H), 4.2–4.25 (m, 1H), 4.95–5.05 (m, 2H), 5.7–5.85 (m, 1H).

Example V-6

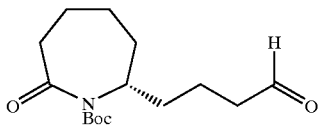

A three neck 3 L flask containing the product of Example V-5 (150 g, 0.533) dissolved in 3 L of $CH_2Cl_2$ was cool to −78° C. A stream of $O_3$ was passed through the solution for 2.5 h until the color of the reaction mixture turned blue. Argon was then bubbled through the solution maintained at −60° C. to −70° C. until the solution became clear and colorless (~30 min.). Dimethylsulfide (DMS, 500 mL) was then added before the reaction was brought to reflux and this reflux was continued for 24 h. Another 100 mL of DMS was added and reflux was continued for 12 h. Another 100 mL of DMS was added and reflux continued for an additional 12 h. The solvent and excess DMS were then stripped on a rotary evaporator at 20° C. The residual yellow oil obtained was diluted with 500 mL of DI water and extracted with 3×300 mL of EA. The EA layer was dried over anhydrous $MgSO_4$, treated with 20 g of DARCO, filtered through a thin layer of celite topped with anhydrous $MgSO_4$, and stripped of all solvent under reduced pressure to yield 156 g of the crude title product as orange yellow oil.

$^1$H NMR ($CDCl_3$, δ ppm): 1.3–1.6 (m, 4H), 1.5 (s, 9H), 1.6–1.9 (m, 6H), 2.45–2.75 (m, 4H), 4.2–4.25 (m, 1H), 9.75 (s, 1H).

Example V-7

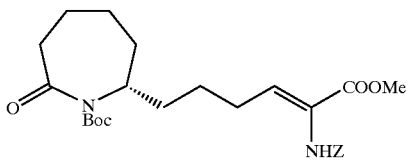

To a sample of N-(Benzyloxycarbonyl)-alpha-phosphonoglycine trimethyl ester (160 g, 0.48 mol) dissolved in 1 L of dichloromethane ($CH_2Cl_2$) and cooled to 0° C. was added a solution of DBU (110.29 g, 0.72 mol) in 100 mL of $CH_2Cl_2$. This clear colorless reaction mixture was stirred for 1 h at 0° C. to 6° C. before the Boc-aldehyde product of Example V-6 (150 g, 0.53 mol) in 600 mL of $CH_2Cl_2$ was added drop wise at −5° C. to −1° C. The reaction mixture was stirred for 30 min. at this temperature before it was slowly warmed to 10° C. in approximately 1 h. The reaction mixture was washed with 1N $KHSO_4$ (500 mL), saturated aq. $NaHCO_3$ (200 mL) and 50 aq. NaCl (200 mL). The organic layer was then dried over anhydrous $MgSO_4$, treated with 40 g of DARCO, filtered through a thin layer of celite topped with anhydrous $MgSO_4$, and concentrated to give 258 g of the crude title product as an yellow oil. Chromatographic purification of this material gave 130 g (55%) of the pure title product.

Elemental analyses Calcd for $C_{26}H_{36}N_2O_7$: C, 63.96; H, 7.42; N, 5.77. Found: C, 63.42; H, 8.16; N, 5.31. $^1$H NMR ($CDCl_3$, δ ppm): 1.25 (m, 2H), 1.5 (s, 9H), 1.51–1.9 (bm, 8H), 2.25 (m, 2H), 2.5 (m, 1H), 2.65 (m, 1H), 3.75 (s, 3H), 4.12 (m, 1H), 5.15 (s, 2H), 6.3 (bs, 1H), 6.55 (t, 1H), 7.45 (m,5H). $^{13}$C NMR ($CDCl_3$, δ ppm): 14.04, 22.62, 23.46, 24.08, 25.27, 27.89, 27.92, 28.34, 28.95, 31.81, 31.86, 32.05, 39.18, 52.31, 54.65, 67.27, 82.62, 128.07, 128.18, 128.46, 135.98, 136.82, 154.50, 164.92, 176.68. $[α]^{25}$=+10.9° ($CHCl_3$) at 365 nm.

Example V-8

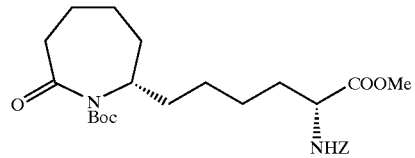

To a MeOH (1 L) solution of the product of Example V-7 (91.3 g, 0.19 mol) was added 2.5 g of S,S-Rh-DIPAMP catalyst followed by hydrogen. The hydrogenation was carried out at 25° C. in 1.5 h in a Parr apparatus. The reaction mixture was filtered through celite before concentrating to provide the crude title product (90 g, 98%) as a brown oil.

$^1$H NMR ($CDCl_3$, δ ppm): 1.35 (m, 4H), 1.5 (s, 9H), 1.55–1.95 (m, 10H), 2.4–2.7 (m, 2H), 3.75 (s, 3H), 4.2 (m, 1H), 4.4 (m, 1H), 5.1 (m, 2H), 5.35 (d, 1H), 7.35 (m, 5H).

Example V-9

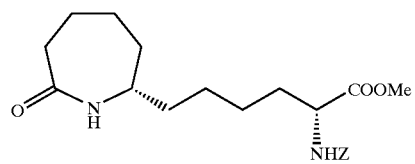

To a solution of the product of Example V-8 (90 g,) in 200 mL of glacial acetic acid was added 200 mL of 4N HCl in dioxane. The reaction mixture was stirred at 25° C. for 20 min. before it was stripped of all solvent under reduced pressure at 40° C. to give a red brown oil. This oily product was treated with 500 mL of water and extracted 2×300 mL of dichloromethane. The combined organic layer was washed with satd. sodium bicarbonate solution (100 mL), dried over magnesium sulfate, filtered and stripped of all solvent to give the crude title product. This material was chromatographed to provide 45 g (62%) of the pure title product.

Elemental analyses Calcd for $C_{21}H_{30}N_2O_5$: C, 64.02; H, 7.68; N, 7.17. Found: C, 63.10; H, 7.88; N, 6.60. $^1$H NMR ($CDCl_3$, δ ppm): 1.2–2.0 (m, 14H), 2.45 (t, 2H), 3.25 (m,1H), 3.75 (s, 3H), 4.38 (m, 1H), 5.1 (s, 2H), 5.3 (d, 1H), 5.45 (bs, 1H), 7.35 (m, 5H). $^{13}$C NMR ($CDCl_3$, δ ppm): 14.09, 23.11, 24.89, 25.41, 29.53, 32.33, 35.52, 35.79, 36.68, 52.26, 53.51, 53.55, 53.60, 60.26, 66.86, 127.97, 128.05, 128.40, 136.18, 155.85, 172.85, 177.80. $[α]^{25}$=−9.9° ($CHCl_3$) at 365 nm.

Example V-10

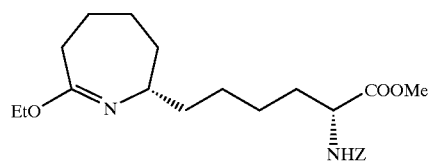

To a 45.0 g (0.115 mol) sample of the product of Example V-9 in 300 mL of dichloromethane purged with argon was added 23.0 g (0.121 mol) of triethyloxonium tetrafluoroborate. This mixture was stirred for 1 h at 25° C. before 150 mL of satd. aq. sodium bicarbonate solution was added. The dichloromethane layer was separated, washed with 150 mL of 50% aq. NaCl solution, dried over sodium sulfate, filtered through celite and concentrated at 25° C. to give a clear yellow oil, 47.0 g (97%) of the title product Elemental analyses Calcd for $C_{23}H_{34}N_2O_5$: C, 60.01; H, 8.19; N, 6.69. Found: C, 65.13; H, 8.45; N, 6.64. $^1$H NMR (CDCl$_3$, δ ppm): 1.2 (t, 3H), 1.25–1.74 (m, 12H), 1.75–1.95 (m, 2H), 2.2–2.3 (m, 1H), 2.4–2.5 (m, 1H), 3.1 (m, 1H), 3.7 (s, 3H), 3.9–4.0 (m, 2H), 4.35 (m, 1H), 5.1 (s, 2H), 5.25 (d, 1H), 7.35 (m, 5H). $^{13}$C NMR (CDCl$_3$, δ ppm): 14.23, 23.38, 25.01, 25.21, 26.10, 30.24, 32.16, 32.77, 33.92, 39.15, 52.22, 53.91, 58.05, 60.19, 66.92, 128.11, 128.33, 128.48, 136.27, 155.83, 166.29, 173.11, 177.64.

Example V-11

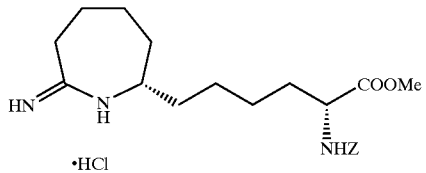

To 7.0 g (0.130 mol) of ammonium chloride in 500 mL methanol was added 31.2 g of the title material of Example V-10 (45.0 g, 0.107 mol). The reaction was refluxed at 65° C. for 5 h before all solvent was removed under reduced pressure to yield 40 g (87%) of the crude product as a foamy viscous mass. This material was purified by column chromatography to provide 37 g (81%) of the title product.

Elemental analyses Calcd for $C_{21}H_{31}N_3O_4$: C, 59.22; H, 7.57; N, 9.86; Cl, 8.32. Found for $C_{21}H_{31}N_3O_4$+1.2 HCl+0.5 H$_2$O: C, 57.20; H, 7.99; N, 9.66; Cl, 9.62. IR (Neat, λ max cm$^{-1}$): 2935, 1716, 1669. $^1$H NMR (CDCl$_3$, δ ppm): 1.2–2.0 (m, 13H), 2.5 (t, 1H), 2.95 (m, 1H), 3.4 (bs, 1H), 3.7 (s, 3H), 4.3 (m, 1H), 5.1 (s, 2H), 5.55 (d, 1H), 7.3 (m, 5H), 8.75 (bs,1H), 8.9 (bs, 1H), 9.5 (s, 1H). $^{13}$C NMR (CDCl$_3$, δ ppm): 23.20, 24.95, 25.22, 28.94, 31.80, 32.05, 33.75, 34.89, 52.33, 53.76, 56.07, 66.83, 127.93, 128.04, 128.43, 136.26, 156.00, 172.24, 172.87. Mass (ESI): M/Z, 390. $[α]^{25}$=+31.5° at 365 nm.

Example V

The title product of Example V-11 (36.0 g, 0.084 mol) in 1 L of 2.3 N HCl was refluxed for 3 h. After cooling to room temperature, the solution was washed with 2×150 mL of CH$_2$Cl$_2$ and then stripped of all solvent in vacuo to give 25.6 g (96%) of the title amino acid product as a pale yellow foam.

Elemental analyses Calcd for $C_{12}H_{23}N_3O_2$·2HCl: C, 46.02; H, 8.01; N, 13.39; Cl 22.45. Found for $C_{12}H_{23}N_3O_2$+2.2 HCl+0.1 H$_2$O: C, 42.76; H,8.02; N, 12.41; Cl, 22.79. IR (Neat, λ max, cm$^{-1}$): 2930, 2861, 1738, 1665. $^1$H NMR (CD$_3$OD, δ ppm): 1.3–2.5 (m, 16H), 2.6 (dd, 1H), 2.8 (t, 1H), 3.65 (m, 1H), 4.0 (t, 1H), 7.85 (s, 1H), 8.85 (s, 1H), 8.95 (s, 1H). $^{13}$C NMR (CD$_3$OD, δ ppm): 24.49, 25.67, 26.33, 29.71, 31.26, 32.45, 35.04, 35.87, 53.73, 57.21, 171.77, 173.96. UV, 282 nm, abs 0.015. Mass (M$^{+1}$)=242. $[α]^{25}$=−47.4° (MeOH) at 365 nm. ee=91% as determined by CE at λ=214 nm.

Example W (αS,2R)-α-aminohexahydro-7-imino-1H-azepine-2-hexanoic acid, trihydrate hydrochloride

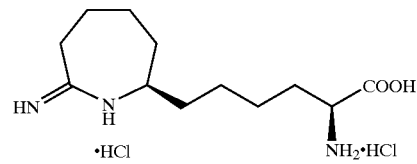

Example W-1

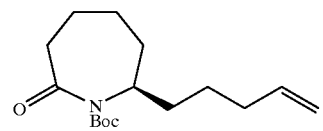

The S-isomer product of Example V-4 (5.45 g, 0.030 mol) was converted to its Boc derivative by the method of Example V-5. After chromatography, this reaction yielded 6.3 g (75%) of the desired title product.

$^1$H NMR (CDCl$_3$, δ ppm): 1.3–1.6 (m, 4H), 1.5 (s, 9H), 1.6–1.9 (m, 6H), 1.95–2.05 (m, 2H), 2.5–2.7 (m, 2H), 4.2–4.25 (m, 1H), 4.95–5.05 (m, 2H), 5.7–5.85 (m, 1H).

Example W-2

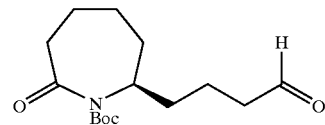

The product of Example W-1 (6.3 g, 0.025 mol) was ozonized by the method of Example V-6 to produce 8.03 g of the crude title aldehyde that was used without further purification.

$^1$H NMR (CDCl$_3$, δ ppm): 1.3–1.6 (m, 4H), 1.5 (s, 9H), 1.6–1.9 (m, 6H), 2.45–2.75 (m, 4), 4.2–4.25 (m, 1H), 9.75 (s, 1H).

Example W-3

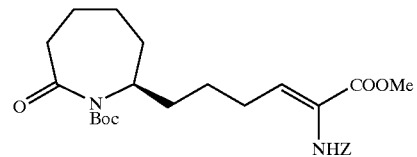

The product of Example W-2 (8.03 g, 0.024 mol) was condensed with N-(Benzyloxycarbonylalpha-phosphonoglycine trimethyl ester (7.9 g, 0.024 mol) utilizing the procedure of Example V-7 to produce 4.9 g (44%) of the desired title product after chromatography.

$^1$H NMR (CDCl$_3$, δ ppm): 1.25 (m, 2H), 1.5 (s, 9H), 1.51–1.9 (bm, 8H), 2.25 (m, 2H), 2.5 (m, 1H), 2.65 (m, 1H), 3.75 (s, 3H), 4.15–4.25 (m, 1H), 5.15 (s, 2H), 6.3–6.4 (bs, 1H), 6.45–6.55 (t, 1H), 7.3–7.4 (m,5H).

Example W-4

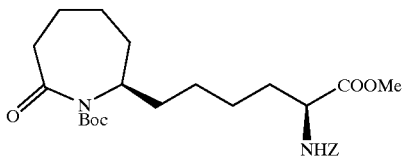

The product of Example W-3 (4.8 g, 0.010 mol) was reduced in the presence of R,R-Rh-DIPAMP catalyst by the method of Example V-8 to produce 2.9 g (60%) of the desired title product after chromatography.

Example W-5

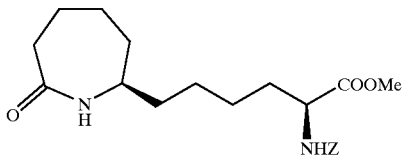

The product of Example W-4 (2.9 g, 0.006 mol) was deprotected by treatment with HCl using the method of Example V-9 to produce 2.3 g (100%) of the desired title product.

$^1$H NMR (CDCl$_3$, δ ppm): 1.3–2.0 (m, 14H), 2.45 (t, 2H), 3.25 (m, 1H), 3.75 (s, 3H), 4.38 (m, 1H), 5.1 (s, 2H), 5.3 (d, 1H), 5.45 (bs, 1H), 7.35 (m, 5H).

Example W-6

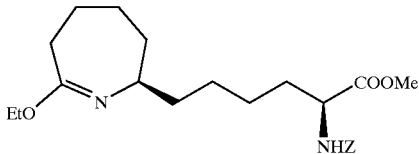

The product of Example W-5 (0.56 g, 0.0015 mol) was alkylated with triethyloxonium tetrafluoroborate using the method of Example V-10 to produce 0.62 g (98%) of the desired title product.

Example W-7

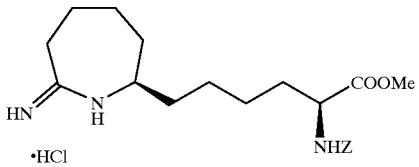

The product of Example W-6 (0.62 g, 0.0015 mol) was treated with ammonium chloride in methanol using the method of Example V-11 to produce 0.50 g (88%) of the desired title product after chromatographic purification.

Example W-8

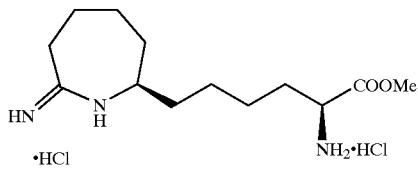

The product of Example W-7 (0.37 g, 0.0009 mol) dissolved in MeOH was added to a Parr hydrogenation apparatus. To this vessel was added a catalytic amount of 5% Pd/C. Hydrogen was introduced and the reaction was carried out at room temperature at pressure of 5 psi over a 7 hr period. The catalyst was removed by filtration and all solvent was removed under reduced pressure from the filtrate to produce 0.26 g (quantitative) of the desired title product.

Example W

A solution of the product of Example W-8 dissolved in 2N HCl (30 mL) was maintained at reflux for 2 h before it was cooled to room temperature. All solvent was removed under reduced pressure and the residue was dissolved in 50 mL of water. This solution was again stripped of all solvent under reduced pressure before it was again dissolved in 12 mL of water and then lyophilized to generated 0.245 g (71%) of the title compound.

Elemental analyses Calcd for C$_{12}$H$_{23}$N$_3$O$_2$.2.3 HCl.1.9 H$_2$O: C, 40.10; H, 8.16; N, 11.69; Cl, 22.69. Found for C$_{12}$H$_{23}$N$_3$O$_2$+2.1 HCl+0.7 H$_2$O: C, 40.27; H, 8.28; N, 11.62; Cl, 22.70. $^1$H NMR (CD$_3$OD, δ ppm): 1.4–2.1 (m, 16H), 2.6 (dd, 1H), 2.8 (t, 1H), 3.65 (m, 1H), 4.0 (t, 1H), 7.85 (s, 1H), 8.45 (s, 1H), 8.9 (s, 1H). $^{13}$C NMR (CD$_3$OD, δ ppm): 24.46, 25.64, 26.31, 29.69, 31.24, 32.54, 35.00, 35.83, 53.75, 57.20, 171.85, 173.93. [α]$^{25}$=+25.7° (MeOH) at 365 nm.

Example X (αS,2S)-α-aminohexahydro-7-imino-1H-azepine-2-hexanoic acid, trihydrate hydrochloride

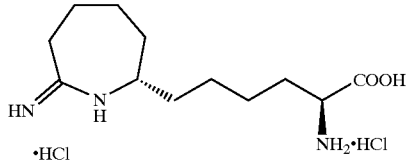

Example X-1

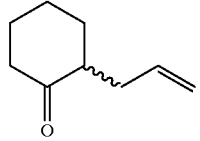

To a 22 L round bottom flask equipped with overhead stirrer, half moon shape paddle, heating mantle, thermocouple, and a silver vacuum jacketed distillation column (5 plates) was charged cyclohexanone (4500.0 g, 45.85 mol), acetone dimethyl acetal (5252.6 g, 50.43 mol), allyl alcohol (6390.87 g, 110.04 mol) and p-toluene sulfonic acid (PTSA) (0.256 g, 0.001 mol). After the stirring was started (137 rpm) the pot was heated slowly with the initial set point being 70° C. Heating was increased step wise to a final pot temperature of 150° C. The decision to increase the reactor set point was made based on distillation rate. If the rate of distillate slowed or stopped, additional heat was applied. The additional heating to 150° C. allowed the Claisen rearrangement to occur. After the pot temperature was raised to 150° C. and no distillate was observed, the heating mantle was lowered and the reaction mixture allowed to cool to 130° C. The PTSA was then neutralized with 3 drops of 2.5 N NaOH. The vacuum stripping was then started with the heating mantle lowered away from the flask. Evaporative cooling was used to lower the pot temperature, and the pressure was gradually lowered to 40 mm Hg. When the pot temperature had decreased to ~100° C., the heating mantle was raised back into the proper position for heating. Unreacted cyclohexanone and low boiling impurities were distilled off. The pot temperature was slowly raised (the maximum temperature deferential between the pot and vapor was ~12° C.). The product was isolated at 109–112° C. @ 40 mm Hg. Typical yields were 40–45%. Fractions which were <95% by area (GC) were combined and redistilled to afford the title product in a total yield of 55%.

$^1$H NMR (CDCl$_3$, δ ppm): 5.8–5.6 (m, 1H), 4.8–5.0 (m, 2H), 2.5–2.4 (m, 1H), 2.3–2.1 (m, 3H), 2.1–1.2 (m, 7H). $^{13}$C NMR (CDCl$_3$, δ ppm): 212.53, 136.62, 116.32, 50.39, 42.18, 33.91, 33.52, 28.09, 25.10. GC/MS m/z=138.

Example X-2

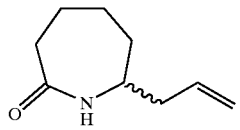

Hydroxyl amine-O-sulfonic acid (91.8 g) dissolved in acetic acid (470 g) was added to a 1 L Bayer flask equipped with a mechanical stirrer, thermocouple, condenser chilled to 0° C., and an addition funnel and heated to 70° C. The allyl cyclohexone (100 g) was added dropwise in approximately 40 min to the above solution while maintaining the temperature between 70 and 78° C. During the addition, the reaction appearance changed from a white slurry to a clear orange solution. After the addition, the reaction was heated and stirred for an additional 5 h at 75° C. An IPC sample was taken each hour. After the reaction was complete, the acetic acid was stripped at 50° C. under reduced pressure on a rotary evaporator. Water (200 mL) was then added to the residue and the solution extracted with toluene (2×300 mL). The organic layers were combined, treated with water (150 ml) and stirred for 10 min. A sodium hydroxide solution (79.4 g of 50 solution) was added until the aqueous layer turned basic (pH 12). The neutralization was carried out in the reactor by controlling the temperature below 40° C. The layers were then separated and the toluene layer was passed through a filter to remove any solids or tarry material. The organic solution was then stripped at 50° C. under reduced pressure on a rotary evaporator. The residue was taken up in a mixture of toluene (510 mL) and heptanes (2040 mL) and heated to 60° C. in a 3 L reactor. A clear yellow-orange solution was obtained. The title product began to crystallize at 53° C. as the solution was slowly cooled to 5° C. while being stirred. The solid was filtered, washed with heptanes (50 mL) and dried over night at 40° C. under house vacuum to produce 66.3 g (60%) of title product as off-white crystals obtained. A portion of this material was recrystallized from toluene and heptane to generate the title product as a white crystalline solid.

$^1$H NMR (CDCl$_3$, δ ppm): 5.8–5.6 (m, 1H), 5.5 (bs, 1H), 4.8–5.0 (m, 2H), 3.4–3.3 (m, 1H), 2.5–2.3(m, 2H), 2.3–2.1 (m, 2H) 2.0–1.2 (m, 6H) $^{13}$C NMR (CDCl$_3$, δ ppm): 117.73, 133.83, 119.31, 52.88, 40.95, 37.20, 35.75, 29.96, 23.33. GC/MS (EI mode)=153. m.p.=97–99° C.

Example X-3

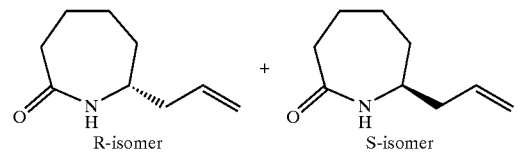

The racemic product mixture of Example X-2 was subjected to chiral chromatographic separation on a Chiralpac AS 20 um column eluting with 100% acetonitrile. A 220 nM wavelength was employed in the detector. A sample loading of 0.08 g/mL of acetonitrile was used to obtain 90% recovery of separated isomers each with >95% ee. A portion of the R-isomer material was recrystallized from toluene and heptane to generate the R-isomer title product as a white crystalline solid.

R-isomer: m.p.=81–82° C.

Example X-4

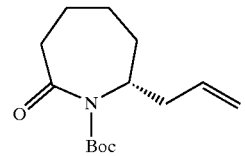

A five necked flat bottom flask equipped with dropping funnel, thermometer and mechanical overhead stirrer was evacuated and purged with nitrogen three times. The R-isomer product lactam of Example X-3 (100.0 g, 0.653 mol), DMAP (7.98 g, 65 mmol) and N-diisopropylethyl amine (Hunigs base, 113.3 g, 0.876 mol) were dissolved in toluene (350 mL) and Di-tert-butyl dicarbonate (170.2 g, 0.78 mol) dissolved in toluene (100 mL) was added. (Note: the reaction works better, when 2.0 eq of Hunigs base were used). The mixture was heated to 65° C. (Note: Steady offgasing during the reaction was observed). After 1.5 h another 86.25 g of Di-tert-butyl-dicarbonate (0.395 mol) dissolved in toluene (50 mL) were added. Heating was continued for 17 h and IPC by HPLC showed 75 conversion. Another 42.78 g of Di-tert-butyl dicarbonate (0.196 mol) in toluene (30 mL) were added and the brown mixture was heated 5.5 h. After cooling to ambient temperature, the mixture was treated with 4M HCl (215 mL), and the aqueous layer was extracted with toluene (2×80 mL). The combined organic layers were washed with NaHCO$_3$ (170 mL) and 250 ml of water (Note: the internal temperature during the quench was controlled by external cooling with ice/water). Gas evolution was observed. The organic layer was evaporated to give 257.4 g brown liquid. This crude material was purified by plug filtration over SiO$_2$ (950 g) using toluene/EtOAc 9/1 (6 L) and toluene/AcOEt 1/1 (0.5 L) as eluent giving 139.5 g (51%) of the yellow liquid title product.

Example X-5

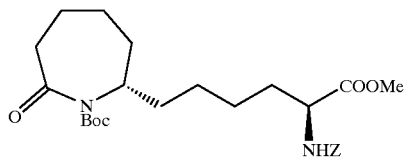

Example X-6

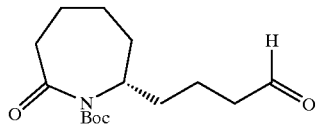

Example 1f

Into a 2-L stainless steel autoclave equipped with baffles and a six-bladed gas dispersing axial impeller was charged Rh(CO)$_2$(acac) (0.248 g, 0.959 mmol), BIPHEPHOS (structure shown below and prepared as described in Example 13 of U.S. Pat. No. 4,769,498, 2.265 g, 2.879 mmol), the product of Example X-4 (N-(tert-butoxycarbonyl)S-7-allylcaprolactam

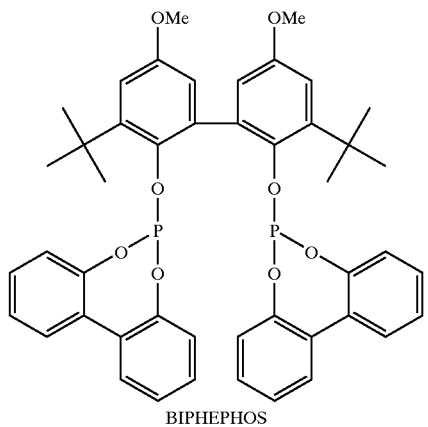

BIPHEPHOS (242.9 g, 0.959 mol), and toluene (965 g). The reactor was sealed and purged 100% carbon monoxide (8×515 kPa). The reactor was pressurized to 308 kPa (30 psig) with 100% carbon monoxide and then a 1:1 CO/H$_2$ gas mixture was added to achieve a total pressure of 515 kPa (60 psig). With vigorous mechanical agitation, the mixture was heated to 50° C. with a 1:1 CO/H$_2$ gas mixture added so as to maintain a total pressure of about 515 kPa (60 psig). After 22 h, the mixture was cooled to about 25° C. and the pressure was carefully released. Vacuum filtration of the product mixture and evaporation of the filtrate under reduced pressure afforded a 267.7 g of a light yellow oil. Analysis by $^1$H NMR was consistent with essentially quantitative conversion of the starting material with about 96% selectivity to the corresponding aldehyde product of Example V-6. This oil was used without further purification in the following example.

$^1$H NMR (CDCl$_3$) δ 1.47 (s, 9H), 1.6–1.80 (m, 9H), 1.84–1.92(m, 1H), 2.41–2.58 (m, 3H), 2.61–2.71 (m, 1H), 4.2 (d, J=5.2 Hz, 1H), 9.74 (s, 1H).

Example X-8

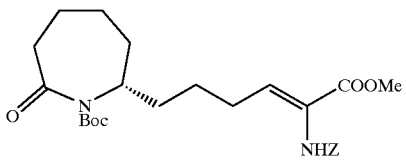

Example 1g

To a sample of N-(Benzyloxycarbonyl)-alpha-phosphonoglycine trimethyl ester (901.8 g, 2.7 mol) dissolved in CH$_2$Cl$_2$ and cooled to 0° C. was added a solution of DBU (597.7 g, 3.9 mol) in CH$_2$Cl$_2$. This clear colorless reaction mixture was stirred for 1 h at 0° C. to 6° C. before a sample of the Boc-aldehyde product Example V-6 (812.0 g, 2.9 mol) in CH$_2$Cl$_2$ was added drop wise at −5° C. to −1° C. The reaction, work up, and purification was completed as described in Example V-7 to give 1550 g of the title product of Example V-7 containing a small amount of CH$_2$Cl$_2$.

Example X-9

To a MeOH (1 L) solution of the product of Example V-7 (100 g, 0.20 mol) was added 3 g of RR-Rh-DIPAMP catalyst. The hydrogenation was carried out at 25° C. in 1.5 h in a Parr apparatus. The reaction mixture was filtered through celite before concentrating to provide the crude Example X-9 title product as a brown oil (100 g).

$^1$H NMR (CDCl$_3$, δ ppm): 1.35 (m, 4H), 1.5 (s, 9H), 1.6–1.9(m, 10H), 2.5–2.8 (m, 2H), 3.75 (s, 3H), 4.25 (m, 1H), 4.45 (m, 1H), 5.1 (m, 2H), 5.65 (d, 1H), 7.35 (m, 5H).

Example X-10

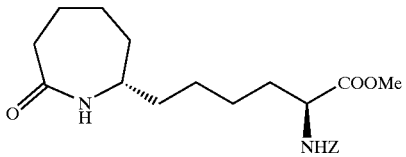

To a solution of the product of Example V-8 (100 g) in 200 mL glacial acetic acid was added 25 mL 4N HCl in dioxane. The reaction mixture was stirred at 25° C. for 20 min. before it was stripped of all solvent under reduced pressure at 40° C. to give 105 g of red brown oil. This oily product was treated with 500 mL of water and extracted 2×300 mL of dichloromethane. The combined organic layer was washed with satd. sodium bicarbonate solution (100 mL), dried over magnesium sulfate, filtered and stripped of all solvent to give 99.9 g of the title product as a red brown oil.

$^1$H NMR (CDCl$_3$, δ ppm): 1.25–2.0 (m, 14H), 2.45 (t, 2H), 3.25 (m,1H), 3.7 (s, 3H), 4.35 (m, 1H), 5.1 (s, 2H), 5.5 (d, 1H), 6.45 (bs, 1H), 7.35 (m, 5H). ee=95% as determined by chiral HPLC.

Example X-11

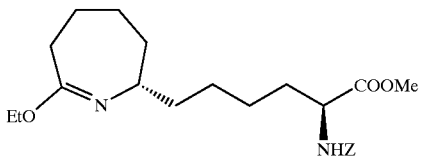

To a 30.0 g (0.077 mol) sample of the product of Example X-10 in 600 mL dichloromethane purged with argon was added 15.7 g (0.082 mol) of triethyloxonium tetrafluoroborate. This mixture was stirred for 1 h at 25° C. before 300 mL of satd. aq. sodium bicarbonate solution was added. The dichloromethane layer was separated, washed with 300 mL 50% aq. NaCl solution, dried over sodium sulfate, filtered through celite and concentrate at 25° C. to give a clear yellow oil, 31.2 g (~97%) of the title product.

Elemental analyses Calcd for $C_{23}H_{34}N_2O_5$: C, 60.01; H, 8.19; N, 6.69. Found for $C_{23}H_{34}N_2O_5$+0.5 $H_2O$: C, 64.66; H, 8.24;N,6.59. $^1H$ NMR (CDCl$_3$, δ ppm): 1.25(t, 3H), 1.28–1.75 (m, 12H), 1.8–1.98 (m, 2H), 2.2–2.3 (m, 1H), 2.4–2.5 (m, 1H), 3.1 (m, 1H), 3.78 (s, 3H), 3.9–4.0 (m, 2H), 4.35 (m, 1H), 5.1 (s, 2H), 5.25 (d, 1H), 7.35 (m, 5H). $^{13}C$ NMR (CDCl$_3$, δ ppm): 14.27, 23.36, 25.21, 25.53, 26.09, 30.22, 32.15, 32.73, 33.90, 39.14, 52.21, 53.89, 58.04, 60.33, 66.89, 128.11, 128.35, 128.48, 136.29, 155.86, 166.30, 173.14, 177.69. IR (Neat, λ max, cm$^{-1}$): 3295, 2920, 1739, 1680. UV, 257 nm, abs 0.015. $[α]^{25}$=+39.8° (CHCl$_3$) at 365 nm.

Example X-12

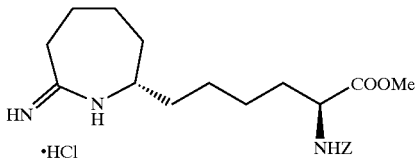

To 4.2 g (0.078 mol) of ammonium chloride in 500 mL methanol was added 31.2 g of the title material of Example X-11. The reaction was refluxed at 65° C. for 5 h before all solvent was removed under reduced pressure to yield 29 g (92%) of the crude product as a foamy viscous mass. This material was purified by column chromatography to provide 23 g (70%) of the title product.

Elemental analyses Calcd for $C_{21}H_{31}N_3O_4$·1HCl) C, 59.28; H, 7.57; N, 9.89; Cl, 8.39. Found (For $C_{21}H_{31}N_3O_4$+ 1HCl+1 $H_2O$): C, 56.73; H, 7.74; N, 9.40; Cl, 8.06. IR (Neat, λ max cm$^{-1}$): 3136, 30348, 2935, 1716, 1669. $^1H$ NMR (CDCl$_3$, δ ppm): 1.3–2.05 (m, 13H), 2.5 (t, 1H), 2.98 (m, 1H), 3.4 (bs, 1H), 3.75 (s, 3H), 4.35 (m, 1H), 5.1 (s, 2H), 5.5 (d, 1H), 7.35 (m, 5H), 8.75 (s,1H), 9.0 (s, 1H), 9.5 (s, 1H). $^{13}C$ NMR (CDCl$_3$, δ ppm): 23.25, 25.01, 25.34, 29.01, 31.88, 32.26, 33.89, 35.06, 52.33, 53.73, 56.20, 66.89, 127.95, 128.06, 128.45, 136.27, 155.93, 172.27, 172.80. UV, 257 nm, abs 0.009. Mass (ESI): M/Z, 390. $[α]^{25}$=−42.80 (MeOH) at 365 nm. ee=96% as determined by chiral HPLC.

Example X

The title product of Example X-12 (23 g) in 500 mL 2N HCl was refluxed for 5 h. All solvent was then removed in vacuo and the residue redissolved in water was washed with 2×300 mL of $CH_2Cl_2$. The aqueous was then concentrated in vacuo to give 17 g (100%) of the light brown hygroscopic solid title product.

Elemental analyses Calcd for $C_{12}H_{23}N_3O_2$·2HCl: C, 45.86; H, 8.02; N, 13.37; Cl, 22.56. Found for $C_{12}H_{23}N_3O_2$+ 2.1 HCl+0.7 $H_2O$: C, 43.94; H, 8.65; N, 12.52; Cl, 22.23IR (Neat, λ max, cm$^{-1}$): 2936, 1742, 1669. $^1H$ NMR (CD$_3$OD, δ ppm): 1.3–2.1 (m, 16H), 2.6 (dd, 1H), 2.8 (t, 1H), 3.65 (m, 1H), 4.0 (t, 1H), 7.85 (s, 1H), 8.4 (s, 1H), 8.95 (s, 1H). $^{13}C$ NMR (CD$_3$OD, δ ppm): 24.49, 25.67, 26.33, 29.71, 31.26, 32.45, 35.04, 35.87, 53.73, 57.21, 171.77, 173.96. UV, 209 nm, abs 0.343. Mass (M$^{+1}$)=242. $[α]^{25}$=+60.0° (MeOH) at 365 nm. ee=92% as determined by CE at λ=210 nm.

Example Y (αR,2S)-α-aminohexahydro-7-imino-1H-azepine-2-hexanoic acid, trihydrate hydrochloride

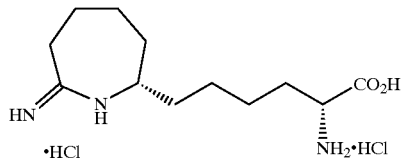

Example Y-1

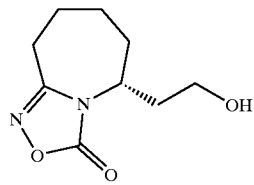

A solution of Example X-3 (3.0 g, 0.015 mol) in methylene chloride and methanol (75/45 mL) was cooled to −78° C. in a dry ice bath. The reaction stirred as ozone was bubble through the solution at a 3ml/min flow rate. When the solution stayed a consistent deep blue, the ozone was remove and the reaction was purged with nitrogen. To the cold solution was added sodium borohydride (2.14 g, 0.061 mol) very slowly to minimize the evolution of gas at one time. To the reaction was added glacial acetic acid slowly to bring the pH to 3. The reaction was then neutralized with saturated sodium bicarbonate. The oraganics were then washed 3×50 mL with brine, dried over magnesium sulfate anhydrous, removed under reduced pressure. The pale oil was run through a plug of silica (15 g) to afford the alcohol 5.15 g, 0.026 mol (64%). $C_9H_{14}N_2O_3$.

$^1H$ NMR (CDCl$_3$, δ ppm) 1.18–2.15(m, 8H), 3.59(m, 2H), 4.39(m, 1H). $^{13}C$ NMR (CDCl$_3$, δ ppm) 24.45, 25.71, 26.47, 32.56, 34.67, 51.16, 58.85, 160.66, 160.89.

Example Y-2

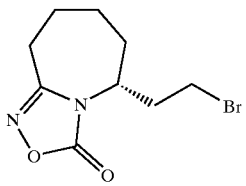

To a solution of Example Y-1 (5.15 g, 0.026 mol) in methylene chloride (100 mL) at 0° C. in an ice bath was added carbon tetrabromide(10.78 g, 0.033 mol). The solution was cooled to 0° C. in an ice bath. Then triphenylphosphine (10.23 g, 0.39 mol) was added portion wise as not to allow the temperature raise above 3° C. The reaction was stirred for 2 hours and the solvent was removed in vacuo. The crude was purified by flash chromatography to yield the bromide (5.9 g, 0.023 mol) in 87% yield.

Elemental analysis calculated for $C_{10}H_{16}N_2O_3$: C, 41.40; H, 5.02; N, 10.73; Br, 30.60. Found: C, 41.59; H, 5.07; N, 10.60, Br, 30.86. $^1$H NMR (CDCl$_3$, δ ppm) 1.50–2.60 (m, 9H), 2.99 (dd, 1H), 3.35 (m, 2H), 4.41 (m, 1H). $^{13}$C NMR (CDCl$_3$, δ ppm) 23.89, 25.33, 26.04, 28.06, 31.59, 35.05, 52.79, 159.3, 160.2.

Example Y-3

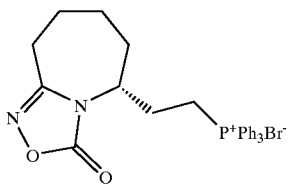

To a solution of Example Y-2 (5.71 g, 0.026 mol) in toluene (25 mL) was added triphenyl phosphine (7.17 g, 0.027 mol). The reaction refluxed in an oil bath for 16 hours. After cooling, the toluene was decanted from the glassy solid. The solid was triturated with diethyl ether overnight to afford the phosphonium bromide (10.21 g, 0.020 mol) in 90% yield.

$^1$H NMR (CDCl$_3$, δ ppm): 1.50–2.9 (m, 1H), 3.58 (m, 1H), 4.16 (m, 1H), 4.41 (m, 1H), 7.6–8.0 (m, 15H). $^{13}$CNMR(CDCl$_3$, δ ppm): 24.43, 24.97, 25.50, 55.08, 55.27, 116.9, 118.1, 130.4, 130.6, 133.5, 135.1, 135.2, 159.4, 160. $^{31}$P NMR (CDCl$_3$, δ ppm) 26.0.

Example Y-4

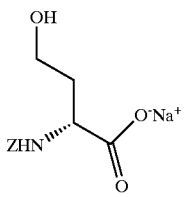

To a 1 L Round Bottom Flask was added N-benzyloxycarbonyl-D-homoserine lactone (97 g, 0.442 mol) in ethanol (500 mL). To the reaction was added solution of sodium hydroxide (1M, 50 mL). The reaction was monitored by thin layer chromatography for 12 hours until the starting material had been consumed. Toluene (60 mL) was added and then solvent was removed in vacuo. The residue was carried on with no further purification.

Example Y-5

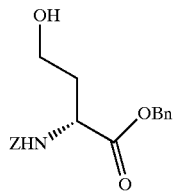

The residue from Example Y-4 was suspended in DMF in a 1 L Round Bottom Flask. To the suspension was added benzyl bromide (76.9 g, 0.45 mol, 53.5 mL) and the mixture was stirred for 1 hour. A sample was quenched and analyzed by mass spec to indicate the consumption of the starting material and that there was no lactone reformation. To the reaction was added 1 L of ethyl acetate and 500 mL of brine. The aqueous layer was washed 2 additional times with 500 mL of ethyl acetate. The organics were combined, dried over MgSO$_4$ and concentrated. Silica gel chromatography provided N-benzyloxycarbonyl-S-homoserine benzyl ester as a white solid (80 g).

Example Y-6

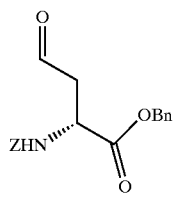

To a 2 L Round Bottom Flask was added pyridinium chlorochromate (187 g, 0.867 mol) and silica gel (197 g) suspended in CH$_2$Cl$_2$ (600 mL). To the slurry was added a solution of the product of Example Y-5 (80 g, 0.233 mol) in CH$_2$Cl$_2$ (600 mL). The mixture was stirred for 4 hours. Thin layer chromatography indicated that the starting material was consumed. To the reaction was added 1 L of diethyl ether. The solution was then filtered through a pad of ceilite followed by a pad of silica gel. The solvent was removed in vacuo and the resulting oil was purified by silica gel chromatography to afford the aldehyde (58.8 g) in 38% overall yield.

MH$^+$342.5, MH+NH$_4$$^+$359.5. $^1$H NMR (CDCl$_3$, δ ppm) 3.15 (q, 2H), 4.12 (m, 1H), 5.15 (s, 2H), 5.20 (s, 2H), 7.31 (m, 10H), 9.72 (s,1H).

Example Y-7

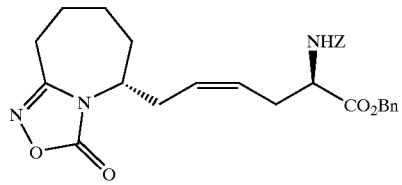

To a 3 L 3-neck flask was added the phosphonium salt from Example Y-3 (56.86 g, 0.11 mol) that had been dried over P$_2$O$_5$ under a vacuum in THF (1 L). The slurry was cooled to −78° C. in a dry-ice bath. To the cold slurry was added KHMDS (220 mL, 0.22 mol) dropwise so that the temperature did not rise above −72° C. The reaction was stirred at −78° C. for 20 minutes and then −45° C. for 2 hours. The temperature was then dropped back to −78° C. and the aldehyde (15.9 g, 0.047 mol) from Example Y-6 was added in THF (50 mL) dropwise over 45 minutes. The reaction was stirred at −77° C. for 30 minutes then warmed to −50° C. for 1 hour before it was warmed to room temperature over 4 hours. To the reaction was added ethyl acetate (200 mL) and saturated ammonium chloride. The organics were collected, dried over MgSO$_4$ and concentrated in vacuo. The crude oil was purified on silica chromatography to afford the olefin compound (45.1 g) in 81% yield as a pale yellow viscous oil.

$^1$H NMR (CDCl$_3$, δ ppm) 1.4–2.6 (m, 10H), 2.92(d, 1H), 4.17(m, 1H), 4.38(m, 1H), 5.05(q, 2H), 5.40(m, 2H), 7.3(m, 10H). $^{13}$C NMR (CDCl$_3$, δ ppm) 29.49, 29.64, 31.32, 39.60, 49.56, 53.98, 61.01, 65.25, 124.14, 127.81, 128.20, 128.55, 128.79, 129.30, 130.96, 135.68, 137.31, 152.59, 157.57, 171.61.

Example Y

To a 20 mL vial was added the product from Example Y-7 (19.77 g, 0.039 mol) in Dioxane (50 mL) and 4N aqueous HCl (250 mL). This solution was added a cat. amount of 10% Pd on carbon in a hydrogenation flask. The flask was pressurized with H$_2$ (50 psi) for five hours. The reaction was monitored by mass spec and the starting material had been consumed. The solution was filtered through a pad of celite and washed with water. The solvent was removed by lyophollization to afford the title compound (7.52 g) in 81% yield.

MH$^+$242.2, MH+NH$_4$$^+$259.2. $^1$H NMR (CD$_3$OD δ ppm) 1.2–2.0 (m, 15H), 2.42 (d, 1H), 2.65 (dd, 1H), 3.49 (m, 1H), 3.98 (t, 1H), 7.26 (s), 8.05 (s), 8.35 (s). $^{13}$C NMR (CDCl$_3$, δ ppm) 24.43, 25.58, 26.00, 26.10, 32.75, 33.45, 35.31, 53.76, 54.55, 157.27, 175.13.

Example Z (αS,2S)-α-aminohexahydro-7-imino-1H-azepine-2-hexanoic acid, trihydrate hydrochloride

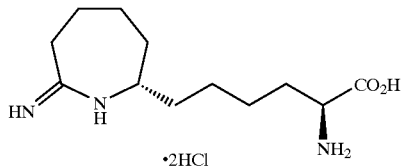

Example Z-1

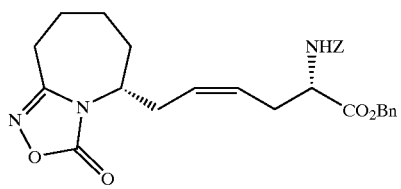

To a 1 L 3-neck flask was added the phosphonium salt from Example Y-3 (21.21 g, 0.041 mol) in THF (200 mL). The slurry was cooled to −78° C. in a dry-ice bath. To the cold slurry was added KHMDS (88 mL, 0.044 mol) dropwise so that the internal temperature did not rise above −72° C. The reaction stirred at −78° C. for 20 minutes then −45° C. for 1 hour. The temperature was then dropped back to −78° C. and the aldehyde (15.9 g, 0.047 mol) (prepared as in Example Y(4–6) using N-benzyloxycarbonyl-L-homoserine lactone) was added in THF (50 mL) dropwise over 45 minutes. The reaction was stirred at −77° C. for 30 minutes then warmed to −50° C. for 30 minutes then warmed to room temperature over 4 hours. To the reaction was added ethyl acetate (100 mL) and saturated ammonium chloride. The organics were collected, dried over MgSO$_4$ and concentrated in vacuo. The crude oil was purified on silica chromatography to afford the olefin compound (9.0 g) in 45% yield as a pale yellow viscous oil.

$^1$H NMR (CDCl$_3$, δ ppm) 1.4–2.6 (m, 10H), 2.92 (d, 1H), 4.17 (m, 1H), 4.38 (m, 1H), 5.05 (q, 2H), 5.40 (m, 2H), 7.3 (m,10H). $^{13}$C NMR (CDCl$_3$, δ ppm) 29.49, 29.64, 31.32, 39.60, 49.56, 53.98, 61.01, 65.25, 124.14, 127.81, 128.20, 128.55, 128.79, 129.30, 130.96, 135.68, 137.31, 152.59, 157.57, 171.71.

Example Z

To a 20 mL vial was added the product from Example Z-1 in dioxane (5 mL) and 4N aqueous HCl (16 mL). This solution was added a cat. amount of 10% Pd on carbon in a hydrogenation flask. The flask was pressurized with H$_2$ (50 psi) for five hours. The reaction was monitored by mass spec and the starting material had been consumed. The solution was filtered through a pad of ceilite and washed with water. The solvent was removed by lyophilization to afford the title compound (98.7 mg) in 79.4% yield.

MH$^+$242.2, MH+NH$_4$$^+$259.2. $^1$H NMR (CD$_3$OD, δ ppm) 1.2–2.0 (m, 15H), 2.42 (d, 1H), 2.6 (dd, 1H), 3.49 (m, 1H), 3.98 (t, 1H). $^{13}$C NMR (CDCl$_3$, δ ppm) 24.43, 25.58, 26.00, 26.10, 32.75, 33.45, 35.31, 53.76, 54.55, 157.27, 175.13.

Example AA (2S,4Z)-2-amino-6-[(2R)-hexahydro-7-imino-1H-azepin-2-yl]-4-hexenoic acid

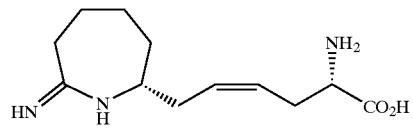

Example AA-1

(2S,4Z)-6-[(2R)-hexahydro-7-imino-1H-azepin-2-yl]-2-[[(phenylmethoxy)carbonyl]amino]-4-hexenoic acid, phenylmethyl ester

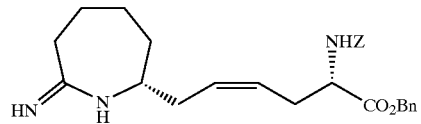

To a 50 mL flask was added a sample of Example Z-1 (1.5 g, 2.97 mmol) in methanol (25 mL). A 60% solution of glacial acetic acid (16 mL) was then added to the reaction mixture. A precipitate was observed. Additional methanol was added to dissolve the solid (1 mL). To the reaction was then added zinc dust (0.200 g). The reaction was sonicated for 4 hours during which the temperature was maintained at 37° C. The reaction was monitored by TLC and MS until the starting material was consumed and a mass corresponding to the product was observed. The solution was decanted from the zinc and a 30% solution of acetonitrile/water (100 mL) was added to the filtrate. The reaction was purified with 52% acetonitrile/water in two runs on the Waters Preparatory HPLC [a gradient of from 20% to 70% acetonitrile over 30 minutes]. Lyophilization of the resulting product afforded the title material of Example AA-1 (1.01 g) in 73% yield as a white solid.

$MH^+464.4$, $MH+Na^+486.4$. $^1H$ NMR ($CD_3OD$, δ ppm): 1.2–2.0 (m, 8H), 2.42 (m, 2H), 2.6 (m, 5H), 3.49 (q, 1H), 4.31 (t, 1H), 5.15 (s, 2H), 5.22 (s, 2H), 5.43 (q, 1H), 5.59(q, 1H), 7.25 (bs, 10H). $^{13}C$ NMR ($CDCl_3$, δ ppm): 24.37, 29.61, 30.76, 32.45, 33.73, 34.42, 55.40, 57.09, 68.06, 68.07, 122.3, 124.9, 128.76, 129.09, 129.28, 129.39, 129.51, 129.61, 155.71, 158.35, 173.90.

Example AA

To a 250 mL flask was added the product of Example AA-1 (1.0 g, 2.2 mmol) in 4 M HCl (100 mL). The reaction was refluxed overnight, monitored by MS until the starting material had been consumed and the mass for the product was observed. The reaction, without further work up was purified in two runs on the Water's prep reverse phase column using 18% acetonitrile/water [0% to 30% acetonitrile/water over 30 minutes]. Lyophilization of the combined fractions afforded the title product (0.34 g) in 64% yield as a cream colored foam.

$MH^+240.3$, $MH+Na^+486.4$. $^1H$ NMR ($CD_3OD$, δ ppm): 1.2–2.0 (m, 6H), 2.35 (m, 2H), 2.45 (dd, 2H), 2.69 (m, 2H), 3.61 (dt, 1H), 3.98 (t, 1H), 5.59(m, 1H), 5.65 (m, 1H). $^{13}C$ NMR ($CDCl_3$, δ ppm): 23.65, 24.66, 32.51, 32.84, 33.1, 33.25, 54.10, 56.1, 126.80, 129.33, 153.33, 172.52.

Example BB (2S,4E)-2-amino-6-[(2R)-hexahydro-7-imino-1H-azepin-2-yl]-4-hexenoic acid

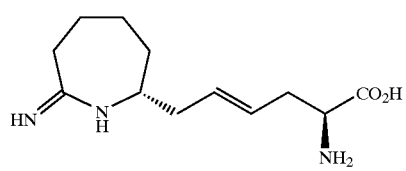

Example BB-1

(2S,4E)-2-[[(phenylmethoxy)carbonyl]amino]-6-[(5R)-6,7,8,9-tetrahydro-3-oxo-3H,5H-[1,2,4]oxadiazolo[4,3-a]azepin-5-yl]-4-hexenoic acid, phenylmethyl ester

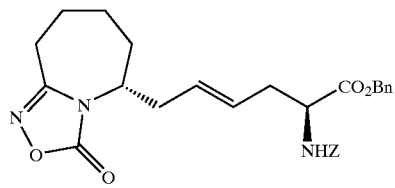

To a 250 mL flask was added Example Z-1 (2.0 g, 3.9 mmol) and phenyl disulfide (0.860 g, 3.9 mmol) in a cyclohexane (70 mL)/benzene(40 mL) solution. Nitrogen was bubbled through the solution to purge the system of oxygen. The reaction was exposed to a short wave UV lamp for the weekend. The reaction was evaluated by normal phase HPLC (ethyl acetate/hexane). 71% of the trans isomer and 29% of the cis isomer was observed. The reaction was subjected to an additional 3 days of UV upon which 84% of the starting material converted to the trans isomer and 16% of the starting cis isomer remained. Purification by chromatography afforded Example BB-1 (0.956 g) in 48% yield.

$MH^+506.1$, $MH+NH4^+523.2$. $^1H$ NMR ($CD_3OD$, δ ppm): 1.2–2.0 (m, 8H), 2.42–2.6 (m, 6H), 2.91 (dd, 1H), 4.19 (m, 1H), 4.31 (dt, 1H), 5.09 (s, 2H), 5.11 (s, 2H), 5.18 (dt, 1H), 5.27(m, 1H), 7.25 (bs, 10H).

Example BB-2

(2S,4E)-6-[(2R)-hexahydro-7-imino-1H-azepin-2-yl]-2-[[(phenylmethoxy)carbonyl]amino]-4-hexenoic acid, phenylmethyl ester, monohydrochloride

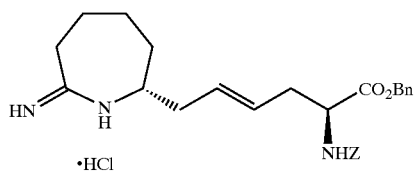

A sample of the product of Example BB-1 (0.956 g, 1.9 mmol) in MeOH (80 mL) was deprotected by method of Example AA-1 with Zn dust (1.5 g) and 60% $HOAc/H_2O$ (40 mL). The resulting product was purified by reverse phase chromatography to afford the title material (0.248 g) in 28% yield.

Example BB

The product of Example BB-2 (0.248 g, 0.53 mmol) was transformed into the title product by the method of Example AA using HCl (2 mL), $H_2O$ (2mL), $CH_3CN$ (4 mL). The crude product was purified by reverse phase chromatography to afford the title product of Example BB (0.073 g) in 57% yield.

$MH^+240.3$, $MH+Na^+486.4$. $^1H$ NMR ($CD_3OD$, δ ppm) 1.2–2.0 (m, 6H), 2.35 (t, 2H), 2.55–2.82 (m, 4H), 3.68 (dt, 1H), 4.05 (t, 1H), 5.65 (m, 2H).

Example CC (E)-2-amino-2-methyl-6-[(1-iminoethyl)amino]-4-hexenoic acid, dihydrochloride

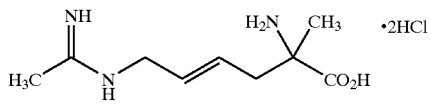

Example CC-1

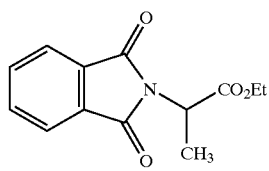

DL-Alanine ethyl ester hydrochloride (5 g, 32.5 mmol) was suspended in toluene (50 mL). Triethyl amine (4.5 mL, 32.5 mmol) was added followed by phthalic anhydride (4.8 g, 32.5 mL). The reaction flask was outfitted with a Dean-Stark trap and reflux condenser and the mixture was heated at reflux overnight. Approximately 10 mL of toluene/water was collected. The reaction mixture was cooled to room temperature and diluted with aqueous $NH_4Cl$ and EtOAc. The layers were separated and the aqueous layer was extracted with EtOAc (3×). The ethyl acetate extract was washed with brine, dried over $MgSO_4$, filtered and concentrated in vacuo to give the title phthalyl-protected amino ester as a white crystalline solid in near quantitative yield.

$^1$H NMR (400 MHz, $CDCl_3$, δ ppm): 1.2 (t, 3H), 1.6 (d, 3H), 4.2 (m, 2H), 4.9 (q, 1H), 7.7 (m, 2H), 7.9 (m, 2H)

Example CC-2

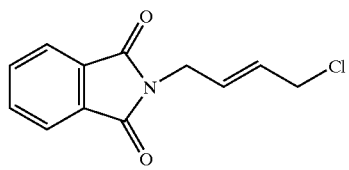

Potassium phthalimide (18.5 g, 0.1 mol) was added to a 250 mL round bottomed flask containing 1,4-butene dichloride (25 g, 0.2 mol). The reaction mixture was heated to 150° C. for 1.5 h. The mixture was cooled to room temperature and was partitioned between brine and $Et_2O$. The organic layer was dried with $MgSO_4$, filtered and concentrated in vacuo. The residue was recrystallized from hot ethanol to give the title 1-chloro-4-phthalimidobutene (8.9 g, 39%) as orange crystals.

HRMS calcd. For $C_{12}H_{10}ClNO_2$: m/z=236.0478 [M+H]. Found: 236.0449. $^1$H NMR (300 MHz, $CDCl_3$, δ ppm): 4.1 (d, 2H), 4.3 (d, 2H), 5.9 (m, 2H), 7.7 (m, 2H), 7.9 (m, 2H)

Example CC-3

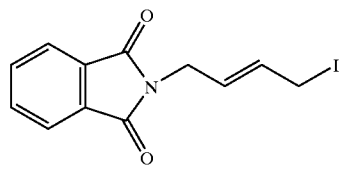

A sample of the product of Example CC-2 (2.3 g, 9.8 mmol) was dissolved in acetone (50 mL). NaI (3.2 g, 21 mmol) was added and the mixture was refluxed overnight. After cooling to room temperature, $Et_2O$ was added and the mixture was washed sequentially with sodium thiosulfate and brine. The organic layer was dried with $MgSO_4$, filtered and concentrated in vacuo to give the title iodide (2.8 g, 87.5%) as a light yellow solid that was used without further purification.

$^1$H NMR (400 MHz, $CDCl_3$, δ ppm): 3.8 (d, 2H), 4.2 (d, 2H), 5.7 (m, 1H), 6.0 (m, 1H), 7.7 (m, 2H), 7.9 (m, 2H) Mass (M+1)=328

Example CC-4

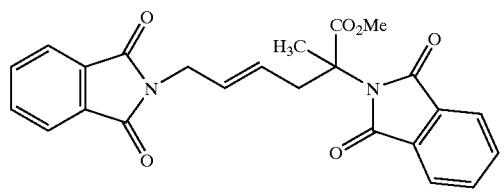

A solution of KHMDS (2.6 g, 13.3 mmol) in THF (50 mL) was cooled to −78° C. A solution of the product of Example CC-1 (2.2 g, 8.87 mmol) in THF (15 mL) was added and 1,3-dimethyl-3,4,5,6-tetrahydro-2(1H)-pyrimidinone (DMPU, 1.0 mL, 8.87 mL) was added immediately thereafter. After the solution was stirred at −78° C. for 40 minutes, a solution of the product of Example CC-3 (2.9 g, 8 87 mmol) in THF (15 mL) was added. The flask was removed from the cold bath and was stirred at room temperature for 3 h. The reaction mixture was partitioned between saturated aqueous $NaHCO_3$ and EtOAc. The organic extract was washed with brine, dried over $MgSO_4$, filtered and concentrated in vacuo to give the desired bis-pththalyl protected amino ester as a yellow solid. This residue was chromatographed on silica gel (1:1 hexanes:EtOAc) and gave 1.4 g (35%) of the title material as a white solid.

$^1$H NMR (300 MHz, $CDCl_3$, δ ppm): 1.2 (t, 3H), 1.6 (d, 3H), 2.8 (dd, 1H), 3.1 (dd, 1H), 4.2 (m, 4H), 5.6 (m, 1H), 5.8 (m, 1H), 7.6 (m, 4H), 7.7 (m, 2H), 7.9 (m, 2H) Mass (M+H)=447

Example CC-5

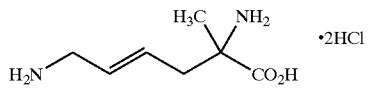

The product of Example CC-4 (0.78 g, 1.76 mmol) was dissolved in a mixture of formic acid (10 mL, 95%) and HCl (20 mL, concentrated HCl) and was refluxed for 3 days. The reaction mixture was cooled to 0° C. and filtered to remove phthalic anhydride. After concentrating in vacuo (T<40° C.), the title unsaturated alpha methyl lysine was obtained as a white solid (0.38 g, 95%), which was used without further purification.

$^1$H NMR (300 MHz, D$_2$O, δ ppm): 1.4 (s, 3H), 2.4 (dd, 1H), 2.6 (dd, 1H), 3.5 (d, 2H), 5.7 (m, 2H) Mass(M+H)=317

Example CC

The product of Example CC-5 (0.2 g, 0.86 mmol) was dissolved in H$_2$O (8 mL) and was brought to pH 9 with 2.5 N NaOH. Ethyl acetimidate—HCl (0.42 g, 3.4 mmol) was added in four portions over 1 h. After 1 h, the mixture was acidified to pH 4 with 10% HCl and was concentrated in vacuo. The residue was then passed through a water-washed DOWEX 50WX4-200 column (H form, 0.5 N NH$_4$OH eluent). The residue was concentrated in vacuo, acidified to pH 4 with 10% HCl, and concentrated to give the title product (17 mg, 6%) as an oil.

HRMS calcd. For C$_9$H$_{17}$N$_3$O$_2$: m/z=200.1399 [M+H]. Found: 200.1417. $^1$H NMR (400 MHz, D$_2$O, δ ppm): 1.4 (s, 3H), 2.1 (s, 3H), 2.5 (dd, 1H), 2.6 (dd, 1H), 3.8 (d, 2H), 5.6 (m, 2H)

Example DD (R,E)-2-amino-2-methyl-6-[(1-iminoethyl)amino]-4-hexenoic acid, dihydrochloride

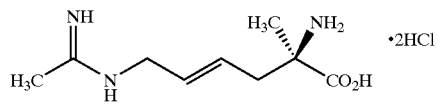

Example DD-1

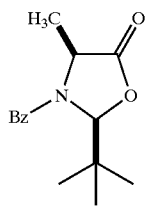

(2S,4S)-3-Benzoyl-2-(tert-butyl)-4-methyl-1,3-oxazolidin-5-one was prepared according to Seebach's procedure. Seebach, D.; Fadel, A. Helvetica Chimica Acta 1985, 68, 1243.

Example DD-2

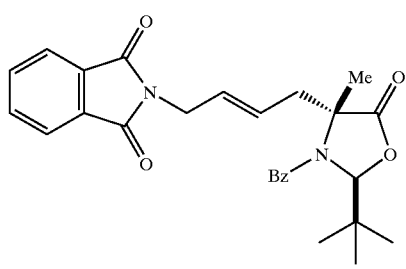

A solution of KHMDS (0.65 g, 3.24 mmol), DMPU (0.33 mL, 2.7 mmol) and THF (40 mL) was cooled to −78° C. A solution of (2S,4S)-3-benzoyl-2-(tert-butyl)-4-methyl-1,3-oxazolidin-5-one (Example DD-1) (0.70 g, 2.7 mmol) in THF (10 mL) was added dropwise. After 45 min, a solution of the product of Example CC-3 (0.88 g, 2.7 mmol) in THF (10 mL) was added. The reaction mixture was stirred at room temperature for 2 h and quenched with saturated aqueous NaHCO$_3$. The layers were separated and the aqueous layer was extracted with EtOAc. The organic layers were combined and washed with brine, dried over MgSO$_4$, filtered and concentrated in vacuo. The resulting yellow oil was chromatographed on silica gel (9:1 then 4:1 hexanes/ethyl acetate) to give the title protected unsaturated alpha methyl D-lysine (0.26 g, 20%) as a colorless oil.

HRMS calcd. For C$_{27}$H$_{28}$N$_2$O$_5$: m/z=461.2076[M+H]. Found: 461.2033. $^1$H NMR (400 MHz, CDCl$_3$, δ ppm): 0.9 (s, 9H), 1.5 (s, 3H), 4.3 (m, 2H), 5.5 (m, 2H), 5.6 (m, 2H), 6.1 (m, 1H), 7.5 (m, 5H), 7.7 (m, 2H), 7.9 (m, 2H)

Example DD-3

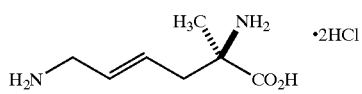

The product of Example DD-2 (0.255 mg, 0.55 mmol) was dissolved in 6N HCl (6 mL) and formic acid (6 mL) and was heated to reflux for 24 h. The reaction mixture was cooled to room temperature and concentrated in vacuo. The residue was suspended in water and washed with CH$_2$Cl$_2$. The aqueous layer was concentrated and passed through a water-washed DOWEX 50WX4-200 column (H form, 0.5 N NH$_4$OH eluent). The residue was concentrated in vacuo, acidified to pH 4 with 10% HCl, and concentrated to give the title unsaturated D-lysine (71 mg, 55%) as an oil which was used without further purification.

$^1$H NMR (400 MHz, D$_2$O, δ ppm): 1.4 (s, 3H), 2.5 (dd, 1H), 2.6 (dd, 1H), 3.4 (d, 2H), 5.6 (m, 2H), 5.7 (m, 2H)

Example DD

The product of Example DD-3 (13 mg, 0.056 mmol) was dissolved in H$_2$O (5 mL) and was brought to pH 9 with 2.5 N NaOH. Ethyl acetimidate—HCl (27 mg, 0.2 mmol) was added in four portions over 2 h. After 2 h, the mixture was acidified to pH 4 with 10% HCl and was concentrated in vacuo. The residue was passed through a water-washed DOWEX 50WX4-200 column (H form, 0.5 N NH$_4$OH eluent). The residue was concentrated in vacuo, acidified to pH 4 with 10% HCl, and concentrated to give the title product (45 mg) as an oil.

HRMS calcd. For C$_9$H$_{17}$N$_3$O$_2$: m/z=200.1399 [M+H]. Found: 200.1386. $^1$H NMR (400 MHz, D$_2$O, δ ppm): 1.4 (s, 3H), 2.1 (s, 3H), 2.5 (dd, 1H), 2.6 (dd, 1H), 3.8 (d, 2H), 5.6 (m, 2H)

Example E (S,E)-2-amino-2-methyl-6-[(1-iminoethyl)amino]-4-hexenoic acid, dihydrochloride

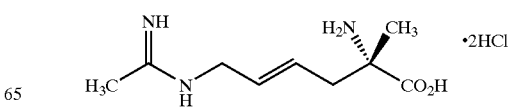

Example EE-1

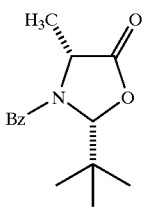

(2R, 4R)-3-Benzoyl-2-(tert-butyl)-4-methyl-1,3-oxazolidin-5-one was prepared according to Seebach's procedure. Seebach, D.; Fadel, A. Helvetica Chimica Acta 1985, 68, 1243.

Example EE-2

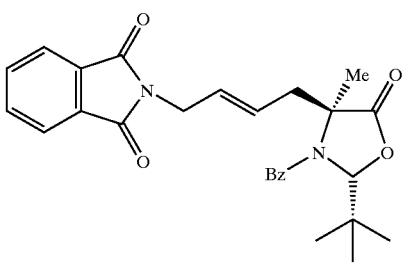

A solution of the (2R, 4R)-3-benzoyl-2-(tert-butyl)-4-methyl-1,3-oxazolidin-5-one product of Example EE-1 (2.0 g, 7.6 mmol) in THF (50 mL) was cooled to −78° C. A −78° C. solution of KHMDS (0.65 g, 3.24 mmol) in THF (25 mL) was added dropwise. After 30 min, a solution of the product of Example CC-3 (2.8 g, 8.6 mmol) in THF (25 mL) was added. The reaction mixture was stirred at room temperature for 1 h and quenched with saturated aqueous NaHCO$_3$. The layers were separated and the aqueous layer was extracted with EtOAc. The organic layers were combined and washed with brine, dried with MgSO$_4$, filtered and concentrated in vacuo. The resulting orange oil was chromatographed on silica gel (9:1 then 4:1 hexanes/ethyl acetate) to give the protected title unsaturated alpha methyl L-lysine (0.5 g, 15%) as a white solid.

HRMS calcd. For C$_{27}$H$_{28}$N$_2$O$_5$: m/z=461.2076[M+H]. Found: 461.2043. $^1$H NMR (400 MHz, CDCl$_3$, δ ppm): 0.9 (s, 9H), 1.5 (s, 3H), 4.3 (m, 2H), 5.5 (m, 2H), 5.6 (m, 2H), 6.1 (m, 1H), 7.5 (m, 5H), 7.7 (m, 2H), 7.9 (m, 2H)

Example EE-3

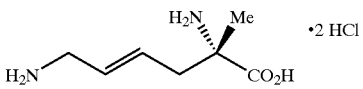

The product of Example EE-2 (0.5 g, 1 mmol) was dissolved in 12N HCl (10 mL) and formic acid (5 mL) and this mixture was heated to reflux for 12 h. The reaction mixture was cooled in the freezer for 3 h and the solids were removed by filtration. The residue was washed with CH$_2$Cl$_2$ and EtOAc. The aqueous layer was concentrated in vacuo and gave the title unsaturated alpha methyl L-lysine (0.26 g, 99%) as an oil which was used without further purification.

$^1$H NMR (300 MHz, D$_2$O, δ ppm): 1.4 (s, 3H), 2.5 (dd, 1H), 2.6 (dd, 1H), 3.4 (d, 2H), 5.7 (m, 2H)

Example EE

The product of Example EE-3 (0.13 g, 0.56 mmol) was dissolved in H$_2$O (1 mL) and was brought to pH 9 with 2.5 N NaOH. Ethyl acetimidate—HCl (0.28 g, 2.2 mmol) was added in four portions over 1 h. After 1 h, the mixture was acidified to pH 4 with 10% HCl and was concentrated in vacuo. The residue was and passed through a water-washed DOWEX 50WX4-200 column (0.5 N NH$_4$OH eluent). The residue was concentrated in vacuo, acidified to pH 4 with 10% HCl, and concentrated to give the title product as an oil (40 mg).

HRMS calcd. For C$_9$H$_{17}$N$_3$O$_2$: m/z=222.1218 [M+Na]. Found: 222.1213. $^1$H NMR (300 MHz, D$_2$O, δ ppm): 1.4 (s, 3H), 2.1 (s, 3H), 2.4 (dd, 1H), 2.6 (dd, 1H), 3.8 (d, 2H), 5.6 (m, 2H)

Example FF 2-amino-2-methyl-6-[(1-iminoethyl)amino]-4-hexynoic acid, dihydrochloride

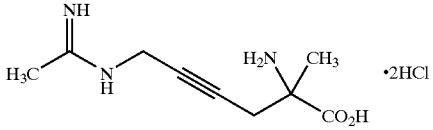

Example FF-1

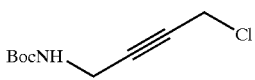

The N-boc-1-amino-4-chlorobut-2-yne was prepared following the procedure described in Tetrahedron Lett. 21, 4263 (1980).

Example FF-2

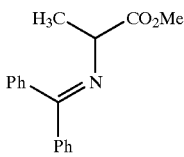

Methyl N-(diphenylmethylene)-L-alaninate was prepared by following the procedure described in J. Org. Chem., 47, 2663 (1982).

Example FF-3

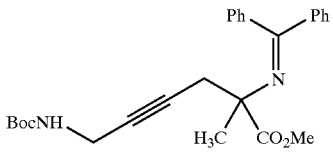

Dry THF (1000 mL) was placed in a flask purged with argon and 60% NaH dispersed in mineral oil (9.04 g, 0.227 mol) was added. To this mixture was added the product of Example FF-2 (30.7 g, 0.114 mol). The reaction mixture was then stirred at 10° C.–15° C. for 30 min. Potassium iodide (4 g) and iodine (2 g) were added and immediately followed by the addition of the product of Example FF-2 (23 g, 0.113 mol in 200 mL THF) in 30 min. The reaction mixture was then stirred at 55° C. until the starting material disappeared (~2 h). The reaction mixture was then cooled to room temperature and the solvent was evaporated. Ethyl acetate (500 mL) was added and the mixture was carefully washed with 2×200 mL deionized water. The organic layer was dried over anhydrous MgSO$_4$, filtered and evaporated to give 44 g of crude product. Purification by chromatography using 20% ethyl acetate in hexane afforded the title protected unsaturated alpha-methyl lysine (28 g, 57%).

Anal.Calcd for $C_{26}H_{30}N_2O_4$ and 0.5 ethylacetate: C,70.42; H, 7.14; N, 5.91. Found: C, 70.95; H, 7.73; N, 6.09. IR (Neat, λ max, cm$^{-1}$): 2981, 1714, 1631 $^1$H NMR (CDCl$_3$, δ ppm): 1.28 (s, 9H), 1.4 (s, 3H), 2.65–2.76(m, 2H), 3.15 (s, 3H), 3.7 (bs, 2H), 4.6 (bs, 1H), 6.95–7.4 (m, 10H) $^{13}$C NMR (CDCl$_3$, δ ppm): 24.29, 28.33, 28.39, 33.24, 51.60, 53.55, 127.79, 127.97, 128.26, 128.36, 128.43, 128.54, 128.66, 130.05, 130.22, 132.39 Mass (M+1)=435 DSC purity: 261.95° C.

Example FF-4

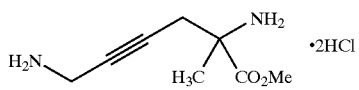

The product of Example FF-3 (16 g, 0.0368 mol) was dissolved in 1N HCl (300 mL) and stirred at 25° C. for 2 h. The reaction mixture was washed with ether (2×150 mL) and the aqueous layer separated and decolorized with charcoal. Concentration afforded ~9 g (100% yield) of the deprotected unsaturated alpha-methyl lysine ester FF-4 as white foamy solid.

Anal.Calcd for $C_8H_{14}N_2O_2$ containing 2.26 HCl and 1.19 H$_2$O: C, 35.06; H, 6.86; N, 10.22; Cl, 29.24. Found: C, 35.31; H, 7.38; N, 10.70; Cl, 29.77. $^1$H NMR (D$_2$O, δ ppm): 1.56 (s, 3H), 2.8–3.0 (2 dt, 2H), 3.75(s, 2H), 3.79 (s, 3H), $^{13}$C NMR (D$_2$O, δ ppm): 23.89, 29.81, 32.05, 57.08, 61.90, 79.57, 82.43, 173.92 Mass (M+1)=171 DSC purity: 114.22° C. UV=206 nm,abs 0.013 [a]$_{25}$ in methanol=0 at 365 nm Example FF-5

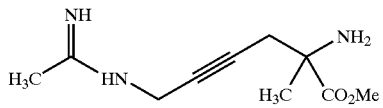

The product of Example FF-4 (2.43 g, 0.01 mol) was dissolved in deionized water (25 mL). A solution of NaOH (400 mg, 0.01 mol) in deionized water (25 mL) was added at 25° C. to bring the pH to ~7.95 and stirring was continued another 10 min. Ethylacetimidate hydrochloride (988 mg, 0.008 mol) was added to the reaction mixture with simultaneous adjustment of the pH to ~8.5 by adding 1N NaOH. The reaction mixture was stirred at pH 8 to 8.5 for 3 h following acetimidate addition. 1N HCl was added to the reaction mixture (4.1 pH). The solvent was evaporated at 50° C. to afford a yellow crude hygroscopic residue (4 g, >100% yield). Purification was carried out on the Gilson chromatography system using 0.1% AcOH/CH$_3$CN/H$_2$O.

Anal.Calcd for $C_{10}H_{17}N_3O_2$ containing 2.25 HCl and 1.7 H$_2$O: C, 37.08; H, 7.05; N, 12.97; Cl, 24.63. Found: C, 37.01; H, 6.79; N, 12.76; Cl, 24.87. IR (Neat, λ max, cm$^{-1}$): 2953, 2569, 1747, 1681, 1631 $^1$H NMR (D$_2$O, δ ppm): 1.52 (s, 3H), 2.12 (s, 3H), 2.74–2.96 (2 dt, 2H), 3.75 (s, 3H), 3.95 (t, 2H) $^{13}$C NMR (D$_2$O, δ ppm): 23.89, 29.81, 32.05, 57.08, 61.90, 79.57, 82.43, 173.92 Mass (M+1)=212

Example FF

The product of Example FF-5 (100 mg, 0.0005 mol) was dissolved in 8N HCl (20 mL) and stirred for 10 h at reflux. The reaction mixture was cooled to room temperature and the aq. HCl was evaporated on rotavap. The residue was dissolved in deionized water (10 mL) and water and reconcentrated under vacuum to afford the title product as a yellow glassy solid in almost quantitative yield (88 mg).

Anal.Calcd for $C_9H_{15}N_3O_2$ containing 2.4 HCl and 1.8 H$_2$O: C, 34.08; H, 6.67; N, 13.25; Cl, 26.83. Found: C, 34.32; H, 6.75; N, 13.63; Cl, 26.47. IR (Neat, λ max, cm$^{-1}$): 1738, 1677, 1628, 1587 $^1$H NMR (D$_2$O, δ ppm): 1.6 (s, 3H), 2.24 (s, 3H), 2.8–3.0 (2 dt, 2H), 4.1 (s, 2H) $^{13}$C NMR (D$_2$O, δ ppm): 21.22, 24.10, 29.88, 34.58, 80.04, 80.99, 128.39, 168.07, 176.13 Mass (M+1)=198

Example GG

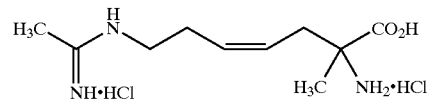

(2R/S,4Z)-2-amino-2-methyl-7-[(1-iminoethyl) amino]-4-heptenoic acid, dihydrochloride

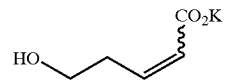

Example GG-1

5,6 dihydropyran-2-one (49.05 g, 0.5 mol) was dissolved in 200 mL of water. Potassium hydroxide (35 g, 0.625 mol) was added and the reaction mixture stirred at ambient temperature for 5 hours. The solvent was removed in vacuo to yield a colorless glassy solid (65 g, 84%) that was characterized by NMR to be predominantly the cis isomer of the title compound.

$^1$H NMR (CDCl$_3$) δ: 2.7 (m, 2H), 3.6 (t, 2H), 5.8–5.85(m, 1H), 5.9–5.97 (m, 1H).

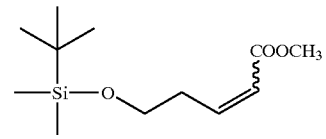

Example GG-2

The product of Example GG-1 was dissolved in 100 mL of dimethyl formamide. Methyl Iodide (52 mL, 0.84 mol) was then added resulting in an exotherm to 40° C. The reaction mixture was stirred at room temperature for 10 hours and partitioned between 150 mL of ethylacetate/ diethylether in a 20/80 ratio and ice water. The aqueous layer was separated and re-extracted with 100 mL of diethyl ether.

The organic layers were combined, dried (Na₂SO₄), filtered and stripped of all solvent to yield the desired methyl ester product (40 g, 71%). This material was dissolved in 200 mL of methylene chloride and the solution cooled to 0° C. Tertiarybutyl dimethylsilylchloride, triethylamine and dimethylaminopyridine were added. The reaction mixture was slowly warmed to room temperature and stirred for 10 hours under nitrogen. The reaction was extracted with 100 mL of 1N aqueous potassium bisulfate solution. The organic layer was washed with 2×100 mL of brine and then with 3×150 mL of water. The organic layer was dried (Na₂SO₄), filtered and stripped to yield 42 g (56%) of the title material.

¹H NMR (CDCl₃) 67 : 0.02 (s, 6H), 0.085 (s, 9H), 2.8–2.85 (m, 2H), 3.65 (s, 3H), 3.66–3.7 (m, 2H), 5.8 (m, 1H), 6.3 (m, 1H)

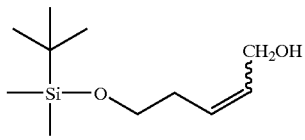

Example GG-3

The material from Example GG-2 was dissolved in 25 mL of toluene and cooled to 0° C. Diisobutylaluminum hydride (1.0 M in toluene, 32 mL, 48 mmol) was added dropwise maintaining the temperature between 5 and −10° C. The reaction mixture was stirred for 1.5 hours between 6 and −8° C. before it was cooled to −25° C. To this mixture was added 100 mL of 0.5N sodium potassium tartarate. The reaction mixture was allowed to warm up to room temperature and stir for an hour. A gelatinous precipitate was formed which was filtered. The aqueous was extracted with 2×100 mL EtOAc. The combined organic layers were dried (sodium sulfate), filtered and concentrated in vacuo to yield title product (3.45 g, 66%) as a colorless oil.

¹H NMR (CDCl₃) 67 : 0.02 (s, 6H), 0.085 (s, 9H), 2.25–2.32 (m, 2H), 2.6 (bs, 1H), 3.6 (t, 2H), 4.08 (d, 2H), 5.45–5.55 (m, 1H), 5.7–5.75 (m, 1H)

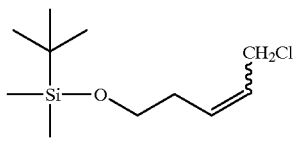

Example GG-4

The product (8 g, 37 mmol) from Example GG-3 was dissolved in 100 mL methylene chloride and this solution was cooled to 0° C. Methanesulfonyl chloride was then added and this mixture was stirred for 5 min. Triethylamine was then added. The temperature maintained between 0 and −10° C. during the addition of the aforementioned reagents. The reaction mixture was subsequently warmed up to room temperature and stirred for 24 hours. It was then extracted with 100 mL of 50% aqueous sodium bicarbonate solution. The organic layer was washed with 100 mL of saturated aqueous brine solution, dried (sodium sulfate), filtered and stripped in vacuo to yield the title material (8.2 g, 94%).

¹H NMR (CDCl₃) 67 : 0.02 (s, 6H), 0.085 (s, 9H), 2.25–2.32 (m, 2H), 3.6 (t, 2H), 4.08 (d, 2), 5.6–5.7 (m, 2H)

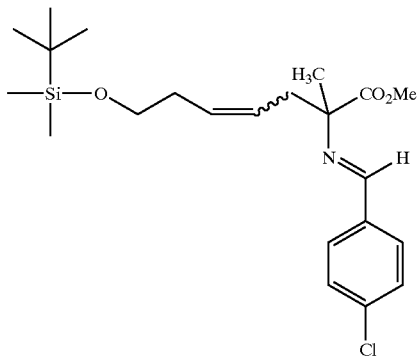

Example GG-5

A solution of N-p-chloro phenylimine alanine methyl ester (8.85 g, 34 mmol) dissolved in 59 mL of tetrahydrofuran was purged with Argon. NaH (1.64 g, 41 mmol) was added whereupon the solution turned bright orange and subsequently a deep red. A solution of the title material from Example GG-4 (8 g, 34 mmol) in 40 mL of tetrahydrofuran was added to the above anionic solution. An exotherm was observed raising the temperature to almost 40° C. The reaction mixture was maintained between 48 and −52° C. for 2 hours. It was then cooled to room temperature and filtered. Filtrate was stripped in vacuo to yield the title material (8.4 g, 50% crude yield) as a yellow oil.

¹H NMR (CDCl₃) 67 : 0.02 (s, 6H), 0.085 (s, 9H), 1.45 (s, 3H), 1.6 (s, 1H), 2.2–2.25(m, 2H), 2.65 (d, 2H), 3.55 (m, 2H), 3.7 (s, 3H), 5.45–5.55 (m, 2H), 7.35–7.7 (m, 4H)

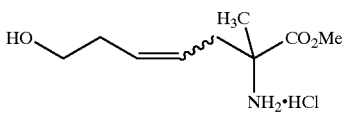

Example GG-6

The title material from Example GG-5 (8.4 g, 18.2 mmol) was treated with 125 mL 1N hydrochloric acid and the reaction was stirred for an hour at room temperature. After the reaction mixture had been extracted 2×75 mL of ethylacetate the aqueous layer was stripped in vacuo at 56° C. to yield 4 g of the title material (100% crude yield).

¹H NMR (CD₃OD) 67 : 1.6 (s, 3H), 2.3–2.4 (m, 2H), 2.65–2.8 (m, 2H), 3.6–3.65 (m, 2H), 3.87 (s, 3H), 5.4–5.5 (m, 1H), 5.75–5.85 (m, 1H)

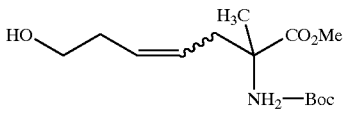

Example GG-7

The title product of Example GG-6 (1.9 g, 8.5 mmol) was dissolved in a mixture of 15 mL dioxane and 8 mL of water. Solid potassium bicarbonate was then carefully added to avoid foaming. The reaction mixture was stirred for 10 min before tertiarybutyloxycarbonyl anhydride was added portionwise and reaction mixture was stirred at ambient temperature for 24 hours. The reaction mixture was diluted with 100 mL of ethylacetate and 50 mL of water before it was poured into a separatory funnel. The organic layer was separated, dried (Na$_2$SO$_4$), filtered and stripped to yield the title material as a colorless oil (1.9 g, 78% crude yield).

$^1$H NMR (CDCl$_3$) 67 : 1.42 (s, 9H), 1.55 (s, 3H), 2.3–2.36 (m, 2H), 2.58–2.65 (m, 2H), 3.65–3.7 (t, 2H), 3.75 (s, 3H), 5.42–5.5 (m, 1H), 5.55–5.62 (m, 1H)

Example GG-8

Another 1.9 g sample of the title material from Example GG-6 was converted by the methods of Example GG-7 to the crude Z/E mixture of the title product of Example GG-7. This material further purified on silica with a solvent system of ethylacetate/hexane in a 20/80 ratio to obtain the minor E-isomer as well as the major Z-isomer.

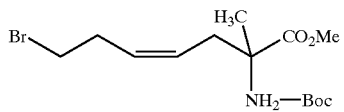

Example GG-9

The title Z-isomer from Example GG-8 (1.8 g, 6.25 mmol) was dissolved in 20 mL of acetonitrile and this solution was cooled to 0° C. Pyridine (0.76 g,9.4mmol) was then added followed by the portion-wise addition of solid dibromotriphenylphosphorane (3.46 g, 8.2 mmol) over 10 min. The reaction mixture was stirred under Argon for 24 hours at room temperature. The precipitate that formed was filtered off. The filtrate was concentrated in vacuo to give 2.8 g of an oil that was purified on silica gel using a solvent system of ethylacetate/hexane in a 60/40 ratio. The 1.1 g of title material (50%) was characterized by NMR.

$^1$H NMR (CDCl$_3$) δ: 1.44 (s, 9H), 1.55 (s, 3H), 2.6–2.65 (m, 4H), 3.35–3.4 (m, 2H), 3.75 (s, 3H), 5.4–5.45 (m, 1H), 5.55–5.6 (m, 1H)

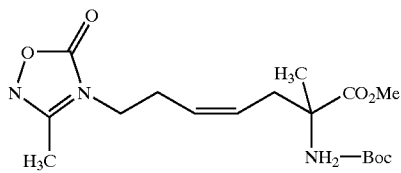

Example GG-10

The title material from Example GG-8 (300 mg, 0.86 mmol) was dissolved in 25 mL of dimethylformamide (DMF). The potassium salt of 3-methyl-1,2,4-oxadiazolin-5-one (130 mg, 0.94 mmol) was added and the reaction mixture was heated to 52° C. and maintained there for 18 hours with stirring. It was then cooled to room temperature before the DMF was stripped in vacuo at 60° C. The residue was purified on silica gel with a gradient of 60/40 to 90/10 ethyl acetate/hexane to yield 300 mg (95%) of the title material.

$^1$H NMR (CD$_3$OD) δ: 1.35 (s, 3H), 1.43 (s, 9H), 2.32 (s, 3H), 2.45–2.55 (m, 4H), 3.65–3.7 (m, 2H), 3.72 (t, 3H), 5.5–5.6 (m, 2H)

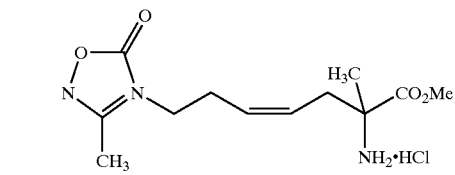

Example GG-11

The product of Example GG-10 (300 mg) was treated with 0.05 N of aqueous HCl and this solution was stirred for 30 min. The solvent was removed in vacuo to afford the desired material in nearly quantitative yield.

$^1$H NMR (CD$_3$OD) δ: 1.6 (s, 3H), 2.25 (s, 3H), 2.45–2.55 (m, 2H), 2.7–2.8 (m, 2H), 3.3–3.4 (m, 5H), 5.5–5.6 (m, 1H), 5.7–5.8 (m, 1H)

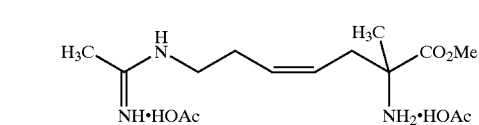

Example GG-12

The title material from Example GG-11 (198 mg, 0.54 mmol) was dissolved in 50 mL of MeOH. Formic acid (40 mg) was then added followed by Palladium on Calcium carbonate (400 mg). The reaction mixture was heated to 65° C. with stirring in a sealed tube for 24 hours. It was then cooled to room temperature and filtered. The filtrate was concentrated in vacuo and the residue purified by reverse phase HPLC to yield 115 mg (75%) of the title material.

$^1$H NMR (CD$_3$OD) δ: 1.4 (s, 3H), 1.95 (s, 3H), 2.25 (s, 3H), 2.4–2.52 (m, 4H), 3.25–3.35 (m, 2H), 3.75 (t, 3H), 5.54–5.62 (m, 2H)

Example GG

The title material (75 mg) from Example GG-12 was dissolved in 15 mL of 2N hydrochloric acid. The reaction mixture was heated to a reflux and stirred for 6 hours before ot was cooled to room temperature. The solvent was removed in vacuo. The residue was dissolved in 25 mL of water and stripped on the rotary evaporator to remove excess hydrochloric acid. The residue was dissolved in water and lyophilized to give 76 mg (~100%) of the title material.

Elemental analyses Calcd for C$_{10}$H$_{19}$N$_3$O$_2$+2.2HCl+2.2 H$_2$O: C, 36.06; H, 7.75; N, 12.61. Found for C$_{10}$H$_{19}$N$_3$O$_2$+2.2HCl+2.2 H$_2$O: C, 35.91; H, 7.61; N, 12.31

$^1$H NMR (CD$_3$OD) δ: 1.47 (s, 3H), 2.32 (s, 3H), 2.45–2.64 (m, 4H), 2.58–2.65 (m, 2H), 3.65–3.7 (t, 2H), 5.55–5.65 (m, 2H)

Example HH

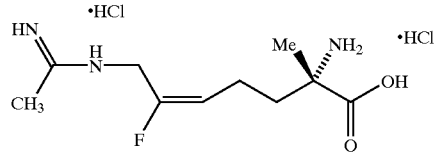

(2S,5E)-2-amino-2-methyl-6-fluoro-7-[(1-iminoethyl)amino]-5-heptenoic acid, dihydrochloride

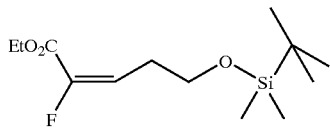

Example-HH-1

To a cold (−78° C.) solution of triethyl 2-fluorophosphonoacetate (25.4 g, 105 mmol) in 100 mL of THF was added n-butyl lithium (63 mL of 1.6 M in hexane, 101 mmol). This mixture was stirred at −78° C. for 20 min producing a bright yellow solution. A solution of crude 3-[(tert-butyldimethylsilyl)oxy]propanal (*J. Org. Chem.*, 1994, 59, 1139–1148) (20.0 g, 105 mmol) in 120 mL of THF was then added dropwise over ten minutes, and the resulting mixture was stirred for 1.5 h at −78° C., at which time analysis by thin layer chromatography (5% ethyl acetate in hexane) showed that no starting material remained. The reaction was quenched at −78° C. with sat. aqueous NH$_4$Cl (150 mL). The organic layer was collected, and the aqueous layer was extracted with diethyl ether (300 mL). The combined organics were washed with brine (200 mL), dried over MgSO$_4$, filtered and concentrated. The crude material was filtered through a plug of silica gel (150 g) eluting with hexane (2 L) to give 14.38 g (52%) of the desired (2E)-5-[[(1,1-dimethylethyl)di-methylsilyl]oxy]-2-fluoro-2-pentenoic acid ethyl ester product as a clear oil. $^1$H NMR and $^{19}$F NMR indicated that the isolated product had an approximate E:Z ratio of 95:5.

HRMS calcd. for C$_{13}$H$_{26}$FO$_3$Si: m/z=277.1635 [M+H]$^+$, found: 277.1645. $^1$H NMR (CDCl$_3$) δ 0.06 (s, 6H), 0.94 (s, 9H), 1.38 (t, 3H), 2.74 (m, 2H), 3.70 (m, 2H), 431 (q, 2H), 6.0 (dt, vinyl, 1H). $^{19}$F NMR (CDCl$_3$) δ −129.78 (d, 0.05 F,J=35 Hz, 5% Z-isomer), −121.65 (d, 0.95 F,J=23 Hz, 95% E-isomer).

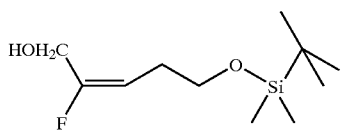

Example-HH-2

To a solution of Example-HH-1 (6.76 g, 24.5 mmol) in 100 mL of methanol at room temperature was added solid NaBH$_4$ (4.2 g, 220 mmol) in 1.4 g portions over three hours. After 3.5 hours water was added (10 mL). Additional solid NaBH$_4$ (4.2 g, 220 mmol) was added in 1.4 g portions over three hours. The reaction was quenched with 150 mL of sat. aqueous NH$_4$Cl and extracted with diethyl ether (2×250 mL). The organic layers were combined, dried over MgSO$_4$, filtered and concentrated. The crude material, 4.81 g of clear oil, was purified by flash column chromatography on silica gel eluting with 10% ethyl acetate in hexane to give 2.39 g (42%) of the desired (2E)-5-[[(1,1-dimethylethyl)dimethylsilyl]oxy]-2-fluoro-2-penten-1-ol product as a clear oil, that contained an approximate E:Z ratio of 93:7 by $^{19}$F NMR.

HRMS calcd. for C$_{11}$H$_{24}$FO$_2$Si: m/z=235.1530 [M+H]$^+$, found: 235.1536. $^1$H NMR (CDCl$_3$) δ 0.06 (s, 6H), 0.88 (s, 9H), 2.35 (m, 2H), 3.62 (t, 2H), 4.19 (dd, 2H), 5.2 (dt, vinyl, 1H). $^{19}$F NMR (CDCl$_3$) δ −120.0 (dt, 0.07F, 7% Z-isomer), −109.82 (q, 0.93 F,J=21 Hz, 93% E-isomer).

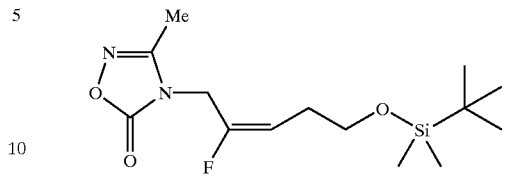

Example-HH-3

To a mixture of Example-HH-2 (2.25 g, 9.58 mmol), polymer-supported triphenylphosphine (3 mmol/g, 1.86 g, 15 mmol) and 3-methyl-1,2,4-oxadiazolin-5-one (1.25 g, 12.5 mmol) in 60 mL of THF was added dropwise diethylazodicarboxylate (2.35 mL, 14.7 mmol). The reaction mixture was stirred for 1 h at room temperature, and additional 3-methyl-1,2,4-oxadiazolin-5-one (0.30 g, 3.0 mmol) was added. After 30 minutes, the mixture was filtered through celite, and the filtrate was concentrated. The resulting yellow oil was triturated with diethyl ether (30 mL) and the solid removed by filtration. The filtrate was concentrated, triturated with hexane (30 mL) and filtered. The filtrates was concentrated to an oil which was purified by flash column chromatography on silica gel eluting with 15% ethyl acetate in hexane to give 1.83 g (60%) of the desired 4-[(2E)-5-[[(1,1-dimethylethyl)dimethylsilyl]oxy]-2-fluoro-2-pentenyl]-3-methyl-1,2,4-oxadi-azol-5(4H)-one product as a clear oil, that contained only the desired E-isomer by $^{19}$F NMR.

HRMS calcd. for C$_{14}$H$_{26}$FN$_2$O$_3$Si: m/z=317.1697 [M+H]$^+$, found: 317.1699. $^1$H NMR (CDCl$_3$) δ 0.04 (s, 6H), 0.85 (s, 9H), 2.28 (s, 3H), 2.37 (m, 2H), 3.64 (t, 2H), 4.32 (d, 2H), 5.4 (dt, vinyl, 1H). $^{19}$F NMR (CDCl$_3$) δ −110.20 (q, 1 F,J=21 Hz).

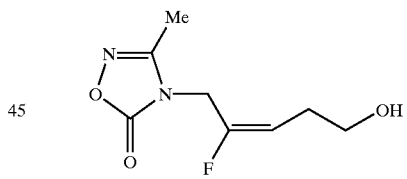

Example-HH-4

A solution of Example-HH-3 (1.83 g, 5.78 mmol) in a mixture of acetic acid (6 mL), THF (2 mL) and water (2 mL) was stirred at room temperature for 2.5 hours. The resulting solution was concentrated in vacuo to an oil which was dissolved in diethyl ether (50 mL). The organic layer was washed with saturated NaHCO$_3$, and the aqueous layer was extracted with diethyl ether (2×50 mL) and ethyl acetate (2×50 mL). The combined organic layers were dried (MgSO$_4$), filtered and evaporated to give 1.15 g (98%) of the desired 4-[(2E)-2-fluoro-5-hydroxy-2-pentenyl]-3-methyl-1,2,4-oxadiazol-5(4H)-one product as a clear colorless oil.

HRMS calcd. for C$_8$H$_{12}$FN$_2$O$_3$: m/z=203.0832 [M+H]$^+$, found: 203.0822. $^1$H NMR (CDCl$_3$) δ 2.31 (3H), 2.4 (m, 2H), 3.66 (t, 2H), 4.37 (d, 2H), 5.42 (dt, vinyl, 1H). $^{19}$F NMR (CDCl$_3$) δ −110.20(q, 1 F,J=21 Hz).

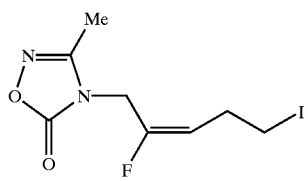

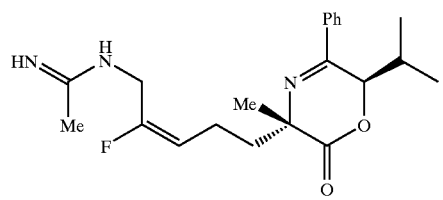

Example-HH-5

To a CH$_2$Cl$_2$ (2 mL) solution of triphenylphosphine (238 mg, 0.91 mmol) and imidazole (92 mg) at 0° C. was added solid iodine (230 mg, 0.91 mmol), and the mixture was stirred for 5 minutes. To the resulting yellow slurry was added a CH$_2$Cl$_2$ (1.5 mL) solution of Example-HH-4 (0.15 g, 0.74 mmol). The slurry was allowed to warm to room temperature and stirred 30 minutes. The reaction mixture was diluted with CH$_2$Cl$_2$ (10 mL), washed with saturated Na$_2$S$_2$O$_3$ (5 mL) and brine (5 mL), dried (MgSO$_4$), filtered and evaporated to an oil. Addition of diethyl ether (10 mL) to the oil gave a white precipitate that was removed by filtration and the filtrate was concentrated to an oil. The crude material was purified by flash column chromatography on silica gel eluting with 30% ethyl acetate in hexane to give 0.18 g (78%) of the desired 4-[(2E)-2-fluoro-5-iodo-2-pentenyl]-3-methyl-1,2,4-oxadiazol-5(4H)-one product as a clear oil, which solidified upon standing, mp=58.1–58.6° C.

Anal. calcd. for C$_8$H$_{10}$FIN$_2$O$_2$: C, 30.79; H, 3.23; N, 8.98. Found: C, 30.83; H, 3.11; N, 8.85. HRMS calcd. for C$_8$H$_{11}$FIN$_2$O$_2$: m/z=330.0115 [M+H]$^+$, found: 330.0104. $^1$H NMR (CDCl$_3$) δ2.31 (s, 3H), 2.75 (q, 2H), 3.21 (t, 2H), 4.31 (d, 2H), 5.39 (dt, vinyl, 1H). $^{19}$F NMR (CDCl$_3$) δ–108.21 (q, 1F,J=21 Hz).

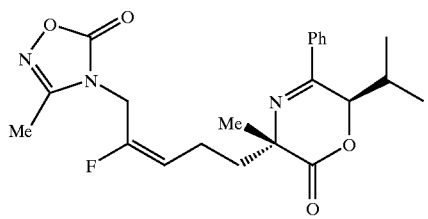

Example-HH-6

To a 1-methyl-2-pyrrolidinone (12 mL) solution of (3S,6R)-6-isopropyl-3-methyl-5-phenyl-3,6-dihydro-2H-1,4-oxazin-2-one (*Synthesis*, 1999, 4, 704–717) (1.10 g, 4.76 mmol), LiI (0.63 g, 4.76 mmol) and Example-HH-5 (0.85 g, 2.72 mmol) in an ice bath was added 2-tert-butylimino-2-diethylamino-1,3-dimethylperhydro-1,3,2-diazaphosphorine (1.38 mL, 4.76 mmol). The yellow solution became orange upon addition of the base, and the resulting solution was allowed to stir at room temperature for 1 hour. The reaction mixture was diluted with ethyl acetate (100 mL), washed with water (2×30 mL), dried (MgSO$_4$), filtered and evaporated to a yellow oil. The crude material was purified by flash column chromatography on silica gel eluting with 30% ethyl acetate in hexane to give 0.64 g (57%) of the desired alkylated product as a clear oil.

$^1$H NMR (C$_6$D$_6$) δ 0.57 (d, 3H), 0.89 (d, 3H), 1.30 (s, 3H), 1.65 (s, 3H), 1.8 (m, 2H), 2.0 (m, 2H), 2.1 (m, 1H), 3.22 (m, 2H), 4.88 (dt, vinyl, 1H), 5.49 (d, 1H), 7.1 (m, 3H), 7.6 (m, 3H), 7.6 (m, 2H). $^{19}$F NMR (CDCl$_3$) δ –110.37 (q, 1 F,J=21 Hz).

Example-HH-7

To a methanol (20 mL) solution of Example-HH-6 (0.13 g, 0.31 mmol) was added Lindlar catalyst (1.0 g). The stirred slurry was heated to 60° C. for 1 hour, and additional Lindlar catalyst (0.30 g) was added. The slurry was stirred an additional 1 hour at 60° C., then cooled to room temperature. The catalyst was removed by filtration through celite, and the filtrate was stripped to give 0.58 g (100%) of the desired deprotected amidine product as a pale yellow oil.

MS: m/z=374.2 [M+H]$^{+1}$H NMR (CD$_3$OD) δ 0.77 (d, 3H), 1.07 (d, 3H), 1.58 (s, 3H), 2.02 (s, 3H), 1.8–2.2 (m, 5H), 3.83 (d, 2H), 5.20 (dt, vinyl, 1H), 5.69 (d, 1H), 7.4 (m, 3H), 7.7 m, 2H) $^{19}$F NMR (CDCl$_3$) δ –109.4 (m, 1F,J=21 Hz)

Example-HH

A solution of the product from Example-HH-7 (0.58 g, 1.54 mmol) in 1.5 N HCl (25 mL) was washed with diethyl ether (2×20 mL) and refluxed for 1 hour. The solvent was stripped and the crude amino acid ester was dissolved in 6 N HCl (15 mL) and heated to reflux. After six hours, the solvent was removed in vacuo, and the resulting foam was purified by reverse-phase HPLC eluting with a 30 minute gradient of 0–40% CH$_3$CN/H$_2$O (0.25% acetic acid). Fractions containing product were combined and concentrated to a foam. The product was dissolved in 1 N HCl and the solvent removed in vacuo (2×) to give 0.15 g (29%) of the desired (2S,5E)-2-amino-2-methyl-6-fluoro-7-[(1-iminoethyl)amino]-5-heptenoic acid, dihydrochloride product.

HRMS calcd. for C$_{10}$H$_{19}$FN$_3$O$_2$: m/z=232.1461 [M+H]$^+$, found: 232.1485. $^1$H NMR (D$_2$O ) δ 1.43 (s, 3H), 2.10 (s, 3H), 1.8–2.1 (m, 4H), 3.98 (d, 2H) 5.29 (dt, vinyl, 1H). $^{19}$F NMR (CDCl$_3$) δ –109.97 (q, 1 F,J=21 Hz).

Example 11

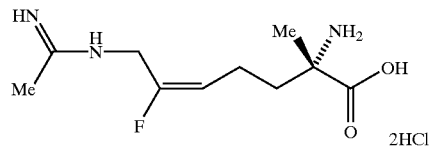

(2S,5E)-2-amino-2-methyl-6-fluoro-7-[(1-iminoethyl)amino]-5-heptenoic acid, dihydrochloride

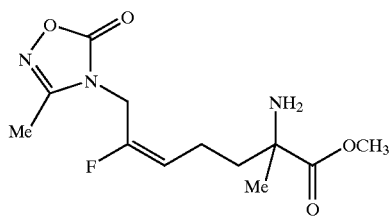

Example-II-1

To a 1-methyl-2-pyrrolidinone (7500 mL) solution of methyl N-[(3,4-dichlorophenyl)-methylene]-alaninate (748.5 g, 2.88 mol) under nitrogen was added LiI (385.5 g, 2.88 mol) and the resulting slurry stirred approximately 20 minutes to give a clear solution. The solid from Example-HH-5 (750 g, 2.40 mol) was then added and the resulting solution cooled in an ice bath to ~0° C. Neat BTPP (900 g, 2.88 mol) was added dropwise over 25 minutes maintaining the internal temperature below 5° C. After stirring for an additional 1.5 hour at 5° C., the reaction was determined to be complete by HPLC. At this time, 7500 mL of methyl t-butyl ether (MTBE) was added followed by addition of 9750 mL of a water/crushed ice mixture. The temperature rose to 20° C. during this operation. After stirring vigorously for 5–10 minutes, the layers were separated and the aqueous layer washed with twice with 6000 mL of MTBE. The MTBE layers were combined and washed two times with 7500 mL of water. The resulting MTBE solution was then concentrated to ~5000 mL, treated with 11625 mL of 1.0 N HCl, and stirred vigorously at room temperature for one hour. The layers were separated and the aqueous layer washed with 7500 ml of MTBE. About 1 kg of sodium chloride was added to the aqueous layer and the resulting mixture stirred until all the salt had dissolved. At this point, 7500 mL of ethyl acetate was added, the resulting mixture cooled to 10° C., and 2025 mL of 6.0 N sodium hydroxide added with good agitation. The resulting pH should be about 9. The layers were separated and the aqueous layer was saturated with sodium chloride and extracted again with 7500 mL of ethyl acetate. The combined ethyl acetate extracts were dried (MgSO$_4$) and concentrated to a light oil. It should be noted that the ethyl acetate was not complete removed. With agitation, 3000 ml of hexane then is added to generate a slurry that was cooled to 10° C. The granular solid was collected by filtration and washed with 1500 mL of hexane. About 564 g (82% yield) of the desired pure aminoester (>95% pure by HPLC) was obtained as a white solid, m.p. 82.9–83.0° C. LCMS: m/z=288.2 [M+H]$^+$. Chiral HPLC (Chiralpak-AD normal phase column, 100% acetonitrile, 210 nm, 1 mL/min): Two major peaks at 4.71 and 5.36 min (1:1).

1H NMR (CDCl$_3$): δ 1.40 (s, 3H), 1.7–1.8 (m, 2H), 2.0 (br s, 2H), 2.2 (m, 2H, 2.29 (s, 3H), 3.73 (s, 3H), 4.34 (dd, 2H), 5.33 (dt, 1H).

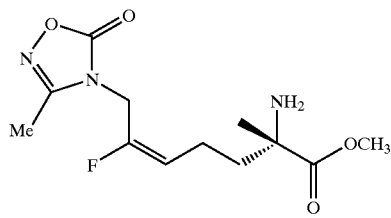

Example II-2

Separation of the individual enantiomers of the product from Example-II-1 was accomplished on preparative scale using chiral HPLC chromatography (ChiralPak-AD, normal phase column, 100% acetonitrile) to give the desired pure (2S)-2-methyl amino ester product title product. ChiralPak-AD, normal phase column, 100% acetonitrile, 210 nm, 1 mL/min): 5.14 min (99%).

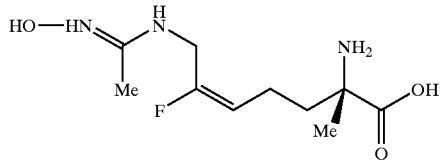

Example-II-3

A slurry of the product of Example-II-2 (2.30 g, 8.01 mmol) in 0.993 M NaOH (30.0 ml, 29.79 mmol) was stirred 2 hours at room temperature. To the resulting clear colorless solution was added 1.023 M HCl (29.10 mL, 29.76 mmol). The resulting clear solution was concentrated until a precipitate began to form (approx. 30 mL). The slurry was warmed to give a clear solution that was allowed to stand at room temperature overnight. The precipitate was isolated by filtration. The solid was washed with cold water (2×10 mL), cold methanol (2×10 mL) and Et$_2$O (2×20 mL). The white solid was dried in vacuo at 40° C. 4 hours to give 1.04 g (53%) of the desired N-hydroxy illustrated product. mp=247.2° C.

Anal. calcd. for C$_{10}$H$_{18}$FN$_3$O$_3$: C, 48.57; H, 7.34; N, 16.99; Cl, 0.0. Found: C, 48.49; H, 7.37; N, 16.91; Cl, 0.0. HRMS calcd. for C$_{10}$H$_{19}$FN$_3$O$_3$: m/z=248.1410 [M+H]$^+$, found: 248.1390. $^1$H NMR (D$_2$O ) δ 1.35 (s, 3H), 1.81 (s, 3H), 1.7–2.0 (m, 4H), 3.87 (d, 2H) 5.29 (dt, vinyl, 1H). $^{19}$F NMR(CDCl$_3$)δ -112.51 (q, 1 F,J=21 Hz).

Example-II-4

To a solution of Example-II-3 in methanol is added Lindlar catalyst. The stirred slurry is refluxed for 2 hours, then cooled to room temperature. The catalyst is removed by filtration through celite, and the filtrate is stripped. The resulting solid is dissolved in water and concentrated repeatedly from 1.0 N HCl to give the desired (2R,5E)-2-amino-2-methyl-6-fluoro-7-[(1-iminoethyl)amino]-5-heptenoic acid, dihydrochloride product.

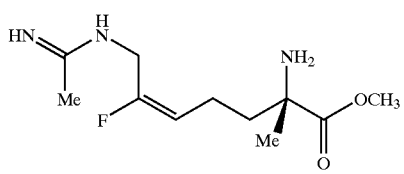

Example-II-5

A solution of 73.5 g (0.3 mol) of the product from Example-II-2 was dissolved in 300 mL of methanol and added dropwise to a preformed mixture of 13.7 g of Lindlar catalyst and 73.5 g of formic acid (1.53 mol) in 312 mL of methanol while maintaining the reaction temperature between 22° C. and 26° C. After stirring at room temperature for an additional ~15 hrs, the reaction was determined to be complete by $F^{19}$ NMR. The resulting reaction mixture was filtered through celite and the celite washed 3 times with 125 mL of methanol. The methanol filtrates were combined and concentrated to generate 115 g of the desired amidine title product as a viscous oil.

MS: m/z=246 (M+H)$^+$. $^1$H NMR (CD$_3$OD) δ 1.6 (s, 3H) 2.0–2.2 (m, 4H) 2.3 (s, 3H), 3.9 (s, 3H), 4,2 (d, 2H), 5.4 (dt,vinyl), 8.4 (s, 3H). $F^{19}$NMR (CD$_3$OD) δ −110.4 (q, J=21 Hz) −111.7 (q, J=21 Hz).

In order to remove trace levels of lead, the crude product was dissolved in 750 mL of methanol and 150 g of a thiol-based resin (Deloxan THP 11) was added. After stirring 3 hrs at room temperature, the resin was filtered off and washed 2 times with 500 mL methanol. The filtrates were collected and concentrated to 99 g of the desired amidine title product as a viscous oil.

Alternatively:

A total of 5.0 g of the product from Example-II-2 (0.0174 mole, 1.0 equiv) was mixed with 5.0 g of zinc dust (0.0765 moles, 4.39 equiv) in 40 mL of 1-butanol and 10 mL of acetic acid. After stirring for 5 hrs at 50° C., LC analyses indicated the reaction to be complete. The solids were readily filtered off. The filtrate, after cooling in ice water to 7° C., was treated with 30 mL of 6 N NaOH (0.180 moles) in one portion with vigorous stirring. After cooling the reaction mixture from 33° C. to 20° C., the clear butanol layer was separated off and the aqueous layer extracted again with 40 mL of 1-butanol. The butanol extracts were combined, washed with 30 mL of brine followed by approx 10 mL of 6N HCl. After concentration at 70° C., a clear glass resulted which was identified as the desired amidine title product.

Example-II

A solution of 99 g of the product from Example-II-5 in 6 N HCl was refluxed for 1 hr at which time LC analyses indicated the reaction to be complete. The solvent was removed in vacuo to yield 89.2 g of a glassy oil which was dissolved in a mixture of 1466 mL ethanol and 7.5 ml of deionized water. THF was added to this agitated solution at ambient temperature until the cloud point was reached (5.5 liters). An additional 30 ml of deionized water was added and the solution agitated overnight at room temperature. The resulting slurry was filtered and washed with 200 mL of THF to yield 65 g of a white solid identified as the desired title product.

$[\alpha]_D^{25}$=+7.2 (c=0.9, H$_2$O) mp=126–130° C. MS: m/z= 232 (M+H)$^+$. Anal. Calcd for C$_{10}$H$_{22}$N$_3$F$_1$O$_3$Cl$_2$: C, 37.28; H, 6.88; N, 13.04; Cl, 22.01. Found: C, 37.52, H, 6.84, N, 13.21, Cl, 21.81. $^1$H NMR (D$_2$O) δ 1.4 (s, 3H), 1.8–2.1 (m, 4H), 1.9 (s,3H), 4.0(d, 2H), 5.3(dt, vinyl, 1H). $F^{19}$NMR (D$_2$O) δ −109.6 (q, J=21 Hz) −112.1 (q, J=21 Hz).

Example JJ

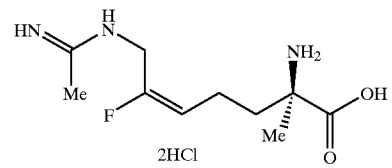

(2R,5E)-2-amino-2-methyl-6-fluoro-7-[(1-iminoethyl)amino]-5-heptenoic acid, dihydrochloride

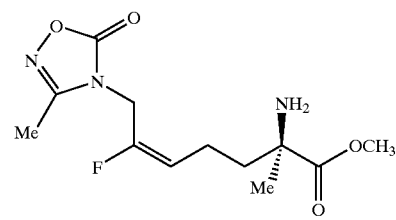

Example-JJ-1

Separation of the individual enantiomers of the product from Example-II-1 was accomplished on preparative scale using chiral HPLC chromatography to give the desired pure (2R)-2-methyl amino ester product.

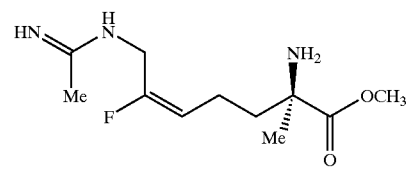

Example-JJ-2

The product from Example-JJ-1 is dissolved in water and acetic acid. Zinc dust is added, and the mixture is heated at 60° C. until HPLC analysis shows that little of the starting material remains. The Zn is filtered through celite from the reaction mixture, and the filtrate is concentrated. The crude material is purified by reverse-phase HPLC column chromatography. Fractions containing product are combined and concentrated affording the desired (2R)-2-methyl acetamidine product.

Example-JJ

A solution of Example-JJ-2 in 2.0 N HCl is refluxed for 2 h. The solvent is removed in vacuo. The resulting solid is dissolved in water and concentrated repeatedly from 1.0 N HCl to give the desired (2R,5E)-2-amino-2-methyl-6-fluoro-7-[(1-iminoethyl)amino]-5-heptenoic acid, dihydrochloride product.

Example KK

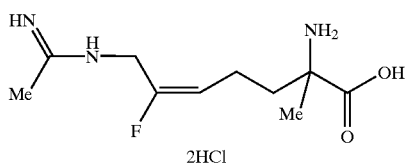

2HCl (2R/S,5E)-2-amino-2-methyl-6-fluoro-7-[(1-iminoethyl)amino]-5-heptenoic acid, dihydrochloride

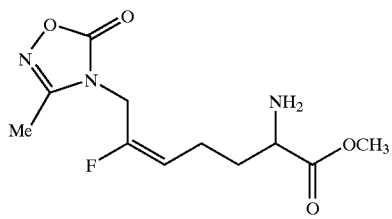

Example-KK-1

To an 1-methyl-2-pyrrolidinone (5 mL) solution of methyl N-[(4-chlorophenyl)methylene]-glycinate (0.33 g, 1.6 mmol), LiI (0.20 g, 1.0 mmol) and a sample of the product of Example-HH-5 (0.30 g, 0.96 mmol) in an ice bath was added 2-tert-butylimino-2-diethylamino-1,3-dimethylperhydro-1,3,2-diazaphosphorine (0.433 mL, 1.5 mmol). The solution was allowed to stir at room temperature for 1.5 hours. The reaction mixture was diluted with ethyl acetate (30 mL), washed with water (2×20 mL), dried (MgSO$_4$), filtered, and evaporated to give the crude desired racemic alkylated imine as a yellow oil.

The crude material was dissolved in ethyl acetate (10 mL) and 1N HCl (10 mL) was added. The mixture was stirred for 2 hours at room temperature, and the organic layer was separated. The aqueous layer was neutralized with solid NaHCO$_3$ and extracted with ethyl acetate (2×30 mL). The organic layer was dried (MgSO$_4$), filtered and evaporated to give 0.13 g of the desired title racemic amino ester product as a yellow oil. This product was used in the next step without further purification. LCMS: m/z=288.2 [M+H]$^+$.

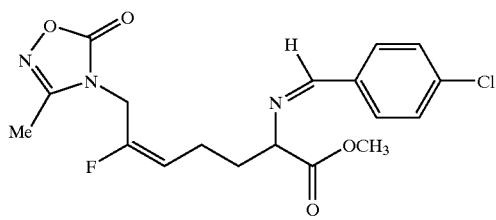

Example-KK-2

To a CH$_2$Cl$_2$ (15 mL) solution of Example-KK-1 (1.36 g, 4.98 mmol) was added 4-chlorobenzaldehyde (0.70 g, 5.0 mmol) and MgSO$_4$ (~5 g). The slurry was stirred at room temperature for 18 hours. The slurry was filtered, and the filtrate stripped to give 1.98 g (100%) of the desired title imine product as a pale yellow oil. This product was used in the next step without further purification.

$^1$H NMR (C$_6$D$_6$) δ 1.34 (s, 3H), 2.0 (br m, 4H), 3.32 (s, 3H), 3.42 (m, 2H), 3.83 (t, 1H), 4,98 (dt, vinyl, 1H).

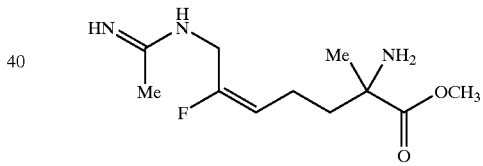

Example-KK-3

To a CH$_2$Cl$_2$ (2 mL) solution of the product of Example-KK-2 (0.25 g, 0.63 mmol) was added methyl iodide (0.200 mL, 3.23 mmol) and O(9)-allyl-N-(9-anthracenylmethyl)-cinchonidinium bromide (40 mg, 0.066 mmol). The solution was cooled to −78° C. and neat BTPP (0.289 mL, 0.95 mmol) was added. The resulting orange solution was stirred at −78° C. for 2 hours and allowed to reach −50° C. After 2 hours at −50° C., the solution was diluted with CH$_2$Cl$_2$ (10 mL), washed with water (10 mL), dried (MgSO$_4$), filtered, and evaporated to give the crude desired racemic alkylated imine as a yellow oil.

The crude material was dissolved in ethyl acetate (10 mL) and 1N HCl (10 mL) was added. The mixture was stirred for 1 hour at room temperature, and the organic layer was separated. The aqueous layer was neutralized with solid NaHCO$_3$ and extracted with ethyl acetate (2×30 mL). The organic layer was dried (MgSO$_4$), filtered and evaporated to give 0.16 g of the desired racemic 2-methylamino ester product as a yellow oil. The product was used in the next step without further purification. LCMS: m/z=288.2 [M+H]$^+$.

Example-KK-4

The racemic product from Example-KK-3 is dissolved in water and acetic acid. Zinc dust is added, and the mixture is heated at 60° C. until HPLC analysis shows that little of the starting material remains. The Zn dust is filtered through celite from the reaction mixture, and the filtrate is concentrated. The crude material is purified by reverse-phase HPLC column chromatography. Fractions containing product are combined and concentrated affording the desired acetamidine product.

Example-KK

A solution of racemic Example-KK-4 in 2.0 N HCl is refluxed for 1 h. The solvent is removed in vacuo. The resulting solid is dissolved in water and concentrated repeatedly from 1.0 N HCl to give the desired title (2R/S,5E)-2-amino-2-methyl-6-fluoro-7-[(1-iminoethyl)amino]-5-heptenoic acid, dihydrochloride product.

Example LL

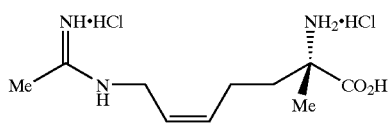

(2S,5Z)-2-amino-2-methyl-7-[(1-iminoethyl)amino]-
5-heptenoic acid, dihydrochloride

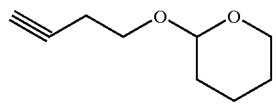

4-[(Tetrahydropyranyl)oxy]butyne

Example LL-1

A mixture of 4-dihydro-2H-pyridine (293.2 g 3.5 mol) and concentrated HCl (1.1 mL) was cooled to 5° C. While continuing to cool externally, 3-butyn-1-ol (231.5 g, 3.3 mol) was added over a period of 30 minutes allowing the temperature to reach 50° C. Reaction was held with mixing at room temperature for 2.5 hours before it was diluted with MTBE (1.0 L). The resulting mixture was washed with saturated sodium bicarbonate (2×150 mL). The organic phase was dried over sodium sulfate and concentrated under reduced pressure to afford 500 g (98% crude yield) of product; GC area % of 96%.

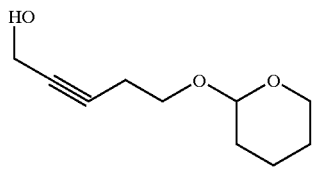

5-(Tetrahydro-pyran-2-yloxy)-pent-2-yn-1-ol

Example LL-2

To a solution of the 4-[(tetrahydropyranyl)oxy]butyne product of Example LL-1 (50.0 g, 0.33 mol) in THF (125 mL) was added a solution of 2N EtMgCl in THF (242 mL, 0.48 mol) under a nitrogen atmosphere over a 30 minute period, allowing the temperature to rise to 48° C. Mixture was further heated to 66° C. and was held at this temperature for 2 hours before cooling to ambient temperature. Paraformaldehyde (14.5 g, 0.48 mol) was added (small exotherm was observed) and the resulting mixture was heated to 45° C. After 1 hour of controlling the temperature between 45–55° C., the mixture turned clear. At this point, the mixture was heated up to 66° C. and stirred for 2.5 hours. Mixture was cooled to room temperature and saturated ammonium chloride (125 mL) was added slowly over 30 minutes (strong exotherm was observed) keeping the temperature below 40° C. The liquid phase was separated by decantation; ethyl acetate (250 mL) and brine (50 mL) were added. The organic phase was separated and washed with brine (2×50 mL) and water (1×50 mL). The organic layer was dried over sodium sulfate and concentrated under reduced pressure to afford 51 g of a lightly yellow colored oil (85% crude yield); GC area %=88% title product, 6% starting material.

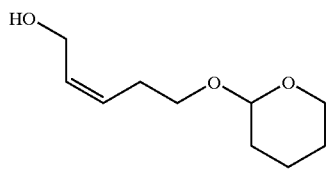

5-(Tetrahydro-pyran-2-yloxy)-pent-2-en-1-ol

Example LL-3

To a 500 mL Parr bottle, under a nitrogen atmosphere, was charged the 5-(tetrahydro-pyran-2-yloxy)-pent-2-yn-1-ol product of Example LL-2 (40.2 g, 0.22 mol), Lindlar catalyst (2.0 g), ethanol (120 mL), hexane (120 mL), and 2,6-lutidine (457 mg). Reaction mixture was purged five times each with nitrogen and hydrogen gas. Parr bottle was pressurized with hydrogen to 5 psi and shaken until 98% of the theoretical hydrogen was consumed. Hydrogen was released from the vessel and the reaction was purged with nitrogen five times. Mixture was filtered through a pad of Solka Floc and the catalyst was rinsed with ethanol (2×50 mL). The filtrate and rinses were combined and concentrated under reduced pressure to afford 40.3 g (99% yield) of the title material as a yellow colored oil (GC area %=96%).

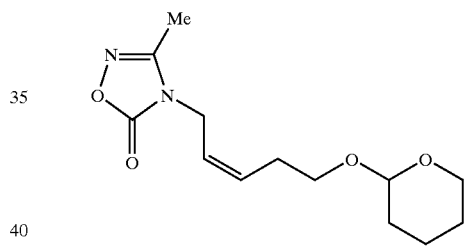

3-Methyl-4-[5-(tetrahydro-pyran-2-yloxy)-pent-2-enyl]-4H-[1,2,4]oxadiazol-5-one

Example LL-4

To a solution of the 5-(tetrahydro-pyran-2-yloxy)-pent-2-en-1-ol product of Example LL-3 (11.8 g, 0.063 mol) in toluene (42 mL) was added) triethylamine (6.4 g, 0.063 mol). The mixture was cooled to −5° C. and methanesulfonyl chloride (7.3 g, 0.63 mol) was added via syringe at such rate as to keep the pot temperature below 10° C. The mixture was allowed to warm to room temperature and stirred for two hours. The mixture was filtered by suction and rinsed on the filter with toluene (2×20 mL). The filtrate and washes were added to a mixture of the sodium salt of 3-methyl-1,2,4-oxadiazolin-5-one (8.6 g, 0.063 mol) in DMF (10 mL). The mixture was stirred with a mechanical stirrer and heated at 45° C. for 5 hours. Water (40 mL) was added and the mixture was stirred for 5 minutes and then the layers were separated. The toluene layer was washed with water (3×20 mL), dried over MgSO$_4$, and concentrated to afford 16.5 g (97.3%) of an orange colored crude product (area % GC consisted of 71% title product, 18% toluene, and 4% of an impurity).

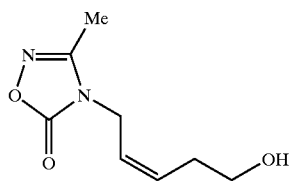

4-(5-Hydroxy-pent-2-enyl)-3-methyl-4H-[1,2,4]
oxadiazol-5-one

Example LL-5

To a solution the 3-methyl-4-[5-(tetrahydro-pyran-2-yloxy)-pent-2-enyl]-4H-[1,2,4]oxadi-az-ol-5-one product of Example LL-4 (16 g, 0.06 mol) in methanol (48 mL) was added p-toluenesulfonic acid (0.34 g, 2.0 mmol). The mixture was stirred at room temperature for four hours. Sodium bicarbonate (0.27 g, 3.0 mmol) was added and the mixture was concentrated on a rotary evaporator. The residue was diluted with saturated NaHCO$_3$ (20 mL) and the resulting mixture was extracted with ethyl acetate (2×60 mL). Extracts were combined and washed with water (2×25 mL), dried over MgSO$_4$, and concentrated to afford 8.4 g of the crude, orange colored oil title product (area % GC=80%).

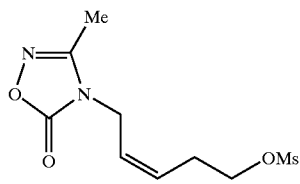

Methanesulfonic acid 5-(3-methyl-5-oxo-[1,2,4]
oxadiazol-4-yl)-pent-3-enyl ester Example LL-6

To a solution of the 4-(5-Hydroxy-pent-2-enyl)-3-methyl-4H-[1,2,4]oxadiazol-5-one product of Example LL-5 (8.27 g, 0.045 mol) in methylene chloride (33 mL) was added triethylamine (5.0 g, 0.49 mol). The mixture was cooled to −5° C. and methanesulfonyl chloride (5.5 g, 0.048 mol) was added at such rate as to keep the temperature below 8° C. The cooling bath was removed and the mixture was stirred for 3 hours as it warmed up to room temperature. Water (15 mL) was added and the mixture was stirred for 5 minutes and then the layers were separated. The organic phase was washed with water (10 mL), dried over MgSO$_4$, and concentrated to give a light amber colored residue. The residue was dissolved in ethyl acetate (8 mL) and kept at 5° C. overnight. Precipitated solids were filtered off by suction and rinsed on the filter with minimum volume of ethyl acetate and then air-dried on the filter to afford 6.8 g (58% yield) of the title product.

$^1$H NMR (CDCl$_3$) δ 5.76 (dtt, J=10.9, 7.5, 1.5 Hz, 1H), δ 5.59 (dtt, J=10.9, 7.0, 1.5 Hz, 1H) δ 4.31 (t, J=6.3 Hz, 2H), δ 4.27 (dd, J=7.0, 1.5 Hz, 2H), δ 3.04 (s, 3H), δ 2.67 (q, J=6.7 Hz, 2H), δ 2.28 (s, 3H) $^{13}$C (CDCl$_3$) δ 159.0, 156.3, 129.9, 125.1, 68.4, 38.9, 37.2, 27.5, 10.2. IR (cm$^{-1}$) 1758, 1605, 1342, 1320, 1170. Anal. Calcd. for C$_9$H$_{14}$N$_2$O$_5$S: C, 41.21; H, 5.38; N, 10.68. Found: C, 41.15; H, 5.41; N, 10.51.

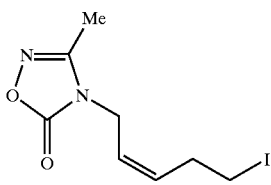

4-(5-Iodo-pent-2-enyl)-3-methyl-4H-[1,2,4]
oxadiazol-5-one

Example LL-7

To a solution of the methanesulfonic acid 5-(3-methyl-5-oxo-[1,2,4]oxadiazol-4-yl)-pent-3-enyl ester product of Example LL-6 (20.0 g, 0.076 mol) in acetone (160 ml) was added sodium iodide (17.15 g, 0.114 mol). The mixture was heated to reflux and was stirred for 3 hours. External heating was stopped and the mixture was held at room temperature overnight. Solids were removed by filtration and rinsed on the filter. The filtrate and washes were combined and concentrated and the heterogeneous residue was extracted with ethyl acetate (120 mL). The organic layer was washed with water (60 mL), 15% aqueous solution of sodium thiosulfate (60 mL) and water (60 mL); dried over MgSO$_4$ and concentrated under reduced pressure to afford 22.1 g (98% yield) of the title oil product.

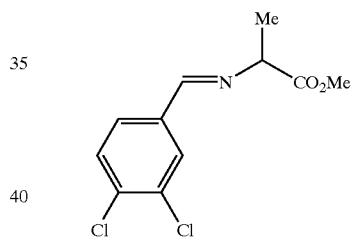

2-[(3,4-Dichloro-benzylidene)-amino]-propionic
acid methyl ester

Example LL-8

To a mechanically stirred slurry of L-alanine methyl ester hydrochloride (200.0 g, 1.43 mol) in methylene chloride (2.1 L) under a nitrogen atmosphere was added triethylamine (199.7 mL, 1.43 mol) over 12 min (during the addition solids partially dissolved and then reprecipitated). After 10 min, 3,4-dichlorobenzaldehyde (227.5 g, 1.30 mol) and magnesium sulfate (173.0 g, 1.43 mol) were added (temperature increased 6° C. over 30 min). After 2.5 h, the mixture was filtered. The filtrate was washed with water (1×1 L) and brine (1×500 mL), dried over sodium sulfate, filtered and concentrated to give 313.3 g, 92.4% yield of oil product.

$^1$HNMR (400 MHz, CDCl3) δ 8.25 (s, 1H), 7.91 (d, 1H), 7.58 (dd, 1H), 7.49 (d, 1H), 4.17 (t, 1H), 3.76 (s, 3H), 1.53 (d, 3H). Anal. Calcd for C$_{11}$H$_{11}$Cl$_2$NO$_2$: C, 50.79; H, 4.26; Cl, 27.26; N, 5.38. Found: C, 50.37; H, 4.10; Cl, 26.87; N, 5.38.

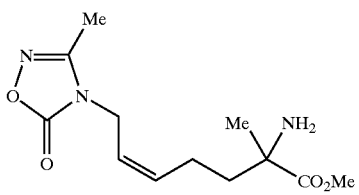

Rac-2-Amino-2-methyl-7-(3-methyl-5-oxo-[1,2,4] oxadiazol-4-yl)-hept-5-enoic acid methyl ester

Example LL-9

Method 1. A solution of the product of Example LL-7 (114.2 g, 0.39 mol) and the product of Example LL-8 (151.5 g, 0.58 mol) in dimethylformamide (1.4 L) under nitrogen atmosphere was cooled to −8° C. Lithium iodide (78.1 g, 0.58 mol) was then added in 3 equal portions over 19 min. The mixture was stirred for 20 min at −7° C. and then (tert-butylimino)-tris(pyr-rolidino)phosphorane (194.0 mL, 0.62) was added over 36 min (maximum temperature=−2.6° C.). After 10 min, the cooling bath was removed and the solution was stirred at ambient temperature for 1 h. The mixture was then poured into cold water (1.4 L) and extracted with ethyl acetate (2×1.0 L). The combined organic layers were washed with water (2×400 mL) and brine. The ethyl acetate layer was treated with 1 N HCl (780 mL) and stirred for 1 h. The aqueous layer was separated and extracted with ethyl acetate (2×400 mL) and then neutralized with sodium bicarbonate (110 g). The mixture was extracted with ethyl acetate (1×500 mL). The organic layer was dried over sodium sulfate, filtered, concentrated and then treated with methyl t-butyl ether to give a crystalline product: first crop 14.4 g; second crop 6.6 g (GC purity=96.2 and 91.9%, respectively). The aqueous phase was saturated with sodium chloride and extracted with ethyl acetate (4×500 mL). The combined organic layers were dried over sodium sulfate, filtered, concentrated and then treated with methyl t-butyl ether to give a crystalline product: first crop 33.4 g; second crop 10.8 g (GC purity=89.6 and 88.8%, respectively). Total crude yield 65.2 g, 62.4%.

Method 2. To a solution of the product of Example LL-7 (20.7 g, 0.070 mol) and the product of Example LL-8 (22.9 g, 0.088 mol) in dimethylformamide (207 mL) under a nitrogen atmosphere was added cesium carbonate (29.8 g, 0.092). The mixture was stirred at rt for 16 h and then diluted with water (300 mL) and extracted with ethyl acetate (2×200 mL). The combined ethyl acetate layers were washed with water (3×100 mL) and brine and then treated with 1 N HCl (184 mL). After 1 h, the layers were separated and the aqueous layer was extracted with ethyl acetate (3×100 mL) and then neutralized with sodium bicarbonate (15.5 g). The mixture was extracted with ethyl acetate (1×150 mL). The aqueous layer was saturated with sodium chloride and extracted with ethyl acetate (3×100 mL). The combined organic layers were dried over sodium sulfate, filtered and concentrated to give a yellow solid, 11.9 g, 62.9%; GC purity=96.6%. The crude product was recrystallized from warm methyl t-butyl ether or ethyl acetate.

$^1$H NMR (400 MHz, CDCl$_3$) δ 5.68 (m, 1H), 5.36 (m, 1H), 4.23 (d, 2H), 3.73 (s, 3H), 2.43 (s, 3H), 2.18 (m, 2H), 1.81 (m, 1H), 1.69 (s, br, 2H), 1.66 (m, 1H), (1.36, 3H) $^{13}$C NMR (400 MHz, CDCl$_3$) δ 177.60, 159.01, 156.10, 135.12, 121.82, 57.48, 52.29, 40.12, 39.00, 26.62, 22.56, 10.41

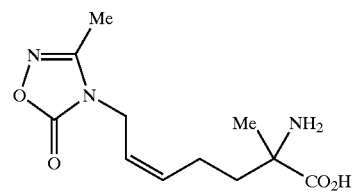

Rac-2-Amino-2-methyl-7-(3-methyl-5-oxo-[1,2,4] oxadiazol-4-yl)-hept-5-enoic acid

Example LL-10

The product of Example LL-9 (0.269 g, 1 mmol) was dissolved in 5 mL 2 N HCl and heated to reflux under argon. After refluxing for 6 hrs followed by stirring at room temperature for 72 hours, an aliquot was removed and checked by $^1$H NMR. Approximately 6% of unreacted starting ester remained along with the desired product (verified by LC-MS). The aqueous portion was removed in vacuo, leaving 0.38 g of a thick, amber oil. After purification via reverse phase chromatography, followed by lyophilization, one obtained 0.23 g, 90.2% of the title compound as white, non-deliquescent solids.

Anal. Calcd. for C$_{11}$H$_{17}$N$_3$O$_4$·0.77H$_2$O: C, 49.09; H, 6.94; N, 15.61. Found: C, 48.71; H, 6.94; N, 15.98 Mass spec: M+1=256.

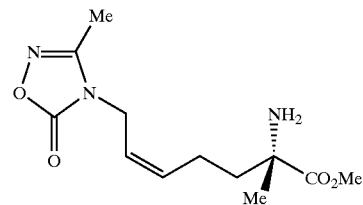

(2S,5Z)-2-Amino-2-methyl-7-(3-methyl-5-oxo-[1,2,4]oxadiazol-4-yl)-hept-5-enoic acid methyl ester

Example LL-11

The title compound (827.3 g) was separated from its R enantiomer by preparative chiral chromatography using Novaprep 200 instrument with steady state recycling option. The material was dissolved in absolute ethanol at a concentration of 40 mg/ml and loaded on a 50×500 mm prepacked Chiral Technologies stainless steel column. The adsorbent was 20μ ChiralPak AD. The mobile phase was ethanol/triethylamine 100/0.1; the flow rate equaled 125 ml per min. The crude solution (25 mL) was loaded on the column every 12 mins. A steady state recycling technique was used. Solvent was removed using a rotovap. The final product was isolated as gold oil which solidified on standing; 399.0 g (96.4% recovery).

$^1$H (400 MHz, CD$_3$OD) δ 5.68 (dtt, 1H,J$_{olefinic}$=10.7 Hz), 5.43 (dtt, 1H, J$_{olefinic}$=10.7 Hz), 4.82 (s, br, 2H), 4.28 (d, 2H,J=5.5 Hz), 3.73 (s, 3H), 2.27 (s, 3H), 2.26 (m, 1H), 2.14 (m, 1H), 1.82 (ddd, 1H,J=13.6, 11.3, 5.4 Hz), 1.67 (ddd, 1H,J=13.6, 11.2, 5.5 Hz), 1.34 (s, 3H) $^{13}$C NMR (400 MHz, CD$_3$OD) δ 178.49, 161.13, 158.70, 135.92, 123.47, 58.55, 52.77, 41.38, 39.96, 26.23, 23.47, 10.23 Anal. Calcd for C$_{12}$H$_{19}$N$_3$O$_4$: C, 53.52; H, 7.11; N, 15.60. Found: C, 52.35; H, 7.20; N, 15.60.

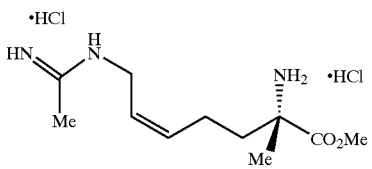

(2S,5Z)-7-Acetimidoylamino-2-amino-2-methyl-hept-5-enoic acid methyl ester, dihydrochloride hydrate

Example LL-12

To a solution of the product of Example LL-11 (114.5 g, 0.425 mol) in methanol (2.4 L) was added the solid dibenzoyl-L-tartaric acid (152.5 g, 0.425 mol) and 88% formic acid (147 mL, 3.428 mol) at ambient temperature. A slurry of Lindlar catalyst, 5 wt % palladium on calcium carbonate poisoned with lead acetate (37.9 g), in methanol (200 mL) was prepared under nitrogen. The solution of starting material was then added at ambient temperature to the light grey catalyst slurry followed by a methanol rinse (200 mL). The heterogeneous reaction mixture was heated at 45° C. for 1½ hours. Steady gas evolution was observed starting at about 40° C., which indicated the ongoing reaction. The mixture was cooled in an ice/water bath and then filtered through a plug of Supercell HyFlo. The yellow solution was concentrated in vacuo to give a viscous oil, which was dissolved and partitioned between 2 N aqueous HCl (2 L) and ethyl acetate (0.8 L). Layers were separated and the aqueous layer was washed once with ethyl acetate (0.8 L). Solvent and volatiles were removed in vacuo at elevated temperatures (=70° C.). The intermediate product was used in next the step without further purification or characterization. LC-MS [M+H]+=228.

Example LL

The crude product of Example LL-12 (170 g) was dissolved in 2 N aqueous HCl (1 L). The resulting orange solution was refluxed overnight before it was allowed to cool back to ambient temperature. The reaction mixture was concentrated to about ⅓ of its volume, and the acidic solution was passed through a solid phase extraction cartridge (25 g of C18 silica) to remove color and other impurities. Solvent was removed in vacuo (=70° C.) to give 208 g of crude product as yellowish gum.

The crude gum (31.3 g) was taken up in water (250 mL) and the material was loaded onto a pretreated ion exchange column packed with the acidic resin Dowex 50WX4–400 (about 600 g). The resin was first washed with water (1 L), then with dilute aqueous HCl (1 L of 10/90 v/v conc. HCl/water). The product was eluted off the resin with higher ion strength aqueous HCl (1.5 L of 20/90 v/v to 25/75 v/v conc. HCl/water). The aqueous solvent was removed in vacuo (=70° C.), and the gummy residue was taken up in 4 vol % aqueous trifluoroacetic acid (100 mL). The aqueous solvent was removed in vacuo (=70° C.), and the procedure was repeated once more. The residue was then dried under high vacuum to give 32.2 g of gum as the trifluoroacetic acid salt.

Crude (2S,5Z)-7-acetimidoylamino-2-amino-2-methyl-hept-5-enoic acid, ditrifluoroace-tic acid salt hydrate (32.2 g) was purified by reverse-phase preparative chromatography. The crude was dissolved in 0.1% aqueous TFA (50 ml) and loaded onto a 2-inch ID×1 meter stainless steel column packed with adsorbent (BHK polar W/S, 50μ, 1.16 kg). The product was eluted at a flow rate of 120 mL/min with a step gradient from 0.1% aqueous TFA to 25/75/0.1 acetonitrile/water/TFA. The loading ratio was 36:1 w/w silica to sample. Solvent was removed in vacuo, and the material was converted into the HCl salt by repeated rinses with dilute aqueous HCl and solvent removals in vacuo. Drying under high vacuum gave 27.4 g of the title dihydrochloride hydrate as yellowish gum.

LC-MS [M+H]+=214.16 Da $^1$H NMR (D$_2$O, δ): 1.48 (s, 3H), 1.8–1.9 (AB, 2H), 2.10 (s, 3H), 2.01/2.12 (AB, 2H), 3.78 (d, 2H), rotamere 3.87 (d, 2H), 5.6/5.5 (dt, 2H, 11 Hz) $^{13}$C NMR (D2O) δ: 18.7, 21.5, 21.6, 36.4, 39.1, 59.8, 122.6, 134.3, 164.5, 173.7 Elemental Anal. Calcd. for C$_{10}$H$_{19}$N$_3$O$_2$.2.2HCl.2 H$_2$O: C, 36.21; H, 8.33; N, 12.67; Cl, 23.51. Found: C, 36.03; H, 7.72; N, 12.67; Cl, 23.60.

Example MM

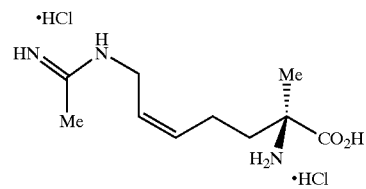

(2R,5Z)-2-amino-2-methyl-7-[(1-iminoethyl)amino]-5-heptenoic acid, dihydrochloride The R-enantiomer isolated during the separation described in Example LL-11 (1.13 g, 4.2 mmol) was dissolved in 11 mL 25% aqueous acetic acid and heated to 60° C. Zinc dust (1.10 g) was then added in 4 equal portions at 30-minute intervals. After heating for a total of 3 hours, an aliquot was removed and checked by LC-MS, which indicated only a trace of unreacted starting material remaining, along with desired product. The mixture was cooled to room temperature, filtered and stripped in vacuo, leaving 2.31 g of a slushy white solid. The methyl ester was hydrolysed with dilute hot HCl to the title compound. After purification by reverse phase chromatography followed by lyophilization, 0.3 1 g of the title compound as a glassy solid was obtained.

Anal. Calcd. for C$_{10}$H$_{19}$N$_3$O$_2$.1.22 HCl.1.15 H$_2$O: C, 46.13; H, 8.15; N, 15.09; Cl, 15.53. Found: C, 46.38; H, 8.51; N, 15.13; Cl, 15.80. Mass spec: M+1=214

Example NN

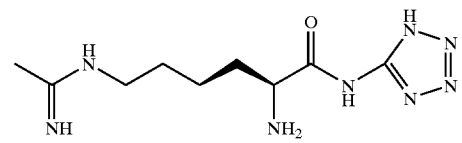

2S-amino-6-[(1-iminoethyl)amino]-N-(1H-tetrazol-5-yl)hexanamide, hydrate, dihydrochloride NN-1 To a stirring solution of Boc-L-Lys(Cbz)-OH (5 g, 13.18 mmol), 5-aminotetrazole monohydrate (1.36 g, 13.18 mmol) and N,N-diisopropylethylamine (DIPEA) (5.1 g 6.9 mL, 39.54 mmol) in 20 mL of dimethylformamide (DMF) at ambient temperature was added benzotriazol-1-yl-oxy-tris-(dimethylamino)phosphonium hexafluorophosphate (BOP) (6.4 g, 14.49 mmol).

After being stirred for 1 h, the reaction mixture was concentrated under vacuum. The residue was distributed between 60 mL of ethyl acetate (EtOAc) and 50 mL of water. The layers were separated. The organic layer was washed with 50 mL of 1M $KHSO_4$ solution and 2 times with 50 mL of water. The product started to precipitate and the suspension was concentrated in vacuum giving 9 g of crude compound. After drying, the product was purified by boiling in methylene chloride followed by filtration, giving 3.7 g of 1A (62.7%). The compound was characterized by $^1H$ NMR.

NN-2 (2 g, 4.5 mmol) was reduced under catalytic hydrogenation conditions using Pd black at 5 psi in 50% EtOH/AcOH solution for 12 h, giving 1.55 g (100%) of NN-2. The compound was characterized by $^1H$ NMR.

NN-3 To a stirring solution of NN-2 (1.55 g, 4.15 mmol) and methyl acetimidate hydrochloride (0.91 g, 8.31 mmol) in 25 mL of DMF was added triethylamine (TEA) (1.26 g, 1.74 mL, 12.45 mmol). After being stirred 16 h at ambient temperature, the reaction mixture was filtered from triethylamine hydrochloride and the filtrate was concentrated in vacuum. The residue was dissolved in 50% AcOH and lyophilized. The crude product (2 g) was purified using reverse-phase chromatography on a C-18 column giving 0.9 g (52.3%) of 1C. The product was characterized by $^1H$ NMR.

NN-4 (0.9 g, 2.17 mmol) was dissolved in 30 mL of acetic acid and 3 mL of 4 N HCl/dioxane were added. The reaction was stirred for 20 min. at ambient temperature then 150 mL of ethyl ether were added. After 2 h, the precipitate was filtered, washed with ethyl ether, and dried giving 0.78 g of 1 (96%). Anal. Calcd. for $C_9H_{18}N_8O,2HCl, 1.25H_2O$: C, 30.91; H, 6.48; N, 32.04; Cl, 20.27. Found: C, 31.64; H, 6.43; N, 32.19; Cl, 20.19. DSC mp 144.9° C.

Example NN is a more potent i-NOS inhibitor than 2S-amino-6-[(1-iminoethyl)amino]hexanamide (NIL amide) or NIL dimethylamide Example 1 is also more selective. Example NN is a nicely crystalline product as is all its intermediates. In contrast, NIL is a glass which makes it difficult to handle.

c. NSAIDS and Cyclooxygenase-2 Selective Inhibitors

The present invention is also directed to combinations comprising an iNOS selective inhibitor and an inhibitor of cyclooxegenase, such as, for example aspirin, indomethacin, sulindac, etodolac, mefenamic acid, tolmetin, ketorolac, diclofenac, ibuprofen, naproxen, fenoprofen, ketoprofen, oxaprozin, flurbiprofen, piroxicam, tenoxicam, phenylbutazone, apazone, or nimesulide or a pharmaceutically acceptable salt or derivative or prodrug thereof.

The present invention is further directed to combinations comprising an iNOS selective inhibitor and a cyclooxygenase-2 inhibitor. The present invention preferably includes compounds which selectively inhibit cyclooxygenase-2 over cyclooxygenase-1. In one embodiment, the compounds have a selectivity ratio of cyclooxygenase 2 inhibition over cyclooxygenase-1 inhibition of at least 50, and in another embodiment have a selectivity ratio of at least 100. Such selectivity ratios may indicate an ability to reduce the incidence of common NSAID-induced side effects.

In one embodiment, the combination is a pharmaceutical composition comprising an iNOS selective inhibitor and a cyclooxygenase-2 inhibitor.

A class of selective cyclooxygenase-2 inhibiting agents useful in the present invention include compounds of Formula 1:

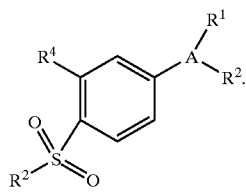

wherein A is a 5- or 6-member ring substituent selected from partially unsaturated or unsaturated heterocyclo and carboxcyclic rings, wherein A is optionally substituted with one or more radicals selected from alkyl, halo, oxo, and alkoxy;

wherein $R^1$ is selected from cyclohexyl, pyridinyl, and phenyl, wherein cyclohexyl, pyridinyl, or phenyl are optionally substituted with one or more radicals selected from alkyl, haloalkyl, cyano, carboxyl, alkoxycarbonyl, hydroxyl, hydroxyalkyl, haloalkoxy, amino, alkylamino, phenylamino, nitro, alkoxyalkyl, alkylsulfinyl, halo, alkoxy, and alkylthio;

wherein $R^2$ is selected from alkyl and amino;

wherein $R^3$ is a radical selected from halo, alkyl, alkenyl, alkynyl, aryl, heteroaryl, oxo, cyano, carboxyl, cyanoalkyl, heterocyclyloxy, alkyloxy, alkylthio, alkylcarbonyl, cycloalkyl, phenyl, haloalkyl, heterocyclo, cycloalkenyl, phenylalkyl, heterocyclylalkyl, alkylthioalkyl, hydroxyalkyl, alkoxycarbonyl, phenylcarbonyl, phenylalkylcarbonyl, phenylalkenyl, alkoxyalkyl, phenylthioalkyl, phenyloxyalkyl, alkoxyphenylalkoxyalkyl, alkoxycarbonylalkyl, aminocarbonyl, aminocarbonylalkyl, alkylaminocarbonyl, N-phenylaminocarbonyl, N-alkyl-N-phenylaminocarbonyl, alkylaminocarbonylalkyl, carboxyalkyl, alkylamino, N-arylamino, N-arylkylamino, N-alkyl-N-arylkylamino, N-alkyl-N-arylamino, aminoalkyl, alkylaminoalkyl, N-phenylaminoalkyl, N-phenylalkylaminoalkyl, N-alkyl-N-phenylalkylaminoalkyl, N-alkyl-N-phenylaminoalkyl, phenyloxy, phenylalkoxy, phenylthio, phenylalkylthio, alkylsulfinyl, alkylsulfonyl, aminosulfonyl, alkylaminosulfonyl, Nphenylaminosulfonyl, phenylsulfonyl, and N-alkyl-N-phenylaminosulfonyl; and wherein $R^4$ is selected from hydrido and halo;

or a pharmaceutically-acceptable salt thereof.

Within Formula 1 there is a subclass of compounds of particular interest wherein A is selected from thienyl, oxazolyl, furyl, furanone, pyrrolyl, thiazolyl, imidazolyl, benzofuryl, indenyl, benzithienyl, isoxazolyl, pyrazolyl, cyclopentenyl, cyclopentadienyl, benzindazolyl, cyclopentenone, benzopyranopyrazolyl, phenyl, and pyridyl;

wherein $R^1$ is selected from cyclohexyl, pyridinyl, and phenyl, wherein cyclohexyl, pyridinyl, or phenyl is substituted with one or more radicals selected from $C_{1-2}$ alkyl, $C_{1-2}$ haloalkyl, cyano, carboxyl, $C_{1-2}$ alkoxycarbonyl, hydroxyl, $C_{1-2}$ hydroxyalkyl, $C_{1-2}$ haloalkoxy, amino, $C_{1-2}$ alkylamino, phenylamino, nitro, $C_{1-2}$ alkoxy-$C_{1-2}$-alkyl, $C_{1-2}$ alkylsulfinyl, $C_{1-2}$ alkoxy, halo, alkoxy, and $C_{1-2}$ alkylthio;

wherein $R^2$ is selected from alkyl and amino;

wherein $R^3$ is a radical selected from halo, $C_{1-2}$ alkyl, $C_{2-3}$ alkenyl, $C_{2-3}$ alkynyl, aryl, heteroaryl, oxo, cyano, carboxyl, cyano-$C_{1-3}$-alkyl, heterocyclyloxy, $C_{1-3}$ alkyloxy, alkylthio, alkylcarbonyl, cycloalkyl, phenyl, $C_{1-3}$ haloalkyl, heterocyclo, cycloalkenyl, phenyl-$C_{1-3}$-alkyl, heterocyclyl- $C_{1-3}$-alkyl, $C_{1-3}$ alkylthio-$C_{1-3}$-alkyl, $C_{1-3}$ hydroxyalkyl, $C_{1-3}$ alkoxycarbonyl, phenylcarbonyl, phenyl-$C_{1-3}$-alkylcarbonyl, phenyl-$C_{2-3}$-alkenyl, $C_{1-3}$ alkoxy-$C_{1-3}$-alkyl, phenylthio-$C_{1-3}$-alkyl, phenylyloxyalkyl, alkoxyphenylalkoxyalkyl, alkoxycarbonylalkyl, aminocarbonyl, aminocarbonyl-$C_{1-3}$-alkyl, $C_{1-3}$ alkylaminocarbonyl, N-phenylaminocarbonyl, N-$C_{1-3}$ alkyl-N-phenylaminocarbonyl, $C_{1-3}$ alkylaminocarbonyl-$C_{1-3}$-alkyl, carboxy-$C_{1-3}$-alkyl, $C_{1-3}$ alkylamino, N-arylamino, N-arylkylamino, N-$C_{1-3}$ alkyl-N-arylkylamino, N-$C_{1-3}$ alkyl-N-arylamino, amino-$C_{1-3}$-alkyl, $C_{1-3}$ alkylaminoalkyl, N-phenylamino-$C_{1-3}$-alkyl, N-phenyl-$C_{1-3}$-alkylaminoalkyl, N-$C_{1-3}$ alkyl-N-phenyl-$C_{1-3}$-alkylamino-$C_{1-3}$-alkyl, N-$C_{1-3}$ alkyl-N-phenylamino-$C_3$-alkyl, phenyloxy, phenylalkoxy, phenylthio, phenyl-$C_{1-3}$-alkylthio, $C_{1-3}$ alkylsulfinyl, $C_{1-3}$ alkylsulfonyl, aminosulfonyl, $C_{1-3}$ alkylaminosulfonyl, N-phenylaminosulfonyl, phenylsulfonyl, and N-$C_{1-3}$ alkyl-N-phenylaminosulfonyl; and wherein $R^4$ is selected from hydrido and halo;

or a pharmaceutically-acceptable salt thereof.

Another class of compounds within Formula 1 of even more interest include compounds wherein A is substituted with one or more radicals selected from alkyl, halo, oxo, and alkoxy;

wherein $R^1$ is selected from pyridyl, cyclohexyl, and phenyl, wherein pyridyl, cyclohexyl, or phenyl is optionally substituted with one or more radicals selected from alky, halo, and alkoxy;

wherein $R^2$ is $C_{1-2}$ alkyl or amino;

wherein $R^3$ is a radical selected from halo, $C_{1-2}$ alkyl, cyano, carboxyl, $C_{1-2}$ alkyloxy, phenyl, C1–2 haloalkyl, and $C_{1-2}$ hydroxyalkyl; and wherein $R^4$ is selected from hydrido and fluoro;

or a pharmaceutically-acceptable salt thereof.

A family of specific compounds within Formula 1 of particular interest include compounds and pharmaceutically-acceptable salts thereof, as follows:

C1)

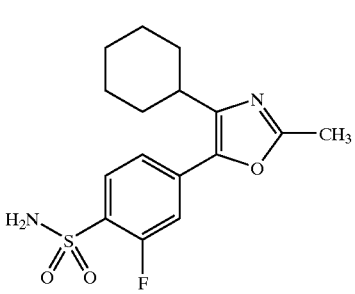

4-(4-cyclohexyl-2-methloxazol-5-yl)-2-fluorobenzenesulfonamide;

C2)

5-chloro-3-(4-(methylsulfonyl)phenyl)-2-(methyl-5-pyridine;

C3)

2-(3,5-difluorophenyl)-3-4-(methylsulfonyl)phenyl)-2-cyclopenten-1-one;

C4)

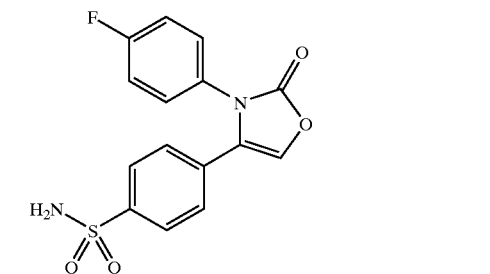

4-[5-(4-methylphenyl)-3-(trifluoromethyl)-1H-pyrazol-1-yl]-benzenesulfonamide;

C5)

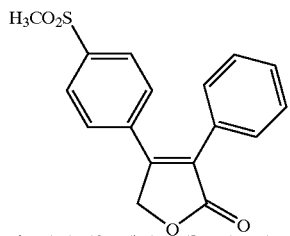

4-(4-(methylsulfonyl)phenyl]-3-phenyl-2(5H)-furanone;

C6)

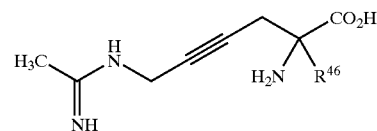

4-(5-methyl-3-phenylisoxazol-4-yl)benzenesulfonamide;

C7)

N-[[4-(5-methyl-3-phenylisoxazol-4yl]phenyl]sulfonyl]propanamide:

C8)

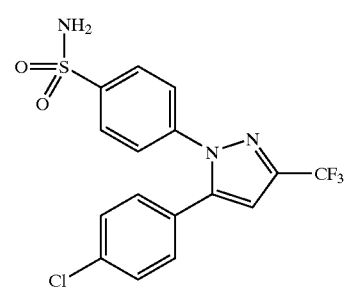

4-[5-(4-chorophenyl)-3-(trifluoromethyl)-1H-pyrazole-1-yl]benzenesulfonamide;

C9)

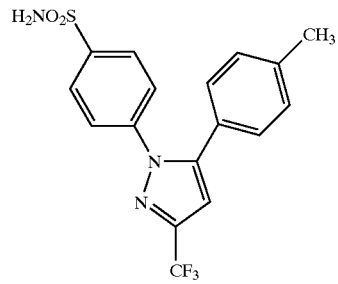

3-(4-chlorophenyl)-4-[4-methylsulfonyl)phenyl]-2(3H)-oxazolone;

C10)

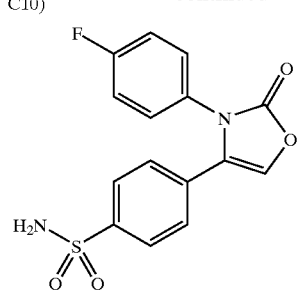

4-[3-(4-fluorophenyl)-2,3-dihydro-2-oxo-4-oxazolyl]benzenesulfonamide;

C11)

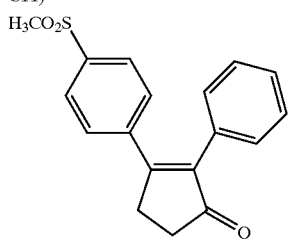

3-[4-(methylsulfonyl)phenyl]-2-phenyl-2-cyclopenten-1-one;

C12)

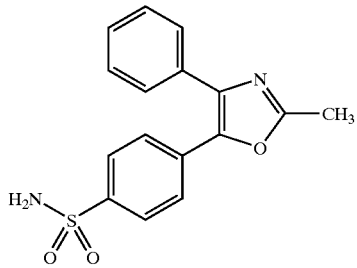

4-(2-methyl-4-phenyl-5-oxazolyl)benzenesulfonamide;

C13)

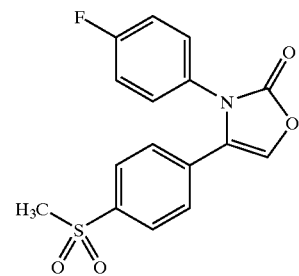

3-(4-fluorophenyl)-4-[4-(methylsulfonyl)phenyl]-2(3H)-oxazolone;

C14)

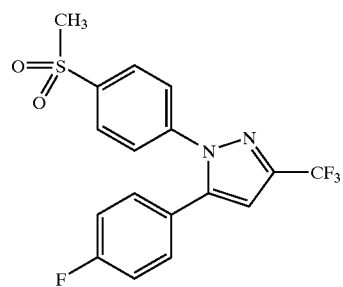

5-(4-fluorophenyl)-1-[4-(methylsulfonyl)phenyl]-3-(trifluoromethyl)-1H-pyrazole;

C15)

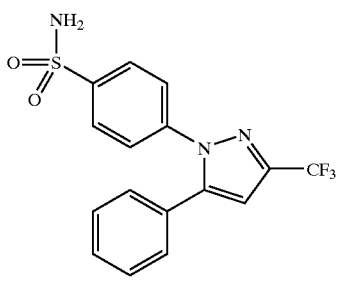

4-[5-phenyl)-3-(trifluoromethyl)-1H-pyrazol-1-yl]benzenesulfonamide;

C16)

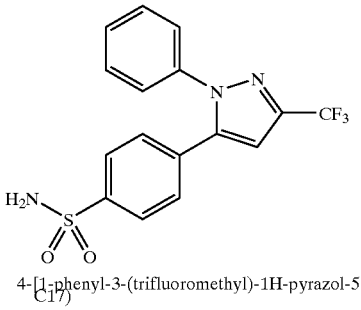

4-[1-phenyl-3-(trifluoromethyl)-1H-pyrazol-5-yl]benzenesulfonamide;

C17)

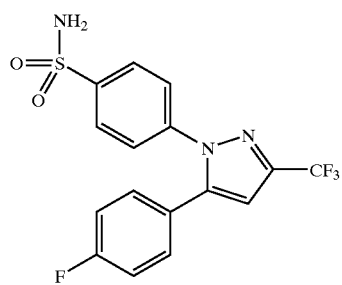

4-[5-(4-fluorophenyl)-3-(trifluoromethyl)-1H-pyrazol-1-yl]benzenesulfonamide;

C18)

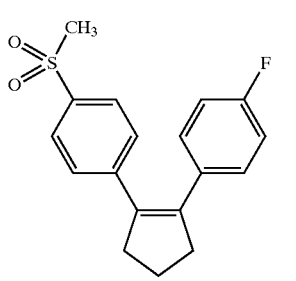

1-fluoro-4-[2-[4-(methylsulfonyl)phenyl]cyclopenten-1-yl]benzene;

C19)

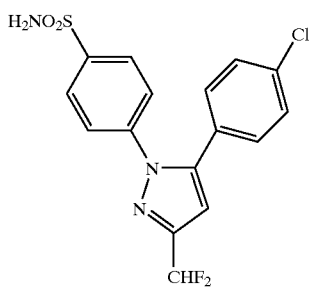

4-[5-(4-chloropheynl)-3-(difluoromethyl)-1H-pyrazol-1-yl]benzenesulfonamide;

C20)

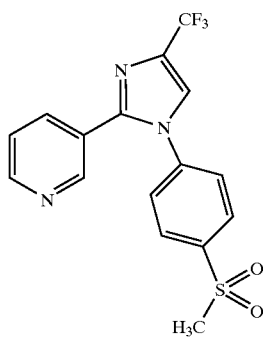

3-[1-[4-(methylsulfonyl)phenyl]-4-(trifluoromethyl)-1H-imidazol-2-yl]pyridine;

C21)

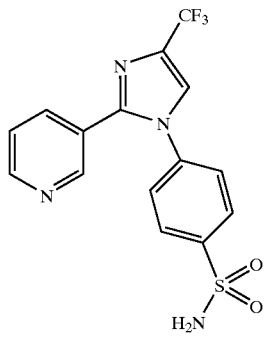

4-[2-(3-pyridinyl)-4-(trifluoromethyl)-1H-imidazol-1-yl]benzenesulfonamide;

C22)

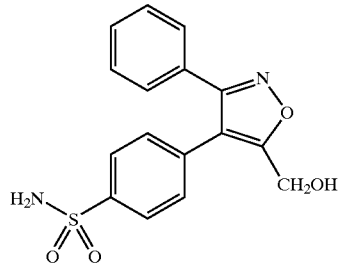

4-[5-(hydroxymethyl)-3-phenylisoxazol-4-yl]benzenesulfonamide;

C23)

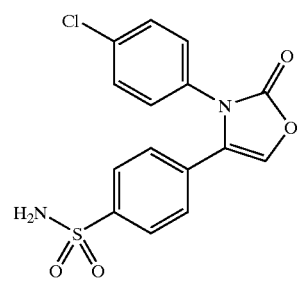

4-[3-(4-chlorophenyl)-2,3-dihydro-2-oxo-4-oxazolyl]benzenesulfonamide;

C24)

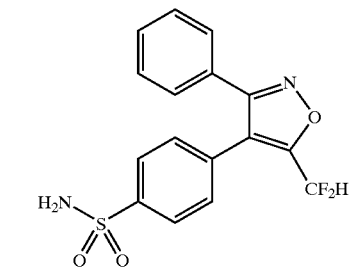

4-[5-difluoromethyl)-3-phenylisoxazol-4-yl]benzenesulfonamide;

C25)

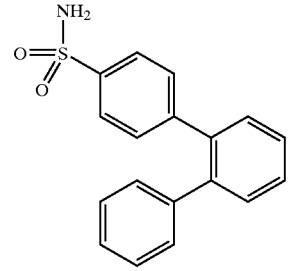

[1,1':2',1''-terphenyl]-4-sulfonamide;

C26)

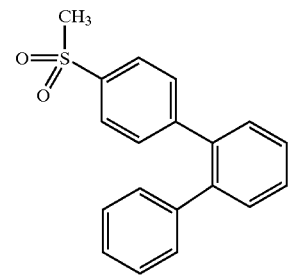

4-(methylsulfonyl)-1,1':2],1''-terphenyl;

C27)

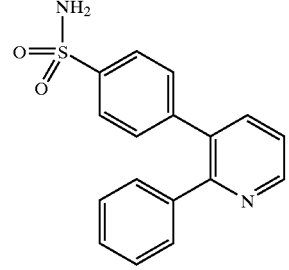

4-(2-phenyl-3-pyridinyl)benzenesulfonamide;

C28)

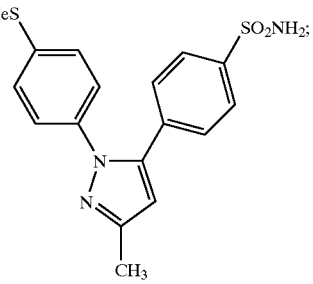

C29)

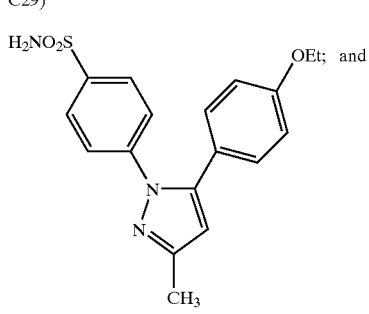

C30)

2-(6-methylpyrid-3-yl)-3-(4-methylsulfinylphenyl)-5-chloropyridine.

Additional specific compounds of particular interest within Formula I include each of the compounds and pharmaceutically-acceptable salts thereof as follows:

4-(4-cyclohexyl-2-methyloxazol-5-yl)-2-fluorobenzenesulfonamide,
4-(4-(methylsulfonyl)phenyl]-3-phenyl-2(5H)-furanone,
2-(6-methylpyrid-3-yl)-3-(4-methylsulfinylphenyl)-5-chloropyridine:

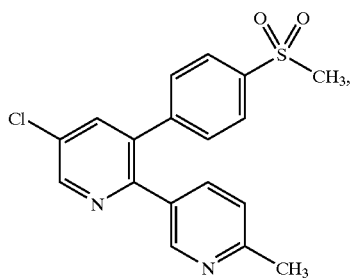

4-[5-(4-methylphenyl)-3-(trifluoromethyl)-1H-pyrazol-1-yl]-benzenesulfonamide,
4-(4-(methylsulfonyl)phenyl]-3-phenyl-2(5H)-furanone,
4-[5-(4-chorophenyl)-3-(trifluoromethyl)-1H-pyrazole-1-yl]benzenesulfonamide,
4-(4-cyclohexyl-2-methyloxazol-5-yl)-2-fluorobenzenesulfonamide,
5-chloro-3-(4-(methylsulfonyl)phenyl)-2-(methyl-5-pyridinyl)pyridine,
2-(3,5-difluorophenyl)-3-4-(methylsulfonyl)phenyl2-cyclopenten-1-one,
4-(4-(methylsulfonyl)phenyl]-3-phenyl-2(5H)-furanone,
4-[5-methyl-3-phenyl-isoxazol-4-yl] benzenesulfonamide, and
N-[[4-(5-methyl-3-phenylisoxazol-4-yl]phenyl]sulfonyl] propanamide.

In another embodiment of the invention the cyclooxygenase-2 selective inhibitor is preferably of the chromene structural class that is a substituted benzopyran or a substituted benzopyran analog, and even more preferably selected from the group consisting of substituted benzothiopyrans, dihydroquinolines, or dihydronaphthalenes having the general Formula II shown below and possessing, by way of example and not limitation, the structures disclosed in Table 3, including the diastereomers, enantiomers, racemates, salts, esters, amides and prodrugs thereof. Furthermore, benzopyran COX-2 selective inhibitors useful in the practice of the present invention are described in International publication WO/00/23433, U.S. Pat. Nos. 6,034,256 and 6,077,850 herein incorporated by reference.

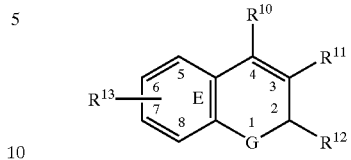

II wherein G is selected from the group consisting of O or S or $NR^a$; wherein $R^a$ is alkyl;

wherein $R^{10}$ is selected from the group consisting of H and aryl wherein $R^{11}$ is selected from the group consisting of carboxyl, aminocarbonyl, alkylsulfonylaminocarbonyl and alkoxycarbonyl;

wherein $R^{12}$ is selected from the group consisting of haloalkyl, alkyl, aralkyl, cycloalkyl and aryl optionally substituted with one or more radicals selected from alkylthio, nitro and alkylsulfonyl; or wherein $R^{13}$ is selected from the group consisting of one or more radicals selected from H, halo, alkyl, aralkyl, alkoxy, aryloxy, heteroaryloxy, aralkyloxy, heteroaralkoxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, hydroxyarylcarbonyl, nitroaryl, optionally substituted aryl, optionally substituted heteroaryl, aralkylcarbonyl, heteroarylcarbonyl, arylcarbonyl, aminocarbonyl, and alkylcarbonyl;

or wherein $R^{13}$ together with ring E forms a naphthyl radical; or an isomer or pharmaceutically acceptable salt thereof, such as, for example the compounds shown in table 3:

TABLE 3

Examples of Chromene COX-2 Selective Inhibitors as Embodiments

| Compound Number | Structural Formula |
|---|---|
| C-31 | ![structure] 6-Nitro-2-trifluoromethyl-2H-1-benzopyran-3-carboxylic acid |
| C-32 | ![structure] 6-Chloro-8-methyl-2-trifluoromethyl-2H-1-benzopyran-3-carboxylic acid |

TABLE 3-continued

Examples of Chromene COX-2 Selective Inhibitors as Embodiments

| Compound Number | Structural Formula |
|---|---|
| C-33 | ((S)-6-Chloro-7-(1,1-dimethylethyl)-2-(trifluoromethyl-2H-1-benzopyran-3-carboxylic acid |
| C-34 | 2-Trifluoromethyl-2H-naphtho[2,3-b]pyran-3-carboxylic acid |
| C-35 | 6-Chloro-7-(4-nitrophenoxy)-2-(trifluoromethyl)-2H-1-benzopyran-3-carboxylic acid |
| C-36 | ((S)-6,8-Dichloro-2-(trifluoromethyl)-2H-1-benzopyran-3-carboxylic acid |
| C-37 | 6-Chloro-2-(trifluoromethyl)-4-phenyl-2H-1-benzopyran-3-carboxylic acid |
| C-38 | 6-(4-Hydroxybenzoyl)-2-(trifluoromethyl)-2H-1-benzopyran-3-carboxylic acid |
| C-39 | 2-(Trifluoromethyl)-6-[(trifluoromethyl)thio]-2H-1-benzothiopyran-3-carboxylic acid |
| C-40 | 6,8-Dichloro-2-trifluoromethyl-2H-1-benzothiopyran-3-carboxylic acid |
| C-41 | 6-(1,1-Dimethylethyl)-2-(trifluoromethyl)-2H-1-benzothiopyran-3-carboxylic acid |
| C-42 | 6,7-Difluoro-1,2-dihydro-2-(trifluoromethyl)-3-quinolinecarboxylic acid |
| C-43 | 6-Chloro-1,2-dihydro-1-methyl-2-(trifluoromethyl)-3-quinolinecarboxylic acid |
| C-44 | 6-Chloro-2-(trifluoromethyl)-1,2-dihydro[1,8]naphthyridine-3-carboxylic acid |

TABLE 3-continued

Examples of Chromene COX-2 Selective Inhibitors as Embodiments

| Compound Number | Structural Formula |
|---|---|
| C-45 | 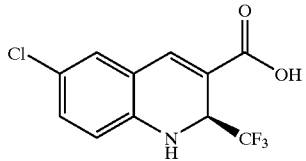<br>((S)-6-Chloro-1,2-dihydro-2-(trifluoromethyl)-3-quinolinecarboxylic acid |
| C-46 | 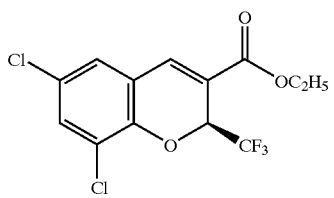<br>6,8-Dichloro-2-(trifluoromethyl)-2H-1 benzopyran-3-ethyl acetate |
| C-47 | 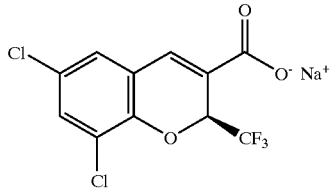<br>Sodium 6,8-Dichloro-2-(trifluoromethyl)-2H-1 benzopyran-3-carboxylate |
| C-48 | 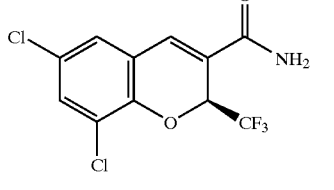<br>6,8-Dichloro-2-(trifluoromethyl)-2H-1 benzopyran-3-carboxamide |

Additional Cyclooxygenase-2 selective inhibitors advantageously employed in the combination therapy of the present invention include:

C-49)

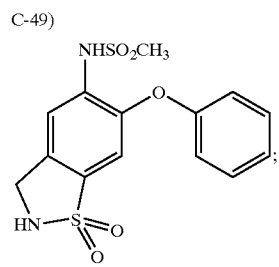

C-50)

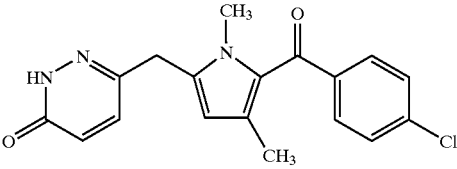

RS 57067, 6-[[5-(4-chlorobenzoyl)-1,4-dimethyl-1H-pyrrol-2-yl]methyl]-3(2H)-pyridazinone, (CAS registry number 179382-91-3);

C-51)

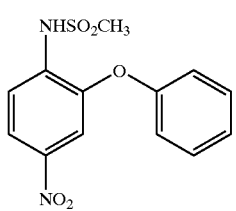

N-(4-nitro-2-phenoxyphenyl)methanesulfonamide;

C-52)

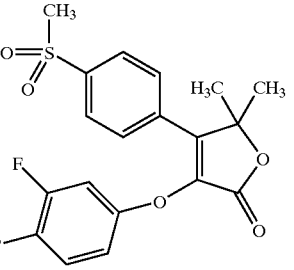

3-(3,4-difluorophenoxy)-5,5-dimethyl-4-[4-(methylsulfonyl)phenyl]-2(5H)-furanone;

C-53)

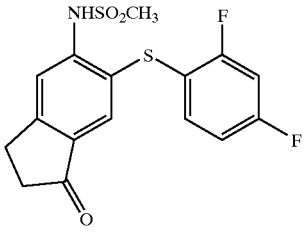

N-[6-[(2,4-difluorophenyl)thio]-2,3-dihydro-1-oxo-1H-inden-5-yl]methanesulfonamide;

C-54)

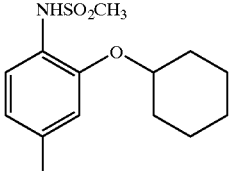

N-[2-(cyclohexyloxy)-4-nitrophenyl]methanesulfonamide;

C-55)

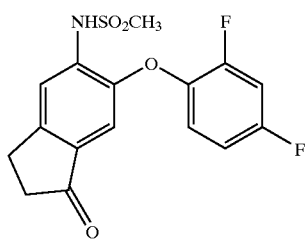

N-[6-(2,4-difluorophenoxy)-2,3-dihydro-1-oxo-1H-inden-5-yl]methanesulfonamide;

C-56)

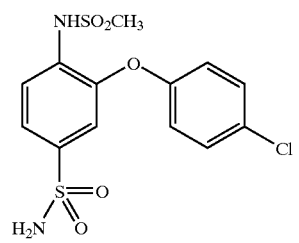

3-(4-chlorophenoxy)-4-[(methylsulfonyl)amino]benzenesulfonamide;

C-57)

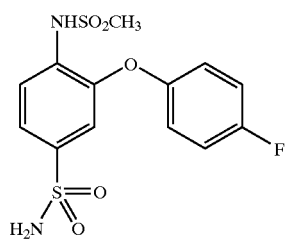

3-(4-fluorophenoxy)-4-[(methylsulfonyl)amino]benzenesulfonamide;

C-58)

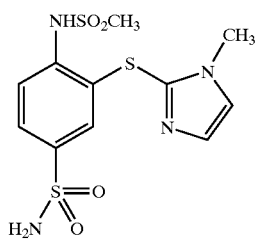

3-[(1-methyl-1H-imidazol-2-yl)thio]-4[(methylsulfonyl)amino]benzenesulfonamide;

C-59)

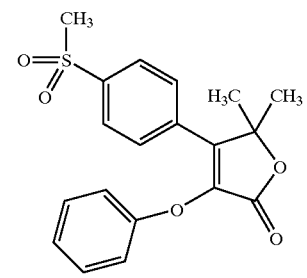

5,5-dimethyl-4-[4-(methylsulfonyl)phenyl]-3-phenoxy-2(5H)-furanone;

C-60)

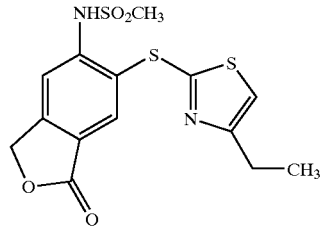

N-[6-[(4-ethyl-2-thiazolyl)thio]-1,3-dihydro-1-oxo-5-isobenzofuranyl]methanesulfonamide;

C-61)

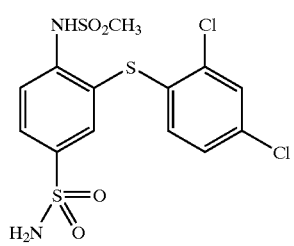

3-[(2,4-dichlorophenyl)thio]-4-[(methylsulfonyl)amino]benzenesulfonamide;

C-62)

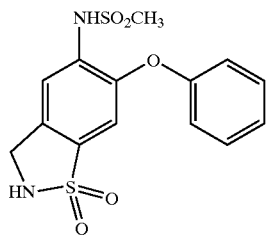

N-(2,3-dihydro-1,1-dioxido-6-phenoxy-1,2-benzisothiazol-5-yl)methanesulfonamide;

C-63)

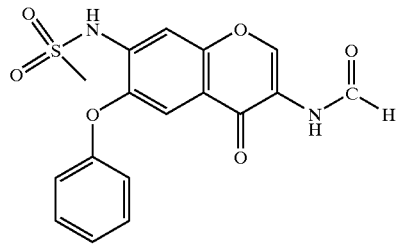

N-[3-(formylamino)-4-oxo-6-phenoxy-4H-1-benzopyran-7-yl]methanesulfonamide;

and

C-64)

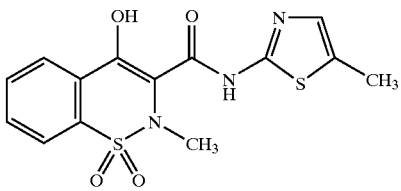

Meloxicam, (CAS registry number 71125-38-7)

In another embodiment of the invention, the compound ABT-963 having the formula C-66 that has been previously described in International Publication number WO 00/24719 (which is herein incorporated by reference), is another tricyclic cyclooxygenase-2 selective inhibitor which may be advantageously employed in the combination therapy of the present invention.

C-66)

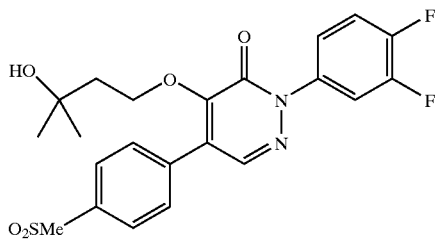

In another embodiment of the present invention, the Cyclooxygenase-2 selective inhibitor is COX-189, Novartis AG, Basel, Switzerland, formula C-67:

C-67)

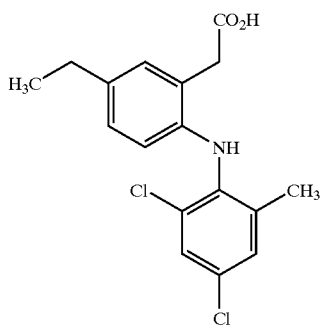

In another embodiment of the present invention, the Cyclooxygenase-2 selective inhibitor is Formula C-68, JTE 522.

C-68)

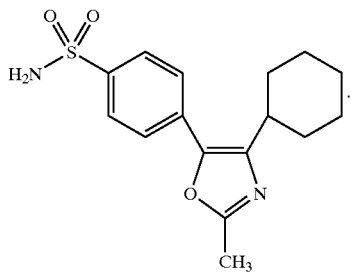

Derivatives are intended to encompass any compounds which are structurally related to the cyclooxygenase-2 inhibitors or which possess the substantially equivalent biologic activity. By way of example, such inhibitors may include, but are not limited to, prodrugs thereof.

In another embodiment of the invention the cyclooxygenase-2 selective inhibitor represented by the above Formula 1 is selected from the group of compounds, consisting of celecoxib (C4; described in U.S. Pat. No. 5,466,823, herein incorporated by reference), valdecoxib (C6), deracoxib, rofecoxib (C5; described in U.S. Pat. No. 5,474,955, herein incorporated by reference), etoricoxib (MK-663; C30), JTE-522 (C68), or a pharmaceutically acceptable salt or prodrug thereof.

d. Combinations

The therapeutic combinations of the present invention have a number of uses. For example, through dosage adjustment and medical monitoring of the subject, the dosage of each therapeutic compound as used in the therapeutic combinations is lower than the dosage of each therapeutic compound typically used when administering the compounds individually in monotherapy. The dosage reduction would provide advantages such as reducing the side effects produced by the individual therapeutic compounds when administered at the higher doses typically used in monotherapy. In addition, patients would be likely to be more compliant with a therapy regimen that produces fewer side effects.

The combinations of the present invention are useful for the prevention or treatment of colorectal cancer. The method can be also used to treat subjects having adenomatous polyps, including those with familial adenomatous polyposis (FAP). Additionally, the method can be used to prevent polyps from forming in patients at risk of FAP.

In addition, the combinations of the present invention would be useful for the prevention or treatment of other neoplasias including brain cancer, bone cancer, and epithelial cell-derived neoplasias (epithelial carcinomas) such as basal cell carcinoma, adenocarcinoma, gastrointestinal cancer such as lip cancer, mouth cancer, esophogeal cancer, small bowel cancer and stomach cancer, liver cancer, bladder cancer, pancreatic cancer, ovarian cancer, cervical cancer, lung cancer, breast cancer and skin cancer, such as melanoma, squamous cell and basal cell cancers, prostate cancer, renal cell carcinoma, and other known cancers that effect epithelial cells throughout the body. Preferably, neoplasia is selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The combinations could also be used to treat the fibrosis which occurs with radiation therapy.

e. Dosages, Formulations and Routes of Administration

Many of the compounds useful in the present invention can have at least two asymmetric carbon atoms, and therefore include racemates and stereoisomers, such as diastereomers and enantiomers, in both pure form and in admixture. Such stereoisomers can be prepared using conventional techniques, either by reacting enantiomeric starting materials, or by separating isomers of compounds of the present invention. Isomers may include geometric isomers, for example cis-isomers or trans-isomers across a double bond. All such isomers are contemplated among the compounds useful in the present invention. The compounds useful in the present invention also include tautomers. The compounds useful in the present invention also include their salts, solvates and prodrugs.

Suitable routes of administration of the combinations of the present invention for the prophylaxis and treatment of colorectal cancer and adenomatous polyps include any means that produce contact of these compounds with their site of action in the subject's body, for example in the ileum of a mammal such as a human. More specifically, suitable routes of administration include oral, intravenous, subcutaneous, rectal, topical, buccal (i.e. sublingual), intramuscular, and intradermal. In an exemplary embodiment, the combinations are orally administered.

For the prophylaxis or treatment of neoplasia and neoplasia-related conditions, such as colorectal cancer and other epithelial cell-derived cancers, as well as leukemias and lymphomas, the compounds useful in the present invention can be used in the combinations as the compound per se. Pharmaceutically acceptable salts are particularly suitable for medical applications because of their greater solubility relative to the parent compound. Such salts must clearly have a pharmaceutically acceptable anion or cation. Suitable pharmaceutically acceptable acid addition salts of the compounds of the present invention include when possible include those derived from inorganic acids, such as hydrochloric, hydrobromic, phophoric, metaphosphoric, nitric, sulfonic, sulfuric acids, and organic acids such as acetic, benzenesulfonic, benzoic, citric, ethanesulfonic, fumaric, gluconic, glycolic, isotho9nic, lactic, lactobionic, maleic, malic, methanesulfonic, succinic, toluenesulfonic, tartaric, and trifluoroacetic acids. The chloride salt is especially suitable for medical purposes. Suitable pharmaceutically acceptable base salts include ammonium salts, alkali metal salts such as sodium and potassium salts, and alkaline earth salts such as magnesium and calcium salts.

In one embodiment, the combinations useful in the present invention are presented with an acceptable carrier in the form of a pharmaceutical combination. The carrier must be acceptable in the sense of being compatible with the other ingredients of the pharmaceutical combination and must not be deleterious to the subject. Suitable forms for the carrier include solid or liquid or both, and in an exemplary embodiment the carrier is formulated with the therapeutic compound as a unit-dose combination, for example as a tablet that contains from about 0.05% to about 95% by weight of the active compound. In alternative embodiments, other pharmacologically active substances are also present, including other compounds of the present invention. The pharmaceutical combinations of the present invention are prepared by any of the well-known techniques of pharmacy, consisting essentially of admixing the ingredients.

Preferred unit dosage formulations are those containing an effective dose, as herein below described, or an appropriate fraction thereof, of one or more of the therapeutic compounds of the combinations.

In general, a total daily dose of an iNOS selective inhibitor in the combinations is in the range of about 0.001 mg/kg body weight/day to about 2500 mg/kg body weight/day. The dose range for adult humans is generally from about 0.005 mg to about 10 g per day. Tablets or other forms of presentation provided in discrete units may conveniently contain an amount of a therapeutic compound of the combinations of the present invention, the amount being effective at such dosage, or at a multiple of the same. For instance, iNOS selective compounds of the combinations of the present invention can be presented in units containing 5 mg to 500 mg, and typically around 10 mg to about 200 mg.

In general, a total daily dose of a cyclooxygenase-2 inhibitor in the combinations is in the range of about 0.3 to about 100 mg/kg body weight/day, preferably from about 1 mg to about 50 mg/kg body weight/day, and more preferably from about 3 mg to about 10 mg/kg body weight/day.

In the case of pharmaceutically acceptable salts of the therapeutic compounds, the weights indicated above refer to the weight of the acid equivalent or the base equivalent of the therapeutic compound derived from the salt.

It should be understood that the amount of each compound that is required to achieve the desired biological effect of the combination depends on a number of factors such as the specific individual compounds chosen, the specific use for which it is intended, the route of administration, the clinical condition of the subject, and the age, weight, gender, and diet of the subject.

The daily doses described in the preceding paragraphs for the various therapeutic compounds are administered in a single dose, or in proportionate multiple subdoses. Subdoses are administered from two to six times per day. In one embodiment, doses are administered in sustained release form effective to obtain the desired biological effect.

Oral delivery of the combinations of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small intestine, slow erosion of a tablet or capsule, retention in the stomach based on physical properties of the formulation, bioadhesion of the dosage form to the mucosal lining of the intestinal tract, or enzymatic release of the active drug from the dosage form.

Oral delivery of the combinations of the present invention can be achieved using a solid, semi-solid or liquid dosage form. Suitable semi-solid and liquid forms include, for example, a syrup or liquid contained in a gel capsule.

Pharmaceutical compositions suitable for oral administration can be presented in discrete units, such as capsules, cachets, lozenges, or tablets, each containing a predetermined amount of at least one of the therapeutic compounds useful in the combinations of the present invention; as a powder or in granules; as a solution or a suspension in an aqueous or non-aqueous liquid; or as an oil-in-water or water-in-oil emulsion.

f. Biological Assays of Utility

The utility of the combinations of the present invention is shown by the following assays performed in animal models using procedures recognized to show the utility of the present invention.

Citrulline Assay for Nitric Oxide Synthase

Nitric oxide synthase (NOS) activity can be measured by monitoring the conversion of L-[2,3-$^3$H]-arginine to L-[2,3-$^3$H]-citrulline (Bredt and Snyder, Proc. Natl. Acad. Sci. U.S.A., 87, 682–685, 1990 and Moore et al, J. Med. Chem., 39, 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a ?cDNA library made from RNA extracted from a colon sample from a patient with ulcerative colitis. The cDNA for human endothelial constitutive NOS (hecNOS) is isolated from a λcDNA library made from RNA extracted from human umbilical vein endothelial cells (HUVEC) and the cDNA for human neuronal constitutive NOS (hncNOS) is isolated from a λcDNA library made from RNA extracted from human cerebellum obtained from a cadaver. The recombinant enzymes are expressed in Sf9 insect cells using a baculovirus vector (Rodi et al, in The Biology of Nitric Oxide, Pt. 4: Enzymology, Biochemistry and Immunology; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 µL of enzyme is added to 40 µL of 50 mM Tris (pH 7.6) in the presence or absence of test compounds and the reaction initiated by the addition of 50 µL of a reaction mixture containing 50 mM Tris (pH 7.6), 2.0 mg/mL bovine serum albumin, 2.0 mM DTT, 4.0 mM $CaCl_2$, 20 µM FAD, 100 µM tetrahydrobiopterin, 0.4 mM NADPH and 60 µM L-arginine containing 0.9 µCi of L-[2,3-³H]-arginine. The final concentration of L-arginine in the assay is 30 µM. For hecNOS or hncNOS, calmodulin is included at a final concentration of 40–100 nM. Following incubation at 37° C. for 15 minutes, the reaction is terminated by addition of 400 µL of a suspension (1 part resin, 3 parts buffer) of Dowex 50W X-8 cation exchange resin in a stop buffer containing 10 mM EGTA, 100 mM HEPES, pH 5.5 and 1 mM L-citrulline. After mixing the resin is allowed to settle and L-[2,3-³H]-Citrulline formation is determined by counting aliquots of the supernatant with a liquid scintillation counter. Results are reported in Table I as the $IC_{50}$ values of compounds for hiNOS, hecNOS and hncNOS.

Raw Cell Nitrite Assay

RAW 264.7 cells can be plated to confluency on a 96-well tissue culture plate grown overnight (17 h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 µL of buffer containing L-arginine (30 µM)+/−inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite. T. P. Misko et al, *Analytical Biochemistry,* 214, 11–16 (1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 15–45 mg in weight and one or two explants per well are placed into either 96 or 48 well culture plates with 200–500 µL of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 µM L-Arginine (Sigma), 2 mM L-glutamine, 1X HL-1 supplement (BioWihittaker), 50 mg/ml ascorbic acid (Sigma) and 150 pg/ml recombinant human IL-1β (RD Systems) to induce nitric oxide synthase. Compounds are then added in 10 µL aliquots and the explants incubated at 37° C. with 5% $CO_2$ for 18–24 hours. The day old supernatant is then discarded and replaced with fresh culture media containing recombinant human IL-1? and compound and incubated for another 20–24 hours. This supernatant is analyzed for nitrite with a fluorometric assay (Misko et al, *Anal. Biochem.,* 214, 11–16, 1993). All samples are done in quadruplicate. Unstimulated controls are cultured in media in the absence of recombinant human IL-1β. $IC_{50}$ values (Table I) are determined from plotting the percent inhibition of nitrite production at six different concentrations of inhibitor.

Table I shows examples of biological activity for some of the compounds of the present invention.

TABLE I

Biological Activity: Values represent averages across all experiments and all lots studied.

| Example Number of Compound | hiNOS $IC_{50}$ (µM) | hecNOS $IC_{50}$ (µM) | hncNOS $IC_{50}$ (µM) | Human Cartilage $IC_{50}$ (µM) |
|---|---|---|---|---|
| Example A | 0.36 | 68 | 3.6 | 0.1 |
| Example B | 2.2 | 195 | 21 | 0.2 |
| Example C | 12 | 303 | 105 | |
| Example D | 8.6 | 112 | 65 | 2.5 |
| Example E | <5 | 279 | 29 | |
| Example I | 3.1 | 77 | 15 | 0.7 |
| Example J | 4.4 | 302 | 58 | 8.2 |
| Example K | 74 | 266 | 86 | |
| Example L | 197 | 1100 | 539 | |
| Example M | 3.4 | 78 | 17 | |
| Example N | 0.9 | 26 | 6.0 | |
| Example O | 7.2 | >100 | 36 | 0.7 |
| Example P | 12 | >100 | 181 | |
| Example Q | 12 | 1080 | 220 | |
| Example S | 172 | 1490 | 523 | |
| Example T | 0.9 | 89 | 8 | 0.1 |
| Example U | 20 | 418 | 150 | |
| Example V | <3 | >30 | >3 | <10 |
| Example W | <5 | >150 | >10 | >30 |
| Example X | <3 | >15 | >3 | <10 |
| Example Y | <3 | >30 | >3 | <10 |
| Example Z | <3 | >15 | >3 | <10 |
| Example AA | <3 | >5 | <3 | <3 |
| Example BB | <10 | >25 | <10 | |
| Example CC | 2.9 | 29 | 9.9 | 0.5 |
| Example DD | 10 | 74 | 31 | 1.8 |
| Example EE | 1.4 | 18 | 5.8 | 0.5 |

TABLE I-continued

Biological Activity: Values represent averages across all experiments and all lots studied.

| Example Number of Compound | hiNOS IC$_{50}$ ($\mu$M) | hecNOS IC$_{50}$ ($\mu$M) | hncNOS IC$_{50}$ ($\mu$M) | Human Cartilage IC$_{50}$ ($\mu$M) |
|---|---|---|---|---|
| Example FF | 16 | 86 | 45 | |
| Example GG | 34 | 386 | 122 | |
| Example HH | 0.4 | 37 | 7.6 | 0.4 |
| Example JJ | 56 | 352 | 584 | |
| Example KK | 0.57 | 52 | 13 | |
| Example LL | 0.7 | 31 | 12 | 0.8 |
| Example MM | 121 | 1930 | 1480 | |
| Example NN | 21.4 | 2425 | | |

In Vivo Assay

Rats can be treated with an intraperitoneal injection of 1–12.5 mg/kg of endotoxin (LPS) with or without oral administration of the nitric oxide synthase inhibitors. Plasma nitrite/nitrate levels can be determined 5 hours post-treatment. The results can be used to show that the administration of the nitric oxide synthase inhibitors decreases the rise in plasma nitrite/nitrate levels, a reliable indicator of the production of nitric oxide induced by endotoxin. As shown in Table II, Example A ((2S,5E)-2-amino-6-fluoro-7-[(1-iminoethyl)amino]-5-heptenoic acid, dihydrochloride) inhibited the LPS-induced increase in plasma nitrite/nitrate levels with an observed ED$_{50}$ value of <0.1 mg/kg, demonstrating the ability to inhibit inducible nitric oxide synthase activity in vivo.

TABLE II

ED$_{50}$'s for Compounds Determined in Endotoxin-Treated Rats
All compounds administered orally unless otherwise noted.

| Compound | ED$_{50}$ (mg/kg) |
|---|---|
| Example A | <0.1 |
| Example D | >10 |
| Example G | <0.1 |
| Example H | <0.3 |
| Example V | <3 |
| Example W | >10 |
| Example X | <5 |
| Example Y | <3 |
| Example Z | <5 |
| Example AA | <10 |
| Example CC | <3 |
| Example EE | 0.2 |
| Example HH | 0.4 |
| Example KK | 0.3 |
| Example LL | 0.3 |

Assay for Time Dependent Inhibition

Compounds are evaluated for time dependent inhibition of human NOS isoforms by preincubation of the compound with the enzyme at 37° C. in the presence of the citrulline enzyme assay components, minus L-arginine, for times ranging from 0–60 minutes. Aliquots (10 $\mu$L) are removed at 0, 10, 21 and 60 minutes and immediately added to a citrulline assay enzyme reaction mixture containing L-[2,3-$^3$H]-arginine and a final L-arginine concentration of 30 $\mu$M in a final volume of 100 $\mu$L. The reaction is allowed to proceed for 15 minutes at 37° C. and terminated by addition of stop buffer and chromatography with Dowex 50W X-8 cation exchange ion exchange resin as described for the citrulline NOS assay. The % inhibition of NOS activity by an inhibitor was taken as the percent inhibition in activity compared to control enzyme preincubated for the same time in the absence of inhibitor. Data shown in Table III is the % inhibition after 21 and 60 minutes preincubation of inhibitor with enzyme.

TABLE III

| Example No. | hiNOS | heeNOS | hncNOS |
|---|---|---|---|
| V | 75% @ 2.8 $\mu$M @ 21 min | 11% @ 33 $\mu$M @ 21 min | 0% @ 5 $\mu$M @ 21 min |
|   | 76% @ 2.8 $\mu$M @ 60 min | 11% @ 33 $\mu$M @ 60 min | 0% @ 5 $\mu$M @ 60 min |
| W | 34% @ 4.2 $\mu$M @ 21 min | 9% @ 173 $\mu$M @ 21 min | 0% @ 13 $\mu$M @ 21 min |
|   | 38% @ 4.2 $\mu$M @ 60 min | 0% @ 173 $\mu$M @ 60 min | 0% @ 13 $\mu$M @ 60 min |
| X | 86% @ 2.2 $\mu$M @ 21 min | 18% @ 15 $\mu$M @ 21 min | 0% @ 3 $\mu$M @ 21 min |
|   | 85% @ 2.2 $\mu$M @ 60 min | 16% @ 15 $\mu$M @ 60 min | 0% @ 3 $\mu$M @ 60 min |
| Y | 75% @ 2.8 $\mu$M @ 21 min | 11% @ 33 $\mu$M @ 21 min | 0% @ 5 $\mu$M @ 21 min |
|   | 76% @ 2.8 $\mu$M @ 60 min | 11% @ 33 $\mu$M @ 60 min | 0% @ 5 $\mu$M @ 60 min |
| Z | 86% @ 2.2 $\mu$M @ 21 min | 18% @ 15 $\mu$M @ 21 min | 0% @ 3 $\mu$M @ 21 min |
|   | 85% @ 2.2 $\mu$M @ 60 min | 16% @ 15 $\mu$M @ 60 min | 0% @ 3 $\mu$M @ 60 min |
| AA | 96% @ 2.2 $\mu$M @ 21 min | 58% @ 5.7 $\mu$M @ 21 min | 34% @ 0.9 $\mu$M @ 21 min |
|   | 97% @ 2.2 $\mu$M @ 60 min | 55% @ 2.2 $\mu$M @ 60 min | 0% @ 0.9 $\mu$M @ 60 min |

In Vivo Assay of Chemopreventive Effects of Therapeutic Compounds in Rats with Azoxymethane-induced Aberrant Crypt Foci Azoxymethane (AOM) (CAS:25843-45-2) was purchased from Ash Stevens (Detroit, Mich.). iNOS and COX-2 selective inhibitors were provided by Pharmacia, (St. Louis, Minn.). Sulindac, a non-selective inhibitor of COX-isoforms and a known inhibitor of colon carcinogenesis, was supplied by the Chemoprevention Branch of the National Cancer Institute (Bethesda, Md.). Weanling male F344 rats were purchased from Charles River Breeding Laboratories (Kingston, N.Y.). All ingredients of the semipurified diet were obtained from Dyets Inc., (Bethlehem, Pa.) and were stored at 4° C. until the experimental diets were prepared. The rats were held in quarantine for 1 week and had access to modified AIN-76A semipurified control diet (Reddy et al., *Cancer Res.* 50: 2562–2568, 1990, which is herein incorporated by reference.). They were randomly distributed into various dietary groups and were transferred to an animal holding room where they were housed, three rats to a plastic cage, under controlled conditions of a 12-h light/12-h dark cycle, 50% relative humidity and 21° C. room temperature. Experimental diets were prepared by mixing chemopreventive agents with modified AIN-76A control diet.

At five weeks of age, groups of male F344 rats (16–21 rats/group) were fed the modified AIN-76A (control) or experimental diets containing 10, 30, or 100 ppm of iNOS-selective inhibitor compound XI (supra), or 1800 ppm aminoguanidine (an iNOS nonselective inhibitor), or 500 ppm celecoxib (a COX-2 selective inhibitor, compound B-18 supra). Other groups of the same size were given 30 ppm compound XI+500 ppm celecoxib, 100 ppm compound XI+500 ppm celecoxib, or 320 ppm sulindac. At seven weeks of age, all animals except the vehicle-treated rats received azoxymethane (AOM) by subcutaneous injection once weekly for two weeks at a dose rate of 15 mg/kg body weight per week. Control animals intended for vehicle treatment were given an equal volume of normal saline. One day prior to the first azoxymethane injection and 4 and 8 weeks after the second azoxymethane treatment, while the rats were maintained on control or experimental diets, blood samples were taken from animals in each group from the ocular vein under halothane anesthesia for analysis of iNOS and COX-2 inhibitors in blood plasma. All rats were killed by $CO_2$ euthanasia, 8 weeks after the second azoxymethane injection. The colons were removed (12/group), flushed with Krebs Ringer solution, opened from cecum to anus, and fixed flat between two pieces of filter paper in 10% buffered formalin for aberrant crypt foci analysis. Rats intended for the analysis of $Ca^{+2}$-dependent and $Ca^{+2}$-independent NOS, and COX-1 and COX-2 activities, were killed by $CO_2$ euthanasia and their colonic mucosae were scraped, frozen under liquid $N_2$ and stored at −70° C. for further analysis.

To quantify aberrant crypt foci, after a minimum of 24 h in buffered formalin, the colons were cut into 2-cm segments starting at the anus; for the next 5–10 min they were placed in a Petri dish containing 0.2% methylene blue in Krebs Ringer solution. They were then placed, mucosal side up, on a microscope slide and observed through a light microscope. Aberrant crypt foci were recorded according to standard procedures that are being used routinely in our laboratory (Rao et al., *Carcinogenesis* 21: 617–21, 2000; Rao et al., *Cancer Res.* 53:4182–88, 1993, which are herein incorporated by reference.). Aberrant crypts were distinguished from the surrounding normal crypts by their increased size, significantly increased distance from lamina to basal surfaces of cells, and the easily discernible pericryptal zone. The parameters used to assess the aberrant crypts were their occurrence and multiplicity. Crypt multiplicity was determined as the number of crypts in each focus and categorized as containing up to 3, or 4 or more aberrant crypts/focus. All colons were scored by one observer who did not know the identity of agents under study; scores were checked at random by a second observer. All results were expressed as the means±SEM.

The body weights of rats treated with vehicle or AOM and fed the control or experimental diets containing iNOS and COX-2 inhibitors or sulindac were comparable throughout the study period. In vehicle-treated rats, feeding the experimental diets containing selective iNOS-COX-2 inhibitors or its combinations, or sulindac did not produce any toxicity or any gross changes in the liver, kidney, intestine and lungs.

Table 4 shows the chemopreventive effect of iNOS-selective inhibitors and celecoxib, a COX-2 selective inhibitor, individually and in combination, on azoxymethane-induced colonic aberrant crypt foci formation in male F344 rats. The control rats treated with saline and fed the regular or experimental diets showed no evidence of aberrant crypt foci (ACF) formation in the colon. In rats fed the control diet, azoxymethane treatment induced, on average, about 120 ACF/colon and 29 foci that contained multiple (4 or more) aberrant crypts/focus (Table 4). ACF were predominantly observed in the distal colons. Efficacy endpoints used in this study were the inhibition of occurrence of ACF as well as reduction of the number of multicrypt clusters (4 or more) of aberrant crypts. As expected, administration of sulindac (positive control), a non-selective COX-inhibitor, was also found to be an effective inhibitor of total ACF/colon (40%) and of multicrypt clusters containing 4 or more aberrant crypts/focus (50%). None of the test agents had any measurable impact on the formation of 1 or 2 aberrant crypt foci formation but inhibitor effects were seen with respect to 3-crypt foci formation (Table 4). Administration of low dose levels (10 or 30 ppm) of iNOS selective inhibitor compound XI or 500 ppm of the COX-2 inhibitor celecoxib had minimal inhibitory effect on the total ACF (5–20% inhibition). However, high dose levels of iNOS-selective inhibitors (100 ppm of iNOS inhibitor compound XI and 1,800 ppm of aminoguanidine) suppressed AOM-induced total colonic ACF and multicrypt clusters of 4 or more crypts as compared to control diet. Importantly, combination of iNOS (30 ppm iNOS selective inhibitor compound XI) and COX-2 (500 ppm celecoxib) inhibitors decreased total colonic ACF and aberrant crypt multiplicities (4 or more per focus). Further, the data on the colonic ACF by iNOS-selective inhibitors suggest a trend toward greater supression of crypt multiplicities than of the total ACF inhibition.

TABLE 4

Chemopreventive effect of by iNOS-selective inhibitors and celecoxib individually and in combination on AOM-induced colonic ACF formation in male F344 rats. (Mean ± SEM (N = 12–16))

| Experimental Group | Foci containing | | | | Total ACF incidence |
|---|---|---|---|---|---|
| | 1 Crypt | 2 Crypt | 3 Crypt | ≧4 Crypts | |
| 1 Control | 23.4 ± 1.9 | 30.8 ± 2.6 | 37.6 ± 2.2 | 28.9 ± 2.0 | 120 ± 6.7 |
| 2 10 ppm compound XI | 28.2 ± 1.8 | 31.7 ± 2.7 | 29.3 ± 2.3 | 25.6 ± 1.8 | 115 ± 4.8 |
| 3 30 ppm compound XI | 28.7 ± 2.9 | 32.6 ± 1.8 | 24.8 ± 1.7 | 22 ± 2.7 | 108 ± 5.5 |
| 4 100 ppm compound XI | 28.6 ± 2.2 | 33.6 ± 2.1 | 17.7 ± 1.1 | 13.9 ± 1.1 | 93.8 ± 4.2 |
| 5 1800 ppm aminoguanidine | 28.0 ± 2.4 | 29.3 ± 1.3 | 17.8 ± 1.0 | 14.6 ± 1.8 | 89.8 ± 4.5 |
| 6 500 ppm Celecoxib | 26.8 ± 2.1 | 27.3 ± 2.0 | 23.7 ± 2.3 | 23.3 ± 2.7 | 102 ± 7.5 |
| 7 30 ppm compound XI + 500 ppm Celecoxib | 29.3 ± 3.0 | 31.2 ± 2.3 | 21.6 ± 2.0 | 17.6 ± 1.9 | 99.7 ± 7.5 |
| 8 100 ppm compound XI + 500 ppm Celecoxib | 26.3 ± 2.9 | 27.4 ± 2.2 | 16.3 ± 1.9 | 12.6 ± 1.8 | 84.3 ± 6.3 |
| 9 320 ppm Sulindac | 23.3 ± 1.8 | 28.0 ± 1.5 | 17.3 ± 1.7 | 16.5 ± 0.9 | 84.9 ± 4.1 |

Abbreviations: AOM, azoxymethane; ACF, aberrant crypt foci.

In Vivo Assay of Modulation of Colonic Mucosal Activities of NOS and COX isoforms by iNOS and COX-2 Inhibitors NOS and iNOS activities were determined in colonic samples as prepared and described above. Conversion of L-arginine to L-citrulline was measured by a modification of an earlier described method (Rao et al, *Carcinogenesis* 21, supra; Ambs et al., *Cancer Res.* 58:334–41, 1998, which is herein incorporated by reference). The assay was carried out by adding 100 μg sample protein to 150 μl of assay buffer [50 mM HEPES, 1 mM DTT, 1 mM $MgCl_2$, 5 mg/L pepstatin A, 0.1 mM PMSF, and 3 mg/L aprotinin, pH 7.4] containing 70 μM arginine, 250,000 dpm L-[$^3$H]-arginine, 2 mM NADPH, 5μM tetrahydro biopterin, 5 μM flavin adenine dinucleotide, and 0.5 mM $CaCi_2$ to measure total NOS activity, or 1 mM EGTA (without calcium) to determine $Ca^{+2}$-independent iNOS activity. After 30 min at 37° C., the reaction was stopped with 100 μl of 1M trichloroacetic acid. Then the samples were adjusted to pH 4.6 by adding 500 μl of 20 mM HEPES and loaded on to Dowex AG 50W-X8 resin columns. L-[$^3$H]-citrulline was eluted and separated on TLC. Radioactivity was counted by a BioScan Radiomatic detector. Results are expressed as pmol L-[$^3$H]-citrulline released/mg protein/min.

Colonic samples as prepared and described above were assayed for COX-1 and COX-2 activities, using a slight modification of previously published methods (Rao et al., *Carcinogenesis* 21, supra; Rao et al., *Cancer Res.* 55:2310–15, 1995, which is herein incorporated by reference). Briefly, 150 μl of the reaction mixture contained 12 μM $^{14}$C-AA ($^{14}$C-labeled arachidonic acid; 420,000 dpm), 1 mM epinephrine, 1 mM glutathione in 50 mM of phosphate buffer (pH 7.4) and 20–30 μg of microsomal protein. For measuring COX-1 activity, proteins were preincubated with 25 μM of celecoxib, a COX-2 specific inhibitor, to block the COX-2 isoform activity. For determining COX-2 activity, proteins were preincubated with 50 μM of aspirin to block the activity of COX-1. After incubation at 37° C. for 15 min, the reaction was terminated by adding 40 μl of 0.2 M HCl. The COX-mediated metabolites of arachidonic acid were extracted with ethyl acetate (3×0.5 ml). The combined extracts were evaporated to dryness under $N_2$, redissolved in chloroform, and subjected to thin layer chromatography on precoated TLC plastic plates (silica G 60, 20×20 cm, layer thickness 150 μm). The TLC plates were developed with a solvent system containing chloroform/methanol/acetic acid/water (100/15/1.25/1, v/v/v/v) and exposed in an iodide chamber for 5 min to visualize the standards. The metabolites of $^{14}$C-AA corresponding to $PGE_2$, $PGF_{2\alpha}$, $PGD_2$, 6-Keto $PGF_{1\alpha}$, and $TXB_2$ were detected by their comigration (Rf-values) with authentic standards. The area of each metabolite was determined in a Bioscan System 200 image scanning counter (Bioscan Inc., Washington, D.C.) equipped with β-detector. All results were expressed as the means±SEM.

Table 5 summarizes the modulation of colonic mucosal activities of NOS and COX isoforms by iNOS- and COX-2-inhibitors. Administration of AOM increased iNOS activity in the colonic mucosa but had minimal effect on $Ca^{+2}$-dependent NOS activity. AOM treatment induced both isoforms of COX activities, but the effect is more pronounced on COX-2 activity than on COX-1 activity (~4-fold). Selective inhibitors of iNOS such as compound XI administered at 100 ppm and aminoguanidine at 1800 ppm levels suppressed the AOM-induced colonic mucosal iNOS activity by ~37% and 50%, respectively. Administration of 500 ppm celecoxib had a moderate inhibitory effect on the AOM-induced COX-2 activity. Interestingly, administration of 100 ppm of iNOS selective inhibitor compound XI plus 500 ppm celecoxib produced selective suppression of iNOS and COX-2 activities in colonic mucosa.

TABLE 5

Effect of iNOS and COX-2 selective inhibitors on
AOM-induced colonic mucosal
NOS, iNOS, COX-1 and COX-2 activities in male F344 rats.

| Experimental Group | NOS Activity pmoles [$^3$H]-citrulline/mg protein/min | | COX-Activity pmoles [$^{14}$C]-AA metabolized/mg protein/min | |
|---|---|---|---|---|
| | NOS | iNOS | COX-1 | COX-2 |
| Vehicle-treated Control | 8.2 ± 1.4 | ≦0.1 | 7.7 ± 1.0 | 0.2 ± 0.1 |
| AOM-treated Control | 10.5 ± 1.9 | 2.4 ± 0.5 | 14.2 ± 2.3 | 2.6 ± 0.4 |
| 100 ppm compound XI | 9.8 ± 1.5 | 1.6 ± 0.2 | 11.3 ± 1.4 | 1.8 ± 0.3 |
| 1800 ppm aminoguanidine | 7.9 ± 1.7 | 1.1 ± 0.1 | 10.8 ± 1.9 | 1.2 ± 0.2 |
| 500 ppm celecoxib | 11.3 ± 2.1 | 2.7 ± 0.4 | 12.9 ± 2.0 | 1.1 ± 0.2 |
| 100 ppm compound XI + 500 ppm celecoxib | 7.8 ± 1.3 | 1.2 ± 0.2 | 10.5 ± 1.1 | 0.6 ± 0.1 |

Mean ± SEM (n = 4–6)
Abbreviations: AA, arachidonic acid; AOM, azoxymethane acetate:0.2% acetic acid in water by volume. The extracts were analyzed by LC using a ZORBAX NH$_2$ analytical column. Inducible NOS was detected by tandom mass spectrometry in a PE Sciex API 2000 MS/MS instrument (Perkin-Elmer, Foster City, Calif.). All results were expressed as the means±SEM.

Table 6 shows the plasma levels of iNOS and COX-2 inhibitors in the subject rats. The results summarized in Table 6 indicate that the plasma levels of celecoxib administered at 500 ppm ranged from 1.07 to 1.70 µg/ml during various time points. Dose-dependant absorption of compound XI was observed when rats were administered with 3 dose levels of test agent (10 ppm, 461, 341 and 254 ηg/ml; 30 ppm, 1315, 821, and 742 ηg/ml; and 100 ppm, 4306, 2811 and 2639 ηg/ml, reflecting 3 time points respectively. The results also indicate that administration of 30 or 100 ppm iNOS selective inhibitor compound XI in combination with 500 celecoxib had no time-dependent increase in the plasma.

TABLE 6

Plasma levels of iNOS and COX-2 inhibitors in male F344 rats.

| | Chemopreventive Agent | Early One week on diet | Mid 5 weeks on diet | Late 9 weeks on diet |
|---|---|---|---|---|
| 1 | 10 ppm compound XI | 461 ± 15 | 341 ± 9.7 | 254 ± 13 |
| 2 | 20 ppm compound XI | 1315 ± 71 | 821 ± 32 | 742 ± 7 |
| 3 | 100 ppm compound XI | 4306 ± 146 | 2811 ± 82 | 2639 ± 268 |
| 4 | 500 ppm Celecoxib | 1440 ± 118 | 1706 ± 176 | 1072 ± 358 |
| 5 | 30 ppm compound XI + 500 ppm Celecoxib | 1240 ± 37 + 1066 ± 43 | 901 ± 5.0 + 1660 ± 153 | 788 ± 63 2534 ± 96 |
| 6 | 100 ppm compound XI + 500 ppm Celecoxib | 4370 ± 112 + 1475 ± 72 | 3096 ± 344 + 1547 ± 92 | 2477 ± 204 + 1959 ± 191 |

Values are ηg/ml plasma, Mean ± SEM (N = 4)

Plasma Levels of iNOS and COX-2 Inhibitors

To establish dose-relevance and pharmacological interactive effects of celecoxib and iNOS selective inhibitor compound XI in rats fed given both agents, plasma levels were examined at various time points as described above. Celecoxib in plasma was determined as described previously using reverse phase high-performance liquid chromatography and a fluorescence detector with excitation at 240 ηm and emission at 380 ηm (Kawamori et al., *Cancer Res.* 58:409–12, 1998, which is herein incorporated by reference). To assess compound XI, plasma samples (0.2 ml) containing compound XI and an internal standard were acidified with formic acid. The samples were first extracted with a solid phase extraction (Bond Elut PRS 100 mg sorbent mass, 1 cc columns). The samples were eluted with 1:10 ammonium hydroxide: methanol and the eluates were evaporated under N$_2$ and redissovled in a mobile phase consisting of 45:35:20 acetonitrile:25 mM ammonium j. Example of Embodiment The following non-limiting examples serve to illustrate various aspects of the present invention.

EXAMPLE 1

Pharmaceutical Compositions 100 mg tablets of the composition set forth in Table 7 can be prepared using wet granulation techniques:

TABLE 7

| Ingredient | Weight (mg) |
|---|---|
| Compound I | 5 |
| Lactose | 74 |
| Microcrystalline Cellulose | 15 |
| Hydroxypropyl Methylcellulose | 3 |

TABLE 7-continued

| Ingredient | Weight (mg) |
|---|---|
| Croscarmelose Sodium | 2 |
| Magnesium Stearate | 1 |
| Total Tablet Weight | 100 |

EXAMPLE 2

Pharmaceutical Compositions 100 mg tablets of the composition set forth in Table 8 can be prepared using direct compression techniques:

TABLE 8

| Ingredient | Weight (mg) |
|---|---|
| Compound I | 5 |
| Compound C4 (celecoxib) | 20 |
| Microcrystalline Cellulose | 69.5 |
| Colloidal Silicon Dioxide | 0.5 |
| Talc | 2.5 |
| Croscarmelose Sodium | 0.5 |
| Magnesium Stearate | 1 |
| Total Tablet Weight | 100 |

The examples described herein can be performed by substituting the generically or specifically described therapeutic compounds or inert ingredients for those used in the preceding examples.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed:

1. A method for treating a cancer in a subject in need of such treatment, said method consisting of administering to the subject an effective amount of a pharmaceutical composition consisting essentially of an inducible nitric oxide synthase selective inhibitor or pharmaceutically acceptable salt thereof or prodrug thereof, wherein the inducible nitric oxide synthase inhibitor is a compound having a structure corresponding to Formula II

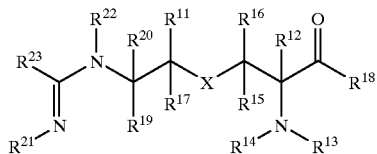

or a pharmaceutically acceptable salt thereof, wherein X is —S—, $R^{12}$ is $C_1$ $R^{18}$ is —$OR^{24}$ $R^{13}$ is —H, $R^{14}$ is —H, $R^{11}$, $R^{15}$, $R^{16}$, and $R^{17}$ are —H, $R^{19}$ and $R^{20}$ —H, $R^{21}$ —H, $R^{22}$ is —H, $R^{23}$ is $C_1$ alkyl, and $R^{24}$ is —H.

2. The method of claim 1 wherein said cancer is selected from the group consisting of: acute lymphoblastic leukemia; acute myeloid leukemia; adrenocortical carcinoma; aids-related lymphoma; aids-related malignancies; anal cancer; cerebellar astrocytoma; extrahepatic bile duct cancer; bladder cancer; osteosarcoma/malignant fibrous histiocytoma; brain stem glioma; ependymoma; medulloblastoma; supratentorial primitive neuroectodermal and pineal tumors; visual pathway and hypothalamic gliomas; breast cancer; bronchial adenomas/carcinoids; carcinoid tumors; gastrointestinal carcinoid tumors; carcinoma; adrenocortical; islet cell carcinoma; carcinoma of unknown primary; primary central nervous system lymphoma; cerebellar astrocytoma; cervical cancer; chronic lymphocytic leukemia; chronic myelogenous leukemia; clear cell sarcoma of tendon sheaths; colon cancer; colorectal cancer; cutaneous t-cell lymphoma; endometrial cancer; ependymoma; ovarian epithelial cancer; esophageal cancer; ewing's sarcoma/family of tumors; extracranial germ cell tumors; extragonadal germ cell tumors; extrahepatic bile duct cancer; eye cancers; including intraocular melanoma; and retinoblastoma; gallbladder cancer; gastric (stomach) cancer; gastrointestinal carcinoid tumor; ovarian germ cell tumor; geetational trophoblastic tumor; hairy cell leukemia; head and neck cancer; primary hepatocellular cancer; Hodgkin's disease; including Hodgkin's disease during pregnancy; hypopharyngeal cancer; hypothalamic and visual pathway glioma; intraocular melanoma; islet cell carcinoma (endocrine pancreas); Kaposi's sarcoma; kidney cancer; laryngeal cancer; acute lymphoblastic leukemia; acute myeloid leukemia; chronic lymphocytic; leukemia; chronic myelogenous leukemia; hairy cell; lip and oral cavity cancer; liver cancer; non-small cell lung cancer; small cell lung cancer; Hodgkin's disease; non-Hodgkin's lymphoma; Waldenstrom's macroglobulinemia; male breast cancer; malignant mesothelioma; malignant thymoma; medulloblastoma; melanoma; intraocular melanoma; merkel cell carcinoma; malignant mesothelioma; metastatic squamous neck cancer with occult primary; multiple endocrine neoplasia syndrome; multiple myeloma/plasma cell neoplasm; mycosis fungoides; myelodysplastic syndrome; chronic myelogenous leukemia; myeloid leukemia; multiple myeloma; myeloproliferative disorders; nasal cavity and paranasal sinus cancer; nasopharyngeal cancer; neuroblastoma; oral cancer; oral cavity and lip cancer; oropharyngeal cancer; osteosarcoma/malignant fibrous histiocytoma of bone; ovarian epithelial cancer; ovarian low malignant potential tumor; pancreatic cancer; pancreatic cancer; islet cell; paranasal sinus and nasal cavity cancer; parathyroid cancer; penile cancer; pheochromocytoma; pineal and supratentorial primitive neuroectodermal tumors; pituitary tumor; pleuropulmonary blastoma; prostate cancer; rectal cancer; renal cell (kidney) cancer; transitional cell cancer (e.g. renal pelvis and ureter); retinoblastoma; rhabdomyosarcoma; salivary gland cancer; Ewing's family of tumors/primitive neuroectodermal tumor (pnet); malignant fibrous histiocytoma of bone; soft tissue sarcoma; sezary syndrome; skin cancer; small intestine cancer; stomach (gastric) cancer; supratentorial primitive neuroectodermal and pineal tumors; cutaneous t-cell lymphoma; testicular cancer; malignant thyrnoma; thyroid cancer; transitional cell cancer of the renal pelvis and ureter; gestational trophoblastic tumor; cancer of unknown primary site; unusual cancers of childhood; urethral cancer; uterine sarcoma; vaginal cancer; vulvar cancer; and Wilms' tumor.

3. The method of claim 2 wherein said cancer is selected from the group consisting of: gastrointestinal cancer; liver cancer; bladder cancer; pancreas cancer; ovary cancer; prostate cancer; cervical cancer; lung cancer; breast cancer; multiple myeloma, chronic lymphocytic leukemia, and skin cancer.

4. The method of claim 1 wherein said cancer is selected from the group consisting of: brain cancer; bone cancer; a leukemia; a lymphoma; epithelial cell-derived neoplasia; adenocarcinoma; gastrointestinal cancer; liver cancer; bladder cancer; pancreas cancer; ovary cancer; cervical cancer; lung cancer; breast cancer; skin cancer; prostate cancer; and renal cell carcinoma.

5. A method for treating a cancer in a subject in need of such treatment, said method consisting essentially of administering to the subject an effective amount of an inducible nitric oxide synthase selective inhibitor or pharmaceutically acceptable salt thereof or prodrug thereof, wherein the inducible nitric oxide synthase inhibitor is S-[2-[(1-Iminoethyl)amino]ethyl]-2-methyl-L-cysteine, or a pharmaceutically acceptable salt thereof.

* * * * *